(12) United States Patent
Cronin et al.

(10) Patent No.: US 7,326,552 B1
(45) Date of Patent: Feb. 5, 2008

(54) WILD-TYPE KINASE DOMAIN OF HUMAN EPHRIN RECEPTOR A2 (EPHA2) AND CRYSTALLIZATION THEREOF

(75) Inventors: Ciaran N. Cronin, San Diego, CA (US); Jacek Nowakowski, San Diego, CA (US); Nikola P. Pavletich, New York, NY (US); Devon A. Thompson, San Diego, CA (US)

(73) Assignee: Takeda San Diego, Inc., San Diego, CA (US)

( * ) Notice: Subject to any disclaimer, the term of this patent is extended or adjusted under 35 U.S.C. 154(b) by 452 days.

(21) Appl. No.: 10/601,324

(22) Filed: Jun. 20, 2003

Related U.S. Application Data

(60) Provisional application No. 60/390,356, filed on Jun. 21, 2002.

(51) Int. Cl.
C07K 14/00 (2006.01)
G01N 31/00 (2006.01)
C12N 9/12 (2006.01)
C12Q 1/48 (2006.01)

(52) U.S. Cl. ............................ 435/194; 436/4; 435/15; 702/27; 530/350

(58) Field of Classification Search ................ 435/194
See application file for complete search history.

(56) References Cited

OTHER PUBLICATIONS

Creighton. T., "Encyclopedia of Molecular Biology", John Wiley and Sons, Inc. New York, 1999, pp. 586 and 2725.*
Giege et al., Acta Cryst.-D, vol. 50, pp. 339-350, 1994.*
Kierzek et al., Biophys. Chem., vol. 91, pp. 1-20, 2001.*
Wiencek, Annu. Rev. Biomed. Eng., vol. 1, pp. 505-534, 1999.*
Ke & Doudna, Methods, vol. 34, pp. 408-414, 2004.*
Derewenda et al. Acta Crystallogr. D., vol. 62, pp. 116-124, 2006.*
Buts et al., Acta Crystallogr. D., vol. 61, pp. 1149-1159, 2005.*
Witkowski et al., Biochemistry, vol. 38, pp. 11643-11650, 1999.*
Lindberg et al., Mol. Cell. Biol., vol. 10, pp. 6316-6324, 1990.*
Dale et al. The Protein as a Variable in Protein Crystallization. Journal of Structural Biology. 2003. vol. 142, pp. 88-97.*
McPherson, A. Current Approaches to Macromolecular Crystallization. European Journal of Biochemistry. 1990. vol. 189, pp. 1-23.*
CCP4 Bulletin Board—His- Tags. Dec. 21, 2001 http://www.ysbl.york.ac.uk/ccp4bb/2001/msg01286.html.*
Lauri, Georges et al., CAVEAT: A program to facilitate the design of organic molecules, Journal of Computer-Aided Molecular Design, (1994), vol. 8, pp. 51-66.

* cited by examiner

*Primary Examiner*—David J. Steadman
*Assistant Examiner*—Suzanne M. Noakes
(74) *Attorney, Agent, or Firm*—David J. Weitz

(57) ABSTRACT

Provided are crystals relating to human Ephrin Receptor A2 and its various uses.

15 Claims, 90 Drawing Sheets

FIGURE 1

Amino acid sequence for full length human wild type EPHA2 [SEQ ID NO: 1]

(Residues 596-900 are underlined)

```
MELQAARACFALLWGCALAAAAAAQGKEVVLLDFAAAGGELGWLTHPYGK        50
GWDLMQNIMNDMPIYMYSVCNVMSGDQDNWLRTNWVYRGEAERNNFELNF       100
TVRDCNSFPGGASSCKETFNLYYAESDLDYGTNFQKRLFTKIDTIAPDEI       150
TVSSDFEARHVKLNVEERSVGPLTRKGFYLAFQDIGACVALLSVRVYYKK       200
CPELLQGLAHFPETIAGSDAPSLATVAGTCVDHAVVPPGGEEPRMHCAVD       250
GEWLVPIGQCLCQAGYEKVEDACQACSPGFFKFEASESPCLECPEHTLPS       300
PEGATSCECEEGFFRAPQDPASMPCTRPPSAPHYLTAVGMGAKVELRWTP       350
PQDSGGREDIVYSVTCEQCWPESGECGPCEASVRYSEPPHGLTRTSVTVS       400
DLEPHMNYTFTVEARNGVSGLVTSRSFRTASVSINQTEPPKVRLEGRSTT       450
SLSVSWSIPPPQQSRVWKYEVTYRKKGDSNSYNVRRTEGFSVTLDDLAPD       500
TTYLVQVQALTQEGQGAGSKVHEFQTLSPEGSGNLAVIGGVAVGVVLLLV       550
LAGVGFFIHRRRKNQRARQSPEDVYFSKSEQLKPLKTYVDPHTYEDPNQA       600
VLKFTTEIHPSCVTRQKVIGAGEFGEVYKGMLKTSSGKKEVPVAIKTLKA       650
GYTEKQRVDFLGEAGIMGQFSHHNIIRLEGVISKYKPMMIITEYMENGAL       700
DKFLREKDGEFSVLQLVGMLRGIAAGMKYLANMNYVHRDLAARNILVNSN       750
LVCKVSDFGLSRVLEDDPEATYTTSGGKIPIRWTAPEAISYRKFTSASDV       800
WSFGIVMWEVMTYGERPYWELSNHEVMKAINDGFRLPTPMDCPSAIYQLM       850
MQCWQQERARRPKFADIVSILDKLIRAPDSLKTLADFDPRVSIRLPSTSG       900
SEGVPFRTVSEWLESIKMQQYTEHFMAAGYTAIEKVVQMTNDDIKRIGVR       950
LPGHQKRIAYSLLGLKDQVNTVGIPI                              976
```

FIGURE 1A

Human cDNA sequence encoding residues 596-900 of EPHA2 [SEQ ID NO: 2]

| | |
|---|---|
| GACCCCAACCAGGCTGTGTTGAAGTTCACTACCGAGATCCATCCATCCTG | 50 |
| TGTCACTCGGCAGAAGGTGATCGGAGCAGGAGAGTTTGGGGAGGTGTACA | 100 |
| AGGGCATGCTGAAGACATCCTCGGGGAAGAAGGAGGTGCCGGTGGCCATC | 150 |
| AAGACGCTGAAAGCCGGCTACACAGAGAAGCAGCGAGTGGACTTCCTCGG | 200 |
| CGAGGCCGGCATCATGGGCCAGTTCAGCCACCACAACATCATCCGCCTAG | 250 |
| AGGGCGTCATCTCCAAATACAAGCCCATGATGATCATCACTGAGTACATG | 300 |
| GAGAATGGGGCCCTGGACAAGTTCCTTCGGGAGAAGGATGGCGAGTTCAG | 350 |
| CGTGCTGCAGCTGGTGGGCATGCTGCGGGGCATCGCAGCTGGCATGAAGT | 400 |
| ACCTGGCCAACATGAACTATGTGCACCGTGACCTGGCTGCCCGCAACATC | 450 |
| CTCGTCAACAGCAACCTGGTCTGCAAGGTGTCTGACTTTGGCCTGTCCCG | 500 |
| CGTGCTGGAGGACGACCCCGAGGCCACCTACACCACCAGTGGCGGCAAGA | 550 |
| TCCCCATCCGCTGGACCGCCCCGGAGGCCATTTCCTACCGGAAGTTCACC | 600 |
| TCTGCCAGCGACGTGTGGAGCTTTGGCATTGTCATGTGGGAGGTGATGAC | 650 |
| CTATGGCGAGCGGCCCTACTGGGAGTTGTCCAACCACGAGGTGATGAAAG | 700 |
| CCATCAATGATGGCTTCCGGCTCCCCACACCCATGGACTGCCCCTCCGCC | 750 |
| ATCTACCAGCTCATGATGCAGTGCTGGCAGCAGGAGCGTGCCCGCCGCCC | 800 |
| CAAGTTCGCTGACATCGTCAGCATCCTGGACAAGCTCATTCGTGCCCTG | 850 |
| ACTCCCTCAAGACCCTGGCTGACTTTGACCCCGCGTGTCTATCCGGCTC | 900 |
| CCCAGCACGAGCGGC | 915 |

Amino acid sequence for residues 596-900 of EPHA2 with a cleavable (rTev) N-terminal 6x-histidine tag [SEQ ID NO: 3]
(6x-histidine tag and cleavage site are underlined)

| | |
|---|---|
| MSYYHHHHHHDYDIPTTENLYFQGAMGSDPNQAVLKFTTEIHPSCVTRQK | 50 |
| VIGAGEFGEVYKGMLKTSSGKKEVPVAIKTLKAGYTEKQRVDFLGEAGIM | 100 |
| GQFSHHNIIRLEGVISKYKPMMIITEYMENGALDKFLREKDGEFSVLQLV | 150 |
| GMLRGIAAGMKYLANMNYVHRDLAARNILVNSNLVCKVSDFGLSRVLEDD | 200 |
| PEATYTTSGGKIPIRWTAPEAISYRKFTSASDVWSFGIVMWEVMTYGERP | 250 |
| YWELSNHEVMKAINDGFRLPTPMDCPSAIYQLMMQCWQQERARRPKFADI | 300 |
| VSILDKLIRAPDSLKTLADFDPRVSIRLPSTSG | 333 |

FIGURE 3

LEGEND

Column headings from left to right are (A)'Atom Number', (B)'Atom Type', (C)'Amino Acid', (D)'Chain Identifier', (E)'Amino Acid Number' (SEQ ID NO: 1), (F)'X Coordinate', (G)'Y Coordinate', (H)'Z Coordinate', (I)'Occupancy' (OCC) and (J)'B factor'.

| A | B | C | D | E | F | G | H | I | J |
|---|---|---|---|---|---|---|---|---|---|
| 1 | N | ALA | A | 605 | 47.239 | 45.529 | 67.448 | 1.00 | 51.83 |
| 2 | CA | ALA | A | 605 | 46.929 | 45.860 | 66.049 | 1.00 | 52.40 |
| 3 | CB | ALA | A | 605 | 45.751 | 44.876 | 65.490 | 1.00 | 51.40 |
| 4 | C | ALA | A | 605 | 46.433 | 47.259 | 66.307 | 1.00 | 51.78 |
| 5 | O | ALA | A | 605 | 46.252 | 47.630 | 67.422 | 1.00 | 52.61 |
| 6 | N | THR | A | 606 | 46.218 | 48.048 | 65.302 | 1.00 | 51.19 |
| 7 | CA | THR | A | 606 | 45.719 | 49.337 | 65.564 | 1.00 | 49.98 |
| 8 | CB | THR | A | 606 | 46.128 | 50.120 | 64.454 | 1.00 | 48.98 |
| 9 | OG1 | THR | A | 606 | 47.553 | 50.041 | 64.401 | 1.00 | 50.88 |
| 10 | CG2 | THR | A | 606 | 45.766 | 51.541 | 64.651 | 1.00 | 48.25 |
| 11 | C | THR | A | 606 | 44.201 | 49.397 | 65.650 | 1.00 | 50.57 |
| 12 | O | THR | A | 606 | 43.487 | 48.868 | 64.787 | 1.00 | 51.60 |
| 13 | N | GLU | A | 607 | 43.680 | 50.086 | 66.646 | 1.00 | 49.68 |
| 14 | CA | GLU | A | 607 | 42.264 | 50.182 | 66.717 | 1.00 | 47.97 |
| 15 | CB | GLU | A | 607 | 41.796 | 50.123 | 68.130 | 1.00 | 47.41 |
| 16 | CG | GLU | A | 607 | 40.323 | 50.414 | 68.279 | 1.00 | 50.07 |
| 17 | CD | GLU | A | 607 | 39.394 | 49.230 | 68.074 | 1.00 | 39.82 |
| 18 | OE1 | GLU | A | 607 | 39.796 | 48.072 | 68.195 | 1.00 | 38.52 |
| 19 | OE2 | GLU | A | 607 | 38.260 | 49.515 | 67.856 | 1.00 | 41.61 |
| 20 | C | GLU | A | 607 | 41.841 | 51.347 | 65.971 | 1.00 | 48.16 |
| 21 | O | GLU | A | 607 | 42.392 | 52.398 | 66.162 | 1.00 | 48.74 |
| 22 | N | ILE | A | 608 | 40.955 | 51.146 | 64.963 | 1.00 | 50.14 |
| 23 | CA | ILE | A | 608 | 40.531 | 52.309 | 64.228 | 1.00 | 49.42 |
| 24 | CB | ILE | A | 608 | 41.128 | 52.517 | 62.742 | 1.00 | 51.19 |
| 25 | CG1 | ILE | A | 608 | 40.066 | 52.886 | 61.752 | 1.00 | 49.45 |
| 26 | CD1 | ILE | A | 608 | 39.259 | 51.726 | 61.615 | 1.00 | 60.72 |
| 27 | CG2 | ILE | A | 608 | 42.168 | 51.494 | 62.300 | 1.00 | 47.67 |
| 28 | C | ILE | A | 608 | 39.135 | 52.787 | 64.481 | 1.00 | 51.43 |
| 29 | O | ILE | A | 608 | 38.254 | 52.049 | 64.879 | 1.00 | 51.22 |
| 30 | N | HIS | A | 609 | 38.983 | 54.090 | 64.361 | 1.00 | 53.40 |
| 31 | CA | HIS | A | 609 | 37.727 | 54.745 | 64.674 | 1.00 | 55.30 |
| 32 | CB | HIS | A | 609 | 37.938 | 56.203 | 65.196 | 1.00 | 57.26 |
| 33 | CG | HIS | A | 609 | 36.715 | 56.776 | 65.835 | 1.00 | 60.02 |
| 34 | ND1 | HIS | A | 609 | 36.486 | 56.686 | 67.186 | 1.00 | 62.57 |
| 35 | CE1 | HIS | A | 609 | 35.313 | 57.221 | 67.471 | 1.00 | 62.48 |
| 36 | NE2 | HIS | A | 609 | 34.764 | 57.635 | 66.348 | 1.00 | 63.53 |
| 37 | CD2 | HIS | A | 609 | 35.606 | 57.345 | 65.301 | 1.00 | 62.09 |
| 38 | C | HIS | A | 609 | 36.701 | 54.718 | 63.557 | 1.00 | 53.34 |
| 39 | O | HIS | A | 609 | 36.943 | 55.109 | 62.474 | 1.00 | 55.03 |
| 40 | N | PRO | A | 610 | 35.517 | 54.263 | 63.854 | 1.00 | 52.90 |
| 41 | CA | PRO | A | 610 | 34.533 | 54.113 | 62.805 | 1.00 | 53.20 |
| 42 | CB | PRO | A | 610 | 33.246 | 53.864 | 63.591 | 1.00 | 52.67 |
| 43 | CG | PRO | A | 610 | 33.753 | 53.087 | 64.713 | 1.00 | 50.94 |

FIGURE 3A

| A | B | C | D | E | F | G | H | I | J |
|---|---|---|---|---|---|---|---|---|---|
| 44 | CD | PRO | A | 610 | 35.069 | 53.682 | 65.133 | 1.00 | 52.08 |
| 45 | C | PRO | A | 610 | 34.421 | 55.273 | 61.903 | 1.00 | 52.69 |
| 46 | O | PRO | A | 610 | 33.935 | 55.146 | 60.793 | 1.00 | 55.21 |
| 47 | N | SER | A | 611 | 34.789 | 56.418 | 62.391 | 1.00 | 52.17 |
| 48 | CA | SER | A | 611 | 34.546 | 57.584 | 61.639 | 1.00 | 52.33 |
| 49 | CB | SER | A | 611 | 34.694 | 58.833 | 62.562 | 1.00 | 54.93 |
| 50 | OG | SER | A | 611 | 35.822 | 58.723 | 63.443 | 1.00 | 49.81 |
| 51 | C | SER | A | 611 | 35.579 | 57.611 | 60.552 | 1.00 | 52.77 |
| 52 | O | SER | A | 611 | 35.394 | 58.256 | 59.545 | 1.00 | 54.01 |
| 53 | N | CYS | A | 612 | 36.679 | 56.915 | 60.701 | 1.00 | 49.87 |
| 54 | CA | CYS | A | 612 | 37.633 | 57.083 | 59.642 | 1.00 | 51.06 |
| 55 | CB | CYS | A | 612 | 39.044 | 56.889 | 60.169 | 1.00 | 50.65 |
| 56 | SG | CYS | A | 612 | 39.193 | 57.805 | 61.702 | 1.00 | 55.75 |
| 57 | C | CYS | A | 612 | 37.445 | 56.214 | 58.426 | 1.00 | 49.07 |
| 58 | O | CYS | A | 612 | 38.215 | 56.286 | 57.479 | 1.00 | 48.12 |
| 59 | N | VAL | A | 613 | 36.470 | 55.349 | 58.497 | 1.00 | 49.20 |
| 60 | CA | VAL | A | 613 | 36.329 | 54.361 | 57.471 | 1.00 | 48.42 |
| 61 | CB | VAL | A | 613 | 36.130 | 52.976 | 58.087 | 1.00 | 49.58 |
| 62 | CG1 | VAL | A | 613 | 35.493 | 52.026 | 57.030 | 1.00 | 46.32 |
| 63 | CG2 | VAL | A | 613 | 37.477 | 52.423 | 58.651 | 1.00 | 46.61 |
| 64 | C | VAL | A | 613 | 35.039 | 54.652 | 56.779 | 1.00 | 47.49 |
| 65 | O | VAL | A | 613 | 34.080 | 55.078 | 57.401 | 1.00 | 46.54 |
| 66 | N | THR | A | 614 | 34.976 | 54.426 | 55.496 | 1.00 | 46.87 |
| 67 | CA | THR | A | 614 | 33.674 | 54.449 | 54.961 | 1.00 | 47.76 |
| 68 | CB | THR | A | 614 | 33.230 | 55.839 | 54.547 | 1.00 | 48.10 |
| 69 | OG1 | THR | A | 614 | 32.501 | 55.759 | 53.312 | 1.00 | 53.74 |
| 70 | CG2 | THR | A | 614 | 34.430 | 56.804 | 54.383 | 1.00 | 48.56 |
| 71 | C | THR | A | 614 | 33.479 | 53.362 | 53.956 | 1.00 | 47.36 |
| 72 | O | THR | A | 614 | 34.145 | 53.317 | 52.971 | 1.00 | 49.44 |
| 73 | N | ARG | A | 615 | 32.519 | 52.496 | 54.192 | 1.00 | 46.37 |
| 74 | CA | ARG | A | 615 | 32.356 | 51.360 | 53.352 | 1.00 | 44.80 |
| 75 | CB | ARG | A | 615 | 31.323 | 50.464 | 53.993 | 1.00 | 43.89 |
| 76 | CG | ARG | A | 615 | 31.817 | 49.366 | 54.921 | 1.00 | 44.82 |
| 77 | CD | ARG | A | 615 | 30.699 | 48.434 | 55.297 | 1.00 | 45.58 |
| 78 | NE | ARG | A | 615 | 29.827 | 49.226 | 56.142 | 1.00 | 49.04 |
| 79 | CZ | ARG | A | 615 | 29.151 | 48.769 | 57.151 | 1.00 | 51.81 |
| 80 | NH1 | ARG | A | 615 | 29.164 | 47.437 | 57.427 | 1.00 | 50.76 |
| 81 | NH2 | ARG | A | 615 | 28.473 | 49.652 | 57.883 | 1.00 | 51.85 |
| 82 | C | ARG | A | 615 | 31.694 | 51.886 | 52.150 | 1.00 | 45.54 |
| 83 | O | ARG | A | 615 | 30.737 | 52.603 | 52.357 | 1.00 | 47.25 |
| 84 | N | GLN | A | 616 | 32.035 | 51.399 | 50.944 | 1.00 | 45.88 |
| 85 | CA | GLN | A | 616 | 31.366 | 51.824 | 49.681 | 1.00 | 46.97 |
| 86 | CB | GLN | A | 616 | 32.323 | 52.657 | 48.734 | 1.00 | 47.24 |
| 87 | CG | GLN | A | 616 | 33.258 | 53.608 | 49.475 | 1.00 | 49.82 |
| 88 | CD | GLN | A | 616 | 34.200 | 54.437 | 48.588 | 1.00 | 55.54 |
| 89 | OE1 | GLN | A | 616 | 35.203 | 53.909 | 48.073 | 1.00 | 56.72 |
| 90 | NE2 | GLN | A | 616 | 33.889 | 55.770 | 48.428 | 1.00 | 56.51 |
| 91 | C | GLN | A | 616 | 30.597 | 50.752 | 48.848 | 1.00 | 46.63 |
| 92 | O | GLN | A | 616 | 29.448 | 50.970 | 48.361 | 1.00 | 48.68 |
| 93 | N | LYS | A | 617 | 31.167 | 49.598 | 48.678 | 1.00 | 44.77 |
| 94 | CA | LYS | A | 617 | 30.497 | 48.628 | 47.857 | 1.00 | 44.21 |
| 95 | CB | LYS | A | 617 | 30.835 | 48.787 | 46.331 | 1.00 | 44.70 |

FIGURE 3B

| A | B | C | D | E | F | G | H | I | J |
|---|---|---|---|---|---|---|---|---|---|
| 96 | CG | LYS | A | 617 | 32.399 | 48.959 | 45.944 | 1.00 | 48.09 |
| 97 | CD | LYS | A | 617 | 32.768 | 48.759 | 44.391 | 1.00 | 58.41 |
| 98 | CE | LYS | A | 617 | 34.285 | 49.300 | 44.085 | 1.00 | 60.72 |
| 99 | NZ | LYS | A | 617 | 35.073 | 48.944 | 42.813 | 1.00 | 59.09 |
| 100 | C | LYS | A | 617 | 31.019 | 47.331 | 48.370 | 1.00 | 43.38 |
| 101 | O | LYS | A | 617 | 32.139 | 47.297 | 48.834 | 1.00 | 42.92 |
| 102 | N | VAL | A | 618 | 30.126 | 46.333 | 48.379 | 1.00 | 42.86 |
| 103 | CA | VAL | A | 618 | 30.376 | 44.945 | 48.657 | 1.00 | 41.23 |
| 104 | CB | VAL | A | 618 | 29.070 | 44.146 | 48.522 | 1.00 | 39.95 |
| 105 | CG1 | VAL | A | 618 | 29.426 | 42.622 | 48.582 | 1.00 | 40.13 |
| 106 | CG2 | VAL | A | 618 | 28.147 | 44.503 | 49.610 | 1.00 | 42.60 |
| 107 | C | VAL | A | 618 | 31.203 | 44.381 | 47.543 | 1.00 | 40.46 |
| 108 | O | VAL | A | 618 | 30.854 | 44.667 | 46.392 | 1.00 | 42.70 |
| 109 | N | ILE | A | 619 | 32.237 | 43.567 | 47.809 | 1.00 | 37.69 |
| 110 | CA | ILE | A | 619 | 33.059 | 43.022 | 46.731 | 1.00 | 33.98 |
| 111 | CB | ILE | A | 619 | 34.521 | 43.786 | 46.495 | 1.00 | 36.65 |
| 112 | CG1 | ILE | A | 619 | 35.584 | 43.320 | 47.540 | 1.00 | 31.94 |
| 113 | CD1 | ILE | A | 619 | 36.383 | 44.380 | 48.493 | 1.00 | 29.73 |
| 114 | CG2 | ILE | A | 619 | 34.380 | 45.336 | 46.302 | 1.00 | 31.41 |
| 115 | C | ILE | A | 619 | 33.357 | 41.588 | 46.995 | 1.00 | 33.91 |
| 116 | O | ILE | A | 619 | 34.185 | 41.024 | 46.280 | 1.00 | 35.83 |
| 117 | N | GLY | A | 620 | 32.752 | 40.970 | 47.989 | 1.00 | 32.82 |
| 118 | CA | GLY | A | 620 | 33.039 | 39.577 | 48.271 | 1.00 | 32.89 |
| 119 | C | GLY | A | 620 | 32.373 | 39.194 | 49.553 | 1.00 | 32.89 |
| 120 | O | GLY | A | 620 | 31.714 | 39.949 | 50.177 | 1.00 | 30.70 |
| 121 | N | ALA | A | 621 | 32.511 | 37.954 | 49.897 | 1.00 | 34.15 |
| 122 | CA | ALA | A | 621 | 31.818 | 37.384 | 51.019 | 1.00 | 35.78 |
| 123 | CB | ALA | A | 621 | 30.777 | 36.453 | 50.533 | 1.00 | 35.84 |
| 124 | C | ALA | A | 621 | 32.833 | 36.551 | 51.687 | 1.00 | 37.56 |
| 125 | O | ALA | A | 621 | 33.491 | 35.782 | 51.007 | 1.00 | 39.38 |
| 126 | N | GLY | A | 622 | 33.026 | 36.691 | 52.986 | 1.00 | 38.91 |
| 127 | CA | GLY | A | 622 | 34.006 | 35.848 | 53.611 | 1.00 | 38.65 |
| 128 | C | GLY | A | 622 | 33.398 | 34.928 | 54.575 | 1.00 | 39.55 |
| 129 | O | GLY | A | 622 | 32.173 | 34.902 | 54.796 | 1.00 | 36.11 |
| 130 | N | GLU | A | 623 | 34.293 | 34.225 | 55.272 | 1.00 | 41.01 |
| 131 | CA | GLU | A | 623 | 33.843 | 33.363 | 56.342 | 1.00 | 41.61 |
| 132 | CB | GLU | A | 623 | 35.046 | 32.793 | 57.068 | 1.00 | 43.27 |
| 133 | CG | GLU | A | 623 | 34.682 | 31.885 | 58.223 | 1.00 | 50.78 |
| 134 | CD | GLU | A | 623 | 35.838 | 31.063 | 58.780 | 1.00 | 65.56 |
| 135 | OE1 | GLU | A | 623 | 36.962 | 31.030 | 58.200 | 1.00 | 64.79 |
| 136 | OE2 | GLU | A | 623 | 35.592 | 30.422 | 59.836 | 1.00 | 72.34 |
| 137 | C | GLU | A | 623 | 32.965 | 34.088 | 57.417 | 1.00 | 40.39 |
| 138 | O | GLU | A | 623 | 32.055 | 33.457 | 57.987 | 1.00 | 38.12 |
| 139 | N | PHE | A | 624 | 33.265 | 35.347 | 57.758 | 1.00 | 37.75 |
| 140 | CA | PHE | A | 624 | 32.522 | 35.965 | 58.889 | 1.00 | 36.41 |
| 141 | CB | PHE | A | 624 | 33.506 | 36.538 | 59.933 | 1.00 | 37.60 |
| 142 | CG | PHE | A | 624 | 34.593 | 35.546 | 60.354 | 1.00 | 34.22 |
| 143 | CD1 | PHE | A | 624 | 34.285 | 34.584 | 61.169 | 1.00 | 32.75 |
| 144 | CE1 | PHE | A | 624 | 35.256 | 33.643 | 61.527 | 1.00 | 42.16 |
| 145 | CZ | PHE | A | 624 | 36.568 | 33.666 | 61.022 | 1.00 | 37.78 |
| 146 | CE2 | PHE | A | 624 | 36.866 | 34.594 | 60.168 | 1.00 | 37.66 |
| 147 | CD2 | PHE | A | 624 | 35.861 | 35.571 | 59.805 | 1.00 | 37.30 |

FIGURE 3C

| A | B | C | D | E | F | G | H | I | J |
|---|---|---|---|---|---|---|---|---|---|
| 148 | C | PHE | A | 624 | 31.569 | 37.066 | 58.437 | 1.00 | 35.68 |
| 149 | O | PHE | A | 624 | 30.875 | 37.739 | 59.261 | 1.00 | 36.44 |
| 150 | N | GLY | A | 625 | 31.557 | 37.336 | 57.140 | 1.00 | 35.15 |
| 151 | CA | GLY | A | 625 | 30.731 | 38.445 | 56.714 | 1.00 | 32.08 |
| 152 | C | GLY | A | 625 | 31.164 | 39.011 | 55.423 | 1.00 | 32.29 |
| 153 | O | GLY | A | 625 | 32.177 | 38.633 | 54.858 | 1.00 | 32.00 |
| 154 | N | GLU | A | 626 | 30.422 | 39.990 | 54.988 | 1.00 | 33.82 |
| 155 | CA | GLU | A | 626 | 30.710 | 40.519 | 53.695 | 1.00 | 37.80 |
| 156 | CB | GLU | A | 626 | 29.534 | 41.289 | 53.103 | 1.00 | 36.83 |
| 157 | CG | GLU | A | 626 | 28.396 | 40.298 | 52.839 | 1.00 | 42.38 |
| 158 | CD | GLU | A | 626 | 27.343 | 40.941 | 51.992 | 1.00 | 45.04 |
| 159 | OE1 | GLU | A | 626 | 27.289 | 40.680 | 50.777 | 1.00 | 47.93 |
| 160 | OE2 | GLU | A | 626 | 26.632 | 41.773 | 52.553 | 1.00 | 43.41 |
| 161 | C | GLU | A | 626 | 31.896 | 41.377 | 53.719 | 1.00 | 37.16 |
| 162 | O | GLU | A | 626 | 32.262 | 41.878 | 54.803 | 1.00 | 35.84 |
| 163 | N | VAL | A | 627 | 32.477 | 41.552 | 52.508 | 1.00 | 35.91 |
| 164 | CA | VAL | A | 627 | 33.711 | 42.268 | 52.392 | 1.00 | 34.05 |
| 165 | CB | VAL | A | 627 | 34.839 | 41.340 | 51.861 | 1.00 | 36.58 |
| 166 | CG1 | VAL | A | 627 | 36.210 | 42.135 | 51.691 | 1.00 | 30.17 |
| 167 | CG2 | VAL | A | 627 | 34.986 | 40.244 | 52.740 | 1.00 | 33.27 |
| 168 | C | VAL | A | 627 | 33.388 | 43.380 | 51.461 | 1.00 | 34.18 |
| 169 | O | VAL | A | 627 | 32.633 | 43.157 | 50.568 | 1.00 | 31.95 |
| 170 | N | TYR | A | 628 | 33.990 | 44.575 | 51.680 | 1.00 | 33.62 |
| 171 | CA | TYR | A | 628 | 33.618 | 45.746 | 50.948 | 1.00 | 33.35 |
| 172 | CB | TYR | A | 628 | 32.892 | 46.766 | 51.894 | 1.00 | 35.70 |
| 173 | CG | TYR | A | 628 | 31.519 | 46.398 | 52.411 | 1.00 | 35.23 |
| 174 | CD1 | TYR | A | 628 | 31.344 | 45.529 | 53.497 | 1.00 | 34.62 |
| 175 | CE1 | TYR | A | 628 | 30.088 | 45.215 | 53.976 | 1.00 | 36.28 |
| 176 | CZ | TYR | A | 628 | 28.935 | 45.759 | 53.348 | 1.00 | 39.83 |
| 177 | OH | TYR | A | 628 | 27.634 | 45.479 | 53.748 | 1.00 | 41.33 |
| 178 | CE2 | TYR | A | 628 | 29.080 | 46.582 | 52.266 | 1.00 | 43.12 |
| 179 | CD2 | TYR | A | 628 | 30.397 | 46.941 | 51.826 | 1.00 | 40.98 |
| 180 | C | TYR | A | 628 | 34.890 | 46.407 | 50.597 | 1.00 | 33.72 |
| 181 | O | TYR | A | 628 | 35.938 | 46.184 | 51.223 | 1.00 | 35.69 |
| 182 | N | LYS | A | 629 | 34.749 | 47.365 | 49.743 | 1.00 | 33.77 |
| 183 | CA | LYS | A | 629 | 35.792 | 48.236 | 49.369 | 1.00 | 36.45 |
| 184 | CB | LYS | A | 629 | 35.613 | 48.688 | 47.939 | 1.00 | 36.34 |
| 185 | CG | LYS | A | 629 | 36.692 | 49.598 | 47.624 | 1.00 | 41.68 |
| 186 | CD | LYS | A | 629 | 36.232 | 50.858 | 47.072 | 1.00 | 45.46 |
| 187 | CE | LYS | A | 629 | 37.426 | 51.809 | 46.890 | 1.00 | 51.36 |
| 188 | NZ | LYS | A | 629 | 36.962 | 53.283 | 46.736 | 1.00 | 49.95 |
| 189 | C | LYS | A | 629 | 35.440 | 49.455 | 50.046 | 1.00 | 37.55 |
| 190 | O | LYS | A | 629 | 34.298 | 49.740 | 50.227 | 1.00 | 37.87 |
| 191 | N | GLY | A | 630 | 36.415 | 50.286 | 50.355 | 1.00 | 41.21 |
| 192 | CA | GLY | A | 630 | 36.010 | 51.559 | 50.912 | 1.00 | 42.33 |
| 193 | C | GLY | A | 630 | 37.204 | 52.450 | 51.067 | 1.00 | 44.89 |
| 194 | O | GLY | A | 630 | 38.205 | 52.287 | 50.392 | 1.00 | 45.71 |
| 195 | N | MET | A | 631 | 37.086 | 53.363 | 52.008 | 1.00 | 46.92 |
| 196 | CA | MET | A | 631 | 38.014 | 54.443 | 52.136 | 1.00 | 48.84 |
| 197 | CB | MET | A | 631 | 37.379 | 55.734 | 51.608 | 1.00 | 49.65 |
| 198 | CG | MET | A | 631 | 37.177 | 55.731 | 50.070 | 1.00 | 51.92 |
| 199 | SD | MET | A | 631 | 38.727 | 55.249 | 49.171 | 1.00 | 57.95 |

FIGURE 3D

| A | B | C | D | E | F | G | H | I | J |
|---|---|---|---|---|---|---|---|---|---|
| 200 | CE | MET | A | 631 | 39.478 | 56.799 | 48.727 | 1.00 | 56.76 |
| 201 | C | MET | A | 631 | 38.379 | 54.619 | 53.587 | 1.00 | 49.23 |
| 202 | O | MET | A | 631 | 37.493 | 54.616 | 54.462 | 1.00 | 47.16 |
| 203 | N | LEU | A | 632 | 39.696 | 54.667 | 53.828 | 1.00 | 47.01 |
| 204 | CA | LEU | A | 632 | 40.144 | 54.951 | 55.148 | 1.00 | 48.50 |
| 205 | CB | LEU | A | 632 | 41.204 | 53.954 | 55.531 | 1.00 | 46.95 |
| 206 | CG | LEU | A | 632 | 41.924 | 54.217 | 56.805 | 1.00 | 47.11 |
| 207 | CD1 | LEU | A | 632 | 40.936 | 53.899 | 57.902 | 1.00 | 45.89 |
| 208 | CD2 | LEU | A | 632 | 43.172 | 53.311 | 56.944 | 1.00 | 47.90 |
| 209 | C | LEU | A | 632 | 40.680 | 56.425 | 55.221 | 1.00 | 50.08 |
| 210 | O | LEU | A | 632 | 41.388 | 56.932 | 54.323 | 1.00 | 47.85 |
| 211 | N | ALA | A | 633 | 40.279 | 57.138 | 56.256 | 1.00 | 52.44 |
| 212 | CA | ALA | A | 633 | 40.873 | 58.465 | 56.388 | 1.00 | 56.35 |
| 213 | CB | ALA | A | 633 | 39.848 | 59.562 | 56.836 | 1.00 | 55.50 |
| 214 | C | ALA | A | 633 | 41.842 | 58.189 | 57.445 | 1.00 | 56.34 |
| 215 | O | ALA | A | 633 | 41.406 | 57.920 | 58.493 | 1.00 | 58.62 |
| 216 | N | ALA | A | 634 | 43.136 | 58.194 | 57.224 | 1.00 | 57.84 |
| 217 | CA | ALA | A | 634 | 43.920 | 57.980 | 58.415 | 1.00 | 61.35 |
| 218 | CB | ALA | A | 634 | 45.364 | 57.774 | 58.115 | 1.00 | 62.22 |
| 219 | C | ALA | A | 634 | 43.771 | 59.263 | 59.222 | 1.00 | 62.67 |
| 220 | O | ALA | A | 634 | 44.422 | 60.208 | 58.850 | 1.00 | 64.38 |
| 221 | N | ALA | A | 638 | 43.383 | 64.048 | 56.993 | 1.00 | 78.26 |
| 222 | CA | ALA | A | 638 | 44.752 | 64.060 | 56.359 | 1.00 | 79.12 |
| 223 | CB | ALA | A | 638 | 45.788 | 63.305 | 57.237 | 1.00 | 78.95 |
| 224 | C | ALA | A | 638 | 44.822 | 63.605 | 54.872 | 1.00 | 79.32 |
| 225 | O | ALA | A | 638 | 45.141 | 64.402 | 54.006 | 1.00 | 79.88 |
| 226 | N | ALA | A | 639 | 44.531 | 62.334 | 54.589 | 1.00 | 78.59 |
| 227 | CA | ALA | A | 639 | 44.620 | 61.761 | 53.238 | 1.00 | 77.38 |
| 228 | CB | ALA | A | 639 | 46.119 | 61.531 | 52.875 | 1.00 | 78.65 |
| 229 | C | ALA | A | 639 | 43.843 | 60.408 | 53.247 | 1.00 | 75.52 |
| 230 | O | ALA | A | 639 | 44.050 | 59.569 | 54.155 | 1.00 | 75.87 |
| 231 | N | GLU | A | 640 | 42.935 | 60.248 | 52.273 | 1.00 | 71.51 |
| 232 | CA | GLU | A | 640 | 41.968 | 59.139 | 52.171 | 1.00 | 66.84 |
| 233 | CB | GLU | A | 640 | 40.701 | 59.599 | 51.433 | 1.00 | 66.51 |
| 234 | CG | GLU | A | 640 | 39.483 | 58.732 | 51.713 | 1.00 | 68.84 |
| 235 | CD | GLU | A | 640 | 38.106 | 59.433 | 51.585 | 1.00 | 70.86 |
| 236 | OE1 | GLU | A | 640 | 37.834 | 60.052 | 50.511 | 1.00 | 71.60 |
| 237 | OE2 | GLU | A | 640 | 37.274 | 59.351 | 52.561 | 1.00 | 70.47 |
| 238 | C | GLU | A | 640 | 42.571 | 58.052 | 51.379 | 1.00 | 63.66 |
| 239 | O | GLU | A | 640 | 43.179 | 58.300 | 50.363 | 1.00 | 64.69 |
| 240 | N | VAL | A | 641 | 42.394 | 56.821 | 51.807 | 1.00 | 60.16 |
| 241 | CA | VAL | A | 641 | 43.028 | 55.721 | 51.100 | 1.00 | 55.19 |
| 242 | CB | VAL | A | 641 | 44.352 | 55.368 | 51.777 | 1.00 | 54.62 |
| 243 | CG1 | VAL | A | 641 | 44.223 | 54.272 | 52.749 | 1.00 | 50.91 |
| 244 | CG2 | VAL | A | 641 | 45.363 | 55.043 | 50.767 | 1.00 | 56.67 |
| 245 | C | VAL | A | 641 | 42.102 | 54.570 | 50.931 | 1.00 | 52.53 |
| 246 | O | VAL | A | 641 | 41.378 | 54.194 | 51.812 | 1.00 | 55.11 |
| 247 | N | PRO | A | 642 | 42.105 | 53.989 | 49.767 | 1.00 | 51.34 |
| 248 | CA | PRO | A | 642 | 41.271 | 52.776 | 49.477 | 1.00 | 47.14 |
| 249 | CB | PRO | A | 642 | 41.664 | 52.399 | 48.064 | 1.00 | 47.64 |
| 250 | CG | PRO | A | 642 | 42.633 | 53.493 | 47.544 | 1.00 | 50.33 |
| 251 | CD | PRO | A | 642 | 42.943 | 54.475 | 48.637 | 1.00 | 50.56 |

FIGURE 3E

| A | B | C | D | E | F | G | H | I | J |
|---|---|---|---|---|---|---|---|---|---|
| 252 | C | PRO | A | 642 | 41.625 | 51.589 | 50.367 | 1.00 | 45.19 |
| 253 | O | PRO | A | 642 | 42.816 | 51.373 | 50.765 | 1.00 | 44.61 |
| 254 | N | VAL | A | 643 | 40.636 | 50.779 | 50.710 | 1.00 | 40.92 |
| 255 | CA | VAL | A | 643 | 40.925 | 49.716 | 51.646 | 1.00 | 37.39 |
| 256 | CB | VAL | A | 643 | 40.652 | 50.209 | 53.117 | 1.00 | 37.96 |
| 257 | CG1 | VAL | A | 643 | 41.889 | 50.869 | 53.733 | 1.00 | 39.75 |
| 258 | CG2 | VAL | A | 643 | 39.377 | 51.186 | 53.225 | 1.00 | 32.90 |
| 259 | C | VAL | A | 643 | 39.921 | 48.664 | 51.373 | 1.00 | 36.92 |
| 260 | O | VAL | A | 643 | 38.827 | 48.941 | 50.848 | 1.00 | 38.74 |
| 261 | N | ALA | A | 644 | 40.226 | 47.464 | 51.769 | 1.00 | 34.90 |
| 262 | CA | ALA | A | 644 | 39.217 | 46.411 | 51.722 | 1.00 | 34.08 |
| 263 | CB | ALA | A | 644 | 39.858 | 45.092 | 51.412 | 1.00 | 31.97 |
| 264 | C | ALA | A | 644 | 38.726 | 46.373 | 53.179 | 1.00 | 35.58 |
| 265 | O | ALA | A | 644 | 39.526 | 46.712 | 54.096 | 1.00 | 30.86 |
| 266 | N | ILE | A | 645 | 37.443 | 45.968 | 53.393 | 1.00 | 36.25 |
| 267 | CA | ILE | A | 645 | 36.922 | 45.950 | 54.744 | 1.00 | 34.97 |
| 268 | CB | ILE | A | 645 | 35.932 | 47.080 | 54.876 | 1.00 | 35.85 |
| 269 | CG1 | ILE | A | 645 | 36.577 | 48.336 | 54.488 | 1.00 | 37.94 |
| 270 | CD1 | ILE | A | 645 | 35.489 | 49.480 | 54.224 | 1.00 | 39.26 |
| 271 | CG2 | ILE | A | 645 | 35.314 | 47.127 | 56.304 | 1.00 | 32.71 |
| 272 | C | ILE | A | 645 | 36.201 | 44.682 | 55.066 | 1.00 | 33.98 |
| 273 | O | ILE | A | 645 | 35.113 | 44.491 | 54.584 | 1.00 | 36.64 |
| 274 | N | LYS | A | 646 | 36.714 | 43.846 | 55.922 | 1.00 | 34.87 |
| 275 | CA | LYS | A | 646 | 36.008 | 42.632 | 56.289 | 1.00 | 38.18 |
| 276 | CB | LYS | A | 646 | 37.040 | 41.499 | 56.633 | 1.00 | 39.75 |
| 277 | CG | LYS | A | 646 | 37.905 | 41.096 | 55.427 | 1.00 | 44.65 |
| 278 | CD | LYS | A | 646 | 38.718 | 39.873 | 55.721 | 1.00 | 47.74 |
| 279 | CE | LYS | A | 646 | 38.775 | 38.957 | 54.557 | 1.00 | 56.44 |
| 280 | NZ | LYS | A | 646 | 40.016 | 39.325 | 53.698 | 1.00 | 67.82 |
| 281 | C | LYS | A | 646 | 35.078 | 42.871 | 57.482 | 1.00 | 37.98 |
| 282 | O | LYS | A | 646 | 35.524 | 43.217 | 58.526 | 1.00 | 39.11 |
| 283 | N | THR | A | 647 | 33.779 | 42.703 | 57.344 | 1.00 | 38.53 |
| 284 | CA | THR | A | 647 | 32.898 | 42.869 | 58.518 | 1.00 | 35.17 |
| 285 | CB | THR | A | 647 | 31.620 | 43.563 | 58.086 | 1.00 | 35.95 |
| 286 | OG1 | THR | A | 647 | 30.886 | 42.779 | 57.136 | 1.00 | 31.75 |
| 287 | CG2 | THR | A | 647 | 31.977 | 44.751 | 57.224 | 1.00 | 26.19 |
| 288 | C | THR | A | 647 | 32.581 | 41.580 | 59.205 | 1.00 | 35.41 |
| 289 | O | THR | A | 647 | 32.741 | 40.482 | 58.693 | 1.00 | 36.20 |
| 290 | N | LEU | A | 648 | 32.208 | 41.704 | 60.429 | 1.00 | 35.38 |
| 291 | CA | LEU | A | 648 | 31.915 | 40.572 | 61.187 | 1.00 | 37.01 |
| 292 | CB | LEU | A | 648 | 32.612 | 40.708 | 62.523 | 1.00 | 36.29 |
| 293 | CG | LEU | A | 648 | 32.176 | 39.634 | 63.510 | 1.00 | 34.38 |
| 294 | CD1 | LEU | A | 648 | 32.349 | 38.265 | 63.066 | 1.00 | 33.21 |
| 295 | CD2 | LEU | A | 648 | 32.938 | 39.707 | 64.670 | 1.00 | 38.96 |
| 296 | C | LEU | A | 648 | 30.383 | 40.645 | 61.334 | 1.00 | 39.65 |
| 297 | O | LEU | A | 648 | 29.873 | 41.630 | 61.869 | 1.00 | 41.32 |
| 298 | N | LYS | A | 649 | 29.631 | 39.670 | 60.813 | 1.00 | 39.93 |
| 299 | CA | LYS | A | 649 | 28.175 | 39.764 | 60.832 | 1.00 | 38.04 |
| 300 | CB | LYS | A | 649 | 27.610 | 38.564 | 60.128 | 1.00 | 38.58 |
| 301 | CG | LYS | A | 649 | 27.766 | 37.309 | 60.890 | 1.00 | 38.14 |
| 302 | CD | LYS | A | 649 | 27.679 | 36.238 | 59.889 | 1.00 | 35.47 |
| 303 | CE | LYS | A | 649 | 27.535 | 34.883 | 60.524 | 1.00 | 35.35 |

FIGURE 3F

| A | B | C | D | E | F | G | H | I | J |
|---|---|---|---|---|---|---|---|---|---|
| 304 | NZ | LYS | A | 649 | 27.499 | 33.710 | 59.600 | 1.00 | 36.16 |
| 305 | C | LYS | A | 649 | 27.630 | 39.998 | 62.226 | 1.00 | 38.13 |
| 306 | O | LYS | A | 649 | 28.217 | 39.517 | 63.181 | 1.00 | 38.78 |
| 307 | N | ALA | A | 650 | 26.642 | 40.900 | 62.370 | 1.00 | 38.37 |
| 308 | CA | ALA | A | 650 | 26.009 | 41.267 | 63.688 | 1.00 | 38.30 |
| 309 | CB | ALA | A | 650 | 24.721 | 41.954 | 63.443 | 1.00 | 37.99 |
| 310 | C | ALA | A | 650 | 25.680 | 39.928 | 64.183 | 1.00 | 38.32 |
| 311 | O | ALA | A | 650 | 25.410 | 39.138 | 63.320 | 1.00 | 40.75 |
| 312 | N | GLY | A | 651 | 25.632 | 39.493 | 65.416 | 1.00 | 35.55 |
| 313 | CA | GLY | A | 651 | 25.195 | 38.071 | 65.179 | 1.00 | 36.67 |
| 314 | C | GLY | A | 651 | 26.171 | 36.916 | 65.234 | 1.00 | 33.22 |
| 315 | O | GLY | A | 651 | 25.899 | 35.767 | 65.646 | 1.00 | 30.70 |
| 316 | N | TYR | A | 652 | 27.390 | 37.294 | 65.039 | 1.00 | 34.28 |
| 317 | CA | TYR | A | 652 | 28.455 | 36.416 | 65.446 | 1.00 | 36.25 |
| 318 | CB | TYR | A | 652 | 29.684 | 37.205 | 65.494 | 1.00 | 38.05 |
| 319 | CG | TYR | A | 652 | 29.668 | 38.292 | 66.484 | 1.00 | 38.76 |
| 320 | CD1 | TYR | A | 652 | 30.221 | 38.086 | 67.745 | 1.00 | 36.74 |
| 321 | CE1 | TYR | A | 652 | 30.242 | 39.091 | 68.684 | 1.00 | 34.51 |
| 322 | CZ | TYR | A | 652 | 29.778 | 40.325 | 68.329 | 1.00 | 40.27 |
| 323 | OH | TYR | A | 652 | 29.893 | 41.245 | 69.291 | 1.00 | 42.40 |
| 324 | CE2 | TYR | A | 652 | 29.178 | 40.584 | 67.038 | 1.00 | 34.15 |
| 325 | CD2 | TYR | A | 652 | 29.169 | 39.556 | 66.141 | 1.00 | 38.47 |
| 326 | C | TYR | A | 652 | 28.386 | 35.850 | 66.803 | 1.00 | 35.31 |
| 327 | O | TYR | A | 652 | 27.919 | 36.531 | 67.696 | 1.00 | 34.45 |
| 328 | N | THR | A | 653 | 28.961 | 34.652 | 66.947 | 1.00 | 35.94 |
| 329 | CA | THR | A | 653 | 29.209 | 33.999 | 68.234 | 1.00 | 36.94 |
| 330 | CB | THR | A | 653 | 29.248 | 32.522 | 68.183 | 1.00 | 37.69 |
| 331 | OG1 | THR | A | 653 | 30.427 | 32.201 | 67.433 | 1.00 | 40.83 |
| 332 | CG2 | THR | A | 653 | 28.007 | 31.792 | 67.363 | 1.00 | 32.24 |
| 333 | C | THR | A | 653 | 30.595 | 34.418 | 68.718 | 1.00 | 37.14 |
| 334 | O | THR | A | 653 | 31.347 | 34.985 | 68.015 | 1.00 | 37.03 |
| 335 | N | GLU | A | 654 | 30.831 | 34.210 | 69.998 | 1.00 | 37.12 |
| 336 | CA | GLU | A | 654 | 32.094 | 34.484 | 70.674 | 1.00 | 37.20 |
| 337 | CB | GLU | A | 654 | 32.074 | 33.802 | 72.025 | 1.00 | 34.84 |
| 338 | CG | GLU | A | 654 | 33.380 | 34.188 | 72.705 | 1.00 | 44.32 |
| 339 | CD | GLU | A | 654 | 33.571 | 35.731 | 72.609 | 1.00 | 48.08 |
| 340 | OE1 | GLU | A | 654 | 32.591 | 36.470 | 72.366 | 1.00 | 54.40 |
| 341 | OE2 | GLU | A | 654 | 34.675 | 36.206 | 72.771 | 1.00 | 46.32 |
| 342 | C | GLU | A | 654 | 33.316 | 33.880 | 69.890 | 1.00 | 35.96 |
| 343 | O | GLU | A | 654 | 34.306 | 34.579 | 69.620 | 1.00 | 33.58 |
| 344 | N | LYS | A | 655 | 33.161 | 32.605 | 69.577 | 1.00 | 35.57 |
| 345 | CA | LYS | A | 655 | 34.030 | 31.857 | 68.747 | 1.00 | 39.28 |
| 346 | CB | LYS | A | 655 | 33.532 | 30.394 | 68.482 | 1.00 | 39.74 |
| 347 | CG | LYS | A | 655 | 34.682 | 29.481 | 68.003 | 1.00 | 46.57 |
| 348 | CD | LYS | A | 655 | 34.375 | 28.446 | 66.854 | 1.00 | 53.64 |
| 349 | CE | LYS | A | 655 | 35.674 | 27.584 | 66.374 | 1.00 | 58.92 |
| 350 | NZ | LYS | A | 655 | 37.147 | 28.174 | 66.350 | 1.00 | 58.41 |
| 351 | C | LYS | A | 655 | 34.326 | 32.574 | 67.379 | 1.00 | 38.72 |
| 352 | O | LYS | A | 655 | 35.481 | 32.624 | 67.012 | 1.00 | 41.81 |
| 353 | N | GLN | A | 656 | 33.329 | 33.111 | 66.678 | 1.00 | 35.08 |
| 354 | CA | GLN | A | 656 | 33.583 | 33.809 | 65.411 | 1.00 | 36.08 |
| 355 | CB | GLN | A | 656 | 32.355 | 34.070 | 64.590 | 1.00 | 32.82 |

FIGURE 3G

| A | B | C | D | E | F | G | H | I | J |
|---|---|---|---|---|---|---|---|---|---|
| 356 | CG | GLN | A | 656 | 31.709 | 32.793 | 64.216 | 1.00 | 35.27 |
| 357 | CD | GLN | A | 656 | 30.255 | 32.982 | 63.707 | 1.00 | 37.96 |
| 358 | OE1 | GLN | A | 656 | 29.471 | 33.846 | 64.157 | 1.00 | 30.18 |
| 359 | NE2 | GLN | A | 656 | 29.948 | 32.217 | 62.693 | 1.00 | 42.57 |
| 360 | C | GLN | A | 656 | 34.305 | 35.111 | 65.659 | 1.00 | 35.54 |
| 361 | O | GLN | A | 656 | 35.196 | 35.485 | 64.899 | 1.00 | 35.47 |
| 362 | N | ARG | A | 657 | 33.951 | 35.722 | 66.760 | 1.00 | 35.39 |
| 363 | CA | ARG | A | 657 | 34.557 | 36.985 | 67.147 | 1.00 | 39.00 |
| 364 | CB | ARG | A | 657 | 33.923 | 37.539 | 68.413 | 1.00 | 37.06 |
| 365 | CG | ARG | A | 657 | 34.401 | 38.841 | 68.811 | 1.00 | 40.49 |
| 366 | CD | ARG | A | 657 | 34.033 | 39.137 | 70.269 | 1.00 | 41.44 |
| 367 | NE | ARG | A | 657 | 34.843 | 40.262 | 70.614 | 1.00 | 54.97 |
| 368 | CZ | ARG | A | 657 | 35.982 | 40.205 | 71.383 | 1.00 | 54.52 |
| 369 | NH1 | ARG | A | 657 | 36.451 | 39.051 | 71.945 | 1.00 | 43.49 |
| 370 | NH2 | ARG | A | 657 | 36.616 | 41.349 | 71.556 | 1.00 | 55.48 |
| 371 | C | ARG | A | 657 | 36.017 | 36.717 | 67.311 | 1.00 | 38.95 |
| 372 | O | ARG | A | 657 | 36.826 | 37.240 | 66.592 | 1.00 | 37.52 |
| 373 | N | VAL | A | 658 | 36.331 | 35.771 | 68.150 | 1.00 | 42.72 |
| 374 | CA | VAL | A | 658 | 37.722 | 35.481 | 68.321 | 1.00 | 45.25 |
| 375 | CB | VAL | A | 658 | 37.957 | 34.577 | 69.517 | 1.00 | 47.74 |
| 376 | CG1 | VAL | A | 658 | 39.291 | 33.787 | 69.368 | 1.00 | 48.43 |
| 377 | CG2 | VAL | A | 658 | 37.935 | 35.483 | 70.791 | 1.00 | 49.98 |
| 378 | C | VAL | A | 658 | 38.449 | 35.036 | 67.044 | 1.00 | 45.07 |
| 379 | O | VAL | A | 658 | 39.466 | 35.669 | 66.720 | 1.00 | 44.99 |
| 380 | N | ASP | A | 659 | 37.913 | 34.045 | 66.299 | 1.00 | 42.92 |
| 381 | CA | ASP | A | 659 | 38.561 | 33.655 | 65.043 | 1.00 | 41.99 |
| 382 | CB | ASP | A | 659 | 37.891 | 32.498 | 64.307 | 1.00 | 41.26 |
| 383 | CG | ASP | A | 659 | 37.826 | 31.278 | 65.177 | 1.00 | 45.94 |
| 384 | OD1 | ASP | A | 659 | 37.109 | 30.301 | 64.847 | 1.00 | 46.31 |
| 385 | OD2 | ASP | A | 659 | 38.451 | 31.252 | 66.249 | 1.00 | 43.77 |
| 386 | C | ASP | A | 659 | 38.683 | 34.857 | 64.176 | 1.00 | 39.97 |
| 387 | O | ASP | A | 659 | 39.687 | 35.012 | 63.586 | 1.00 | 36.58 |
| 388 | N | PHE | A | 660 | 37.703 | 35.756 | 64.220 | 1.00 | 38.73 |
| 389 | CA | PHE | A | 660 | 37.765 | 36.881 | 63.312 | 1.00 | 39.49 |
| 390 | CB | PHE | A | 660 | 36.385 | 37.556 | 63.203 | 1.00 | 37.46 |
| 391 | CG | PHE | A | 660 | 36.343 | 38.830 | 62.388 | 1.00 | 33.56 |
| 392 | CD1 | PHE | A | 660 | 36.342 | 40.047 | 62.976 | 1.00 | 32.33 |
| 393 | CE1 | PHE | A | 660 | 36.323 | 41.209 | 62.257 | 1.00 | 28.65 |
| 394 | CZ | PHE | A | 660 | 36.136 | 41.248 | 60.858 | 1.00 | 24.95 |
| 395 | CE2 | PHE | A | 660 | 36.059 | 40.060 | 60.259 | 1.00 | 28.98 |
| 396 | CD2 | PHE | A | 660 | 36.099 | 38.814 | 61.088 | 1.00 | 32.15 |
| 397 | C | PHE | A | 660 | 38.897 | 37.885 | 63.675 | 1.00 | 39.32 |
| 398 | O | PHE | A | 660 | 39.584 | 38.276 | 62.825 | 1.00 | 38.41 |
| 399 | N | LEU | A | 661 | 39.061 | 38.276 | 64.928 | 1.00 | 40.15 |
| 400 | CA | LEU | A | 661 | 40.011 | 39.306 | 65.232 | 1.00 | 42.07 |
| 401 | CB | LEU | A | 661 | 39.711 | 39.915 | 66.582 | 1.00 | 43.38 |
| 402 | CG | LEU | A | 661 | 38.437 | 40.774 | 66.709 | 1.00 | 43.55 |
| 403 | CD1 | LEU | A | 661 | 38.306 | 41.372 | 68.133 | 1.00 | 39.97 |
| 404 | CD2 | LEU | A | 661 | 38.580 | 41.902 | 65.756 | 1.00 | 37.68 |
| 405 | C | LEU | A | 661 | 41.347 | 38.552 | 65.294 | 1.00 | 41.94 |
| 406 | O | LEU | A | 661 | 42.340 | 39.129 | 65.120 | 1.00 | 41.62 |
| 407 | N | GLY | A | 662 | 41.349 | 37.252 | 65.485 | 1.00 | 39.75 |

FIGURE 3H

| A | B | C | D | E | F | G | H | I | J |
|---|---|---|---|---|---|---|---|---|---|
| 408 | CA | GLY | A | 662 | 42.603 | 36.635 | 65.570 | 1.00 | 40.93 |
| 409 | C | GLY | A | 662 | 43.418 | 36.757 | 64.273 | 1.00 | 43.18 |
| 410 | O | GLY | A | 662 | 44.590 | 37.160 | 64.286 | 1.00 | 42.86 |
| 411 | N | GLU | A | 663 | 42.779 | 36.439 | 63.154 | 1.00 | 42.57 |
| 412 | CA | GLU | A | 663 | 43.393 | 36.553 | 61.894 | 1.00 | 42.39 |
| 413 | CB | GLU | A | 663 | 42.379 | 36.281 | 60.792 | 1.00 | 44.11 |
| 414 | CG | GLU | A | 663 | 42.829 | 36.991 | 59.480 | 1.00 | 48.03 |
| 415 | CD | GLU | A | 663 | 42.396 | 36.230 | 58.234 | 1.00 | 54.58 |
| 416 | OE1 | GLU | A | 663 | 41.241 | 35.605 | 58.330 | 1.00 | 52.44 |
| 417 | OE2 | GLU | A | 663 | 43.208 | 36.292 | 57.213 | 1.00 | 53.06 |
| 418 | C | GLU | A | 663 | 43.976 | 37.968 | 61.741 | 1.00 | 40.61 |
| 419 | O | GLU | A | 663 | 45.090 | 38.192 | 61.213 | 1.00 | 37.63 |
| 420 | N | ALA | A | 664 | 43.273 | 38.944 | 62.230 | 1.00 | 38.99 |
| 421 | CA | ALA | A | 664 | 43.939 | 40.237 | 62.062 | 1.00 | 40.23 |
| 422 | CB | ALA | A | 664 | 42.965 | 41.347 | 62.358 | 1.00 | 41.34 |
| 423 | C | ALA | A | 664 | 45.114 | 40.278 | 63.055 | 1.00 | 39.40 |
| 424 | O | ALA | A | 664 | 46.136 | 40.873 | 62.831 | 1.00 | 39.10 |
| 425 | N | GLY | A | 665 | 44.989 | 39.570 | 64.138 | 1.00 | 38.27 |
| 426 | CA | GLY | A | 665 | 46.087 | 39.586 | 65.064 | 1.00 | 42.63 |
| 427 | C | GLY | A | 665 | 47.347 | 39.076 | 64.355 | 1.00 | 44.59 |
| 428 | O | GLY | A | 665 | 48.410 | 39.610 | 64.610 | 1.00 | 45.78 |
| 429 | N | ILE | A | 666 | 47.200 | 38.070 | 63.464 | 1.00 | 44.36 |
| 430 | CA | ILE | A | 666 | 48.295 | 37.277 | 62.941 | 1.00 | 42.46 |
| 431 | CB | ILE | A | 666 | 47.627 | 36.023 | 62.510 | 1.00 | 44.08 |
| 432 | CG1 | ILE | A | 666 | 47.247 | 35.276 | 63.731 | 1.00 | 42.77 |
| 433 | CD1 | ILE | A | 666 | 46.394 | 34.096 | 63.279 | 1.00 | 43.64 |
| 434 | CG2 | ILE | A | 666 | 48.406 | 35.006 | 61.565 | 1.00 | 42.50 |
| 435 | C | ILE | A | 666 | 48.846 | 38.081 | 61.853 | 1.00 | 41.32 |
| 436 | O | ILE | A | 666 | 49.986 | 38.330 | 61.798 | 1.00 | 41.39 |
| 437 | N | MET | A | 667 | 47.988 | 38.726 | 61.143 | 1.00 | 41.98 |
| 438 | CA | MET | A | 667 | 48.371 | 39.417 | 59.971 | 1.00 | 41.72 |
| 439 | CB | MET | A | 667 | 47.073 | 39.871 | 59.303 | 1.00 | 42.41 |
| 440 | CG | MET | A | 667 | 47.154 | 40.885 | 58.149 | 1.00 | 41.60 |
| 441 | SD | MET | A | 667 | 45.384 | 40.798 | 57.345 | 1.00 | 50.77 |
| 442 | CE | MET | A | 667 | 44.917 | 39.215 | 57.870 | 1.00 | 44.36 |
| 443 | C | MET | A | 667 | 49.155 | 40.575 | 60.497 | 1.00 | 42.65 |
| 444 | O | MET | A | 667 | 50.088 | 41.128 | 59.816 | 1.00 | 38.11 |
| 445 | N | GLY | A | 668 | 48.790 | 40.953 | 61.734 | 1.00 | 42.74 |
| 446 | CA | GLY | A | 668 | 49.348 | 42.203 | 62.310 | 1.00 | 42.47 |
| 447 | C | GLY | A | 668 | 50.820 | 42.083 | 62.677 | 1.00 | 40.74 |
| 448 | O | GLY | A | 668 | 51.552 | 43.010 | 62.772 | 1.00 | 39.44 |
| 449 | N | GLN | A | 669 | 51.241 | 40.861 | 62.790 | 1.00 | 40.10 |
| 450 | CA | GLN | A | 669 | 52.563 | 40.577 | 63.149 | 1.00 | 40.54 |
| 451 | CB | GLN | A | 669 | 52.547 | 39.193 | 63.729 | 1.00 | 39.50 |
| 452 | CG | GLN | A | 669 | 52.011 | 39.318 | 65.065 | 1.00 | 43.35 |
| 453 | CD | GLN | A | 669 | 51.833 | 37.999 | 65.772 | 1.00 | 53.41 |
| 454 | OE1 | GLN | A | 669 | 50.716 | 37.616 | 66.048 | 1.00 | 59.36 |
| 455 | NE2 | GLN | A | 669 | 52.917 | 37.334 | 66.121 | 1.00 | 57.56 |
| 456 | C | GLN | A | 669 | 53.472 | 40.657 | 61.955 | 1.00 | 41.95 |
| 457 | O | GLN | A | 669 | 54.683 | 40.622 | 62.152 | 1.00 | 41.00 |
| 458 | N | PHE | A | 670 | 52.922 | 40.908 | 60.729 | 1.00 | 40.25 |
| 459 | CA | PHE | A | 670 | 53.738 | 40.932 | 59.578 | 1.00 | 38.18 |

FIGURE 3I

| A | B | C | D | E | F | G | H | I | J |
|---|---|---|---|---|---|---|---|---|---|
| 460 | CB | PHE | A | 670 | 53.159 | 40.016 | 58.570 | 1.00 | 40.10 |
| 461 | CG | PHE | A | 670 | 52.990 | 38.623 | 59.105 | 1.00 | 35.26 |
| 462 | CD1 | PHE | A | 670 | 51.962 | 37.897 | 58.751 | 1.00 | 33.32 |
| 463 | CE1 | PHE | A | 670 | 51.803 | 36.621 | 59.214 | 1.00 | 35.47 |
| 464 | CZ | PHE | A | 670 | 52.720 | 36.032 | 59.976 | 1.00 | 36.73 |
| 465 | CE2 | PHE | A | 670 | 53.818 | 36.749 | 60.310 | 1.00 | 40.51 |
| 466 | CD2 | PHE | A | 670 | 53.948 | 38.063 | 59.833 | 1.00 | 37.75 |
| 467 | C | PHE | A | 670 | 53.941 | 42.231 | 58.974 | 1.00 | 39.07 |
| 468 | O | PHE | A | 670 | 53.038 | 43.044 | 59.012 | 1.00 | 37.82 |
| 469 | N | SER | A | 671 | 55.170 | 42.491 | 58.485 | 1.00 | 37.93 |
| 470 | CA | SER | A | 671 | 55.327 | 43.719 | 57.712 | 1.00 | 39.08 |
| 471 | CB | SER | A | 671 | 55.937 | 44.825 | 58.533 | 1.00 | 40.17 |
| 472 | OG | SER | A | 671 | 55.915 | 46.032 | 57.754 | 1.00 | 43.39 |
| 473 | C | SER | A | 671 | 56.231 | 43.445 | 56.466 | 1.00 | 41.33 |
| 474 | O | SER | A | 671 | 57.490 | 43.349 | 56.554 | 1.00 | 38.64 |
| 475 | N | HIS | A | 672 | 55.586 | 43.358 | 55.295 | 1.00 | 42.48 |
| 476 | CA | HIS | A | 672 | 56.279 | 42.870 | 54.089 | 1.00 | 42.62 |
| 477 | CB | HIS | A | 672 | 56.565 | 41.391 | 54.190 | 1.00 | 42.23 |
| 478 | CG | HIS | A | 672 | 57.524 | 40.981 | 53.156 | 1.00 | 47.30 |
| 479 | ND1 | HIS | A | 672 | 57.142 | 40.782 | 51.825 | 1.00 | 46.67 |
| 480 | CE1 | HIS | A | 672 | 58.240 | 40.523 | 51.126 | 1.00 | 45.98 |
| 481 | NE2 | HIS | A | 672 | 59.289 | 40.519 | 51.949 | 1.00 | 44.11 |
| 482 | CD2 | HIS | A | 672 | 58.874 | 40.826 | 53.214 | 1.00 | 45.01 |
| 483 | C | HIS | A | 672 | 55.513 | 43.134 | 52.819 | 1.00 | 42.33 |
| 484 | O | HIS | A | 672 | 54.388 | 42.761 | 52.732 | 1.00 | 41.57 |
| 485 | N | HIS | A | 673 | 56.192 | 43.697 | 51.819 | 1.00 | 42.80 |
| 486 | CA | HIS | A | 673 | 55.610 | 44.132 | 50.553 | 1.00 | 42.36 |
| 487 | CB | HIS | A | 673 | 56.722 | 44.316 | 49.548 | 1.00 | 38.97 |
| 488 | CG | HIS | A | 673 | 56.262 | 44.939 | 48.249 | 1.00 | 46.80 |
| 489 | ND1 | HIS | A | 673 | 55.503 | 46.087 | 48.211 | 1.00 | 49.74 |
| 490 | CE1 | HIS | A | 673 | 55.348 | 46.487 | 46.956 | 1.00 | 43.86 |
| 491 | NE2 | HIS | A | 673 | 55.959 | 45.613 | 46.172 | 1.00 | 43.54 |
| 492 | CD2 | HIS | A | 673 | 56.496 | 44.606 | 46.944 | 1.00 | 42.26 |
| 493 | C | HIS | A | 673 | 54.523 | 43.167 | 49.883 | 1.00 | 40.55 |
| 494 | O | HIS | A | 673 | 53.543 | 43.601 | 49.310 | 1.00 | 42.61 |
| 495 | N | ASN | A | 674 | 54.764 | 41.917 | 50.005 | 1.00 | 36.25 |
| 496 | CA | ASN | A | 674 | 54.035 | 40.894 | 49.374 | 1.00 | 38.32 |
| 497 | CB | ASN | A | 674 | 55.074 | 39.876 | 48.740 | 1.00 | 39.80 |
| 498 | CG | ASN | A | 674 | 55.870 | 40.509 | 47.607 | 1.00 | 36.97 |
| 499 | OD1 | ASN | A | 674 | 55.321 | 40.897 | 46.582 | 1.00 | 35.65 |
| 500 | ND2 | ASN | A | 674 | 57.139 | 40.728 | 47.847 | 1.00 | 37.21 |
| 501 | C | ASN | A | 674 | 53.281 | 40.177 | 50.440 | 1.00 | 38.05 |
| 502 | O | ASN | A | 674 | 53.058 | 38.944 | 50.288 | 1.00 | 37.79 |
| 503 | N | ILE | A | 675 | 52.996 | 40.886 | 51.586 | 1.00 | 38.03 |
| 504 | CA | ILE | A | 675 | 52.081 | 40.325 | 52.641 | 1.00 | 36.57 |
| 505 | CB | ILE | A | 675 | 52.790 | 40.111 | 53.920 | 1.00 | 36.46 |
| 506 | CG1 | ILE | A | 675 | 53.903 | 39.127 | 53.672 | 1.00 | 33.71 |
| 507 | CD1 | ILE | A | 675 | 53.464 | 37.726 | 53.483 | 1.00 | 35.15 |
| 508 | CG2 | ILE | A | 675 | 51.921 | 39.461 | 54.965 | 1.00 | 31.06 |
| 509 | C | ILE | A | 675 | 50.979 | 41.344 | 52.797 | 1.00 | 38.05 |
| 510 | O | ILE | A | 675 | 51.256 | 42.562 | 52.869 | 1.00 | 35.21 |
| 511 | N | ILE | A | 676 | 49.724 | 40.902 | 52.661 | 1.00 | 37.36 |

FIGURE 3J

| A | B | C | D | E | F | G | H | I | J |
|---|---|---|---|---|---|---|---|---|---|
| 512 | CA | ILE | A | 676 | 48.617 | 41.868 | 52.857 | 1.00 | 37.03 |
| 513 | CB | ILE | A | 676 | 47.229 | 41.162 | 52.874 | 1.00 | 37.73 |
| 514 | CG1 | ILE | A | 676 | 46.734 | 40.942 | 51.432 | 1.00 | 41.75 |
| 515 | CD1 | ILE | A | 676 | 46.828 | 39.276 | 50.877 | 1.00 | 38.59 |
| 516 | CG2 | ILE | A | 676 | 46.105 | 42.067 | 53.361 | 1.00 | 39.38 |
| 517 | C | ILE | A | 676 | 48.796 | 42.654 | 54.162 | 1.00 | 35.26 |
| 518 | O | ILE | A | 676 | 48.978 | 42.142 | 55.242 | 1.00 | 32.27 |
| 519 | N | ARG | A | 677 | 48.683 | 43.918 | 54.025 | 1.00 | 34.27 |
| 520 | CA | ARG | A | 677 | 48.910 | 44.789 | 55.101 | 1.00 | 36.19 |
| 521 | CB | ARG | A | 677 | 49.494 | 46.075 | 54.510 | 1.00 | 36.64 |
| 522 | CG | ARG | A | 677 | 49.536 | 47.178 | 55.599 | 1.00 | 41.64 |
| 523 | CD | ARG | A | 677 | 50.506 | 48.285 | 55.229 | 1.00 | 47.74 |
| 524 | NE | ARG | A | 677 | 49.825 | 49.350 | 54.572 | 1.00 | 53.55 |
| 525 | CZ | ARG | A | 677 | 49.795 | 49.516 | 53.246 | 1.00 | 61.80 |
| 526 | NH1 | ARG | A | 677 | 50.425 | 48.610 | 52.436 | 1.00 | 54.93 |
| 527 | NH2 | ARG | A | 677 | 49.096 | 50.568 | 52.734 | 1.00 | 55.75 |
| 528 | C | ARG | A | 677 | 47.670 | 45.163 | 55.876 | 1.00 | 35.14 |
| 529 | O | ARG | A | 677 | 46.723 | 45.624 | 55.334 | 1.00 | 37.56 |
| 530 | N | LEU | A | 678 | 47.670 | 44.907 | 57.161 | 1.00 | 36.98 |
| 531 | CA | LEU | A | 678 | 46.577 | 45.306 | 58.012 | 1.00 | 37.75 |
| 532 | CB | LEU | A | 678 | 46.636 | 44.533 | 59.287 | 1.00 | 37.13 |
| 533 | CG | LEU | A | 678 | 45.644 | 45.003 | 60.367 | 1.00 | 38.89 |
| 534 | CD1 | LEU | A | 678 | 44.186 | 44.629 | 59.808 | 1.00 | 40.66 |
| 535 | CD2 | LEU | A | 678 | 45.909 | 44.223 | 61.548 | 1.00 | 36.72 |
| 536 | C | LEU | A | 678 | 46.592 | 46.739 | 58.328 | 1.00 | 36.93 |
| 537 | O | LEU | A | 678 | 47.505 | 47.253 | 58.861 | 1.00 | 37.75 |
| 538 | N | GLU | A | 679 | 45.585 | 47.452 | 57.961 | 1.00 | 40.76 |
| 539 | CA | GLU | A | 679 | 45.583 | 48.829 | 58.351 | 1.00 | 41.67 |
| 540 | CB | GLU | A | 679 | 44.596 | 49.592 | 57.532 | 1.00 | 42.01 |
| 541 | CG | GLU | A | 679 | 45.045 | 49.720 | 56.088 | 1.00 | 43.00 |
| 542 | CD | GLU | A | 679 | 46.208 | 50.642 | 55.968 | 1.00 | 54.85 |
| 543 | OE1 | GLU | A | 679 | 47.055 | 50.299 | 55.162 | 1.00 | 60.51 |
| 544 | OE2 | GLU | A | 679 | 46.321 | 51.678 | 56.698 | 1.00 | 58.17 |
| 545 | C | GLU | A | 679 | 45.182 | 48.939 | 59.817 | 1.00 | 43.77 |
| 546 | O | GLU | A | 679 | 45.579 | 49.921 | 60.483 | 1.00 | 45.58 |
| 547 | N | GLY | A | 680 | 44.383 | 47.987 | 60.317 | 1.00 | 43.57 |
| 548 | CA | GLY | A | 680 | 43.778 | 48.130 | 61.635 | 1.00 | 43.39 |
| 549 | C | GLY | A | 680 | 42.428 | 47.436 | 61.718 | 1.00 | 43.49 |
| 550 | O | GLY | A | 680 | 41.870 | 46.994 | 60.730 | 1.00 | 43.61 |
| 551 | N | VAL | A | 681 | 41.917 | 47.300 | 62.921 | 1.00 | 43.77 |
| 552 | CA | VAL | A | 681 | 40.638 | 46.712 | 63.148 | 1.00 | 45.21 |
| 553 | CB | VAL | A | 681 | 40.739 | 45.577 | 64.095 | 1.00 | 44.87 |
| 554 | CG1 | VAL | A | 681 | 41.831 | 44.596 | 63.645 | 1.00 | 46.36 |
| 555 | CG2 | VAL | A | 681 | 41.163 | 46.141 | 65.458 | 1.00 | 48.19 |
| 556 | C | VAL | A | 681 | 39.714 | 47.667 | 63.826 | 1.00 | 47.24 |
| 557 | O | VAL | A | 681 | 40.146 | 48.697 | 64.420 | 1.00 | 49.54 |
| 558 | N | ILE | A | 682 | 38.444 | 47.292 | 63.827 | 1.00 | 47.38 |
| 559 | CA | ILE | A | 682 | 37.419 | 48.006 | 64.569 | 1.00 | 48.87 |
| 560 | CB | ILE | A | 682 | 36.375 | 48.569 | 63.710 | 1.00 | 48.22 |
| 561 | CG1 | ILE | A | 682 | 36.958 | 49.768 | 62.995 | 1.00 | 48.43 |
| 562 | CD1 | ILE | A | 682 | 35.994 | 50.531 | 62.288 | 1.00 | 44.35 |
| 563 | CG2 | ILE | A | 682 | 35.350 | 49.079 | 64.642 | 1.00 | 51.05 |

FIGURE 3K

| A | B | C | D | E | F | G | H | I | J |
|---|---|---|---|---|---|---|---|---|---|
| 564 | C | ILE | A | 682 | 36.787 | 46.983 | 65.439 | 1.00 | 49.28 |
| 565 | O | ILE | A | 682 | 36.073 | 46.091 | 64.927 | 1.00 | 47.34 |
| 566 | N | SER | A | 683 | 37.128 | 47.028 | 66.720 | 1.00 | 49.45 |
| 567 | CA | SER | A | 683 | 36.611 | 46.043 | 67.629 | 1.00 | 52.94 |
| 568 | CB | SER | A | 683 | 37.745 | 45.283 | 68.237 | 1.00 | 52.37 |
| 569 | OG | SER | A | 683 | 38.501 | 46.148 | 69.035 | 1.00 | 57.12 |
| 570 | C | SER | A | 683 | 35.865 | 46.665 | 68.798 | 1.00 | 55.66 |
| 571 | O | SER | A | 683 | 35.285 | 45.961 | 69.632 | 1.00 | 56.40 |
| 572 | N | LYS | A | 684 | 35.893 | 47.987 | 68.884 | 1.00 | 57.01 |
| 573 | CA | LYS | A | 684 | 35.286 | 48.589 | 70.046 | 1.00 | 57.46 |
| 574 | CB | LYS | A | 684 | 36.154 | 49.729 | 70.595 | 1.00 | 56.07 |
| 575 | CG | LYS | A | 684 | 37.282 | 49.187 | 71.564 | 1.00 | 58.30 |
| 576 | CD | LYS | A | 684 | 38.630 | 49.925 | 71.446 | 1.00 | 58.07 |
| 577 | CE | LYS | A | 684 | 38.562 | 51.505 | 71.950 | 1.00 | 65.46 |
| 578 | NZ | LYS | A | 684 | 39.871 | 52.366 | 71.881 | 1.00 | 62.96 |
| 579 | C | LYS | A | 684 | 33.821 | 48.865 | 69.727 | 1.00 | 57.78 |
| 580 | O | LYS | A | 684 | 32.999 | 48.795 | 70.580 | 1.00 | 58.15 |
| 581 | N | TYR | A | 685 | 33.467 | 48.977 | 68.464 | 1.00 | 58.96 |
| 582 | CA | TYR | A | 685 | 32.075 | 49.289 | 68.086 | 1.00 | 59.96 |
| 583 | CB | TYR | A | 685 | 31.994 | 50.682 | 67.473 | 1.00 | 60.66 |
| 584 | CG | TYR | A | 685 | 32.713 | 51.794 | 68.195 | 1.00 | 63.95 |
| 585 | CD1 | TYR | A | 685 | 32.081 | 53.033 | 68.444 | 1.00 | 68.40 |
| 586 | CE1 | TYR | A | 685 | 32.793 | 54.105 | 69.056 | 1.00 | 72.55 |
| 587 | CZ | TYR | A | 685 | 34.165 | 53.916 | 69.401 | 1.00 | 73.82 |
| 588 | OH | TYR | A | 685 | 34.955 | 54.898 | 70.023 | 1.00 | 70.57 |
| 589 | CE2 | TYR | A | 685 | 34.766 | 52.684 | 69.116 | 1.00 | 70.32 |
| 590 | CD2 | TYR | A | 685 | 34.035 | 51.660 | 68.523 | 1.00 | 65.77 |
| 591 | C | TYR | A | 685 | 31.407 | 48.309 | 67.090 | 1.00 | 60.40 |
| 592 | O | TYR | A | 685 | 32.026 | 47.310 | 66.713 | 1.00 | 61.88 |
| 593 | N | LYS | A | 686 | 30.162 | 48.569 | 66.649 | 1.00 | 59.90 |
| 594 | CA | LYS | A | 686 | 29.579 | 47.680 | 65.656 | 1.00 | 58.82 |
| 595 | CB | LYS | A | 686 | 28.498 | 46.716 | 66.024 | 1.00 | 59.93 |
| 596 | CG | LYS | A | 686 | 29.096 | 45.424 | 66.530 | 1.00 | 59.37 |
| 597 | CD | LYS | A | 686 | 29.072 | 45.326 | 68.040 | 1.00 | 64.32 |
| 598 | CE | LYS | A | 686 | 30.146 | 46.244 | 68.676 | 1.00 | 67.97 |
| 599 | NZ | LYS | A | 686 | 30.718 | 45.703 | 69.957 | 1.00 | 66.41 |
| 600 | C | LYS | A | 686 | 29.658 | 47.859 | 64.242 | 1.00 | 59.00 |
| 601 | O | LYS | A | 686 | 29.403 | 48.925 | 63.673 | 1.00 | 61.49 |
| 602 | N | PRO | A | 687 | 29.432 | 46.717 | 63.735 | 1.00 | 56.91 |
| 603 | CA | PRO | A | 687 | 30.101 | 45.699 | 63.006 | 1.00 | 53.48 |
| 604 | CB | PRO | A | 687 | 29.846 | 46.015 | 61.546 | 1.00 | 55.46 |
| 605 | CG | PRO | A | 687 | 28.763 | 47.004 | 61.470 | 1.00 | 56.97 |
| 606 | CD | PRO | A | 687 | 28.593 | 47.506 | 62.796 | 1.00 | 57.11 |
| 607 | C | PRO | A | 687 | 31.572 | 45.851 | 63.404 | 1.00 | 50.95 |
| 608 | O | PRO | A | 687 | 32.164 | 46.919 | 63.374 | 1.00 | 49.51 |
| 609 | N | MET | A | 688 | 32.169 | 44.784 | 63.861 | 1.00 | 48.57 |
| 610 | CA | MET | A | 688 | 33.610 | 44.783 | 63.904 | 1.00 | 45.58 |
| 611 | CB | MET | A | 688 | 34.037 | 43.690 | 64.784 | 1.00 | 44.26 |
| 612 | CG | MET | A | 688 | 33.358 | 43.867 | 66.128 | 1.00 | 46.14 |
| 613 | SD | MET | A | 688 | 34.181 | 42.726 | 67.123 | 1.00 | 50.45 |
| 614 | CE | MET | A | 688 | 32.972 | 42.348 | 68.460 | 1.00 | 55.70 |
| 615 | C | MET | A | 688 | 34.060 | 44.576 | 62.442 | 1.00 | 45.64 |

FIGURE 3L

| A | B | C | D | E | F | G | H | I | J |
|---|---|---|---|---|---|---|---|---|---|
| 616 | O | MET | A | 688 | 33.364 | 43.928 | 61.647 | 1.00 | 43.85 |
| 617 | N | MET | A | 689 | 35.223 | 45.158 | 62.136 | 1.00 | 44.48 |
| 618 | CA | MET | A | 689 | 35.872 | 45.203 | 60.853 | 1.00 | 41.56 |
| 619 | CB | MET | A | 689 | 35.682 | 46.594 | 60.344 | 1.00 | 40.68 |
| 620 | CG | MET | A | 689 | 34.291 | 46.942 | 60.319 | 1.00 | 37.62 |
| 621 | SD | MET | A | 689 | 33.939 | 48.310 | 59.192 | 1.00 | 42.01 |
| 622 | CE | MET | A | 689 | 34.300 | 49.294 | 60.146 | 1.00 | 46.45 |
| 623 | C | MET | A | 689 | 37.362 | 44.919 | 60.908 | 1.00 | 41.69 |
| 624 | O | MET | A | 689 | 37.977 | 45.178 | 61.897 | 1.00 | 39.55 |
| 625 | N | ILE | A | 690 | 37.940 | 44.373 | 59.830 | 1.00 | 40.03 |
| 626 | CA | ILE | A | 690 | 39.410 | 44.156 | 59.726 | 1.00 | 38.46 |
| 627 | CB | ILE | A | 690 | 39.650 | 42.717 | 59.574 | 1.00 | 38.25 |
| 628 | CG1 | ILE | A | 690 | 39.323 | 42.011 | 60.848 | 1.00 | 33.60 |
| 629 | CD1 | ILE | A | 690 | 39.562 | 40.492 | 60.720 | 1.00 | 36.97 |
| 630 | CG2 | ILE | A | 690 | 41.038 | 42.467 | 59.271 | 1.00 | 40.53 |
| 631 | C | ILE | A | 690 | 39.644 | 44.923 | 58.495 | 1.00 | 38.31 |
| 632 | O | ILE | A | 690 | 38.862 | 44.775 | 57.519 | 1.00 | 38.24 |
| 633 | N | ILE | A | 691 | 40.509 | 45.952 | 58.568 | 1.00 | 39.22 |
| 634 | CA | ILE | A | 691 | 40.764 | 46.894 | 57.444 | 1.00 | 36.53 |
| 635 | CB | ILE | A | 691 | 40.907 | 48.317 | 57.943 | 1.00 | 37.55 |
| 636 | CG1 | ILE | A | 691 | 39.876 | 48.734 | 59.047 | 1.00 | 39.31 |
| 637 | CD1 | ILE | A | 691 | 38.393 | 48.990 | 58.541 | 1.00 | 32.39 |
| 638 | CG2 | ILE | A | 691 | 40.907 | 49.256 | 56.831 | 1.00 | 37.29 |
| 639 | C | ILE | A | 691 | 42.158 | 46.590 | 56.770 | 1.00 | 38.01 |
| 640 | O | ILE | A | 691 | 43.218 | 46.620 | 57.463 | 1.00 | 38.01 |
| 641 | N | THR | A | 692 | 42.182 | 46.381 | 55.445 | 1.00 | 37.20 |
| 642 | CA | THR | A | 692 | 43.445 | 46.080 | 54.734 | 1.00 | 36.47 |
| 643 | CB | THR | A | 692 | 43.566 | 44.593 | 54.387 | 1.00 | 35.20 |
| 644 | OG1 | THR | A | 692 | 42.564 | 44.283 | 53.451 | 1.00 | 35.83 |
| 645 | CG2 | THR | A | 692 | 43.156 | 43.824 | 55.543 | 1.00 | 30.57 |
| 646 | C | THR | A | 692 | 43.683 | 46.861 | 53.537 | 1.00 | 36.06 |
| 647 | O | THR | A | 692 | 42.841 | 47.599 | 53.075 | 1.00 | 37.50 |
| 648 | N | GLU | A | 693 | 44.893 | 46.762 | 53.018 | 1.00 | 36.84 |
| 649 | CA | GLU | A | 693 | 45.200 | 47.581 | 51.862 | 1.00 | 34.75 |
| 650 | CB | GLU | A | 693 | 46.688 | 47.414 | 51.456 | 1.00 | 34.83 |
| 651 | CG | GLU | A | 693 | 47.212 | 45.989 | 51.487 | 1.00 | 37.28 |
| 652 | CD | GLU | A | 693 | 48.611 | 45.888 | 50.934 | 1.00 | 40.39 |
| 653 | OE1 | GLU | A | 693 | 49.308 | 44.958 | 51.275 | 1.00 | 45.33 |
| 654 | OE2 | GLU | A | 693 | 49.039 | 46.754 | 50.177 | 1.00 | 38.27 |
| 655 | C | GLU | A | 693 | 44.262 | 47.082 | 50.823 | 1.00 | 35.09 |
| 656 | O | GLU | A | 693 | 43.970 | 45.920 | 50.773 | 1.00 | 36.98 |
| 657 | N | TYR | A | 694 | 43.698 | 47.978 | 50.038 | 1.00 | 36.62 |
| 658 | CA | TYR | A | 694 | 42.849 | 47.622 | 48.960 | 1.00 | 37.31 |
| 659 | CB | TYR | A | 694 | 42.179 | 48.887 | 48.452 | 1.00 | 37.54 |
| 660 | CG | TYR | A | 694 | 41.184 | 48.414 | 47.412 | 1.00 | 42.14 |
| 661 | CD1 | TYR | A | 694 | 41.184 | 48.943 | 46.116 | 1.00 | 43.68 |
| 662 | CE1 | TYR | A | 694 | 40.308 | 48.458 | 45.146 | 1.00 | 43.19 |
| 663 | CZ | TYR | A | 694 | 39.456 | 47.373 | 45.442 | 1.00 | 43.99 |
| 664 | OH | TYR | A | 694 | 38.543 | 46.885 | 44.453 | 1.00 | 50.45 |
| 665 | CE2 | TYR | A | 694 | 39.497 | 46.773 | 46.700 | 1.00 | 45.46 |
| 666 | CD2 | TYR | A | 694 | 40.400 | 47.254 | 47.673 | 1.00 | 43.35 |
| 667 | C | TYR | A | 694 | 43.600 | 46.896 | 47.705 | 1.00 | 37.33 |

FIGURE 3M

| A | B | C | D | E | F | G | H | I | J |
|---|---|---|---|---|---|---|---|---|---|
| 668 | O | TYR | A | 694 | 44.550 | 47.410 | 47.236 | 1.00 | 36.42 |
| 669 | N | MET | A | 695 | 43.211 | 45.693 | 47.297 | 1.00 | 36.44 |
| 670 | CA | MET | A | 695 | 43.873 | 45.008 | 46.147 | 1.00 | 38.70 |
| 671 | CB | MET | A | 695 | 44.266 | 43.583 | 46.553 | 1.00 | 36.76 |
| 672 | CG | MET | A | 695 | 45.185 | 43.564 | 47.793 | 1.00 | 36.63 |
| 673 | SD | MET | A | 695 | 46.870 | 44.267 | 47.620 | 1.00 | 38.01 |
| 674 | CE | MET | A | 695 | 47.436 | 42.869 | 46.677 | 1.00 | 33.07 |
| 675 | C | MET | A | 695 | 42.889 | 44.957 | 44.909 | 1.00 | 40.11 |
| 676 | O | MET | A | 695 | 42.039 | 44.111 | 44.843 | 1.00 | 42.18 |
| 677 | N | GLU | A | 696 | 43.005 | 45.883 | 43.975 | 1.00 | 40.26 |
| 678 | CA | GLU | A | 696 | 42.088 | 46.032 | 42.896 | 1.00 | 41.93 |
| 679 | CB | GLU | A | 696 | 42.712 | 46.973 | 41.893 | 1.00 | 43.18 |
| 680 | CG | GLU | A | 696 | 42.480 | 48.440 | 42.115 | 1.00 | 48.76 |
| 681 | CD | GLU | A | 696 | 41.565 | 48.937 | 40.999 | 1.00 | 58.48 |
| 682 | OE1 | GLU | A | 696 | 40.566 | 48.194 | 40.663 | 1.00 | 63.90 |
| 683 | OE2 | GLU | A | 696 | 41.916 | 50.017 | 40.443 | 1.00 | 62.65 |
| 684 | C | GLU | A | 696 | 41.889 | 44.764 | 42.103 | 1.00 | 41.93 |
| 685 | O | GLU | A | 696 | 40.789 | 44.446 | 41.706 | 1.00 | 44.34 |
| 686 | N | ASN | A | 697 | 42.922 | 43.979 | 41.880 | 1.00 | 39.85 |
| 687 | CA | ASN | A | 697 | 42.618 | 42.947 | 40.921 | 1.00 | 38.87 |
| 688 | CB | ASN | A | 697 | 43.808 | 42.705 | 39.966 | 1.00 | 38.40 |
| 689 | CG | ASN | A | 697 | 43.812 | 43.672 | 38.784 | 1.00 | 40.20 |
| 690 | OD1 | ASN | A | 697 | 44.849 | 44.178 | 38.347 | 1.00 | 44.17 |
| 691 | ND2 | ASN | A | 697 | 42.558 | 43.959 | 38.269 | 1.00 | 45.86 |
| 692 | C | ASN | A | 697 | 42.157 | 41.756 | 41.647 | 1.00 | 37.90 |
| 693 | O | ASN | A | 697 | 41.992 | 40.689 | 41.026 | 1.00 | 39.69 |
| 694 | N | GLY | A | 698 | 42.062 | 41.848 | 42.992 | 1.00 | 33.49 |
| 695 | CA | GLY | A | 698 | 41.403 | 40.701 | 43.621 | 1.00 | 28.87 |
| 696 | C | GLY | A | 698 | 42.204 | 39.491 | 43.680 | 1.00 | 29.77 |
| 697 | O | GLY | A | 698 | 43.383 | 39.592 | 43.682 | 1.00 | 29.55 |
| 698 | N | ALA | A | 699 | 41.559 | 38.342 | 43.701 | 1.00 | 29.72 |
| 699 | CA | ALA | A | 699 | 42.186 | 37.154 | 43.998 | 1.00 | 29.38 |
| 700 | CB | ALA | A | 699 | 41.204 | 36.198 | 44.395 | 1.00 | 26.29 |
| 701 | C | ALA | A | 699 | 42.995 | 36.675 | 42.794 | 1.00 | 33.59 |
| 702 | O | ALA | A | 699 | 42.596 | 36.859 | 41.676 | 1.00 | 31.03 |
| 703 | N | LEU | A | 700 | 44.050 | 35.887 | 43.011 | 1.00 | 34.21 |
| 704 | CA | LEU | A | 700 | 44.921 | 35.788 | 41.802 | 1.00 | 34.10 |
| 705 | CB | LEU | A | 700 | 46.407 | 35.560 | 42.179 | 1.00 | 32.00 |
| 706 | CG | LEU | A | 700 | 47.319 | 34.761 | 41.280 | 1.00 | 31.11 |
| 707 | CD1 | LEU | A | 700 | 47.764 | 35.687 | 40.259 | 1.00 | 28.00 |
| 708 | CD2 | LEU | A | 700 | 48.550 | 34.238 | 42.076 | 1.00 | 28.60 |
| 709 | C | LEU | A | 700 | 44.409 | 34.800 | 40.866 | 1.00 | 33.32 |
| 710 | O | LEU | A | 700 | 44.504 | 35.041 | 39.691 | 1.00 | 33.33 |
| 711 | N | ASP | A | 701 | 43.814 | 33.697 | 41.348 | 1.00 | 34.11 |
| 712 | CA | ASP | A | 701 | 43.402 | 32.617 | 40.406 | 1.00 | 35.12 |
| 713 | CB | ASP | A | 701 | 42.894 | 31.383 | 41.064 | 1.00 | 33.80 |
| 714 | CG | ASP | A | 701 | 41.715 | 31.594 | 41.891 | 1.00 | 34.53 |
| 715 | OD1 | ASP | A | 701 | 41.531 | 32.676 | 42.421 | 1.00 | 30.09 |
| 716 | OD2 | ASP | A | 701 | 40.923 | 30.670 | 42.118 | 1.00 | 37.42 |
| 717 | C | ASP | A | 701 | 42.326 | 33.068 | 39.463 | 1.00 | 36.51 |
| 718 | O | ASP | A | 701 | 42.123 | 32.568 | 38.350 | 1.00 | 37.86 |
| 719 | N | LYS | A | 702 | 41.562 | 34.003 | 39.970 | 1.00 | 37.59 |

FIGURE 3N

| A | B | C | D | E | F | G | H | I | J |
|---|---|---|---|---|---|---|---|---|---|
| 720 | CA | LYS | A | 702 | 40.659 | 34.530 | 39.118 | 1.00 | 36.66 |
| 721 | CB | LYS | A | 702 | 39.348 | 34.752 | 39.976 | 1.00 | 39.28 |
| 722 | CG | LYS | A | 702 | 38.479 | 35.942 | 39.600 | 1.00 | 40.13 |
| 723 | CD | LYS | A | 702 | 37.311 | 36.218 | 40.641 | 1.00 | 56.19 |
| 724 | CE | LYS | A | 702 | 35.951 | 36.757 | 40.026 | 1.00 | 59.70 |
| 725 | NZ | LYS | A | 702 | 35.195 | 35.733 | 39.227 | 1.00 | 67.51 |
| 726 | C | LYS | A | 702 | 40.878 | 35.646 | 38.132 | 1.00 | 35.74 |
| 727 | O | LYS | A | 702 | 40.206 | 35.681 | 37.082 | 1.00 | 37.89 |
| 728 | N | PHE | A | 703 | 41.549 | 36.665 | 38.605 | 1.00 | 33.13 |
| 729 | CA | PHE | A | 703 | 42.200 | 37.643 | 37.765 | 1.00 | 36.62 |
| 730 | CB | PHE | A | 703 | 43.332 | 38.312 | 38.567 | 1.00 | 34.46 |
| 731 | CG | PHE | A | 703 | 44.012 | 39.505 | 37.876 | 1.00 | 38.02 |
| 732 | CD1 | PHE | A | 703 | 43.177 | 40.498 | 37.330 | 1.00 | 25.27 |
| 733 | CE1 | PHE | A | 703 | 43.732 | 41.626 | 36.757 | 1.00 | 33.70 |
| 734 | CZ | PHE | A | 703 | 45.135 | 41.763 | 36.641 | 1.00 | 34.23 |
| 735 | CE2 | PHE | A | 703 | 45.994 | 40.790 | 37.203 | 1.00 | 37.20 |
| 736 | CD2 | PHE | A | 703 | 45.473 | 39.665 | 37.808 | 1.00 | 29.52 |
| 737 | C | PHE | A | 703 | 42.876 | 36.911 | 36.599 | 1.00 | 35.72 |
| 738 | O | PHE | A | 703 | 42.629 | 37.269 | 35.553 | 1.00 | 37.70 |
| 739 | N | LEU | A | 704 | 43.688 | 35.901 | 36.842 | 1.00 | 33.99 |
| 740 | CA | LEU | A | 704 | 44.382 | 35.252 | 35.803 | 1.00 | 34.00 |
| 741 | CB | LEU | A | 704 | 45.213 | 34.181 | 36.373 | 1.00 | 32.88 |
| 742 | CG | LEU | A | 704 | 46.458 | 34.749 | 37.087 | 1.00 | 36.11 |
| 743 | CD1 | LEU | A | 704 | 47.352 | 33.579 | 37.374 | 1.00 | 37.94 |
| 744 | CD2 | LEU | A | 704 | 47.195 | 36.016 | 36.306 | 1.00 | 37.86 |
| 745 | C | LEU | A | 704 | 43.422 | 34.649 | 34.912 | 1.00 | 36.85 |
| 746 | O | LEU | A | 704 | 43.715 | 34.499 | 33.721 | 1.00 | 35.55 |
| 747 | N | ARG | A | 705 | 42.236 | 34.267 | 35.435 | 1.00 | 38.22 |
| 748 | CA | ARG | A | 705 | 41.330 | 33.575 | 34.495 | 1.00 | 38.60 |
| 749 | CB | ARG | A | 705 | 40.284 | 32.784 | 35.157 | 1.00 | 37.82 |
| 750 | CG | ARG | A | 705 | 40.854 | 31.540 | 35.460 | 1.00 | 40.12 |
| 751 | CD | ARG | A | 705 | 39.889 | 30.555 | 35.686 | 1.00 | 40.84 |
| 752 | NE | ARG | A | 705 | 39.223 | 30.917 | 36.889 | 1.00 | 40.80 |
| 753 | CZ | ARG | A | 705 | 39.621 | 30.530 | 38.094 | 1.00 | 48.75 |
| 754 | NH1 | ARG | A | 705 | 38.912 | 30.876 | 39.157 | 1.00 | 41.80 |
| 755 | NH2 | ARG | A | 705 | 40.700 | 29.778 | 38.239 | 1.00 | 48.73 |
| 756 | C | ARG | A | 705 | 40.673 | 34.528 | 33.555 | 1.00 | 38.66 |
| 757 | O | ARG | A | 705 | 40.320 | 34.170 | 32.473 | 1.00 | 40.65 |
| 758 | N | GLU | A | 706 | 40.500 | 35.728 | 34.028 | 1.00 | 38.10 |
| 759 | CA | GLU | A | 706 | 39.969 | 36.744 | 33.282 | 1.00 | 40.40 |
| 760 | CB | GLU | A | 706 | 39.517 | 37.804 | 34.231 | 1.00 | 40.22 |
| 761 | CG | GLU | A | 706 | 38.247 | 37.363 | 34.881 | 1.00 | 50.24 |
| 762 | CD | GLU | A | 706 | 37.786 | 38.278 | 36.015 | 1.00 | 60.71 |
| 763 | OE1 | GLU | A | 706 | 36.711 | 37.952 | 36.578 | 1.00 | 61.83 |
| 764 | OE2 | GLU | A | 706 | 38.517 | 39.275 | 36.357 | 1.00 | 64.44 |
| 765 | C | GLU | A | 706 | 40.921 | 37.385 | 32.278 | 1.00 | 38.37 |
| 766 | O | GLU | A | 706 | 40.495 | 38.051 | 31.411 | 1.00 | 40.23 |
| 767 | N | LYS | A | 707 | 42.197 | 37.278 | 32.465 | 1.00 | 37.18 |
| 768 | CA | LYS | A | 707 | 43.145 | 38.027 | 31.602 | 1.00 | 35.98 |
| 769 | CB | LYS | A | 707 | 44.085 | 38.856 | 32.502 | 1.00 | 36.31 |
| 770 | CG | LYS | A | 707 | 43.436 | 40.070 | 33.159 | 1.00 | 31.25 |
| 771 | CD | LYS | A | 707 | 42.537 | 40.850 | 32.178 | 1.00 | 41.00 |

FIGURE 3O

| A | B | C | D | E | F | G | H | I | J |
|---|---|---|---|---|---|---|---|---|---|
| 772 | CE | LYS | A | 707 | 41.828 | 42.152 | 32.801 | 1.00 | 43.91 |
| 773 | NZ | LYS | A | 707 | 42.468 | 43.446 | 32.199 | 1.00 | 46.63 |
| 774 | C | LYS | A | 707 | 43.963 | 36.986 | 30.907 | 1.00 | 34.83 |
| 775 | O | LYS | A | 707 | 45.140 | 37.112 | 30.851 | 1.00 | 31.51 |
| 776 | N | ASP | A | 708 | 43.310 | 35.854 | 30.599 | 1.00 | 34.02 |
| 777 | CA | ASP | A | 708 | 43.961 | 34.687 | 30.142 | 1.00 | 34.42 |
| 778 | CB | ASP | A | 708 | 42.937 | 33.630 | 29.906 | 1.00 | 35.74 |
| 779 | CG | ASP | A | 708 | 43.549 | 32.340 | 29.318 | 1.00 | 37.91 |
| 780 | OD1 | ASP | A | 708 | 44.713 | 32.065 | 29.373 | 1.00 | 46.66 |
| 781 | OD2 | ASP | A | 708 | 42.940 | 31.505 | 28.741 | 1.00 | 51.37 |
| 782 | C | ASP | A | 708 | 44.823 | 34.932 | 28.843 | 1.00 | 33.85 |
| 783 | O | ASP | A | 708 | 44.332 | 35.563 | 27.880 | 1.00 | 33.03 |
| 784 | N | GLY | A | 709 | 46.076 | 34.438 | 28.842 | 1.00 | 32.14 |
| 785 | CA | GLY | A | 709 | 46.985 | 34.781 | 27.796 | 1.00 | 32.46 |
| 786 | C | GLY | A | 709 | 47.341 | 36.273 | 27.734 | 1.00 | 33.50 |
| 787 | O | GLY | A | 709 | 48.010 | 36.740 | 26.849 | 1.00 | 32.44 |
| 788 | N | GLU | A | 710 | 47.011 | 37.043 | 28.715 | 1.00 | 33.77 |
| 789 | CA | GLU | A | 710 | 47.365 | 38.445 | 28.521 | 1.00 | 35.02 |
| 790 | CB | GLU | A | 710 | 46.198 | 39.448 | 28.823 | 1.00 | 34.74 |
| 791 | CG | GLU | A | 710 | 44.870 | 39.054 | 28.228 | 1.00 | 33.49 |
| 792 | CD | GLU | A | 710 | 43.843 | 40.107 | 28.521 | 1.00 | 41.03 |
| 793 | OE1 | GLU | A | 710 | 44.173 | 41.360 | 28.693 | 1.00 | 44.53 |
| 794 | OE2 | GLU | A | 710 | 42.704 | 39.661 | 28.521 | 1.00 | 38.77 |
| 795 | C | GLU | A | 710 | 48.602 | 39.017 | 29.221 | 1.00 | 36.64 |
| 796 | O | GLU | A | 710 | 48.820 | 40.227 | 29.192 | 1.00 | 34.62 |
| 797 | N | PHE | A | 711 | 49.403 | 38.185 | 29.832 | 1.00 | 37.09 |
| 798 | CA | PHE | A | 711 | 50.510 | 38.792 | 30.525 | 1.00 | 37.88 |
| 799 | CB | PHE | A | 711 | 50.414 | 38.384 | 32.039 | 1.00 | 38.28 |
| 800 | CG | PHE | A | 711 | 49.322 | 39.225 | 32.812 | 1.00 | 38.60 |
| 801 | CD1 | PHE | A | 711 | 48.302 | 38.610 | 33.509 | 1.00 | 38.93 |
| 802 | CE1 | PHE | A | 711 | 47.359 | 39.316 | 34.196 | 1.00 | 36.81 |
| 803 | CZ | PHE | A | 711 | 47.377 | 40.696 | 34.129 | 1.00 | 43.70 |
| 804 | CE2 | PHE | A | 711 | 48.361 | 41.361 | 33.378 | 1.00 | 42.48 |
| 805 | CD2 | PHE | A | 711 | 49.320 | 40.609 | 32.722 | 1.00 | 36.32 |
| 806 | C | PHE | A | 711 | 51.731 | 38.237 | 29.795 | 1.00 | 38.37 |
| 807 | O | PHE | A | 711 | 51.653 | 37.191 | 29.189 | 1.00 | 38.38 |
| 808 | N | SER | A | 712 | 52.829 | 38.954 | 29.832 | 1.00 | 37.51 |
| 809 | CA | SER | A | 712 | 54.054 | 38.463 | 29.318 | 1.00 | 37.68 |
| 810 | CB | SER | A | 712 | 55.019 | 39.640 | 29.207 | 1.00 | 33.41 |
| 811 | OG | SER | A | 712 | 55.482 | 39.865 | 30.488 | 1.00 | 38.72 |
| 812 | C | SER | A | 712 | 54.533 | 37.373 | 30.343 | 1.00 | 38.11 |
| 813 | O | SER | A | 712 | 54.143 | 37.370 | 31.560 | 1.00 | 36.94 |
| 814 | N | VAL | A | 713 | 55.345 | 36.430 | 29.853 | 1.00 | 36.56 |
| 815 | CA | VAL | A | 713 | 55.970 | 35.463 | 30.743 | 1.00 | 38.74 |
| 816 | CB | VAL | A | 713 | 56.860 | 34.555 | 29.902 | 1.00 | 40.25 |
| 817 | CG1 | VAL | A | 713 | 57.880 | 33.741 | 30.734 | 1.00 | 40.91 |
| 818 | CG2 | VAL | A | 713 | 55.973 | 33.661 | 29.047 | 1.00 | 46.85 |
| 819 | C | VAL | A | 713 | 56.820 | 36.172 | 31.891 | 1.00 | 38.93 |
| 820 | O | VAL | A | 713 | 57.034 | 35.653 | 33.003 | 1.00 | 38.80 |
| 821 | N | LEU | A | 714 | 57.279 | 37.366 | 31.621 | 1.00 | 38.01 |
| 822 | CA | LEU | A | 714 | 58.081 | 38.031 | 32.613 | 1.00 | 40.96 |
| 823 | CB | LEU | A | 714 | 58.951 | 39.068 | 31.898 | 1.00 | 40.30 |

FIGURE 3P

| A | B | C | D | E | F | G | H | I | J |
|---|---|---|---|---|---|---|---|---|---|
| 824 | CG | LEU | A | 714 | 60.120 | 39.781 | 32.561 | 1.00 | 45.88 |
| 825 | CD1 | LEU | A | 714 | 61.094 | 38.833 | 33.052 | 1.00 | 46.43 |
| 826 | CD2 | LEU | A | 714 | 60.780 | 41.002 | 31.669 | 1.00 | 38.74 |
| 827 | C | LEU | A | 714 | 57.168 | 38.638 | 33.698 | 1.00 | 40.29 |
| 828 | O | LEU | A | 714 | 57.505 | 38.570 | 34.844 | 1.00 | 44.01 |
| 829 | N | GLN | A | 715 | 55.998 | 39.165 | 33.341 | 1.00 | 39.22 |
| 830 | CA | GLN | A | 715 | 55.001 | 39.613 | 34.321 | 1.00 | 36.85 |
| 831 | CB | GLN | A | 715 | 53.868 | 40.332 | 33.636 | 1.00 | 38.50 |
| 832 | CG | GLN | A | 715 | 54.218 | 41.672 | 33.012 | 1.00 | 29.96 |
| 833 | CD | GLN | A | 715 | 53.075 | 42.067 | 32.167 | 1.00 | 28.87 |
| 834 | OE1 | GLN | A | 715 | 52.617 | 41.293 | 31.387 | 1.00 | 32.88 |
| 835 | NE2 | GLN | A | 715 | 52.490 | 43.193 | 32.455 | 1.00 | 33.61 |
| 836 | C | GLN | A | 715 | 54.509 | 38.407 | 35.125 | 1.00 | 36.09 |
| 837 | O | GLN | A | 715 | 54.324 | 38.479 | 36.350 | 1.00 | 38.22 |
| 838 | N | LEU | A | 716 | 54.447 | 37.245 | 34.514 | 1.00 | 34.64 |
| 839 | CA | LEU | A | 716 | 54.000 | 36.106 | 35.305 | 1.00 | 34.14 |
| 840 | CB | LEU | A | 716 | 53.658 | 34.883 | 34.441 | 1.00 | 33.25 |
| 841 | CG | LEU | A | 716 | 52.373 | 35.072 | 33.597 | 1.00 | 34.69 |
| 842 | CD1 | LEU | A | 716 | 52.021 | 33.922 | 32.684 | 1.00 | 40.42 |
| 843 | CD2 | LEU | A | 716 | 51.151 | 35.391 | 34.465 | 1.00 | 35.13 |
| 844 | C | LEU | A | 716 | 55.008 | 35.742 | 36.325 | 1.00 | 36.34 |
| 845 | O | LEU | A | 716 | 54.687 | 35.526 | 37.487 | 1.00 | 38.96 |
| 846 | N | VAL | A | 717 | 56.247 | 35.640 | 35.901 | 1.00 | 35.71 |
| 847 | CA | VAL | A | 717 | 57.282 | 35.173 | 36.716 | 1.00 | 33.91 |
| 848 | CB | VAL | A | 717 | 58.571 | 35.031 | 35.931 | 1.00 | 35.17 |
| 849 | CG1 | VAL | A | 717 | 59.687 | 34.711 | 36.866 | 1.00 | 29.77 |
| 850 | CG2 | VAL | A | 717 | 58.367 | 33.983 | 34.852 | 1.00 | 38.75 |
| 851 | C | VAL | A | 717 | 57.580 | 36.125 | 37.850 | 1.00 | 33.83 |
| 852 | O | VAL | A | 717 | 57.880 | 35.699 | 38.947 | 1.00 | 31.28 |
| 853 | N | GLY | A | 718 | 57.534 | 37.416 | 37.555 | 1.00 | 31.97 |
| 854 | CA | GLY | A | 718 | 57.503 | 38.426 | 38.592 | 1.00 | 35.27 |
| 855 | C | GLY | A | 718 | 56.292 | 38.282 | 39.565 | 1.00 | 36.66 |
| 856 | O | GLY | A | 718 | 56.491 | 38.537 | 40.791 | 1.00 | 39.82 |
| 857 | N | MET | A | 719 | 55.089 | 37.891 | 39.114 | 1.00 | 35.07 |
| 858 | CA | MET | A | 719 | 54.036 | 37.707 | 40.103 | 1.00 | 34.57 |
| 859 | CB | MET | A | 719 | 52.605 | 37.454 | 39.502 | 1.00 | 34.98 |
| 860 | CG | MET | A | 719 | 52.011 | 38.624 | 38.740 | 1.00 | 38.87 |
| 861 | SD | MET | A | 719 | 50.791 | 38.025 | 37.564 | 1.00 | 43.45 |
| 862 | CE | MET | A | 719 | 50.085 | 39.579 | 36.958 | 1.00 | 37.28 |
| 863 | C | MET | A | 719 | 54.549 | 36.568 | 40.960 | 1.00 | 34.85 |
| 864 | O | MET | A | 719 | 54.303 | 36.521 | 42.201 | 1.00 | 34.62 |
| 865 | N | LEU | A | 720 | 55.287 | 35.643 | 40.362 | 1.00 | 33.93 |
| 866 | CA | LEU | A | 720 | 55.655 | 34.523 | 41.175 | 1.00 | 35.01 |
| 867 | CB | LEU | A | 720 | 56.042 | 33.265 | 40.370 | 1.00 | 34.91 |
| 868 | CG | LEU | A | 720 | 54.807 | 32.554 | 39.778 | 1.00 | 41.19 |
| 869 | CD1 | LEU | A | 720 | 55.348 | 31.681 | 38.652 | 1.00 | 33.86 |
| 870 | CD2 | LEU | A | 720 | 54.125 | 31.703 | 40.866 | 1.00 | 35.22 |
| 871 | C | LEU | A | 720 | 56.796 | 34.940 | 42.127 | 1.00 | 34.33 |
| 872 | O | LEU | A | 720 | 56.915 | 34.341 | 43.175 | 1.00 | 33.94 |
| 873 | N | ARG | A | 721 | 57.633 | 35.906 | 41.741 | 1.00 | 35.51 |
| 874 | CA | ARG | A | 721 | 58.698 | 36.200 | 42.637 | 1.00 | 37.80 |
| 875 | CB | ARG | A | 721 | 59.987 | 36.862 | 42.044 | 1.00 | 38.19 |

FIGURE 3Q

| A | B | C | D | E | F | G | H | I | J |
|---|---|---|---|---|---|---|---|---|---|
| 876 | CG | ARG | A | 721 | 60.314 | 38.329 | 42.432 | 1.00 | 43.45 |
| 877 | CD | ARG | A | 721 | 61.699 | 38.652 | 43.075 | 1.00 | 44.68 |
| 878 | NE | ARG | A | 721 | 61.671 | 39.968 | 43.738 | 1.00 | 46.01 |
| 879 | CZ | ARG | A | 721 | 62.115 | 40.223 | 45.005 | 1.00 | 47.92 |
| 880 | NH1 | ARG | A | 721 | 62.690 | 39.297 | 45.760 | 1.00 | 42.62 |
| 881 | NH2 | ARG | A | 721 | 62.011 | 41.426 | 45.507 | 1.00 | 42.77 |
| 882 | C | ARG | A | 721 | 58.073 | 36.904 | 43.840 | 1.00 | 35.74 |
| 883 | O | ARG | A | 721 | 58.397 | 36.583 | 44.921 | 1.00 | 36.27 |
| 884 | N | GLY | A | 722 | 57.028 | 37.678 | 43.635 | 1.00 | 36.52 |
| 885 | CA | GLY | A | 722 | 56.397 | 38.422 | 44.757 | 1.00 | 33.29 |
| 886 | C | GLY | A | 722 | 55.861 | 37.381 | 45.691 | 1.00 | 32.31 |
| 887 | O | GLY | A | 722 | 56.178 | 37.333 | 46.854 | 1.00 | 33.65 |
| 888 | N | ILE | A | 723 | 54.965 | 36.546 | 45.211 | 1.00 | 30.16 |
| 889 | CA | ILE | A | 723 | 54.543 | 35.518 | 46.137 | 1.00 | 30.15 |
| 890 | CB | ILE | A | 723 | 53.772 | 34.400 | 45.387 | 1.00 | 29.03 |
| 891 | CG1 | ILE | A | 723 | 52.614 | 35.088 | 44.763 | 1.00 | 28.74 |
| 892 | CD1 | ILE | A | 723 | 51.890 | 34.311 | 43.667 | 1.00 | 22.43 |
| 893 | CG2 | ILE | A | 723 | 53.270 | 33.347 | 46.367 | 1.00 | 23.88 |
| 894 | C | ILE | A | 723 | 55.682 | 34.939 | 46.875 | 1.00 | 29.85 |
| 895 | O | ILE | A | 723 | 55.643 | 34.733 | 48.086 | 1.00 | 28.93 |
| 896 | N | ALA | A | 724 | 56.673 | 34.526 | 46.105 | 1.00 | 30.46 |
| 897 | CA | ALA | A | 724 | 57.762 | 33.758 | 46.736 | 1.00 | 30.64 |
| 898 | CB | ALA | A | 724 | 58.778 | 33.564 | 45.694 | 1.00 | 32.41 |
| 899 | C | ALA | A | 724 | 58.469 | 34.553 | 47.912 | 1.00 | 29.69 |
| 900 | O | ALA | A | 724 | 58.762 | 34.063 | 49.021 | 1.00 | 26.55 |
| 901 | N | ALA | A | 725 | 58.746 | 35.770 | 47.606 | 1.00 | 27.76 |
| 902 | CA | ALA | A | 725 | 59.310 | 36.650 | 48.550 | 1.00 | 30.34 |
| 903 | CB | ALA | A | 725 | 59.330 | 38.044 | 47.843 | 1.00 | 29.68 |
| 904 | C | ALA | A | 725 | 58.500 | 36.648 | 49.943 | 1.00 | 32.46 |
| 905 | O | ALA | A | 725 | 59.049 | 36.269 | 51.069 | 1.00 | 32.65 |
| 906 | N | GLY | A | 726 | 57.186 | 36.806 | 49.778 | 1.00 | 31.30 |
| 907 | CA | GLY | A | 726 | 56.280 | 36.858 | 50.888 | 1.00 | 32.69 |
| 908 | C | GLY | A | 726 | 56.416 | 35.599 | 51.565 | 1.00 | 34.43 |
| 909 | O | GLY | A | 726 | 56.515 | 35.595 | 52.766 | 1.00 | 37.79 |
| 910 | N | MET | A | 727 | 56.508 | 34.533 | 50.825 | 1.00 | 33.96 |
| 911 | CA | MET | A | 727 | 56.597 | 33.296 | 51.482 | 1.00 | 36.78 |
| 912 | CB | MET | A | 727 | 56.397 | 32.063 | 50.534 | 1.00 | 38.17 |
| 913 | CG | MET | A | 727 | 55.028 | 31.722 | 50.128 | 1.00 | 35.85 |
| 914 | SD | MET | A | 727 | 53.739 | 31.892 | 51.569 | 1.00 | 33.45 |
| 915 | CE | MET | A | 727 | 53.924 | 30.327 | 52.256 | 1.00 | 30.52 |
| 916 | C | MET | A | 727 | 58.004 | 33.177 | 52.095 | 1.00 | 40.08 |
| 917 | O | MET | A | 727 | 58.132 | 32.402 | 52.994 | 1.00 | 40.52 |
| 918 | N | LYS | A | 728 | 59.049 | 33.876 | 51.607 | 1.00 | 41.82 |
| 919 | CA | LYS | A | 728 | 60.369 | 33.753 | 52.222 | 1.00 | 43.04 |
| 920 | CB | LYS | A | 728 | 61.552 | 34.367 | 51.426 | 1.00 | 42.93 |
| 921 | CG | LYS | A | 728 | 62.851 | 34.461 | 52.374 | 1.00 | 45.08 |
| 922 | CD | LYS | A | 728 | 64.269 | 34.813 | 51.788 | 1.00 | 48.13 |
| 923 | CE | LYS | A | 728 | 65.367 | 34.940 | 52.974 | 1.00 | 60.10 |
| 924 | NZ | LYS | A | 728 | 65.965 | 33.765 | 53.965 | 1.00 | 59.07 |
| 925 | C | LYS | A | 728 | 60.220 | 34.506 | 53.629 | 1.00 | 43.72 |
| 926 | O | LYS | A | 728 | 60.732 | 34.080 | 54.703 | 1.00 | 42.16 |
| 927 | N | TYR | A | 729 | 59.566 | 35.633 | 53.588 | 1.00 | 41.05 |

FIGURE 3R

| A | B | C | D | E | F | G | H | I | J |
|---|---|---|---|---|---|---|---|---|---|
| 928 | CA | TYR | A | 729 | 59.283 | 36.265 | 54.861 | 1.00 | 40.26 |
| 929 | CB | TYR | A | 729 | 58.511 | 37.417 | 54.525 | 1.00 | 36.34 |
| 930 | CG | TYR | A | 729 | 58.276 | 38.219 | 55.647 | 1.00 | 43.34 |
| 931 | CD1 | TYR | A | 729 | 59.290 | 39.022 | 56.234 | 1.00 | 41.12 |
| 932 | CE1 | TYR | A | 729 | 58.907 | 39.900 | 57.404 | 1.00 | 41.14 |
| 933 | CZ | TYR | A | 729 | 57.600 | 39.837 | 57.863 | 1.00 | 41.39 |
| 934 | OH | TYR | A | 729 | 56.977 | 40.579 | 58.883 | 1.00 | 40.30 |
| 935 | CE2 | TYR | A | 729 | 56.672 | 38.976 | 57.197 | 1.00 | 40.74 |
| 936 | CD2 | TYR | A | 729 | 56.985 | 38.255 | 56.187 | 1.00 | 36.09 |
| 937 | C | TYR | A | 729 | 58.534 | 35.355 | 55.862 | 1.00 | 42.10 |
| 938 | O | TYR | A | 729 | 58.996 | 35.098 | 57.035 | 1.00 | 41.89 |
| 939 | N | LEU | A | 730 | 57.379 | 34.814 | 55.422 | 1.00 | 42.02 |
| 940 | CA | LEU | A | 730 | 56.704 | 33.992 | 56.335 | 1.00 | 39.74 |
| 941 | CB | LEU | A | 730 | 55.411 | 33.422 | 55.779 | 1.00 | 38.11 |
| 942 | CG | LEU | A | 730 | 54.356 | 34.521 | 55.426 | 1.00 | 39.93 |
| 943 | CD1 | LEU | A | 730 | 53.208 | 33.851 | 54.731 | 1.00 | 30.48 |
| 944 | CD2 | LEU | A | 730 | 53.843 | 35.522 | 56.628 | 1.00 | 36.84 |
| 945 | C | LEU | A | 730 | 57.615 | 32.961 | 56.868 | 1.00 | 40.93 |
| 946 | O | LEU | A | 730 | 57.590 | 32.614 | 58.097 | 1.00 | 44.06 |
| 947 | N | ALA | A | 731 | 58.379 | 32.366 | 56.000 | 1.00 | 41.66 |
| 948 | CA | ALA | A | 731 | 59.128 | 31.219 | 56.482 | 1.00 | 43.27 |
| 949 | CB | ALA | A | 731 | 59.665 | 30.304 | 55.365 | 1.00 | 42.98 |
| 950 | C | ALA | A | 731 | 60.252 | 31.695 | 57.426 | 1.00 | 43.66 |
| 951 | O | ALA | A | 731 | 60.645 | 31.018 | 58.306 | 1.00 | 44.04 |
| 952 | N | ASN | A | 732 | 60.709 | 32.885 | 57.279 | 1.00 | 44.35 |
| 953 | CA | ASN | A | 732 | 61.713 | 33.276 | 58.220 | 1.00 | 46.81 |
| 954 | CB | ASN | A | 732 | 62.560 | 34.350 | 57.600 | 1.00 | 43.35 |
| 955 | CG | ASN | A | 732 | 63.616 | 33.729 | 56.588 | 1.00 | 48.96 |
| 956 | OD1 | ASN | A | 732 | 63.954 | 32.507 | 56.609 | 1.00 | 49.17 |
| 957 | ND2 | ASN | A | 732 | 64.077 | 34.565 | 55.670 | 1.00 | 51.65 |
| 958 | C | ASN | A | 732 | 61.050 | 33.532 | 59.645 | 1.00 | 47.03 |
| 959 | O | ASN | A | 732 | 61.593 | 33.105 | 60.645 | 1.00 | 47.94 |
| 960 | N | MET | A | 733 | 59.861 | 34.149 | 59.686 | 1.00 | 47.68 |
| 961 | CA | MET | A | 733 | 59.083 | 34.350 | 60.880 | 1.00 | 45.27 |
| 962 | CB | MET | A | 733 | 57.872 | 35.218 | 60.694 | 1.00 | 43.96 |
| 963 | CG | MET | A | 733 | 58.018 | 36.674 | 60.281 | 1.00 | 48.30 |
| 964 | SD | MET | A | 733 | 59.136 | 37.666 | 61.268 | 1.00 | 58.32 |
| 965 | CE | MET | A | 733 | 58.421 | 37.372 | 62.740 | 1.00 | 52.36 |
| 966 | C | MET | A | 733 | 58.590 | 33.013 | 61.346 | 1.00 | 45.93 |
| 967 | O | MET | A | 733 | 57.762 | 32.977 | 62.179 | 1.00 | 46.67 |
| 968 | N | ASN | A | 734 | 59.121 | 31.890 | 60.885 | 1.00 | 46.78 |
| 969 | CA | ASN | A | 734 | 58.546 | 30.632 | 61.341 | 1.00 | 47.20 |
| 970 | CB | ASN | A | 734 | 58.754 | 30.384 | 62.828 | 1.00 | 50.07 |
| 971 | CG | ASN | A | 734 | 60.243 | 30.038 | 63.145 | 1.00 | 56.81 |
| 972 | OD1 | ASN | A | 734 | 60.886 | 30.656 | 64.048 | 1.00 | 57.16 |
| 973 | ND2 | ASN | A | 734 | 60.803 | 29.077 | 62.372 | 1.00 | 59.81 |
| 974 | C | ASN | A | 734 | 57.069 | 30.458 | 61.090 | 1.00 | 45.73 |
| 975 | O | ASN | A | 734 | 56.373 | 29.743 | 61.797 | 1.00 | 43.13 |
| 976 | N | TYR | A | 735 | 56.542 | 31.043 | 60.042 | 1.00 | 44.71 |
| 977 | CA | TYR | A | 735 | 55.107 | 30.822 | 60.011 | 1.00 | 43.29 |
| 978 | CB | TYR | A | 735 | 54.443 | 32.126 | 59.921 | 1.00 | 42.22 |
| 979 | CG | TYR | A | 735 | 53.029 | 32.009 | 59.724 | 1.00 | 41.13 |

FIGURE 3S

| A | B | C | D | E | F | G | H | I | J |
|---|---|---|---|---|---|---|---|---|---|
| 980 | CD1 | TYR | A | 735 | 52.152 | 32.131 | 60.814 | 1.00 | 40.42 |
| 981 | CE1 | TYR | A | 735 | 50.811 | 32.085 | 60.664 | 1.00 | 47.06 |
| 982 | CZ | TYR | A | 735 | 50.271 | 31.907 | 59.374 | 1.00 | 47.34 |
| 983 | OH | TYR | A | 735 | 48.915 | 31.764 | 59.227 | 1.00 | 46.64 |
| 984 | CE2 | TYR | A | 735 | 51.155 | 31.732 | 58.239 | 1.00 | 47.89 |
| 985 | CD2 | TYR | A | 735 | 52.528 | 31.829 | 58.447 | 1.00 | 42.90 |
| 986 | C | TYR | A | 735 | 54.792 | 29.913 | 58.861 | 1.00 | 41.63 |
| 987 | O | TYR | A | 735 | 55.164 | 30.186 | 57.742 | 1.00 | 42.29 |
| 988 | N | VAL | A | 736 | 54.158 | 28.820 | 59.140 | 1.00 | 38.41 |
| 989 | CA | VAL | A | 736 | 53.937 | 27.923 | 58.084 | 1.00 | 39.18 |
| 990 | CB | VAL | A | 736 | 53.963 | 26.643 | 58.559 | 1.00 | 38.60 |
| 991 | CG1 | VAL | A | 736 | 53.334 | 25.786 | 57.440 | 1.00 | 44.99 |
| 992 | CG2 | VAL | A | 736 | 55.465 | 26.273 | 59.020 | 1.00 | 41.99 |
| 993 | C | VAL | A | 736 | 52.508 | 28.121 | 57.602 | 1.00 | 40.83 |
| 994 | O | VAL | A | 736 | 51.554 | 27.827 | 58.342 | 1.00 | 37.18 |
| 995 | N | HIS | A | 737 | 52.358 | 28.570 | 56.348 | 1.00 | 38.45 |
| 996 | CA | HIS | A | 737 | 51.076 | 29.014 | 55.969 | 1.00 | 38.83 |
| 997 | CB | HIS | A | 737 | 51.218 | 29.539 | 54.599 | 1.00 | 40.55 |
| 998 | CG | HIS | A | 737 | 50.007 | 30.193 | 54.135 | 1.00 | 33.42 |
| 999 | ND1 | HIS | A | 737 | 48.855 | 29.463 | 53.856 | 1.00 | 35.99 |
| 1000 | CE1 | HIS | A | 737 | 47.910 | 30.315 | 53.492 | 1.00 | 39.74 |
| 1001 | NE2 | HIS | A | 737 | 48.385 | 31.563 | 53.591 | 1.00 | 33.63 |
| 1002 | CD2 | HIS | A | 737 | 49.695 | 31.497 | 54.039 | 1.00 | 31.88 |
| 1003 | C | HIS | A | 737 | 49.993 | 28.008 | 55.933 | 1.00 | 41.07 |
| 1004 | O | HIS | A | 737 | 48.797 | 28.237 | 56.357 | 1.00 | 44.04 |
| 1005 | N | ARG | A | 738 | 50.376 | 26.934 | 55.306 | 1.00 | 41.15 |
| 1006 | CA | ARG | A | 738 | 49.618 | 25.687 | 55.197 | 1.00 | 40.70 |
| 1007 | CB | ARG | A | 738 | 48.940 | 25.402 | 56.513 | 1.00 | 42.80 |
| 1008 | CG | ARG | A | 738 | 49.697 | 24.932 | 57.725 | 1.00 | 45.84 |
| 1009 | CD | ARG | A | 738 | 48.687 | 24.798 | 58.849 | 1.00 | 53.31 |
| 1010 | NE | ARG | A | 738 | 49.009 | 23.892 | 59.954 | 1.00 | 67.74 |
| 1011 | CZ | ARG | A | 738 | 48.085 | 23.420 | 60.827 | 1.00 | 72.67 |
| 1012 | NH1 | ARG | A | 738 | 46.820 | 23.728 | 60.649 | 1.00 | 73.68 |
| 1013 | NH2 | ARG | A | 738 | 48.410 | 22.631 | 61.865 | 1.00 | 72.81 |
| 1014 | C | ARG | A | 738 | 48.515 | 25.670 | 54.118 | 1.00 | 38.77 |
| 1015 | O | ARG | A | 738 | 47.921 | 24.641 | 53.870 | 1.00 | 38.45 |
| 1016 | N | ASP | A | 739 | 48.177 | 26.788 | 53.516 | 1.00 | 36.53 |
| 1017 | CA | ASP | A | 739 | 47.072 | 26.753 | 52.631 | 1.00 | 36.55 |
| 1018 | CB | ASP | A | 739 | 45.883 | 27.404 | 53.377 | 1.00 | 39.05 |
| 1019 | CG | ASP | A | 739 | 44.538 | 27.308 | 52.614 | 1.00 | 42.96 |
| 1020 | OD1 | ASP | A | 739 | 43.754 | 28.312 | 52.665 | 1.00 | 43.61 |
| 1021 | OD2 | ASP | A | 739 | 44.148 | 26.255 | 52.038 | 1.00 | 39.35 |
| 1022 | C | ASP | A | 739 | 47.535 | 27.617 | 51.504 | 1.00 | 36.75 |
| 1023 | O | ASP | A | 739 | 46.777 | 28.532 | 50.983 | 1.00 | 36.19 |
| 1024 | N | LEU | A | 740 | 48.780 | 27.439 | 51.069 | 1.00 | 33.43 |
| 1025 | CA | LEU | A | 740 | 49.061 | 28.504 | 50.134 | 1.00 | 33.57 |
| 1026 | CB | LEU | A | 740 | 50.481 | 28.864 | 50.075 | 1.00 | 33.24 |
| 1027 | CG | LEU | A | 740 | 50.940 | 29.335 | 48.750 | 1.00 | 31.68 |
| 1028 | CD1 | LEU | A | 740 | 50.941 | 30.966 | 48.641 | 1.00 | 25.60 |
| 1029 | CD2 | LEU | A | 740 | 52.323 | 28.912 | 48.706 | 1.00 | 23.37 |
| 1030 | C | LEU | A | 740 | 48.490 | 28.150 | 48.796 | 1.00 | 33.56 |
| 1031 | O | LEU | A | 740 | 48.501 | 26.963 | 48.357 | 1.00 | 31.12 |

FIGURE 3T

| A | B | C | D | E | F | G | H | I | J |
|---|---|---|---|---|---|---|---|---|---|
| 1032 | N | ALA | A | 741 | 47.907 | 29.154 | 48.172 | 1.00 | 32.21 |
| 1033 | CA | ALA | A | 741 | 47.206 | 28.832 | 46.941 | 1.00 | 31.18 |
| 1034 | CB | ALA | A | 741 | 45.926 | 27.914 | 47.257 | 1.00 | 29.26 |
| 1035 | C | ALA | A | 741 | 46.846 | 29.993 | 46.143 | 1.00 | 29.34 |
| 1036 | O | ALA | A | 741 | 46.668 | 31.011 | 46.680 | 1.00 | 33.20 |
| 1037 | N | ALA | A | 742 | 46.670 | 29.881 | 44.843 | 1.00 | 30.74 |
| 1038 | CA | ALA | A | 742 | 46.506 | 31.125 | 44.116 | 1.00 | 30.53 |
| 1039 | CB | ALA | A | 742 | 46.415 | 30.932 | 42.505 | 1.00 | 29.25 |
| 1040 | C | ALA | A | 742 | 45.285 | 31.834 | 44.608 | 1.00 | 29.77 |
| 1041 | O | ALA | A | 742 | 45.243 | 33.003 | 44.528 | 1.00 | 31.53 |
| 1042 | N | ARG | A | 743 | 44.245 | 31.119 | 44.944 | 1.00 | 30.98 |
| 1043 | CA | ARG | A | 743 | 43.077 | 31.884 | 45.424 | 1.00 | 34.86 |
| 1044 | CB | ARG | A | 743 | 41.863 | 30.923 | 45.700 | 1.00 | 34.10 |
| 1045 | CG | ARG | A | 743 | 42.121 | 30.047 | 46.920 | 1.00 | 34.44 |
| 1046 | CD | ARG | A | 743 | 41.108 | 28.958 | 47.187 | 1.00 | 39.03 |
| 1047 | NE | ARG | A | 743 | 41.222 | 28.546 | 48.614 | 1.00 | 45.39 |
| 1048 | CZ | ARG | A | 743 | 41.915 | 27.457 | 49.044 | 1.00 | 48.15 |
| 1049 | NH1 | ARG | A | 743 | 42.514 | 26.617 | 48.179 | 1.00 | 45.40 |
| 1050 | NH2 | ARG | A | 743 | 42.006 | 27.199 | 50.343 | 1.00 | 47.01 |
| 1051 | C | ARG | A | 743 | 43.400 | 32.651 | 46.746 | 1.00 | 35.27 |
| 1052 | O | ARG | A | 743 | 42.567 | 33.390 | 47.192 | 1.00 | 35.06 |
| 1053 | N | ASN | A | 744 | 44.557 | 32.422 | 47.395 | 1.00 | 34.09 |
| 1054 | CA | ASN | A | 744 | 44.801 | 33.215 | 48.540 | 1.00 | 33.38 |
| 1055 | CB | ASN | A | 744 | 45.131 | 32.369 | 49.740 | 1.00 | 37.53 |
| 1056 | CG | ASN | A | 744 | 43.885 | 31.484 | 50.204 | 1.00 | 39.21 |
| 1057 | OD1 | ASN | A | 744 | 42.750 | 31.939 | 50.226 | 1.00 | 42.62 |
| 1058 | ND2 | ASN | A | 744 | 44.146 | 30.287 | 50.555 | 1.00 | 40.51 |
| 1059 | C | ASN | A | 744 | 45.837 | 34.214 | 48.356 | 1.00 | 33.36 |
| 1060 | O | ASN | A | 744 | 46.457 | 34.589 | 49.341 | 1.00 | 35.07 |
| 1061 | N | ILE | A | 745 | 46.006 | 34.705 | 47.117 | 1.00 | 30.57 |
| 1062 | CA | ILE | A | 745 | 46.897 | 35.733 | 46.854 | 1.00 | 28.67 |
| 1063 | CB | ILE | A | 745 | 47.832 | 35.223 | 45.714 | 1.00 | 30.71 |
| 1064 | CG1 | ILE | A | 745 | 48.559 | 33.935 | 46.089 | 1.00 | 35.04 |
| 1065 | CD1 | ILE | A | 745 | 49.267 | 33.990 | 47.383 | 1.00 | 35.54 |
| 1066 | CG2 | ILE | A | 745 | 48.729 | 36.302 | 45.150 | 1.00 | 24.18 |
| 1067 | C | ILE | A | 745 | 46.035 | 36.788 | 46.288 | 1.00 | 29.43 |
| 1068 | O | ILE | A | 745 | 45.130 | 36.504 | 45.501 | 1.00 | 31.60 |
| 1069 | N | LEU | A | 746 | 46.311 | 38.021 | 46.582 | 1.00 | 27.98 |
| 1070 | CA | LEU | A | 746 | 45.533 | 39.043 | 46.041 | 1.00 | 30.08 |
| 1071 | CB | LEU | A | 746 | 45.083 | 39.943 | 47.195 | 1.00 | 33.28 |
| 1072 | CG | LEU | A | 746 | 43.629 | 39.785 | 47.648 | 1.00 | 33.99 |
| 1073 | CD1 | LEU | A | 746 | 43.198 | 38.419 | 47.277 | 1.00 | 41.53 |
| 1074 | CD2 | LEU | A | 746 | 43.681 | 39.973 | 49.163 | 1.00 | 38.93 |
| 1075 | C | LEU | A | 746 | 46.416 | 39.870 | 45.214 | 1.00 | 31.34 |
| 1076 | O | LEU | A | 746 | 47.672 | 39.863 | 45.411 | 1.00 | 33.08 |
| 1077 | N | VAL | A | 747 | 45.863 | 40.732 | 44.393 | 1.00 | 32.95 |
| 1078 | CA | VAL | A | 747 | 46.775 | 41.316 | 43.368 | 1.00 | 33.35 |
| 1079 | CB | VAL | A | 747 | 46.535 | 40.592 | 41.936 | 1.00 | 34.25 |
| 1080 | CG1 | VAL | A | 747 | 47.470 | 41.171 | 40.731 | 1.00 | 32.32 |
| 1081 | CG2 | VAL | A | 747 | 46.731 | 39.130 | 42.052 | 1.00 | 28.68 |
| 1082 | C | VAL | A | 747 | 46.354 | 42.728 | 43.243 | 1.00 | 35.15 |
| 1083 | O | VAL | A | 747 | 45.192 | 43.035 | 43.182 | 1.00 | 36.61 |

FIGURE 3U

| A | B | C | D | E | F | G | H | I | J |
|---|---|---|---|---|---|---|---|---|---|
| 1084 | N | ASN | A | 748 | 47.265 | 43.612 | 43.005 | 1.00 | 38.24 |
| 1085 | CA | ASN | A | 748 | 46.877 | 45.028 | 42.924 | 1.00 | 38.34 |
| 1086 | CB | ASN | A | 748 | 47.567 | 45.802 | 44.082 | 1.00 | 36.64 |
| 1087 | CG | ASN | A | 748 | 49.029 | 46.025 | 43.866 | 1.00 | 41.61 |
| 1088 | OD1 | ASN | A | 748 | 49.862 | 46.322 | 44.892 | 1.00 | 43.62 |
| 1089 | ND2 | ASN | A | 748 | 49.440 | 45.937 | 42.561 | 1.00 | 30.49 |
| 1090 | C | ASN | A | 748 | 47.108 | 45.643 | 41.577 | 1.00 | 39.45 |
| 1091 | O | ASN | A | 748 | 47.639 | 44.987 | 40.711 | 1.00 | 40.04 |
| 1092 | N | SER | A | 749 | 46.695 | 46.895 | 41.373 | 1.00 | 42.73 |
| 1093 | CA | SER | A | 749 | 46.786 | 47.496 | 40.099 | 1.00 | 46.89 |
| 1094 | CB | SER | A | 749 | 46.385 | 48.978 | 40.082 | 1.00 | 48.87 |
| 1095 | OG | SER | A | 749 | 45.668 | 49.315 | 41.225 | 1.00 | 54.36 |
| 1096 | C | SER | A | 749 | 48.144 | 47.270 | 39.473 | 1.00 | 47.52 |
| 1097 | O | SER | A | 749 | 48.120 | 47.006 | 38.275 | 1.00 | 50.51 |
| 1098 | N | ASN | A | 750 | 49.269 | 47.369 | 40.208 | 1.00 | 45.78 |
| 1099 | CA | ASN | A | 750 | 50.564 | 47.075 | 39.586 | 1.00 | 45.35 |
| 1100 | CB | ASN | A | 750 | 51.653 | 47.880 | 40.233 | 1.00 | 46.42 |
| 1101 | CG | ASN | A | 750 | 51.353 | 49.378 | 40.146 | 1.00 | 52.77 |
| 1102 | OD1 | ASN | A | 750 | 50.799 | 49.871 | 39.111 | 1.00 | 54.71 |
| 1103 | ND2 | ASN | A | 750 | 51.556 | 50.090 | 41.283 | 1.00 | 54.86 |
| 1104 | C | ASN | A | 750 | 50.867 | 45.596 | 39.508 | 1.00 | 45.29 |
| 1105 | O | ASN | A | 750 | 51.983 | 45.229 | 39.197 | 1.00 | 47.66 |
| 1106 | N | LEU | A | 751 | 49.900 | 44.715 | 39.759 | 1.00 | 43.51 |
| 1107 | CA | LEU | A | 751 | 50.329 | 43.316 | 39.610 | 1.00 | 41.03 |
| 1108 | CB | LEU | A | 751 | 50.906 | 43.089 | 38.217 | 1.00 | 38.31 |
| 1109 | CG | LEU | A | 751 | 50.061 | 43.748 | 37.120 | 1.00 | 41.64 |
| 1110 | CD1 | LEU | A | 751 | 50.758 | 43.503 | 35.751 | 1.00 | 38.27 |
| 1111 | CD2 | LEU | A | 751 | 48.627 | 43.252 | 36.999 | 1.00 | 28.14 |
| 1112 | C | LEU | A | 751 | 51.261 | 42.713 | 40.682 | 1.00 | 38.95 |
| 1113 | O | LEU | A | 751 | 51.616 | 41.503 | 40.614 | 1.00 | 39.08 |
| 1114 | N | VAL | A | 752 | 51.532 | 43.481 | 41.722 | 1.00 | 38.48 |
| 1115 | CA | VAL | A | 752 | 52.201 | 42.927 | 42.911 | 1.00 | 37.62 |
| 1116 | CB | VAL | A | 752 | 52.407 | 44.027 | 43.985 | 1.00 | 41.07 |
| 1117 | CG1 | VAL | A | 752 | 52.935 | 43.433 | 45.248 | 1.00 | 31.93 |
| 1118 | CG2 | VAL | A | 752 | 53.374 | 45.187 | 43.434 | 1.00 | 39.70 |
| 1119 | C | VAL | A | 752 | 51.212 | 41.969 | 43.535 | 1.00 | 36.23 |
| 1120 | O | VAL | A | 752 | 50.109 | 42.327 | 43.656 | 1.00 | 37.11 |
| 1121 | N | CYS | A | 753 | 51.624 | 40.762 | 43.833 | 1.00 | 33.42 |
| 1122 | CA | CYS | A | 753 | 50.883 | 39.701 | 44.373 | 1.00 | 32.01 |
| 1123 | CB | CYS | A | 753 | 51.362 | 38.393 | 43.688 | 1.00 | 27.84 |
| 1124 | SG | CYS | A | 753 | 50.701 | 38.335 | 42.039 | 1.00 | 33.28 |
| 1125 | C | CYS | A | 753 | 51.225 | 39.605 | 45.855 | 1.00 | 32.33 |
| 1126 | O | CYS | A | 753 | 52.398 | 39.547 | 46.172 | 1.00 | 32.32 |
| 1127 | N | LYS | A | 754 | 50.219 | 39.528 | 46.741 | 1.00 | 32.94 |
| 1128 | CA | LYS | A | 754 | 50.507 | 39.386 | 48.166 | 1.00 | 32.10 |
| 1129 | CB | LYS | A | 754 | 50.162 | 40.696 | 48.875 | 1.00 | 33.13 |
| 1130 | CG | LYS | A | 754 | 50.605 | 41.963 | 48.135 | 1.00 | 29.06 |
| 1131 | CD | LYS | A | 754 | 50.285 | 43.144 | 49.026 | 1.00 | 35.71 |
| 1132 | CE | LYS | A | 754 | 50.643 | 44.415 | 48.261 | 1.00 | 35.80 |
| 1133 | NZ | LYS | A | 754 | 51.568 | 45.193 | 49.061 | 1.00 | 43.38 |
| 1134 | C | LYS | A | 754 | 49.841 | 38.219 | 48.816 | 1.00 | 32.31 |
| 1135 | O | LYS | A | 754 | 48.692 | 37.924 | 48.506 | 1.00 | 34.15 |

FIGURE 3V

| A | B | C | D | E | F | G | H | I | J |
|---|---|---|---|---|---|---|---|---|---|
| 1136 | N | VAL | A | 755 | 50.518 | 37.575 | 49.758 | 1.00 | 31.55 |
| 1137 | CA | VAL | A | 755 | 49.978 | 36.428 | 50.386 | 1.00 | 33.31 |
| 1138 | CB | VAL | A | 755 | 51.025 | 35.620 | 51.198 | 1.00 | 30.88 |
| 1139 | CG1 | VAL | A | 755 | 50.350 | 34.441 | 51.795 | 1.00 | 32.21 |
| 1140 | CG2 | VAL | A | 755 | 52.084 | 34.964 | 50.251 | 1.00 | 34.24 |
| 1141 | C | VAL | A | 755 | 48.926 | 37.022 | 51.377 | 1.00 | 35.40 |
| 1142 | O | VAL | A | 755 | 49.168 | 38.016 | 52.005 | 1.00 | 32.54 |
| 1143 | N | SER | A | 756 | 47.774 | 36.361 | 51.457 | 1.00 | 38.43 |
| 1144 | CA | SER | A | 756 | 46.644 | 36.872 | 52.159 | 1.00 | 43.72 |
| 1145 | CB | SER | A | 756 | 45.634 | 37.437 | 51.159 | 1.00 | 44.86 |
| 1146 | OG | SER | A | 756 | 44.645 | 38.014 | 52.000 | 1.00 | 54.93 |
| 1147 | C | SER | A | 756 | 46.074 | 35.651 | 52.814 | 1.00 | 43.72 |
| 1148 | O | SER | A | 756 | 46.719 | 34.651 | 52.765 | 1.00 | 43.99 |
| 1149 | N | ASP | A | 757 | 44.911 | 35.707 | 53.430 | 1.00 | 43.35 |
| 1150 | CA | ASP | A | 757 | 44.410 | 34.492 | 54.043 | 1.00 | 45.65 |
| 1151 | CB | ASP | A | 757 | 44.275 | 33.425 | 53.015 | 1.00 | 46.32 |
| 1152 | CG | ASP | A | 757 | 43.724 | 32.150 | 53.635 | 1.00 | 52.75 |
| 1153 | OD1 | ASP | A | 757 | 44.124 | 30.984 | 53.230 | 1.00 | 56.00 |
| 1154 | OD2 | ASP | A | 757 | 42.867 | 32.274 | 54.510 | 1.00 | 43.97 |
| 1155 | C | ASP | A | 757 | 45.196 | 33.850 | 55.204 | 1.00 | 46.33 |
| 1156 | O | ASP | A | 757 | 45.641 | 32.720 | 55.119 | 1.00 | 45.10 |
| 1157 | N | PHE | A | 758 | 45.277 | 34.549 | 56.314 | 1.00 | 47.63 |
| 1158 | CA | PHE | A | 758 | 46.037 | 34.089 | 57.464 | 1.00 | 49.68 |
| 1159 | CB | PHE | A | 758 | 46.847 | 35.258 | 58.006 | 1.00 | 44.29 |
| 1160 | CG | PHE | A | 758 | 47.817 | 35.731 | 57.094 | 1.00 | 42.30 |
| 1161 | CD1 | PHE | A | 758 | 47.593 | 36.864 | 56.368 | 1.00 | 42.22 |
| 1162 | CE1 | PHE | A | 758 | 48.598 | 37.322 | 55.442 | 1.00 | 39.71 |
| 1163 | CZ | PHE | A | 758 | 49.746 | 36.532 | 55.255 | 1.00 | 36.81 |
| 1164 | CE2 | PHE | A | 758 | 49.877 | 35.352 | 55.943 | 1.00 | 34.18 |
| 1165 | CD2 | PHE | A | 758 | 48.975 | 34.983 | 56.849 | 1.00 | 40.00 |
| 1166 | C | PHE | A | 758 | 44.974 | 33.723 | 58.453 | 1.00 | 52.68 |
| 1167 | O | PHE | A | 758 | 44.200 | 34.528 | 58.838 | 1.00 | 57.15 |
| 1168 | N | GLY | A | 759 | 44.861 | 32.587 | 58.977 | 1.00 | 55.94 |
| 1169 | CA | GLY | A | 759 | 43.688 | 32.622 | 59.798 | 1.00 | 61.61 |
| 1170 | C | GLY | A | 759 | 43.267 | 31.292 | 60.339 | 1.00 | 65.29 |
| 1171 | O | GLY | A | 759 | 42.694 | 30.466 | 59.606 | 1.00 | 67.00 |
| 1172 | N | ALA | A | 760 | 43.669 | 31.122 | 61.603 | 1.00 | 68.87 |
| 1173 | CA | ALA | A | 760 | 43.342 | 30.071 | 62.553 | 1.00 | 70.34 |
| 1174 | CB | ALA | A | 760 | 42.221 | 30.592 | 63.474 | 1.00 | 72.37 |
| 1175 | C | ALA | A | 760 | 43.001 | 28.691 | 62.018 | 1.00 | 70.84 |
| 1176 | O | ALA | A | 760 | 43.734 | 27.741 | 62.273 | 1.00 | 72.10 |
| 1177 | N | LYS | A | 778 | 38.912 | 22.109 | 55.182 | 1.00 | 61.96 |
| 1178 | CA | LYS | A | 778 | 39.123 | 23.434 | 54.474 | 1.00 | 62.02 |
| 1179 | CB | LYS | A | 778 | 39.109 | 24.631 | 55.464 | 1.00 | 61.52 |
| 1180 | CG | LYS | A | 778 | 38.190 | 25.744 | 55.100 | 1.00 | 65.24 |
| 1181 | CD | LYS | A | 778 | 36.788 | 25.579 | 55.739 | 1.00 | 72.35 |
| 1182 | CE | LYS | A | 778 | 35.799 | 26.577 | 55.111 | 1.00 | 76.05 |
| 1183 | NZ | LYS | A | 778 | 34.359 | 26.088 | 55.161 | 1.00 | 78.40 |
| 1184 | C | LYS | A | 778 | 40.461 | 23.466 | 53.662 | 1.00 | 59.65 |
| 1185 | O | LYS | A | 778 | 40.624 | 24.295 | 52.798 | 1.00 | 60.18 |
| 1186 | N | ILE | A | 779 | 41.456 | 22.650 | 53.969 | 1.00 | 56.99 |
| 1187 | CA | ILE | A | 779 | 42.634 | 22.716 | 53.087 | 1.00 | 54.46 |

FIGURE 3W

| A | B | C | D | E | F | G | H | I | J |
|---|---|---|---|---|---|---|---|---|---|
| 1188 | CB | ILE | A | 779 | 44.003 | 22.769 | 53.748 | 1.00 | 54.83 |
| 1189 | CG1 | ILE | A | 779 | 44.106 | 23.930 | 54.709 | 1.00 | 56.87 |
| 1190 | CD1 | ILE | A | 779 | 45.315 | 23.813 | 55.674 | 1.00 | 59.36 |
| 1191 | CG2 | ILE | A | 779 | 45.029 | 22.969 | 52.634 | 1.00 | 51.91 |
| 1192 | C | ILE | A | 779 | 42.605 | 21.521 | 52.188 | 1.00 | 51.97 |
| 1193 | O | ILE | A | 779 | 42.668 | 20.418 | 52.583 | 1.00 | 49.38 |
| 1194 | N | PRO | A | 780 | 42.595 | 21.796 | 50.931 | 1.00 | 51.16 |
| 1195 | CA | PRO | A | 780 | 42.509 | 20.747 | 49.903 | 1.00 | 50.51 |
| 1196 | CB | PRO | A | 780 | 42.343 | 21.559 | 48.651 | 1.00 | 51.35 |
| 1197 | CG | PRO | A | 780 | 43.260 | 22.689 | 48.938 | 1.00 | 51.32 |
| 1198 | CD | PRO | A | 780 | 42.732 | 23.136 | 50.382 | 1.00 | 49.94 |
| 1199 | C | PRO | A | 780 | 43.749 | 19.936 | 49.777 | 1.00 | 49.64 |
| 1200 | O | PRO | A | 780 | 44.947 | 20.334 | 49.770 | 1.00 | 49.57 |
| 1201 | N | ILE | A | 781 | 43.459 | 18.672 | 49.654 | 1.00 | 50.09 |
| 1202 | CA | ILE | A | 781 | 44.559 | 17.737 | 49.516 | 1.00 | 48.15 |
| 1203 | CB | ILE | A | 781 | 43.970 | 16.376 | 49.235 | 1.00 | 48.98 |
| 1204 | CG1 | ILE | A | 781 | 43.156 | 15.898 | 50.458 | 1.00 | 49.76 |
| 1205 | CD1 | ILE | A | 781 | 43.925 | 14.976 | 51.333 | 1.00 | 45.76 |
| 1206 | CG2 | ILE | A | 781 | 45.125 | 15.350 | 48.961 | 1.00 | 49.83 |
| 1207 | C | ILE | A | 781 | 45.512 | 18.088 | 48.393 | 1.00 | 48.04 |
| 1208 | O | ILE | A | 781 | 46.769 | 17.996 | 48.510 | 1.00 | 48.83 |
| 1209 | N | ARG | A | 782 | 44.943 | 18.437 | 47.261 | 1.00 | 47.13 |
| 1210 | CA | ARG | A | 782 | 45.802 | 18.586 | 46.083 | 1.00 | 45.63 |
| 1211 | CB | ARG | A | 782 | 45.053 | 18.378 | 44.769 | 1.00 | 47.26 |
| 1212 | CG | ARG | A | 782 | 44.023 | 19.394 | 44.396 | 1.00 | 44.31 |
| 1213 | CD | ARG | A | 782 | 42.767 | 18.675 | 44.519 | 1.00 | 46.69 |
| 1214 | NE | ARG | A | 782 | 42.141 | 18.708 | 43.274 | 1.00 | 56.04 |
| 1215 | CZ | ARG | A | 782 | 41.462 | 17.713 | 42.740 | 1.00 | 56.10 |
| 1216 | NH1 | ARG | A | 782 | 40.977 | 17.877 | 41.506 | 1.00 | 56.62 |
| 1217 | NH2 | ARG | A | 782 | 41.306 | 16.594 | 43.400 | 1.00 | 52.79 |
| 1218 | C | ARG | A | 782 | 46.663 | 19.814 | 45.954 | 1.00 | 44.90 |
| 1219 | O | ARG | A | 782 | 47.349 | 19.960 | 44.928 | 1.00 | 43.83 |
| 1220 | N | TRP | A | 783 | 46.618 | 20.701 | 46.956 | 1.00 | 42.72 |
| 1221 | CA | TRP | A | 783 | 47.551 | 21.768 | 46.995 | 1.00 | 39.98 |
| 1222 | CB | TRP | A | 783 | 46.868 | 23.004 | 47.412 | 1.00 | 37.95 |
| 1223 | CG | TRP | A | 783 | 46.479 | 23.843 | 46.300 | 1.00 | 35.96 |
| 1224 | CD1 | TRP | A | 783 | 47.144 | 24.953 | 45.829 | 1.00 | 37.75 |
| 1225 | NE1 | TRP | A | 783 | 46.442 | 25.528 | 44.784 | 1.00 | 33.74 |
| 1226 | CE2 | TRP | A | 783 | 45.232 | 24.838 | 44.689 | 1.00 | 27.42 |
| 1227 | CD2 | TRP | A | 783 | 45.234 | 23.816 | 45.630 | 1.00 | 27.27 |
| 1228 | CE3 | TRP | A | 783 | 44.158 | 22.941 | 45.665 | 1.00 | 39.26 |
| 1229 | CZ3 | TRP | A | 783 | 43.124 | 23.079 | 44.774 | 1.00 | 36.66 |
| 1230 | CH2 | TRP | A | 783 | 43.148 | 24.149 | 43.847 | 1.00 | 39.76 |
| 1231 | CZ2 | TRP | A | 783 | 44.221 | 25.011 | 43.792 | 1.00 | 24.85 |
| 1232 | C | TRP | A | 783 | 48.580 | 21.312 | 48.036 | 1.00 | 38.70 |
| 1233 | O | TRP | A | 783 | 49.540 | 21.988 | 48.357 | 1.00 | 35.32 |
| 1234 | N | THR | A | 784 | 48.408 | 20.111 | 48.524 | 1.00 | 40.61 |
| 1235 | CA | THR | A | 784 | 49.172 | 19.762 | 49.727 | 1.00 | 41.41 |
| 1236 | CB | THR | A | 784 | 48.221 | 19.287 | 50.845 | 1.00 | 43.19 |
| 1237 | OG1 | THR | A | 784 | 47.117 | 20.218 | 51.014 | 1.00 | 45.29 |
| 1238 | CG2 | THR | A | 784 | 48.958 | 19.287 | 52.200 | 1.00 | 34.46 |
| 1239 | C | THR | A | 784 | 50.198 | 18.707 | 49.543 | 1.00 | 42.11 |

FIGURE 3X

| A | B | C | D | E | F | G | H | I | J |
|---|---|---|---|---|---|---|---|---|---|
| 1240 | O | THR | A | 784 | 49.985 | 17.747 | 48.813 | 1.00 | 42.17 |
| 1241 | N | ALA | A | 785 | 51.327 | 18.906 | 50.196 | 1.00 | 42.96 |
| 1242 | CA | ALA | A | 785 | 52.418 | 17.963 | 50.141 | 1.00 | 44.73 |
| 1243 | CB | ALA | A | 785 | 53.572 | 18.448 | 50.832 | 1.00 | 42.17 |
| 1244 | C | ALA | A | 785 | 52.037 | 16.627 | 50.734 | 1.00 | 47.53 |
| 1245 | O | ALA | A | 785 | 51.473 | 16.538 | 51.822 | 1.00 | 46.77 |
| 1246 | N | PRO | A | 786 | 52.460 | 15.590 | 50.029 | 1.00 | 48.19 |
| 1247 | CA | PRO | A | 786 | 52.143 | 14.221 | 50.417 | 1.00 | 50.36 |
| 1248 | CB | PRO | A | 786 | 53.099 | 13.338 | 49.569 | 1.00 | 50.74 |
| 1249 | CG | PRO | A | 786 | 53.928 | 14.299 | 48.752 | 1.00 | 49.25 |
| 1250 | CD | PRO | A | 786 | 53.440 | 15.726 | 48.965 | 1.00 | 46.85 |
| 1251 | C | PRO | A | 786 | 52.522 | 14.054 | 51.936 | 1.00 | 52.21 |
| 1252 | O | PRO | A | 786 | 51.679 | 13.490 | 52.651 | 1.00 | 51.09 |
| 1253 | N | GLU | A | 787 | 53.714 | 14.492 | 52.403 | 1.00 | 53.11 |
| 1254 | CA | GLU | A | 787 | 53.970 | 14.318 | 53.884 | 1.00 | 55.40 |
| 1255 | CB | GLU | A | 787 | 55.401 | 14.738 | 54.382 | 1.00 | 54.09 |
| 1256 | CG | GLU | A | 787 | 55.710 | 16.248 | 54.318 | 1.00 | 55.91 |
| 1257 | CD | GLU | A | 787 | 56.214 | 16.661 | 52.939 | 1.00 | 48.91 |
| 1258 | OE1 | GLU | A | 787 | 56.021 | 15.847 | 52.033 | 1.00 | 44.65 |
| 1259 | OE2 | GLU | A | 787 | 56.840 | 17.727 | 52.812 | 1.00 | 45.31 |
| 1260 | C | GLU | A | 787 | 52.848 | 15.012 | 54.726 | 1.00 | 55.92 |
| 1261 | O | GLU | A | 787 | 52.130 | 14.368 | 55.542 | 1.00 | 57.24 |
| 1262 | N | ALA | A | 788 | 52.713 | 16.318 | 54.544 | 1.00 | 54.35 |
| 1263 | CA | ALA | A | 788 | 51.644 | 16.988 | 55.186 | 1.00 | 54.04 |
| 1264 | CB | ALA | A | 788 | 51.446 | 18.323 | 54.578 | 1.00 | 53.00 |
| 1265 | C | ALA | A | 788 | 50.361 | 16.145 | 55.138 | 1.00 | 54.26 |
| 1266 | O | ALA | A | 788 | 49.670 | 16.086 | 56.112 | 1.00 | 54.80 |
| 1267 | N | ILE | A | 789 | 50.025 | 15.490 | 54.028 | 1.00 | 56.51 |
| 1268 | CA | ILE | A | 789 | 48.800 | 14.678 | 54.021 | 1.00 | 57.58 |
| 1269 | CB | ILE | A | 789 | 48.409 | 14.228 | 52.640 | 1.00 | 57.54 |
| 1270 | CG1 | ILE | A | 789 | 47.712 | 15.332 | 51.828 | 1.00 | 59.40 |
| 1271 | CD1 | ILE | A | 789 | 47.797 | 15.085 | 50.262 | 1.00 | 54.27 |
| 1272 | CG2 | ILE | A | 789 | 47.309 | 13.160 | 52.772 | 1.00 | 60.10 |
| 1273 | C | ILE | A | 789 | 48.914 | 13.392 | 54.862 | 1.00 | 58.22 |
| 1274 | O | ILE | A | 789 | 48.062 | 13.049 | 55.692 | 1.00 | 57.15 |
| 1275 | N | SER | A | 790 | 49.990 | 12.659 | 54.690 | 1.00 | 59.69 |
| 1276 | CA | SER | A | 790 | 49.932 | 11.382 | 55.316 | 1.00 | 61.39 |
| 1277 | CB | SER | A | 790 | 50.549 | 10.325 | 54.444 | 1.00 | 61.41 |
| 1278 | OG | SER | A | 790 | 51.936 | 10.499 | 54.315 | 1.00 | 61.74 |
| 1279 | C | SER | A | 790 | 50.226 | 11.364 | 56.846 | 1.00 | 63.87 |
| 1280 | O | SER | A | 790 | 49.485 | 10.710 | 57.593 | 1.00 | 64.38 |
| 1281 | N | TYR | A | 791 | 51.144 | 12.202 | 57.303 | 1.00 | 63.52 |
| 1282 | CA | TYR | A | 791 | 51.439 | 12.287 | 58.665 | 1.00 | 66.15 |
| 1283 | CB | TYR | A | 791 | 52.945 | 12.283 | 58.781 | 1.00 | 68.10 |
| 1284 | CG | TYR | A | 791 | 53.565 | 11.076 | 58.118 | 1.00 | 72.28 |
| 1285 | CD1 | TYR | A | 791 | 54.150 | 11.173 | 56.854 | 1.00 | 75.63 |
| 1286 | CE1 | TYR | A | 791 | 54.755 | 10.071 | 56.241 | 1.00 | 78.33 |
| 1287 | CZ | TYR | A | 791 | 54.770 | 8.841 | 56.900 | 1.00 | 79.84 |
| 1288 | OH | TYR | A | 791 | 55.332 | 7.732 | 56.302 | 1.00 | 78.87 |
| 1289 | CE2 | TYR | A | 791 | 54.210 | 8.722 | 58.176 | 1.00 | 79.39 |
| 1290 | CD2 | TYR | A | 791 | 53.607 | 9.844 | 58.776 | 1.00 | 76.45 |
| 1291 | C | TYR | A | 791 | 50.974 | 13.612 | 59.238 | 1.00 | 66.97 |

FIGURE 3Y

| A | B | C | D | E | F | G | H | I | J |
|---|---|---|---|---|---|---|---|---|---|
| 1292 | O | TYR | A | 791 | 51.182 | 13.912 | 60.434 | 1.00 | 66.84 |
| 1293 | N | ARG | A | 792 | 50.369 | 14.432 | 58.399 | 1.00 | 66.87 |
| 1294 | CA | ARG | A | 792 | 49.970 | 15.760 | 58.851 | 1.00 | 67.30 |
| 1295 | CB | ARG | A | 792 | 48.869 | 15.753 | 59.940 | 1.00 | 68.23 |
| 1296 | CG | ARG | A | 792 | 47.463 | 15.375 | 59.359 | 1.00 | 74.13 |
| 1297 | CD | ARG | A | 792 | 46.869 | 14.030 | 59.780 | 1.00 | 82.23 |
| 1298 | NE | ARG | A | 792 | 45.886 | 14.125 | 60.886 | 1.00 | 89.59 |
| 1299 | CZ | ARG | A | 792 | 45.202 | 13.080 | 61.426 | 1.00 | 92.80 |
| 1300 | NH1 | ARG | A | 792 | 45.357 | 11.829 | 60.958 | 1.00 | 93.06 |
| 1301 | NH2 | ARG | A | 792 | 44.347 | 13.285 | 62.440 | 1.00 | 92.12 |
| 1302 | C | ARG | A | 792 | 51.197 | 16.520 | 59.320 | 1.00 | 65.45 |
| 1303 | O | ARG | A | 792 | 51.139 | 17.269 | 60.315 | 1.00 | 65.77 |
| 1304 | N | ALA | A | 793 | 52.306 | 16.318 | 58.611 | 1.00 | 63.00 |
| 1305 | CA | ALA | A | 793 | 53.519 | 17.103 | 58.883 | 1.00 | 61.10 |
| 1306 | CB | ALA | A | 793 | 54.867 | 16.228 | 58.776 | 1.00 | 60.85 |
| 1307 | C | ALA | A | 793 | 53.648 | 18.397 | 58.049 | 1.00 | 59.08 |
| 1308 | O | ALA | A | 793 | 54.293 | 18.378 | 56.975 | 1.00 | 58.44 |
| 1309 | N | PHE | A | 794 | 53.105 | 19.517 | 58.578 | 1.00 | 56.19 |
| 1310 | CA | PHE | A | 794 | 53.275 | 20.777 | 57.901 | 1.00 | 52.79 |
| 1311 | CB | PHE | A | 794 | 52.133 | 21.718 | 58.149 | 1.00 | 51.44 |
| 1312 | CG | PHE | A | 794 | 50.889 | 21.224 | 57.553 | 1.00 | 53.79 |
| 1313 | CD1 | PHE | A | 794 | 50.266 | 20.110 | 58.096 | 1.00 | 50.68 |
| 1314 | CE1 | PHE | A | 794 | 49.177 | 19.633 | 57.537 | 1.00 | 51.95 |
| 1315 | CZ | PHE | A | 794 | 48.642 | 20.230 | 56.394 | 1.00 | 57.08 |
| 1316 | CE2 | PHE | A | 794 | 49.263 | 21.310 | 55.814 | 1.00 | 48.15 |
| 1317 | CD2 | PHE | A | 794 | 50.350 | 21.819 | 56.416 | 1.00 | 51.41 |
| 1318 | C | PHE | A | 794 | 54.497 | 21.513 | 58.175 | 1.00 | 51.20 |
| 1319 | O | PHE | A | 794 | 54.691 | 21.921 | 59.279 | 1.00 | 51.64 |
| 1320 | N | THR | A | 795 | 55.240 | 21.847 | 57.116 | 1.00 | 49.90 |
| 1321 | CA | THR | A | 795 | 56.318 | 22.788 | 57.254 | 1.00 | 46.99 |
| 1322 | CB | THR | A | 795 | 57.644 | 22.091 | 57.445 | 1.00 | 49.02 |
| 1323 | OG1 | THR | A | 795 | 58.072 | 21.514 | 56.183 | 1.00 | 49.65 |
| 1324 | CG2 | THR | A | 795 | 57.447 | 20.906 | 58.372 | 1.00 | 48.02 |
| 1325 | C | THR | A | 795 | 56.471 | 23.771 | 56.117 | 1.00 | 45.29 |
| 1326 | O | THR | A | 795 | 55.655 | 23.860 | 55.164 | 1.00 | 43.69 |
| 1327 | N | SER | A | 796 | 57.534 | 24.550 | 56.249 | 1.00 | 41.69 |
| 1328 | CA | SER | A | 796 | 57.818 | 25.476 | 55.208 | 1.00 | 41.82 |
| 1329 | CB | SER | A | 796 | 58.981 | 26.331 | 55.547 | 1.00 | 39.66 |
| 1330 | OG | SER | A | 796 | 58.361 | 27.301 | 56.341 | 1.00 | 44.72 |
| 1331 | C | SER | A | 796 | 58.049 | 24.704 | 53.900 | 1.00 | 41.56 |
| 1332 | O | SER | A | 796 | 57.696 | 25.199 | 52.871 | 1.00 | 41.54 |
| 1333 | N | ALA | A | 797 | 58.524 | 23.473 | 53.999 | 1.00 | 40.13 |
| 1334 | CA | ALA | A | 797 | 58.846 | 22.725 | 52.848 | 1.00 | 42.53 |
| 1335 | CB | ALA | A | 797 | 59.884 | 21.556 | 53.214 | 1.00 | 40.83 |
| 1336 | C | ALA | A | 797 | 57.521 | 22.169 | 52.280 | 1.00 | 42.33 |
| 1337 | O | ALA | A | 797 | 57.431 | 21.788 | 51.119 | 1.00 | 42.26 |
| 1338 | N | SER | A | 798 | 56.545 | 22.072 | 53.157 | 1.00 | 40.76 |
| 1339 | CA | SER | A | 798 | 55.253 | 21.629 | 52.760 | 1.00 | 40.11 |
| 1340 | CB | SER | A | 798 | 54.431 | 21.573 | 54.027 | 1.00 | 41.27 |
| 1341 | OG | SER | A | 798 | 53.766 | 20.389 | 53.989 | 1.00 | 46.94 |
| 1342 | C | SER | A | 798 | 54.772 | 22.848 | 51.997 | 1.00 | 39.12 |
| 1343 | O | SER | A | 798 | 54.056 | 22.735 | 51.062 | 1.00 | 39.97 |

FIGURE 3Z

| A | B | C | D | E | F | G | H | I | J |
|---|---|---|---|---|---|---|---|---|---|
| 1344 | N | ASP | A | 799 | 55.130 | 24.050 | 52.406 | 1.00 | 35.77 |
| 1345 | CA | ASP | A | 799 | 54.498 | 25.129 | 51.717 | 1.00 | 34.72 |
| 1346 | CB | ASP | A | 799 | 54.780 | 26.453 | 52.486 | 1.00 | 33.36 |
| 1347 | CG | ASP | A | 799 | 53.791 | 26.726 | 53.664 | 1.00 | 34.25 |
| 1348 | OD1 | ASP | A | 799 | 52.668 | 26.165 | 53.890 | 1.00 | 36.89 |
| 1349 | OD2 | ASP | A | 799 | 54.068 | 27.559 | 54.447 | 1.00 | 37.78 |
| 1350 | C | ASP | A | 799 | 55.132 | 25.237 | 50.316 | 1.00 | 35.69 |
| 1351 | O | ASP | A | 799 | 54.570 | 25.868 | 49.348 | 1.00 | 37.88 |
| 1352 | N | VAL | A | 800 | 56.387 | 24.819 | 50.252 | 1.00 | 34.31 |
| 1353 | CA | VAL | A | 800 | 57.112 | 24.959 | 49.039 | 1.00 | 34.33 |
| 1354 | CB | VAL | A | 800 | 58.663 | 24.654 | 49.163 | 1.00 | 34.63 |
| 1355 | CG1 | VAL | A | 800 | 59.248 | 24.426 | 47.761 | 1.00 | 30.86 |
| 1356 | CG2 | VAL | A | 800 | 59.460 | 25.863 | 49.911 | 1.00 | 29.88 |
| 1357 | C | VAL | A | 800 | 56.427 | 24.040 | 48.023 | 1.00 | 34.69 |
| 1358 | O | VAL | A | 800 | 56.251 | 24.480 | 46.945 | 1.00 | 36.80 |
| 1359 | N | TRP | A | 801 | 56.055 | 22.823 | 48.359 | 1.00 | 32.29 |
| 1360 | CA | TRP | A | 801 | 55.170 | 22.045 | 47.475 | 1.00 | 34.84 |
| 1361 | CB | TRP | A | 801 | 54.679 | 20.731 | 48.117 | 1.00 | 35.44 |
| 1362 | CG | TRP | A | 801 | 53.843 | 19.907 | 47.285 | 1.00 | 33.44 |
| 1363 | CD1 | TRP | A | 801 | 52.561 | 20.102 | 46.984 | 1.00 | 32.49 |
| 1364 | NE1 | TRP | A | 801 | 52.070 | 19.046 | 46.260 | 1.00 | 32.97 |
| 1365 | CE2 | TRP | A | 801 | 53.073 | 18.136 | 46.097 | 1.00 | 33.72 |
| 1366 | CD2 | TRP | A | 801 | 54.183 | 18.623 | 46.756 | 1.00 | 34.03 |
| 1367 | CE3 | TRP | A | 801 | 55.320 | 17.800 | 46.841 | 1.00 | 38.46 |
| 1368 | CZ3 | TRP | A | 801 | 55.378 | 16.614 | 46.143 | 1.00 | 33.13 |
| 1369 | CH2 | TRP | A | 801 | 54.264 | 16.152 | 45.448 | 1.00 | 37.50 |
| 1370 | CZ2 | TRP | A | 801 | 53.088 | 16.888 | 45.430 | 1.00 | 42.25 |
| 1371 | C | TRP | A | 801 | 53.951 | 22.760 | 47.036 | 1.00 | 34.91 |
| 1372 | O | TRP | A | 801 | 53.531 | 22.621 | 45.934 | 1.00 | 38.09 |
| 1373 | N | SER | A | 802 | 53.355 | 23.576 | 47.890 | 1.00 | 35.76 |
| 1374 | CA | SER | A | 802 | 52.126 | 24.274 | 47.503 | 1.00 | 31.87 |
| 1375 | CB | SER | A | 802 | 51.515 | 24.963 | 48.746 | 1.00 | 33.54 |
| 1376 | OG | SER | A | 802 | 50.899 | 23.899 | 49.521 | 1.00 | 30.64 |
| 1377 | C | SER | A | 802 | 52.429 | 25.304 | 46.557 | 1.00 | 31.93 |
| 1378 | O | SER | A | 802 | 51.690 | 25.509 | 45.608 | 1.00 | 34.62 |
| 1379 | N | PHE | A | 803 | 53.536 | 26.007 | 46.779 | 1.00 | 30.27 |
| 1380 | CA | PHE | A | 803 | 53.933 | 27.101 | 45.905 | 1.00 | 29.38 |
| 1381 | CB | PHE | A | 803 | 55.219 | 27.653 | 46.473 | 1.00 | 29.35 |
| 1382 | CG | PHE | A | 803 | 55.817 | 28.671 | 45.639 | 1.00 | 32.84 |
| 1383 | CD1 | PHE | A | 803 | 56.825 | 28.328 | 44.672 | 1.00 | 30.14 |
| 1384 | CE1 | PHE | A | 803 | 57.313 | 29.296 | 43.909 | 1.00 | 28.45 |
| 1385 | CZ | PHE | A | 803 | 56.814 | 30.547 | 43.991 | 1.00 | 26.76 |
| 1386 | CE2 | PHE | A | 803 | 55.846 | 30.877 | 44.932 | 1.00 | 30.61 |
| 1387 | CD2 | PHE | A | 803 | 55.372 | 29.962 | 45.745 | 1.00 | 26.06 |
| 1388 | C | PHE | A | 803 | 54.263 | 26.610 | 44.484 | 1.00 | 30.18 |
| 1389 | O | PHE | A | 803 | 54.033 | 27.263 | 43.432 | 1.00 | 27.18 |
| 1390 | N | GLY | A | 804 | 54.777 | 25.406 | 44.421 | 1.00 | 32.24 |
| 1391 | CA | GLY | A | 804 | 54.953 | 24.865 | 43.033 | 1.00 | 33.84 |
| 1392 | C | GLY | A | 804 | 53.552 | 24.724 | 42.358 | 1.00 | 33.65 |
| 1393 | O | GLY | A | 804 | 53.373 | 25.159 | 41.182 | 1.00 | 31.75 |
| 1394 | N | ILE | A | 805 | 52.558 | 24.215 | 43.119 | 1.00 | 33.22 |
| 1395 | CA | ILE | A | 805 | 51.181 | 24.192 | 42.565 | 1.00 | 33.26 |

FIGURE 3AA

| A | B | C | D | E | F | G | H | I | J |
|---|---|---|---|---|---|---|---|---|---|
| 1396 | CB | ILE | A | 805 | 50.229 | 23.528 | 43.503 | 1.00 | 33.65 |
| 1397 | CG1 | ILE | A | 805 | 50.811 | 22.097 | 43.852 | 1.00 | 37.12 |
| 1398 | CD1 | ILE | A | 805 | 50.975 | 21.032 | 42.698 | 1.00 | 32.87 |
| 1399 | CG2 | ILE | A | 805 | 48.823 | 23.678 | 43.010 | 1.00 | 32.49 |
| 1400 | C | ILE | A | 805 | 50.696 | 25.579 | 42.206 | 1.00 | 31.48 |
| 1401 | O | ILE | A | 805 | 50.103 | 25.710 | 41.183 | 1.00 | 35.71 |
| 1402 | N | VAL | A | 806 | 51.019 | 26.638 | 42.935 | 1.00 | 28.75 |
| 1403 | CA | VAL | A | 806 | 50.549 | 27.991 | 42.575 | 1.00 | 25.41 |
| 1404 | CB | VAL | A | 806 | 50.961 | 29.014 | 43.621 | 1.00 | 25.04 |
| 1405 | CG1 | VAL | A | 806 | 50.941 | 30.522 | 43.191 | 1.00 | 21.16 |
| 1406 | CG2 | VAL | A | 806 | 50.157 | 28.790 | 45.007 | 1.00 | 23.21 |
| 1407 | C | VAL | A | 806 | 51.341 | 28.242 | 41.357 | 1.00 | 29.80 |
| 1408 | O | VAL | A | 806 | 50.912 | 28.993 | 40.455 | 1.00 | 29.17 |
| 1409 | N | MET | A | 807 | 52.538 | 27.649 | 41.280 | 1.00 | 30.71 |
| 1410 | CA | MET | A | 807 | 53.344 | 27.966 | 40.092 | 1.00 | 31.44 |
| 1411 | CB | MET | A | 807 | 54.785 | 27.399 | 40.149 | 1.00 | 32.92 |
| 1412 | CG | MET | A | 807 | 55.817 | 28.157 | 41.066 | 1.00 | 31.62 |
| 1413 | SD | MET | A | 807 | 57.439 | 27.395 | 40.955 | 1.00 | 39.41 |
| 1414 | CE | MET | A | 807 | 57.070 | 26.142 | 40.672 | 1.00 | 45.05 |
| 1415 | C | MET | A | 807 | 52.606 | 27.493 | 38.830 | 1.00 | 31.38 |
| 1416 | O | MET | A | 807 | 52.491 | 28.212 | 37.876 | 1.00 | 33.09 |
| 1417 | N | TRP | A | 808 | 51.936 | 26.352 | 38.875 | 1.00 | 31.98 |
| 1418 | CA | TRP | A | 808 | 51.347 | 25.777 | 37.672 | 1.00 | 32.34 |
| 1419 | CB | TRP | A | 808 | 51.102 | 24.315 | 38.067 | 1.00 | 33.08 |
| 1420 | CG | TRP | A | 808 | 50.501 | 23.517 | 37.005 | 1.00 | 36.11 |
| 1421 | CD1 | TRP | A | 808 | 51.163 | 22.792 | 36.077 | 1.00 | 36.58 |
| 1422 | NE1 | TRP | A | 808 | 50.257 | 22.139 | 35.281 | 1.00 | 38.43 |
| 1423 | CE2 | TRP | A | 808 | 49.005 | 22.468 | 35.660 | 1.00 | 33.35 |
| 1424 | CD2 | TRP | A | 808 | 49.123 | 23.335 | 36.754 | 1.00 | 31.70 |
| 1425 | CE3 | TRP | A | 808 | 47.968 | 23.831 | 37.345 | 1.00 | 35.04 |
| 1426 | CZ3 | TRP | A | 808 | 46.744 | 23.452 | 36.868 | 1.00 | 36.54 |
| 1427 | CH2 | TRP | A | 808 | 46.638 | 22.571 | 35.743 | 1.00 | 38.94 |
| 1428 | CZ2 | TRP | A | 808 | 47.760 | 22.047 | 35.138 | 1.00 | 38.69 |
| 1429 | C | TRP | A | 808 | 50.064 | 26.516 | 37.482 | 1.00 | 33.39 |
| 1430 | O | TRP | A | 808 | 49.612 | 26.851 | 36.402 | 1.00 | 34.70 |
| 1431 | N | GLU | A | 809 | 49.457 | 26.832 | 38.629 | 1.00 | 33.47 |
| 1432 | CA | GLU | A | 809 | 48.354 | 27.714 | 38.567 | 1.00 | 30.38 |
| 1433 | CB | GLU | A | 809 | 47.563 | 28.010 | 39.941 | 1.00 | 30.54 |
| 1434 | CG | GLU | A | 809 | 47.069 | 26.930 | 40.924 | 1.00 | 28.60 |
| 1435 | CD | GLU | A | 809 | 46.429 | 27.611 | 42.127 | 1.00 | 33.46 |
| 1436 | OE1 | GLU | A | 809 | 45.269 | 28.166 | 42.033 | 1.00 | 31.67 |
| 1437 | OE2 | GLU | A | 809 | 47.163 | 27.747 | 43.156 | 1.00 | 40.29 |
| 1438 | C | GLU | A | 809 | 48.610 | 29.024 | 37.793 | 1.00 | 29.74 |
| 1439 | O | GLU | A | 809 | 47.798 | 29.552 | 36.933 | 1.00 | 30.79 |
| 1440 | N | VAL | A | 810 | 49.656 | 29.723 | 38.167 | 1.00 | 28.13 |
| 1441 | CA | VAL | A | 810 | 49.889 | 31.000 | 37.520 | 1.00 | 26.64 |
| 1442 | CB | VAL | A | 810 | 51.022 | 31.716 | 38.242 | 1.00 | 26.67 |
| 1443 | CG1 | VAL | A | 810 | 51.575 | 32.853 | 37.310 | 1.00 | 22.89 |
| 1444 | CG2 | VAL | A | 810 | 50.493 | 32.103 | 39.725 | 1.00 | 27.59 |
| 1445 | C | VAL | A | 810 | 50.319 | 30.755 | 35.999 | 1.00 | 28.59 |
| 1446 | O | VAL | A | 810 | 49.854 | 31.404 | 35.114 | 1.00 | 24.03 |
| 1447 | N | MET | A | 811 | 51.055 | 29.682 | 35.705 | 1.00 | 30.08 |

FIGURE 3AB

| A | B | C | D | E | F | G | H | I | J |
|---|---|---|---|---|---|---|---|---|---|
| 1448 | CA | MET | A | 811 | 51.499 | 29.612 | 34.339 | 1.00 | 31.44 |
| 1449 | CB | MET | A | 811 | 52.744 | 28.783 | 34.201 | 1.00 | 35.04 |
| 1450 | CG | MET | A | 811 | 54.001 | 29.305 | 35.125 | 1.00 | 31.45 |
| 1451 | SD | MET | A | 811 | 54.298 | 30.999 | 34.729 | 1.00 | 37.47 |
| 1452 | CE | MET | A | 811 | 54.782 | 30.847 | 33.012 | 1.00 | 32.94 |
| 1453 | C | MET | A | 811 | 50.347 | 29.060 | 33.524 | 1.00 | 34.61 |
| 1454 | O | MET | A | 811 | 50.403 | 29.178 | 32.332 | 1.00 | 32.60 |
| 1455 | N | THR | A | 812 | 49.276 | 28.501 | 34.133 | 1.00 | 34.24 |
| 1456 | CA | THR | A | 812 | 48.198 | 28.074 | 33.241 | 1.00 | 32.52 |
| 1457 | CB | THR | A | 812 | 47.466 | 26.795 | 33.649 | 1.00 | 34.00 |
| 1458 | OG1 | THR | A | 812 | 47.141 | 26.876 | 35.053 | 1.00 | 32.67 |
| 1459 | CG2 | THR | A | 812 | 48.398 | 25.639 | 33.662 | 1.00 | 30.33 |
| 1460 | C | THR | A | 812 | 47.135 | 29.096 | 33.341 | 1.00 | 31.91 |
| 1461 | O | THR | A | 812 | 46.025 | 28.855 | 32.943 | 1.00 | 30.76 |
| 1462 | N | TYR | A | 813 | 47.464 | 30.243 | 33.834 | 1.00 | 31.56 |
| 1463 | CA | TYR | A | 813 | 46.387 | 31.261 | 33.929 | 1.00 | 31.70 |
| 1464 | CB | TYR | A | 813 | 46.014 | 31.896 | 32.589 | 1.00 | 29.74 |
| 1465 | CG | TYR | A | 813 | 47.044 | 32.836 | 31.958 | 1.00 | 30.09 |
| 1466 | CD1 | TYR | A | 813 | 48.104 | 32.376 | 31.114 | 1.00 | 28.85 |
| 1467 | CE1 | TYR | A | 813 | 49.010 | 33.279 | 30.612 | 1.00 | 29.29 |
| 1468 | CZ | TYR | A | 813 | 48.842 | 34.593 | 30.910 | 1.00 | 29.69 |
| 1469 | OH | TYR | A | 813 | 49.541 | 35.655 | 30.375 | 1.00 | 38.24 |
| 1470 | CE2 | TYR | A | 813 | 47.824 | 35.015 | 31.708 | 1.00 | 31.05 |
| 1471 | CD2 | TYR | A | 813 | 46.969 | 34.162 | 32.203 | 1.00 | 29.25 |
| 1472 | C | TYR | A | 813 | 45.134 | 30.738 | 34.656 | 1.00 | 30.85 |
| 1473 | O | TYR | A | 813 | 44.083 | 30.936 | 34.220 | 1.00 | 30.55 |
| 1474 | N | GLY | A | 814 | 45.270 | 30.031 | 35.753 | 1.00 | 33.19 |
| 1475 | CA | GLY | A | 814 | 44.090 | 29.747 | 36.568 | 1.00 | 35.27 |
| 1476 | C | GLY | A | 814 | 43.411 | 28.377 | 36.403 | 1.00 | 37.11 |
| 1477 | O | GLY | A | 814 | 42.283 | 28.190 | 36.933 | 1.00 | 33.77 |
| 1478 | N | GLU | A | 815 | 44.027 | 27.436 | 35.672 | 1.00 | 36.20 |
| 1479 | CA | GLU | A | 815 | 43.465 | 26.106 | 35.683 | 1.00 | 39.73 |
| 1480 | CB | GLU | A | 815 | 44.122 | 25.206 | 34.568 | 1.00 | 39.41 |
| 1481 | CG | GLU | A | 815 | 43.383 | 23.879 | 34.352 | 1.00 | 45.14 |
| 1482 | CD | GLU | A | 815 | 41.799 | 24.015 | 34.235 | 1.00 | 55.70 |
| 1483 | OE1 | GLU | A | 815 | 41.019 | 24.346 | 35.224 | 1.00 | 48.24 |
| 1484 | OE2 | GLU | A | 815 | 41.307 | 23.789 | 33.053 | 1.00 | 64.63 |
| 1485 | C | GLU | A | 815 | 43.505 | 25.458 | 37.133 | 1.00 | 40.38 |
| 1486 | O | GLU | A | 815 | 44.323 | 25.869 | 37.956 | 1.00 | 41.33 |
| 1487 | N | ARG | A | 816 | 42.636 | 24.460 | 37.433 | 1.00 | 41.29 |
| 1488 | CA | ARG | A | 816 | 42.531 | 23.823 | 38.748 | 1.00 | 42.57 |
| 1489 | CB | ARG | A | 816 | 41.035 | 23.394 | 38.997 | 1.00 | 43.10 |
| 1490 | CG | ARG | A | 816 | 40.769 | 21.927 | 39.483 | 1.00 | 46.76 |
| 1491 | CD | ARG | A | 816 | 39.291 | 21.462 | 39.802 | 1.00 | 54.39 |
| 1492 | NE | ARG | A | 816 | 39.376 | 20.573 | 40.974 | 1.00 | 59.04 |
| 1493 | CZ | ARG | A | 816 | 39.408 | 21.041 | 42.240 | 1.00 | 63.78 |
| 1494 | NH1 | ARG | A | 816 | 39.513 | 20.179 | 43.233 | 1.00 | 65.53 |
| 1495 | NH2 | ARG | A | 816 | 39.304 | 22.384 | 42.511 | 1.00 | 59.05 |
| 1496 | C | ARG | A | 816 | 43.464 | 22.644 | 38.721 | 1.00 | 41.97 |
| 1497 | O | ARG | A | 816 | 43.398 | 21.857 | 37.823 | 1.00 | 42.38 |
| 1498 | N | PRO | A | 817 | 44.469 | 22.608 | 39.597 | 1.00 | 43.68 |
| 1499 | CA | PRO | A | 817 | 45.379 | 21.453 | 39.672 | 1.00 | 41.81 |

FIGURE 3AC

| A | B | C | D | E | F | G | H | I | J |
|---|---|---|---|---|---|---|---|---|---|
| 1500 | CB | PRO | A | 817 | 46.156 | 21.699 | 40.929 | 1.00 | 41.78 |
| 1501 | CG | PRO | A | 817 | 46.031 | 23.202 | 41.122 | 1.00 | 43.11 |
| 1502 | CD | PRO | A | 817 | 44.749 | 23.678 | 40.560 | 1.00 | 40.66 |
| 1503 | C | PRO | A | 817 | 44.627 | 20.101 | 39.695 | 1.00 | 44.30 |
| 1504 | O | PRO | A | 817 | 43.467 | 19.877 | 40.271 | 1.00 | 45.86 |
| 1505 | N | TYR | A | 818 | 45.189 | 19.255 | 38.843 | 1.00 | 44.92 |
| 1506 | CA | TYR | A | 818 | 44.739 | 17.910 | 38.593 | 1.00 | 45.34 |
| 1507 | CB | TYR | A | 818 | 44.740 | 17.159 | 39.884 | 1.00 | 43.91 |
| 1508 | CG | TYR | A | 818 | 46.093 | 17.345 | 40.535 | 1.00 | 42.86 |
| 1509 | CD1 | TYR | A | 818 | 47.185 | 16.479 | 40.253 | 1.00 | 38.28 |
| 1510 | CE1 | TYR | A | 818 | 48.459 | 16.660 | 40.852 | 1.00 | 37.76 |
| 1511 | CZ | TYR | A | 818 | 48.610 | 17.633 | 41.743 | 1.00 | 35.89 |
| 1512 | OH | TYR | A | 818 | 49.875 | 17.735 | 42.212 | 1.00 | 42.19 |
| 1513 | CE2 | TYR | A | 818 | 47.577 | 18.531 | 42.049 | 1.00 | 33.24 |
| 1514 | CD2 | TYR | A | 818 | 46.316 | 18.406 | 41.423 | 1.00 | 37.98 |
| 1515 | C | TYR | A | 818 | 43.336 | 17.995 | 38.033 | 1.00 | 47.01 |
| 1516 | O | TYR | A | 818 | 42.518 | 17.049 | 38.110 | 1.00 | 48.49 |
| 1517 | N | TRP | A | 819 | 43.005 | 19.164 | 37.505 | 1.00 | 47.05 |
| 1518 | CA | TRP | A | 819 | 41.701 | 19.253 | 36.867 | 1.00 | 50.46 |
| 1519 | CB | TRP | A | 819 | 41.740 | 18.432 | 35.528 | 1.00 | 48.43 |
| 1520 | CG | TRP | A | 819 | 42.829 | 18.844 | 34.728 | 1.00 | 46.58 |
| 1521 | CD1 | TRP | A | 819 | 42.959 | 20.031 | 34.004 | 1.00 | 49.18 |
| 1522 | NE1 | TRP | A | 819 | 44.228 | 20.119 | 33.441 | 1.00 | 43.97 |
| 1523 | CE2 | TRP | A | 819 | 44.918 | 18.980 | 33.793 | 1.00 | 43.12 |
| 1524 | CD2 | TRP | A | 819 | 44.087 | 18.187 | 34.609 | 1.00 | 47.93 |
| 1525 | CE3 | TRP | A | 819 | 44.579 | 16.961 | 35.056 | 1.00 | 49.44 |
| 1526 | CZ3 | TRP | A | 819 | 45.822 | 16.613 | 34.720 | 1.00 | 46.77 |
| 1527 | CH2 | TRP | A | 819 | 46.585 | 17.392 | 33.912 | 1.00 | 42.84 |
| 1528 | CZ2 | TRP | A | 819 | 46.157 | 18.598 | 33.464 | 1.00 | 45.34 |
| 1529 | C | TRP | A | 819 | 40.560 | 18.743 | 37.751 | 1.00 | 50.78 |
| 1530 | O | TRP | A | 819 | 40.418 | 19.134 | 38.920 | 1.00 | 52.87 |
| 1531 | N | GLU | A | 820 | 39.757 | 17.855 | 37.170 | 1.00 | 53.15 |
| 1532 | CA | GLU | A | 820 | 38.614 | 17.241 | 37.872 | 1.00 | 54.37 |
| 1533 | CB | GLU | A | 820 | 37.449 | 16.941 | 36.924 | 1.00 | 54.32 |
| 1534 | CG | GLU | A | 820 | 36.366 | 18.002 | 36.896 | 1.00 | 57.57 |
| 1535 | CD | GLU | A | 820 | 36.972 | 19.390 | 36.838 | 1.00 | 61.97 |
| 1536 | OE1 | GLU | A | 820 | 36.651 | 20.232 | 37.703 | 1.00 | 63.58 |
| 1537 | OE2 | GLU | A | 820 | 37.815 | 19.635 | 35.943 | 1.00 | 65.58 |
| 1538 | C | GLU | A | 820 | 38.939 | 15.918 | 38.502 | 1.00 | 54.50 |
| 1539 | O | GLU | A | 820 | 38.032 | 15.090 | 38.695 | 1.00 | 56.40 |
| 1540 | N | LEU | A | 821 | 40.212 | 15.698 | 38.795 | 1.00 | 55.83 |
| 1541 | CA | LEU | A | 821 | 40.604 | 14.432 | 39.369 | 1.00 | 54.87 |
| 1542 | CB | LEU | A | 821 | 42.050 | 14.101 | 39.090 | 1.00 | 54.66 |
| 1543 | CG | LEU | A | 821 | 42.599 | 13.702 | 37.713 | 1.00 | 55.17 |
| 1544 | CD1 | LEU | A | 821 | 44.138 | 14.023 | 37.650 | 1.00 | 59.74 |
| 1545 | CD2 | LEU | A | 821 | 42.372 | 12.223 | 37.358 | 1.00 | 57.81 |
| 1546 | C | LEU | A | 821 | 40.311 | 14.322 | 40.862 | 1.00 | 55.57 |
| 1547 | O | LEU | A | 821 | 40.184 | 15.328 | 41.610 | 1.00 | 52.91 |
| 1548 | N | SER | A | 822 | 40.208 | 13.053 | 41.283 | 1.00 | 55.96 |
| 1549 | CA | SER | A | 822 | 39.800 | 12.777 | 42.619 | 1.00 | 56.75 |
| 1550 | CB | SER | A | 822 | 39.132 | 11.424 | 42.709 | 1.00 | 57.57 |
| 1551 | OG | SER | A | 822 | 40.163 | 10.441 | 42.724 | 1.00 | 61.05 |

FIGURE 3AD

| A | B | C | D | E | F | G | H | I | J |
|---|---|---|---|---|---|---|---|---|---|
| 1552 | C | SER | A | 822 | 41.015 | 12.742 | 43.471 | 1.00 | 56.82 |
| 1553 | O | SER | A | 822 | 42.111 | 12.351 | 43.029 | 1.00 | 55.43 |
| 1554 | N | ASN | A | 823 | 40.752 | 13.039 | 44.733 | 1.00 | 57.38 |
| 1555 | CA | ASN | A | 823 | 41.802 | 13.209 | 45.699 | 1.00 | 58.87 |
| 1556 | CB | ASN | A | 823 | 41.242 | 13.615 | 47.073 | 1.00 | 58.15 |
| 1557 | CG | ASN | A | 823 | 40.815 | 15.094 | 47.094 | 1.00 | 60.32 |
| 1558 | OD1 | ASN | A | 823 | 41.592 | 15.963 | 46.785 | 1.00 | 63.73 |
| 1559 | ND2 | ASN | A | 823 | 39.582 | 15.363 | 47.432 | 1.00 | 61.31 |
| 1560 | C | ASN | A | 823 | 42.513 | 11.941 | 45.660 | 1.00 | 59.12 |
| 1561 | O | ASN | A | 823 | 43.753 | 11.872 | 45.759 | 1.00 | 60.64 |
| 1562 | N | HIS | A | 824 | 41.733 | 10.936 | 45.381 | 1.00 | 58.77 |
| 1563 | CA | HIS | A | 824 | 42.274 | 9.608 | 45.413 | 1.00 | 60.00 |
| 1564 | CB | HIS | A | 824 | 41.115 | 8.627 | 45.445 | 1.00 | 60.99 |
| 1565 | CG | HIS | A | 824 | 41.565 | 7.246 | 45.256 | 1.00 | 67.03 |
| 1566 | ND1 | HIS | A | 824 | 42.251 | 6.566 | 46.238 | 1.00 | 72.16 |
| 1567 | CE1 | HIS | A | 824 | 42.594 | 5.370 | 45.772 | 1.00 | 77.00 |
| 1568 | NE2 | HIS | A | 824 | 42.189 | 5.271 | 44.513 | 1.00 | 75.73 |
| 1569 | CD2 | HIS | A | 824 | 41.551 | 6.441 | 44.161 | 1.00 | 74.03 |
| 1570 | C | HIS | A | 824 | 43.240 | 9.346 | 44.223 | 1.00 | 58.19 |
| 1571 | O | HIS | A | 824 | 44.439 | 9.014 | 44.396 | 1.00 | 55.80 |
| 1572 | N | GLU | A | 825 | 42.701 | 9.531 | 43.014 | 1.00 | 57.37 |
| 1573 | CA | GLU | A | 825 | 43.514 | 9.516 | 41.785 | 1.00 | 56.22 |
| 1574 | CB | GLU | A | 825 | 42.623 | 10.008 | 40.632 | 1.00 | 57.84 |
| 1575 | CG | GLU | A | 825 | 41.881 | 8.907 | 39.881 | 1.00 | 62.50 |
| 1576 | CD | GLU | A | 825 | 40.412 | 9.114 | 39.860 | 1.00 | 67.90 |
| 1577 | OE1 | GLU | A | 825 | 39.948 | 10.076 | 39.213 | 1.00 | 70.44 |
| 1578 | OE2 | GLU | A | 825 | 39.725 | 8.297 | 40.518 | 1.00 | 74.63 |
| 1579 | C | GLU | A | 825 | 44.764 | 10.399 | 42.063 | 1.00 | 54.94 |
| 1580 | O | GLU | A | 825 | 45.937 | 9.927 | 42.067 | 1.00 | 54.45 |
| 1581 | N | VAL | A | 826 | 44.529 | 11.648 | 42.467 | 1.00 | 53.85 |
| 1582 | CA | VAL | A | 826 | 45.667 | 12.540 | 42.776 | 1.00 | 52.93 |
| 1583 | CB | VAL | A | 826 | 45.208 | 13.870 | 43.319 | 1.00 | 51.81 |
| 1584 | CG1 | VAL | A | 826 | 46.447 | 14.871 | 43.452 | 1.00 | 52.68 |
| 1585 | CG2 | VAL | A | 826 | 44.197 | 14.432 | 42.370 | 1.00 | 51.90 |
| 1586 | C | VAL | A | 826 | 46.759 | 11.943 | 43.687 | 1.00 | 53.42 |
| 1587 | O | VAL | A | 826 | 47.967 | 11.917 | 43.378 | 1.00 | 53.40 |
| 1588 | N | MET | A | 827 | 46.363 | 11.447 | 44.821 | 1.00 | 53.41 |
| 1589 | CA | MET | A | 827 | 47.422 | 10.969 | 45.636 | 1.00 | 55.16 |
| 1590 | CB | MET | A | 827 | 47.018 | 10.882 | 47.148 | 1.00 | 55.87 |
| 1591 | CG | MET | A | 827 | 45.490 | 10.429 | 47.445 | 1.00 | 60.83 |
| 1592 | SD | MET | A | 827 | 44.615 | 10.847 | 49.114 | 1.00 | 65.49 |
| 1593 | CE | MET | A | 827 | 46.288 | 11.405 | 49.883 | 1.00 | 54.71 |
| 1594 | C | MET | A | 827 | 48.133 | 9.757 | 44.935 | 1.00 | 54.89 |
| 1595 | O | MET | A | 827 | 49.401 | 9.704 | 44.875 | 1.00 | 55.10 |
| 1596 | N | ALA | A | 828 | 47.375 | 8.861 | 44.295 | 1.00 | 55.10 |
| 1597 | CA | ALA | A | 828 | 48.085 | 7.757 | 43.600 | 1.00 | 55.33 |
| 1598 | CB | ALA | A | 828 | 47.165 | 6.654 | 43.057 | 1.00 | 54.77 |
| 1599 | C | ALA | A | 828 | 49.049 | 8.267 | 42.521 | 1.00 | 54.77 |
| 1600 | O | ALA | A | 828 | 50.167 | 7.792 | 42.403 | 1.00 | 54.26 |
| 1601 | N | ALA | A | 829 | 48.698 | 9.315 | 41.805 | 1.00 | 55.62 |
| 1602 | CA | ALA | A | 829 | 49.672 | 9.732 | 40.804 | 1.00 | 56.05 |
| 1603 | CB | ALA | A | 829 | 49.103 | 10.831 | 39.898 | 1.00 | 56.37 |

FIGURE 3AE

| A | B | C | D | E | F | G | H | I | J |
|---|---|---|---|---|---|---|---|---|---|
| 1604 | C | ALA | A | 829 | 50.966 | 10.177 | 41.468 | 1.00 | 56.31 |
| 1605 | O | ALA | A | 829 | 52.116 | 9.756 | 41.108 | 1.00 | 56.19 |
| 1606 | N | ILE | A | 830 | 50.765 | 11.020 | 42.471 | 1.00 | 56.52 |
| 1607 | CA | ILE | A | 830 | 51.891 | 11.651 | 43.112 | 1.00 | 56.87 |
| 1608 | CB | ILE | A | 830 | 51.446 | 12.581 | 44.293 | 1.00 | 57.35 |
| 1609 | CG1 | ILE | A | 830 | 50.835 | 13.861 | 43.719 | 1.00 | 56.71 |
| 1610 | CD1 | ILE | A | 830 | 51.574 | 14.320 | 42.496 | 1.00 | 47.37 |
| 1611 | CG2 | ILE | A | 830 | 52.641 | 12.975 | 45.149 | 1.00 | 52.92 |
| 1612 | C | ILE | A | 830 | 52.767 | 10.611 | 43.637 | 1.00 | 58.16 |
| 1613 | O | ILE | A | 830 | 54.003 | 10.637 | 43.431 | 1.00 | 58.31 |
| 1614 | N | ASN | A | 831 | 52.120 | 9.692 | 44.344 | 1.00 | 59.54 |
| 1615 | CA | ASN | A | 831 | 52.883 | 8.672 | 45.016 | 1.00 | 60.79 |
| 1616 | CB | ASN | A | 831 | 52.033 | 7.966 | 46.046 | 1.00 | 62.19 |
| 1617 | CG | ASN | A | 831 | 51.972 | 8.768 | 47.324 | 1.00 | 65.87 |
| 1618 | OD1 | ASN | A | 831 | 52.993 | 9.400 | 47.727 | 1.00 | 66.49 |
| 1619 | ND2 | ASN | A | 831 | 50.781 | 8.826 | 47.934 | 1.00 | 68.01 |
| 1620 | C | ASN | A | 831 | 53.492 | 7.757 | 44.044 | 1.00 | 59.66 |
| 1621 | O | ASN | A | 831 | 54.558 | 7.248 | 44.274 | 1.00 | 58.77 |
| 1622 | N | ASP | A | 832 | 52.860 | 7.609 | 42.896 | 1.00 | 59.28 |
| 1623 | CA | ASP | A | 832 | 53.530 | 6.790 | 41.905 | 1.00 | 60.01 |
| 1624 | CB | ASP | A | 832 | 52.494 | 6.118 | 41.014 | 1.00 | 60.55 |
| 1625 | CG | ASP | A | 832 | 52.076 | 4.698 | 41.576 | 1.00 | 66.55 |
| 1626 | OD1 | ASP | A | 832 | 51.135 | 4.051 | 41.007 | 1.00 | 71.66 |
| 1627 | OD2 | ASP | A | 832 | 52.672 | 4.151 | 42.569 | 1.00 | 63.91 |
| 1628 | C | ASP | A | 832 | 54.697 | 7.455 | 41.121 | 1.00 | 59.37 |
| 1629 | O | ASP | A | 832 | 55.088 | 6.979 | 40.039 | 1.00 | 58.56 |
| 1630 | N | GLY | A | 833 | 55.293 | 8.525 | 41.664 | 1.00 | 58.64 |
| 1631 | CA | GLY | A | 833 | 56.220 | 9.303 | 40.850 | 1.00 | 57.55 |
| 1632 | C | GLY | A | 833 | 55.529 | 9.892 | 39.615 | 1.00 | 57.72 |
| 1633 | O | GLY | A | 833 | 55.730 | 9.408 | 38.503 | 1.00 | 61.73 |
| 1634 | N | PHE | A | 834 | 54.711 | 10.932 | 39.806 | 1.00 | 55.50 |
| 1635 | CA | PHE | A | 834 | 53.992 | 11.588 | 38.713 | 1.00 | 52.71 |
| 1636 | CB | PHE | A | 834 | 52.692 | 10.831 | 38.438 | 1.00 | 52.86 |
| 1637 | CG | PHE | A | 834 | 52.758 | 9.760 | 37.377 | 1.00 | 55.68 |
| 1638 | CD1 | PHE | A | 834 | 53.292 | 9.991 | 36.064 | 1.00 | 61.07 |
| 1639 | CE1 | PHE | A | 834 | 53.276 | 8.953 | 35.053 | 1.00 | 58.90 |
| 1640 | CZ | PHE | A | 834 | 52.739 | 7.624 | 35.386 | 1.00 | 60.52 |
| 1641 | CE2 | PHE | A | 834 | 52.202 | 7.400 | 36.702 | 1.00 | 56.50 |
| 1642 | CD2 | PHE | A | 834 | 52.210 | 8.481 | 37.656 | 1.00 | 60.30 |
| 1643 | C | PHE | A | 834 | 53.471 | 12.969 | 39.156 | 1.00 | 50.70 |
| 1644 | O | PHE | A | 834 | 52.879 | 13.061 | 40.234 | 1.00 | 50.00 |
| 1645 | N | ARG | A | 835 | 53.578 | 13.973 | 38.269 | 1.00 | 47.79 |
| 1646 | CA | ARG | A | 835 | 53.278 | 15.397 | 38.529 | 1.00 | 47.62 |
| 1647 | CB | ARG | A | 835 | 54.544 | 16.240 | 38.538 | 1.00 | 47.50 |
| 1648 | CG | ARG | A | 835 | 55.739 | 15.796 | 39.492 | 1.00 | 48.70 |
| 1649 | CD | ARG | A | 835 | 55.161 | 15.694 | 40.870 | 1.00 | 48.58 |
| 1650 | NE | ARG | A | 835 | 56.010 | 15.092 | 41.866 | 1.00 | 46.46 |
| 1651 | CZ | ARG | A | 835 | 55.778 | 13.923 | 42.395 | 1.00 | 45.45 |
| 1652 | NH1 | ARG | A | 835 | 54.763 | 13.179 | 41.994 | 1.00 | 49.16 |
| 1653 | NH2 | ARG | A | 835 | 56.575 | 13.478 | 43.301 | 1.00 | 47.75 |
| 1654 | C | ARG | A | 835 | 52.392 | 16.027 | 37.439 | 1.00 | 44.98 |
| 1655 | O | ARG | A | 835 | 52.160 | 15.415 | 36.403 | 1.00 | 46.68 |

FIGURE 3AF

| A | B | C | D | E | F | G | H | I | J |
|---|---|---|---|---|---|---|---|---|---|
| 1656 | N | LEU | A | 836 | 51.883 | 17.246 | 37.678 | 1.00 | 42.81 |
| 1657 | CA | LEU | A | 836 | 51.065 | 17.947 | 36.699 | 1.00 | 41.01 |
| 1658 | CB | LEU | A | 836 | 50.651 | 19.385 | 37.117 | 1.00 | 38.39 |
| 1659 | CG | LEU | A | 836 | 49.702 | 19.386 | 38.291 | 1.00 | 40.70 |
| 1660 | CD1 | LEU | A | 836 | 49.697 | 20.808 | 38.794 | 1.00 | 38.83 |
| 1661 | CD2 | LEU | A | 836 | 48.341 | 18.855 | 37.832 | 1.00 | 33.85 |
| 1662 | C | LEU | A | 836 | 51.944 | 18.162 | 35.569 | 1.00 | 38.14 |
| 1663 | O | LEU | A | 836 | 53.047 | 18.472 | 35.801 | 1.00 | 38.29 |
| 1664 | N | PRO | A | 837 | 51.413 | 18.144 | 34.359 | 1.00 | 38.07 |
| 1665 | CA | PRO | A | 837 | 52.214 | 18.316 | 33.157 | 1.00 | 36.29 |
| 1666 | CB | PRO | A | 837 | 51.232 | 17.819 | 32.075 | 1.00 | 36.93 |
| 1667 | CG | PRO | A | 837 | 49.907 | 18.505 | 32.492 | 1.00 | 35.54 |
| 1668 | CD | PRO | A | 837 | 49.973 | 18.141 | 34.008 | 1.00 | 37.87 |
| 1669 | C | PRO | A | 837 | 52.525 | 19.778 | 32.964 | 1.00 | 36.09 |
| 1670 | O | PRO | A | 837 | 51.936 | 20.719 | 33.673 | 1.00 | 34.39 |
| 1671 | N | THR | A | 838 | 53.406 | 20.032 | 32.013 | 1.00 | 34.01 |
| 1672 | CA | THR | A | 838 | 53.894 | 21.359 | 31.903 | 1.00 | 35.98 |
| 1673 | CB | THR | A | 838 | 55.120 | 21.485 | 30.963 | 1.00 | 36.64 |
| 1674 | OG1 | THR | A | 838 | 55.395 | 22.892 | 30.765 | 1.00 | 39.83 |
| 1675 | CG2 | THR | A | 838 | 54.736 | 21.181 | 29.545 | 1.00 | 38.71 |
| 1676 | C | THR | A | 838 | 52.803 | 22.116 | 31.252 | 1.00 | 38.36 |
| 1677 | O | THR | A | 838 | 52.197 | 21.670 | 30.274 | 1.00 | 39.45 |
| 1678 | N | PRO | A | 839 | 52.619 | 23.313 | 31.726 | 1.00 | 36.96 |
| 1679 | CA | PRO | A | 839 | 51.719 | 24.197 | 31.114 | 1.00 | 37.46 |
| 1680 | CB | PRO | A | 839 | 51.724 | 25.405 | 32.037 | 1.00 | 34.44 |
| 1681 | CG | PRO | A | 839 | 52.681 | 25.139 | 33.091 | 1.00 | 33.53 |
| 1682 | CD | PRO | A | 839 | 53.318 | 23.890 | 32.865 | 1.00 | 37.82 |
| 1683 | C | PRO | A | 839 | 52.285 | 24.602 | 29.749 | 1.00 | 38.53 |
| 1684 | O | PRO | A | 839 | 53.481 | 24.718 | 29.536 | 1.00 | 40.65 |
| 1685 | N | MET | A | 840 | 51.382 | 24.872 | 28.840 | 1.00 | 40.11 |
| 1686 | CA | MET | A | 840 | 51.632 | 25.423 | 27.501 | 1.00 | 40.90 |
| 1687 | CB | MET | A | 840 | 50.230 | 25.730 | 26.953 | 1.00 | 42.06 |
| 1688 | CG | MET | A | 840 | 50.129 | 26.167 | 25.481 | 1.00 | 50.27 |
| 1689 | SD | MET | A | 840 | 50.014 | 24.569 | 24.486 | 1.00 | 67.03 |
| 1690 | CE | MET | A | 840 | 51.027 | 25.324 | 23.049 | 1.00 | 53.52 |
| 1691 | C | MET | A | 840 | 52.554 | 26.728 | 27.544 | 1.00 | 40.78 |
| 1692 | O | MET | A | 840 | 52.331 | 27.704 | 28.311 | 1.00 | 41.90 |
| 1693 | N | ASP | A | 841 | 53.600 | 26.738 | 26.735 | 1.00 | 39.46 |
| 1694 | CA | ASP | A | 841 | 54.541 | 27.802 | 26.665 | 1.00 | 38.39 |
| 1695 | CB | ASP | A | 841 | 53.847 | 28.967 | 26.104 | 1.00 | 36.97 |
| 1696 | CG | ASP | A | 841 | 53.255 | 28.676 | 24.629 | 1.00 | 40.53 |
| 1697 | OD1 | ASP | A | 841 | 53.550 | 27.617 | 23.972 | 1.00 | 39.77 |
| 1698 | OD2 | ASP | A | 841 | 52.445 | 29.466 | 24.066 | 1.00 | 36.62 |
| 1699 | C | ASP | A | 841 | 55.291 | 28.055 | 28.007 | 1.00 | 39.55 |
| 1700 | O | ASP | A | 841 | 55.749 | 29.129 | 28.326 | 1.00 | 41.50 |
| 1701 | N | CYS | A | 842 | 55.381 | 27.056 | 28.840 | 1.00 | 39.14 |
| 1702 | CA | CYS | A | 842 | 56.121 | 27.250 | 30.088 | 1.00 | 37.64 |
| 1703 | CB | CYS | A | 842 | 55.781 | 26.076 | 31.018 | 1.00 | 35.73 |
| 1704 | SG | CYS | A | 842 | 56.126 | 26.564 | 32.674 | 1.00 | 37.11 |
| 1705 | C | CYS | A | 842 | 57.616 | 27.200 | 29.840 | 1.00 | 36.94 |
| 1706 | O | CYS | A | 842 | 58.077 | 26.258 | 29.219 | 1.00 | 33.74 |
| 1707 | N | PRO | A | 843 | 58.352 | 28.267 | 30.217 | 1.00 | 37.65 |

FIGURE 3AG

| A | B | C | D | E | F | G | H | I | J |
|---|---|---|---|---|---|---|---|---|---|
| 1708 | CA | PRO | A | 843 | 59.804 | 28.178 | 30.251 | 1.00 | 34.75 |
| 1709 | CB | PRO | A | 843 | 60.257 | 29.383 | 31.062 | 1.00 | 31.74 |
| 1710 | CG | PRO | A | 843 | 59.216 | 30.413 | 30.790 | 1.00 | 38.14 |
| 1711 | CD | PRO | A | 843 | 57.864 | 29.626 | 30.588 | 1.00 | 36.86 |
| 1712 | C | PRO | A | 843 | 60.258 | 26.981 | 30.973 | 1.00 | 34.58 |
| 1713 | O | PRO | A | 843 | 59.616 | 26.646 | 32.033 | 1.00 | 34.71 |
| 1714 | N | SER | A | 844 | 61.364 | 26.414 | 30.439 | 1.00 | 30.44 |
| 1715 | CA | SER | A | 844 | 61.947 | 25.239 | 30.957 | 1.00 | 32.01 |
| 1716 | CB | SER | A | 844 | 63.155 | 24.861 | 30.092 | 1.00 | 32.60 |
| 1717 | OG | SER | A | 844 | 63.939 | 23.905 | 30.735 | 1.00 | 32.71 |
| 1718 | C | SER | A | 844 | 62.421 | 25.519 | 32.326 | 1.00 | 33.01 |
| 1719 | O | SER | A | 844 | 62.327 | 24.669 | 33.152 | 1.00 | 34.58 |
| 1720 | N | ALA | A | 845 | 62.988 | 26.690 | 32.593 | 1.00 | 34.49 |
| 1721 | CA | ALA | A | 845 | 63.384 | 26.961 | 34.006 | 1.00 | 36.49 |
| 1722 | CB | ALA | A | 845 | 64.315 | 28.212 | 34.109 | 1.00 | 35.62 |
| 1723 | C | ALA | A | 845 | 62.124 | 27.066 | 34.982 | 1.00 | 34.14 |
| 1724 | O | ALA | A | 845 | 62.137 | 26.522 | 36.021 | 1.00 | 35.47 |
| 1725 | N | ILE | A | 846 | 60.992 | 27.590 | 34.558 | 1.00 | 33.95 |
| 1726 | CA | ILE | A | 846 | 59.787 | 27.597 | 35.457 | 1.00 | 31.95 |
| 1727 | CB | ILE | A | 846 | 58.778 | 28.539 | 34.866 | 1.00 | 33.95 |
| 1728 | CG1 | ILE | A | 846 | 59.535 | 29.848 | 34.737 | 1.00 | 27.88 |
| 1729 | CD1 | ILE | A | 846 | 59.817 | 30.375 | 36.417 | 1.00 | 26.15 |
| 1730 | CG2 | ILE | A | 846 | 57.462 | 28.631 | 35.735 | 1.00 | 28.18 |
| 1731 | C | ILE | A | 846 | 59.233 | 26.236 | 35.656 | 1.00 | 32.51 |
| 1732 | O | ILE | A | 846 | 59.054 | 25.847 | 36.786 | 1.00 | 31.68 |
| 1733 | N | TYR | A | 847 | 59.145 | 25.413 | 34.603 | 1.00 | 35.30 |
| 1734 | CA | TYR | A | 847 | 58.714 | 23.984 | 34.822 | 1.00 | 35.63 |
| 1735 | CB | TYR | A | 847 | 58.713 | 23.167 | 33.520 | 1.00 | 35.69 |
| 1736 | CG | TYR | A | 847 | 57.927 | 21.911 | 33.661 | 1.00 | 32.14 |
| 1737 | CD1 | TYR | A | 847 | 58.477 | 20.696 | 33.310 | 1.00 | 27.77 |
| 1738 | CE1 | TYR | A | 847 | 57.759 | 19.516 | 33.469 | 1.00 | 33.54 |
| 1739 | CZ | TYR | A | 847 | 56.522 | 19.509 | 34.064 | 1.00 | 31.43 |
| 1740 | OH | TYR | A | 847 | 55.943 | 18.320 | 34.231 | 1.00 | 40.26 |
| 1741 | CE2 | TYR | A | 847 | 55.917 | 20.681 | 34.490 | 1.00 | 35.09 |
| 1742 | CD2 | TYR | A | 847 | 56.645 | 21.928 | 34.253 | 1.00 | 32.81 |
| 1743 | C | TYR | A | 847 | 59.577 | 23.180 | 35.723 | 1.00 | 36.62 |
| 1744 | O | TYR | A | 847 | 59.090 | 22.401 | 36.510 | 1.00 | 38.41 |
| 1745 | N | GLN | A | 848 | 60.874 | 23.301 | 35.605 | 1.00 | 38.13 |
| 1746 | CA | GLN | A | 848 | 61.806 | 22.493 | 36.466 | 1.00 | 39.42 |
| 1747 | CB | GLN | A | 848 | 63.262 | 22.533 | 35.863 | 1.00 | 42.35 |
| 1748 | CG | GLN | A | 848 | 63.313 | 21.927 | 34.477 | 1.00 | 38.83 |
| 1749 | CD | GLN | A | 848 | 62.999 | 20.404 | 34.549 | 1.00 | 44.22 |
| 1750 | OE1 | GLN | A | 848 | 62.228 | 19.877 | 33.736 | 1.00 | 48.28 |
| 1751 | NE2 | GLN | A | 848 | 63.569 | 19.735 | 35.485 | 1.00 | 33.20 |
| 1752 | C | GLN | A | 848 | 61.821 | 22.902 | 37.950 | 1.00 | 36.31 |
| 1753 | O | GLN | A | 848 | 61.762 | 22.045 | 38.829 | 1.00 | 35.55 |
| 1754 | N | LEU | A | 849 | 61.847 | 24.194 | 38.200 | 1.00 | 37.37 |
| 1755 | CA | LEU | A | 849 | 61.716 | 24.680 | 39.552 | 1.00 | 38.40 |
| 1756 | CB | LEU | A | 849 | 61.552 | 26.151 | 39.507 | 1.00 | 37.22 |
| 1757 | CG | LEU | A | 849 | 61.237 | 26.406 | 40.933 | 1.00 | 36.60 |
| 1758 | CD1 | LEU | A | 849 | 62.551 | 26.128 | 41.744 | 1.00 | 24.80 |
| 1759 | CD2 | LEU | A | 849 | 60.902 | 27.913 | 40.922 | 1.00 | 33.30 |

FIGURE 3AH

| A | B | C | D | E | F | G | H | I | J |
|---|---|---|---|---|---|---|---|---|---|
| 1760 | C | LEU | A | 849 | 60.521 | 24.099 | 40.250 | 1.00 | 39.79 |
| 1761 | O | LEU | A | 849 | 60.540 | 23.685 | 41.468 | 1.00 | 43.91 |
| 1762 | N | MET | A | 850 | 59.445 | 24.005 | 39.489 | 1.00 | 39.24 |
| 1763 | CA | MET | A | 850 | 58.240 | 23.461 | 40.122 | 1.00 | 39.96 |
| 1764 | CB | MET | A | 850 | 56.904 | 23.372 | 39.299 | 1.00 | 40.95 |
| 1765 | CG | MET | A | 850 | 56.413 | 24.449 | 38.405 | 1.00 | 41.55 |
| 1766 | SD | MET | A | 850 | 55.117 | 23.680 | 37.431 | 1.00 | 39.78 |
| 1767 | CE | MET | A | 850 | 54.574 | 24.992 | 36.847 | 1.00 | 18.82 |
| 1768 | C | MET | A | 850 | 58.422 | 22.040 | 40.423 | 1.00 | 37.52 |
| 1769 | O | MET | A | 850 | 57.783 | 21.573 | 41.370 | 1.00 | 38.53 |
| 1770 | N | MET | A | 851 | 58.853 | 21.295 | 39.415 | 1.00 | 35.10 |
| 1771 | CA | MET | A | 851 | 59.106 | 19.877 | 39.608 | 1.00 | 37.40 |
| 1772 | CB | MET | A | 851 | 59.826 | 19.275 | 38.407 | 1.00 | 36.06 |
| 1773 | CG | MET | A | 851 | 58.932 | 19.130 | 37.200 | 1.00 | 35.21 |
| 1774 | SD | MET | A | 851 | 57.537 | 18.184 | 37.411 | 1.00 | 43.74 |
| 1775 | CE | MET | A | 851 | 58.198 | 16.716 | 37.455 | 1.00 | 39.92 |
| 1776 | C | MET | A | 851 | 60.128 | 19.901 | 40.767 | 1.00 | 40.11 |
| 1777 | O | MET | A | 851 | 60.201 | 18.982 | 41.570 | 1.00 | 38.44 |
| 1778 | N | GLN | A | 852 | 60.894 | 20.980 | 40.908 | 1.00 | 39.68 |
| 1779 | CA | GLN | A | 852 | 61.720 | 20.958 | 42.059 | 1.00 | 42.72 |
| 1780 | CB | GLN | A | 852 | 62.918 | 21.868 | 41.882 | 1.00 | 41.86 |
| 1781 | CG | GLN | A | 852 | 63.758 | 21.298 | 40.778 | 1.00 | 52.95 |
| 1782 | CD | GLN | A | 852 | 65.096 | 22.010 | 40.537 | 1.00 | 62.78 |
| 1783 | OE1 | GLN | A | 852 | 65.118 | 23.232 | 40.419 | 1.00 | 60.88 |
| 1784 | NE2 | GLN | A | 852 | 66.203 | 21.229 | 40.419 | 1.00 | 69.19 |
| 1785 | C | GLN | A | 852 | 60.804 | 21.170 | 43.309 | 1.00 | 43.28 |
| 1786 | O | GLN | A | 852 | 60.916 | 20.491 | 44.309 | 1.00 | 43.36 |
| 1787 | N | CYS | A | 853 | 59.818 | 22.048 | 43.242 | 1.00 | 43.67 |
| 1788 | CA | CYS | A | 853 | 59.046 | 22.136 | 44.454 | 1.00 | 41.63 |
| 1789 | CB | CYS | A | 853 | 58.067 | 23.283 | 44.417 | 1.00 | 40.32 |
| 1790 | SG | CYS | A | 853 | 58.919 | 24.771 | 44.088 | 1.00 | 36.67 |
| 1791 | C | CYS | A | 853 | 58.330 | 20.847 | 44.697 | 1.00 | 42.12 |
| 1792 | O | CYS | A | 853 | 57.934 | 20.608 | 45.832 | 1.00 | 42.69 |
| 1793 | N | TRP | A | 854 | 58.115 | 20.013 | 43.675 | 1.00 | 42.37 |
| 1794 | CA | TRP | A | 854 | 57.383 | 18.705 | 43.926 | 1.00 | 41.75 |
| 1795 | CB | TRP | A | 854 | 56.200 | 18.430 | 42.946 | 1.00 | 38.35 |
| 1796 | CG | TRP | A | 854 | 55.327 | 19.556 | 42.514 | 1.00 | 37.67 |
| 1797 | CD1 | TRP | A | 854 | 54.684 | 20.557 | 43.330 | 1.00 | 35.33 |
| 1798 | NE1 | TRP | A | 854 | 53.972 | 21.386 | 42.509 | 1.00 | 37.18 |
| 1799 | CE2 | TRP | A | 854 | 54.150 | 21.016 | 41.201 | 1.00 | 36.61 |
| 1800 | CD2 | TRP | A | 854 | 54.937 | 19.861 | 41.168 | 1.00 | 38.28 |
| 1801 | CE3 | TRP | A | 854 | 55.238 | 19.302 | 39.913 | 1.00 | 35.92 |
| 1802 | CZ3 | TRP | A | 854 | 54.644 | 19.863 | 38.774 | 1.00 | 35.78 |
| 1803 | CH2 | TRP | A | 854 | 53.886 | 20.998 | 38.860 | 1.00 | 37.11 |
| 1804 | CZ2 | TRP | A | 854 | 53.642 | 21.597 | 40.055 | 1.00 | 36.88 |
| 1805 | C | TRP | A | 854 | 58.249 | 17.379 | 44.163 | 1.00 | 43.48 |
| 1806 | O | TRP | A | 854 | 57.788 | 16.232 | 43.928 | 1.00 | 40.95 |
| 1807 | N | GLN | A | 855 | 59.470 | 17.495 | 44.694 | 1.00 | 46.45 |
| 1808 | CA | GLN | A | 855 | 60.141 | 16.215 | 45.033 | 1.00 | 47.97 |
| 1809 | CB | GLN | A | 855 | 61.562 | 16.399 | 45.421 | 1.00 | 49.14 |
| 1810 | CG | GLN | A | 855 | 62.300 | 17.429 | 44.563 | 1.00 | 53.78 |
| 1811 | CD | GLN | A | 855 | 63.599 | 16.874 | 43.944 | 1.00 | 57.56 |

FIGURE 3AI

| A | B | C | D | E | F | G | H | I | J |
|---|---|---|---|---|---|---|---|---|---|
| 1812 | OE1 | GLN | A | 855 | 64.568 | 17.630 | 43.788 | 1.00 | 58.49 |
| 1813 | NE2 | GLN | A | 855 | 63.597 | 15.574 | 43.550 | 1.00 | 53.02 |
| 1814 | C | GLN | A | 855 | 59.503 | 15.583 | 46.185 | 1.00 | 48.95 |
| 1815 | O | GLN | A | 855 | 59.135 | 16.279 | 47.106 | 1.00 | 48.87 |
| 1816 | N | GLN | A | 856 | 59.417 | 14.251 | 46.193 | 1.00 | 50.70 |
| 1817 | CA | GLN | A | 856 | 58.760 | 13.603 | 47.270 | 1.00 | 51.94 |
| 1818 | CB | GLN | A | 856 | 58.589 | 12.110 | 47.008 | 1.00 | 52.72 |
| 1819 | CG | GLN | A | 856 | 57.987 | 11.341 | 48.190 | 1.00 | 56.53 |
| 1820 | CD | GLN | A | 856 | 56.902 | 10.378 | 47.730 | 1.00 | 67.51 |
| 1821 | OE1 | GLN | A | 856 | 57.145 | 9.159 | 47.626 | 1.00 | 70.03 |
| 1822 | NE2 | GLN | A | 856 | 55.687 | 10.921 | 47.421 | 1.00 | 70.24 |
| 1823 | C | GLN | A | 856 | 59.464 | 13.844 | 48.587 | 1.00 | 52.44 |
| 1824 | O | GLN | A | 856 | 58.839 | 13.901 | 49.641 | 1.00 | 51.92 |
| 1825 | N | GLU | A | 857 | 60.776 | 13.978 | 48.540 | 1.00 | 53.47 |
| 1826 | CA | GLU | A | 857 | 61.455 | 14.329 | 49.763 | 1.00 | 52.94 |
| 1827 | CB | GLU | A | 857 | 62.751 | 13.574 | 49.888 | 1.00 | 55.76 |
| 1828 | CG | GLU | A | 857 | 63.760 | 13.655 | 48.776 | 1.00 | 62.73 |
| 1829 | CD | GLU | A | 857 | 64.555 | 12.357 | 48.808 | 1.00 | 75.13 |
| 1830 | OE1 | GLU | A | 857 | 65.792 | 12.306 | 48.476 | 1.00 | 76.93 |
| 1831 | OE2 | GLU | A | 857 | 63.876 | 11.369 | 49.244 | 1.00 | 80.58 |
| 1832 | C | GLU | A | 857 | 61.642 | 15.763 | 50.058 | 1.00 | 51.09 |
| 1833 | O | GLU | A | 857 | 62.330 | 16.518 | 49.385 | 1.00 | 50.10 |
| 1834 | N | ALA | A | 858 | 61.062 | 16.140 | 51.162 | 1.00 | 51.40 |
| 1835 | CA | ALA | A | 858 | 60.918 | 17.553 | 51.501 | 1.00 | 51.01 |
| 1836 | CB | ALA | A | 858 | 60.376 | 17.634 | 52.879 | 1.00 | 51.91 |
| 1837 | C | ALA | A | 858 | 62.236 | 18.232 | 51.481 | 1.00 | 52.16 |
| 1838 | O | ALA | A | 858 | 62.369 | 19.416 | 51.138 | 1.00 | 49.85 |
| 1839 | N | ALA | A | 859 | 63.210 | 17.476 | 51.999 | 1.00 | 52.64 |
| 1840 | CA | ALA | A | 859 | 64.489 | 18.044 | 52.311 | 1.00 | 51.38 |
| 1841 | CB | ALA | A | 859 | 65.270 | 17.114 | 53.176 | 1.00 | 52.83 |
| 1842 | C | ALA | A | 859 | 65.149 | 18.322 | 51.024 | 1.00 | 50.59 |
| 1843 | O | ALA | A | 859 | 66.033 | 19.188 | 50.921 | 1.00 | 52.09 |
| 1844 | N | ARG | A | 860 | 64.677 | 17.712 | 49.971 | 1.00 | 49.07 |
| 1845 | CA | ARG | A | 860 | 65.287 | 18.206 | 48.702 | 1.00 | 49.33 |
| 1846 | CB | ARG | A | 860 | 65.434 | 17.117 | 47.664 | 1.00 | 49.91 |
| 1847 | CG | ARG | A | 860 | 66.326 | 15.929 | 48.098 | 1.00 | 56.52 |
| 1848 | CD | ARG | A | 860 | 66.767 | 14.950 | 46.979 | 1.00 | 67.86 |
| 1849 | NE | ARG | A | 860 | 67.897 | 15.592 | 46.310 | 1.00 | 79.99 |
| 1850 | CZ | ARG | A | 860 | 67.957 | 15.919 | 45.009 | 1.00 | 84.18 |
| 1851 | NH1 | ARG | A | 860 | 69.035 | 16.555 | 44.538 | 1.00 | 86.30 |
| 1852 | NH2 | ARG | A | 860 | 66.970 | 15.583 | 44.177 | 1.00 | 86.46 |
| 1853 | C | ARG | A | 860 | 64.642 | 19.423 | 48.073 | 1.00 | 47.17 |
| 1854 | O | ARG | A | 860 | 65.289 | 20.026 | 47.190 | 1.00 | 48.00 |
| 1855 | N | ARG | A | 861 | 63.390 | 19.778 | 48.428 | 1.00 | 43.32 |
| 1856 | CA | ARG | A | 861 | 62.722 | 20.886 | 47.710 | 1.00 | 42.70 |
| 1857 | CB | ARG | A | 861 | 61.279 | 21.149 | 48.284 | 1.00 | 43.25 |
| 1858 | CG | ARG | A | 861 | 60.375 | 19.925 | 48.223 | 1.00 | 38.41 |
| 1859 | CD | ARG | A | 861 | 58.992 | 19.969 | 48.886 | 1.00 | 33.61 |
| 1860 | NE | ARG | A | 861 | 58.563 | 18.555 | 48.956 | 1.00 | 39.84 |
| 1861 | CZ | ARG | A | 861 | 57.675 | 18.061 | 49.776 | 1.00 | 40.88 |
| 1862 | NH1 | ARG | A | 861 | 57.041 | 18.838 | 50.621 | 1.00 | 47.18 |
| 1863 | NH2 | ARG | A | 861 | 57.448 | 16.786 | 49.809 | 1.00 | 42.74 |

FIGURE 3AJ

| A | B | C | D | E | F | G | H | I | J |
|---|---|---|---|---|---|---|---|---|---|
| 1864 | C | ARG | A | 861 | 63.548 | 22.127 | 47.982 | 1.00 | 40.90 |
| 1865 | O | ARG | A | 861 | 64.151 | 22.197 | 49.048 | 1.00 | 45.17 |
| 1866 | N | PRO | A | 862 | 63.579 | 23.123 | 47.135 | 1.00 | 38.11 |
| 1867 | CA | PRO | A | 862 | 64.366 | 24.296 | 47.443 | 1.00 | 36.92 |
| 1868 | CB | PRO | A | 862 | 64.173 | 25.174 | 46.248 | 1.00 | 37.49 |
| 1869 | CG | PRO | A | 862 | 62.978 | 24.528 | 45.479 | 1.00 | 34.16 |
| 1870 | CD | PRO | A | 862 | 62.827 | 23.232 | 45.881 | 1.00 | 36.86 |
| 1871 | C | PRO | A | 862 | 63.565 | 24.973 | 48.494 | 1.00 | 40.68 |
| 1872 | O | PRO | A | 862 | 62.378 | 24.679 | 48.675 | 1.00 | 38.28 |
| 1873 | N | LYS | A | 863 | 64.195 | 25.936 | 49.155 | 1.00 | 43.10 |
| 1874 | CA | LYS | A | 863 | 63.626 | 26.658 | 50.273 | 1.00 | 43.38 |
| 1875 | CB | LYS | A | 863 | 64.689 | 26.934 | 51.402 | 1.00 | 44.69 |
| 1876 | CG | LYS | A | 863 | 64.809 | 25.604 | 52.283 | 1.00 | 50.07 |
| 1877 | CD | LYS | A | 863 | 65.801 | 25.501 | 53.459 | 1.00 | 60.38 |
| 1878 | CE | LYS | A | 863 | 65.260 | 26.211 | 54.856 | 1.00 | 67.58 |
| 1879 | NZ | LYS | A | 863 | 66.287 | 26.302 | 55.993 | 1.00 | 63.31 |
| 1880 | C | LYS | A | 863 | 63.235 | 27.905 | 49.612 | 1.00 | 43.27 |
| 1881 | O | LYS | A | 863 | 63.753 | 28.275 | 48.476 | 1.00 | 45.68 |
| 1882 | N | PHE | A | 864 | 62.350 | 28.605 | 50.290 | 1.00 | 40.33 |
| 1883 | CA | PHE | A | 864 | 61.830 | 29.779 | 49.682 | 1.00 | 37.37 |
| 1884 | CB | PHE | A | 864 | 60.731 | 30.422 | 50.528 | 1.00 | 35.46 |
| 1885 | CG | PHE | A | 864 | 59.441 | 29.808 | 50.353 | 1.00 | 32.57 |
| 1886 | CD1 | PHE | A | 864 | 58.869 | 29.099 | 51.365 | 1.00 | 34.21 |
| 1887 | CE1 | PHE | A | 864 | 57.672 | 28.495 | 51.231 | 1.00 | 31.67 |
| 1888 | CZ | PHE | A | 864 | 56.964 | 28.622 | 49.961 | 1.00 | 31.72 |
| 1889 | CE2 | PHE | A | 864 | 57.525 | 29.380 | 48.954 | 1.00 | 30.90 |
| 1890 | CD2 | PHE | A | 864 | 58.743 | 29.927 | 49.129 | 1.00 | 37.14 |
| 1891 | C | PHE | A | 864 | 62.874 | 30.743 | 49.304 | 1.00 | 38.42 |
| 1892 | O | PHE | A | 864 | 62.717 | 31.509 | 48.307 | 1.00 | 40.96 |
| 1893 | N | ALA | A | 865 | 63.875 | 30.905 | 50.126 | 1.00 | 38.95 |
| 1894 | CA | ALA | A | 865 | 64.964 | 31.837 | 49.712 | 1.00 | 40.21 |
| 1895 | CB | ALA | A | 865 | 66.009 | 31.987 | 50.851 | 1.00 | 40.74 |
| 1896 | C | ALA | A | 865 | 65.712 | 31.328 | 48.376 | 1.00 | 39.07 |
| 1897 | O | ALA | A | 865 | 66.186 | 32.133 | 47.578 | 1.00 | 40.17 |
| 1898 | N | ASP | A | 866 | 65.855 | 30.036 | 48.142 | 1.00 | 38.13 |
| 1899 | CA | ASP | A | 866 | 66.437 | 29.657 | 46.850 | 1.00 | 41.20 |
| 1900 | CB | ASP | A | 866 | 66.592 | 28.205 | 46.710 | 1.00 | 42.25 |
| 1901 | CG | ASP | A | 866 | 67.356 | 27.563 | 47.886 | 1.00 | 46.38 |
| 1902 | OD1 | ASP | A | 866 | 68.194 | 28.328 | 48.467 | 1.00 | 45.69 |
| 1903 | OD2 | ASP | A | 866 | 67.164 | 26.319 | 48.255 | 1.00 | 46.52 |
| 1904 | C | ASP | A | 866 | 65.471 | 30.112 | 45.734 | 1.00 | 43.03 |
| 1905 | O | ASP | A | 866 | 65.895 | 30.862 | 44.786 | 1.00 | 43.71 |
| 1906 | N | ILE | A | 867 | 64.154 | 29.834 | 45.959 | 1.00 | 41.85 |
| 1907 | CA | ILE | A | 867 | 63.161 | 30.097 | 44.945 | 1.00 | 39.25 |
| 1908 | CB | ILE | A | 867 | 61.738 | 29.686 | 45.429 | 1.00 | 40.79 |
| 1909 | CG1 | ILE | A | 867 | 61.715 | 28.196 | 45.547 | 1.00 | 37.78 |
| 1910 | CD1 | ILE | A | 867 | 60.587 | 27.644 | 46.393 | 1.00 | 31.95 |
| 1911 | CG2 | ILE | A | 867 | 60.673 | 29.978 | 44.377 | 1.00 | 40.13 |
| 1912 | C | ILE | A | 867 | 63.262 | 31.517 | 44.601 | 1.00 | 38.15 |
| 1913 | O | ILE | A | 867 | 63.383 | 31.839 | 43.478 | 1.00 | 34.00 |
| 1914 | N | VAL | A | 868 | 63.293 | 32.407 | 45.587 | 1.00 | 41.76 |
| 1915 | CA | VAL | A | 868 | 63.363 | 33.826 | 45.221 | 1.00 | 42.24 |

FIGURE 3AK

| A | B | C | D | E | F | G | H | I | J |
|---|---|---|---|---|---|---|---|---|---|
| 1916 | CB | VAL | A | 868 | 63.468 | 34.646 | 46.495 | 1.00 | 43.37 |
| 1917 | CG1 | VAL | A | 868 | 63.906 | 36.180 | 46.204 | 1.00 | 36.83 |
| 1918 | CG2 | VAL | A | 868 | 62.167 | 34.602 | 47.161 | 1.00 | 44.87 |
| 1919 | C | VAL | A | 868 | 64.595 | 34.086 | 44.346 | 1.00 | 43.26 |
| 1920 | O | VAL | A | 868 | 64.566 | 34.653 | 43.250 | 1.00 | 42.88 |
| 1921 | N | SER | A | 869 | 65.709 | 33.593 | 44.819 | 1.00 | 43.82 |
| 1922 | CA | SER | A | 869 | 66.947 | 33.788 | 44.034 | 1.00 | 45.81 |
| 1923 | CB | SER | A | 869 | 68.135 | 33.277 | 44.868 | 1.00 | 46.51 |
| 1924 | OG | SER | A | 869 | 69.256 | 32.973 | 44.081 | 1.00 | 55.81 |
| 1925 | C | SER | A | 869 | 66.932 | 33.161 | 42.595 | 1.00 | 43.21 |
| 1926 | O | SER | A | 869 | 67.448 | 33.748 | 41.646 | 1.00 | 45.11 |
| 1927 | N | ILE | A | 870 | 66.309 | 32.041 | 42.410 | 1.00 | 40.48 |
| 1928 | CA | ILE | A | 870 | 66.341 | 31.421 | 41.081 | 1.00 | 41.53 |
| 1929 | CB | ILE | A | 870 | 65.721 | 30.078 | 41.130 | 1.00 | 40.21 |
| 1930 | CG1 | ILE | A | 870 | 66.726 | 29.091 | 41.617 | 1.00 | 37.62 |
| 1931 | CD1 | ILE | A | 870 | 65.913 | 27.844 | 42.278 | 1.00 | 34.59 |
| 1932 | CG2 | ILE | A | 870 | 65.227 | 29.674 | 39.764 | 1.00 | 37.43 |
| 1933 | C | ILE | A | 870 | 65.551 | 32.101 | 40.057 | 1.00 | 41.17 |
| 1934 | O | ILE | A | 870 | 65.629 | 31.841 | 38.862 | 1.00 | 45.96 |
| 1935 | N | LEU | A | 871 | 64.743 | 32.960 | 40.589 | 1.00 | 42.32 |
| 1936 | CA | LEU | A | 871 | 63.690 | 33.613 | 39.857 | 1.00 | 39.74 |
| 1937 | CB | LEU | A | 871 | 62.477 | 33.514 | 40.715 | 1.00 | 36.70 |
| 1938 | CG | LEU | A | 871 | 61.084 | 32.948 | 40.403 | 1.00 | 42.57 |
| 1939 | CD1 | LEU | A | 871 | 61.128 | 31.584 | 39.753 | 1.00 | 39.10 |
| 1940 | CD2 | LEU | A | 871 | 60.155 | 32.800 | 41.647 | 1.00 | 33.43 |
| 1941 | C | LEU | A | 871 | 64.073 | 35.062 | 39.677 | 1.00 | 40.56 |
| 1942 | O | LEU | A | 871 | 63.729 | 35.716 | 38.685 | 1.00 | 39.95 |
| 1943 | N | ASP | A | 872 | 64.858 | 35.566 | 40.655 | 1.00 | 43.30 |
| 1944 | CA | ASP | A | 872 | 65.641 | 36.754 | 40.333 | 1.00 | 45.25 |
| 1945 | CB | ASP | A | 872 | 66.270 | 37.416 | 41.537 | 1.00 | 44.64 |
| 1946 | CG | ASP | A | 872 | 65.296 | 38.054 | 42.370 | 1.00 | 50.39 |
| 1947 | OD1 | ASP | A | 872 | 64.560 | 38.981 | 41.884 | 1.00 | 58.03 |
| 1948 | OD2 | ASP | A | 872 | 65.222 | 37.729 | 43.584 | 1.00 | 59.66 |
| 1949 | C | ASP | A | 872 | 66.617 | 36.467 | 39.147 | 1.00 | 42.59 |
| 1950 | O | ASP | A | 872 | 66.673 | 37.301 | 38.244 | 1.00 | 40.36 |
| 1951 | N | LYS | A | 873 | 67.123 | 35.244 | 39.030 | 1.00 | 43.85 |
| 1952 | CA | LYS | A | 873 | 68.158 | 35.043 | 37.946 | 1.00 | 46.85 |
| 1953 | CB | LYS | A | 873 | 68.848 | 33.639 | 37.915 | 1.00 | 47.60 |
| 1954 | CG | LYS | A | 873 | 69.201 | 33.005 | 36.461 | 1.00 | 56.65 |
| 1955 | CD | LYS | A | 873 | 70.697 | 32.494 | 36.301 | 1.00 | 64.86 |
| 1956 | CE | LYS | A | 873 | 71.327 | 31.621 | 37.470 | 1.00 | 72.42 |
| 1957 | NZ | LYS | A | 873 | 72.948 | 31.544 | 37.520 | 1.00 | 77.28 |
| 1958 | C | LYS | A | 873 | 67.273 | 35.234 | 36.716 | 1.00 | 45.54 |
| 1959 | O | LYS | A | 873 | 67.554 | 36.043 | 35.848 | 1.00 | 47.71 |
| 1960 | N | LEU | A | 874 | 66.177 | 34.496 | 36.670 | 1.00 | 44.00 |
| 1961 | CA | LEU | A | 874 | 65.345 | 34.413 | 35.523 | 1.00 | 41.76 |
| 1962 | CB | LEU | A | 874 | 64.257 | 33.510 | 35.950 | 1.00 | 42.33 |
| 1963 | CG | LEU | A | 874 | 64.335 | 32.030 | 35.627 | 1.00 | 43.61 |
| 1964 | CD1 | LEU | A | 874 | 65.728 | 31.506 | 34.940 | 1.00 | 39.31 |
| 1965 | CD2 | LEU | A | 874 | 63.820 | 31.183 | 36.838 | 1.00 | 40.93 |
| 1966 | C | LEU | A | 874 | 64.842 | 35.818 | 35.223 | 1.00 | 41.73 |
| 1967 | O | LEU | A | 874 | 64.974 | 36.328 | 34.103 | 1.00 | 40.87 |

FIGURE 3AL

| A | B | C | D | E | F | G | H | I | J |
|---|---|---|---|---|---|---|---|---|---|
| 1968 | N | ILE | A | 875 | 64.356 | 36.539 | 36.219 | 1.00 | 41.36 |
| 1969 | CA | ILE | A | 875 | 63.986 | 37.926 | 35.895 | 1.00 | 41.48 |
| 1970 | CB | ILE | A | 875 | 63.241 | 38.556 | 37.045 | 1.00 | 41.83 |
| 1971 | CG1 | ILE | A | 875 | 61.848 | 37.830 | 37.313 | 1.00 | 41.11 |
| 1972 | CD1 | ILE | A | 875 | 61.307 | 38.014 | 38.707 | 1.00 | 42.11 |
| 1973 | CG2 | ILE | A | 875 | 63.128 | 39.991 | 36.768 | 1.00 | 39.85 |
| 1974 | C | ILE | A | 875 | 65.128 | 38.822 | 35.369 | 1.00 | 43.50 |
| 1975 | O | ILE | A | 875 | 64.949 | 39.592 | 34.357 | 1.00 | 42.05 |
| 1976 | N | ALA | A | 876 | 66.305 | 38.724 | 36.005 | 1.00 | 43.68 |
| 1977 | CA | ALA | A | 876 | 67.460 | 39.526 | 35.543 | 1.00 | 47.29 |
| 1978 | CB | ALA | A | 876 | 68.686 | 39.705 | 36.633 | 1.00 | 45.33 |
| 1979 | C | ALA | A | 876 | 67.981 | 39.177 | 34.150 | 1.00 | 47.94 |
| 1980 | O | ALA | A | 876 | 68.349 | 40.096 | 33.381 | 1.00 | 49.38 |
| 1981 | N | ALA | A | 877 | 67.882 | 37.894 | 33.781 | 1.00 | 49.67 |
| 1982 | CA | ALA | A | 877 | 68.248 | 37.448 | 32.433 | 1.00 | 48.36 |
| 1983 | CB | ALA | A | 877 | 69.359 | 36.469 | 32.485 | 1.00 | 47.02 |
| 1984 | C | ALA | A | 877 | 67.051 | 36.862 | 31.723 | 1.00 | 48.54 |
| 1985 | O | ALA | A | 877 | 66.995 | 35.680 | 31.364 | 1.00 | 48.87 |
| 1986 | N | PRO | A | 878 | 66.165 | 37.720 | 31.333 | 1.00 | 48.50 |
| 1987 | CA | PRO | A | 878 | 64.883 | 37.290 | 30.768 | 1.00 | 50.31 |
| 1988 | CB | PRO | A | 878 | 64.248 | 38.609 | 30.314 | 1.00 | 49.52 |
| 1989 | CG | PRO | A | 878 | 65.076 | 39.594 | 30.795 | 1.00 | 48.76 |
| 1990 | CD | PRO | A | 878 | 66.399 | 39.140 | 31.199 | 1.00 | 47.09 |
| 1991 | C | PRO | A | 878 | 65.005 | 36.339 | 29.595 | 1.00 | 51.52 |
| 1992 | O | PRO | A | 878 | 64.080 | 35.558 | 29.329 | 1.00 | 52.11 |
| 1993 | N | ASP | A | 879 | 66.118 | 36.423 | 28.857 | 1.00 | 53.47 |
| 1994 | CA | ASP | A | 879 | 66.313 | 35.529 | 27.704 | 1.00 | 53.74 |
| 1995 | CB | ASP | A | 879 | 67.561 | 35.840 | 26.877 | 1.00 | 54.59 |
| 1996 | CG | ASP | A | 879 | 67.426 | 37.117 | 26.105 | 1.00 | 57.51 |
| 1997 | OD1 | ASP | A | 879 | 66.311 | 37.639 | 25.969 | 1.00 | 61.05 |
| 1998 | OD2 | ASP | A | 879 | 68.385 | 37.705 | 25.618 | 1.00 | 63.66 |
| 1999 | C | ASP | A | 879 | 66.337 | 34.121 | 28.137 | 1.00 | 52.26 |
| 2000 | O | ASP | A | 879 | 66.064 | 33.243 | 27.320 | 1.00 | 52.16 |
| 2001 | N | SER | A | 880 | 66.687 | 33.897 | 29.401 | 1.00 | 50.31 |
| 2002 | CA | SER | A | 880 | 66.494 | 32.578 | 30.001 | 1.00 | 49.70 |
| 2003 | CB | SER | A | 880 | 66.869 | 32.588 | 31.504 | 1.00 | 52.27 |
| 2004 | OG | SER | A | 880 | 65.870 | 33.209 | 32.357 | 1.00 | 50.20 |
| 2005 | C | SER | A | 880 | 65.026 | 32.063 | 29.841 | 1.00 | 49.60 |
| 2006 | O | SER | A | 880 | 64.796 | 30.895 | 29.773 | 1.00 | 49.66 |
| 2007 | N | LEU | A | 881 | 64.021 | 32.922 | 29.716 | 1.00 | 47.09 |
| 2008 | CA | LEU | A | 881 | 62.691 | 32.401 | 29.788 | 1.00 | 44.70 |
| 2009 | CB | LEU | A | 881 | 61.748 | 33.479 | 30.429 | 1.00 | 42.64 |
| 2010 | CG | LEU | A | 881 | 62.027 | 33.854 | 31.893 | 1.00 | 37.67 |
| 2011 | CD1 | LEU | A | 881 | 61.053 | 35.053 | 32.335 | 1.00 | 46.29 |
| 2012 | CD2 | LEU | A | 881 | 61.905 | 32.636 | 32.698 | 1.00 | 30.01 |
| 2013 | C | LEU | A | 881 | 62.230 | 31.982 | 28.406 | 1.00 | 46.11 |
| 2014 | O | LEU | A | 881 | 61.063 | 31.708 | 28.161 | 1.00 | 46.79 |
| 2015 | N | LYS | A | 882 | 63.166 | 31.996 | 27.480 | 1.00 | 46.05 |
| 2016 | CA | LYS | A | 882 | 62.872 | 31.829 | 26.034 | 1.00 | 44.09 |
| 2017 | CB | LYS | A | 882 | 63.999 | 32.408 | 25.172 | 1.00 | 42.68 |
| 2018 | CG | LYS | A | 882 | 63.822 | 33.855 | 24.808 | 1.00 | 50.65 |
| 2019 | CD | LYS | A | 882 | 64.615 | 34.299 | 23.548 | 1.00 | 57.85 |

FIGURE 3AM

| A | B | C | D | E | F | G | H | I | J |
|---|---|---|---|---|---|---|---|---|---|
| 2020 | CE | LYS | A | 882 | 66.036 | 33.711 | 23.442 | 1.00 | 57.83 |
| 2021 | NZ | LYS | A | 882 | 66.063 | 32.670 | 22.379 | 1.00 | 62.95 |
| 2022 | C | LYS | A | 882 | 62.712 | 30.397 | 25.609 | 1.00 | 39.93 |
| 2023 | O | LYS | A | 882 | 62.057 | 30.189 | 24.624 | 1.00 | 38.21 |
| 2024 | N | THR | A | 883 | 63.413 | 29.481 | 26.255 | 1.00 | 36.09 |
| 2025 | CA | THR | A | 883 | 63.327 | 28.070 | 25.917 | 1.00 | 37.39 |
| 2026 | CB | THR | A | 883 | 64.642 | 27.295 | 26.300 | 1.00 | 38.89 |
| 2027 | OG1 | THR | A | 883 | 65.753 | 27.896 | 25.645 | 1.00 | 45.06 |
| 2028 | CG2 | THR | A | 883 | 64.619 | 25.861 | 25.703 | 1.00 | 34.98 |
| 2029 | C | THR | A | 883 | 62.325 | 27.441 | 26.760 | 1.00 | 37.20 |
| 2030 | O | THR | A | 883 | 62.376 | 27.619 | 27.985 | 1.00 | 38.72 |
| 2031 | N | LEU | A | 884 | 61.468 | 26.653 | 26.136 | 1.00 | 36.33 |
| 2032 | CA | LEU | A | 884 | 60.299 | 26.154 | 26.735 | 1.00 | 37.19 |
| 2033 | CB | LEU | A | 884 | 59.256 | 26.182 | 25.688 | 1.00 | 37.32 |
| 2034 | CG | LEU | A | 884 | 58.405 | 27.401 | 25.764 | 1.00 | 39.51 |
| 2035 | CD1 | LEU | A | 884 | 59.168 | 28.654 | 26.319 | 1.00 | 40.46 |
| 2036 | CD2 | LEU | A | 884 | 57.816 | 27.595 | 24.464 | 1.00 | 39.93 |
| 2037 | C | LEU | A | 884 | 60.536 | 24.812 | 27.146 | 1.00 | 37.90 |
| 2038 | O | LEU | A | 884 | 61.439 | 24.224 | 26.704 | 1.00 | 37.67 |
| 2039 | N | ALA | A | 885 | 59.766 | 24.349 | 28.090 | 1.00 | 40.12 |
| 2040 | CA | ALA | A | 885 | 59.817 | 22.985 | 28.517 | 1.00 | 43.23 |
| 2041 | CB | ALA | A | 885 | 59.092 | 22.789 | 29.809 | 1.00 | 40.83 |
| 2042 | C | ALA | A | 885 | 59.015 | 22.235 | 27.462 | 1.00 | 47.82 |
| 2043 | O | ALA | A | 885 | 58.130 | 22.796 | 26.805 | 1.00 | 48.49 |
| 2044 | N | ASP | A | 886 | 59.249 | 20.942 | 27.379 | 1.00 | 53.03 |
| 2045 | CA | ASP | A | 886 | 58.481 | 20.131 | 26.460 | 1.00 | 57.55 |
| 2046 | CB | ASP | A | 886 | 59.468 | 19.350 | 25.609 | 1.00 | 59.17 |
| 2047 | CG | ASP | A | 886 | 59.801 | 20.080 | 24.316 | 1.00 | 66.52 |
| 2048 | OD1 | ASP | A | 886 | 60.703 | 19.608 | 23.581 | 1.00 | 73.87 |
| 2049 | OD2 | ASP | A | 886 | 59.214 | 21.145 | 23.960 | 1.00 | 73.11 |
| 2050 | C | ASP | A | 886 | 57.476 | 19.113 | 26.984 | 1.00 | 58.65 |
| 2051 | O | ASP | A | 886 | 57.538 | 18.664 | 28.103 | 1.00 | 58.38 |
| 2052 | N | ALA | A | 887 | 56.511 | 18.790 | 26.120 | 1.00 | 62.53 |
| 2053 | CA | ALA | A | 887 | 55.793 | 17.514 | 26.245 | 1.00 | 63.20 |
| 2054 | CB | ALA | A | 887 | 56.793 | 16.396 | 26.732 | 1.00 | 63.87 |
| 2055 | C | ALA | A | 887 | 54.506 | 17.495 | 27.046 | 1.00 | 64.13 |
| 2056 | O | ALA | A | 887 | 53.476 | 18.015 | 26.589 | 1.00 | 64.69 |
| 4115 | O1A | ATP | A | 1000 | 37.488 | 36.083 | 52.431 | 1.00 | 68.23 |
| 4116 | PA | ATP | A | 1000 | 38.403 | 36.497 | 51.393 | 1.00 | 58.85 |
| 4117 | O2A | ATP | A | 1000 | 39.539 | 36.819 | 52.377 | 1.00 | 63.08 |
| 4118 | O3A | ATP | A | 1000 | 38.307 | 35.243 | 50.501 | 1.00 | 64.52 |
| 4119 | PB | ATP | A | 1000 | 37.326 | 34.027 | 51.050 | 1.00 | 65.46 |
| 4120 | O1B | ATP | A | 1000 | 36.977 | 33.851 | 52.487 | 1.00 | 64.98 |
| 4121 | O2B | ATP | A | 1000 | 38.372 | 32.868 | 50.835 | 1.00 | 64.05 |
| 4122 | O3B | ATP | A | 1000 | 36.030 | 33.835 | 50.075 | 1.00 | 61.18 |
| 4123 | PG | ATP | A | 1000 | 36.102 | 33.771 | 48.418 | 1.00 | 64.66 |
| 4124 | O3G | ATP | A | 1000 | 37.337 | 34.705 | 47.992 | 1.00 | 61.28 |
| 4125 | O2G | ATP | A | 1000 | 34.842 | 34.413 | 47.778 | 1.00 | 53.07 |
| 4126 | O1G | ATP | A | 1000 | 36.347 | 32.439 | 47.869 | 1.00 | 55.85 |
| 4127 | O5* | ATP | A | 1000 | 37.771 | 37.754 | 50.611 | 1.00 | 63.69 |
| 4128 | C5* | ATP | A | 1000 | 36.564 | 37.629 | 49.871 | 1.00 | 51.19 |
| 4129 | C4* | ATP | A | 1000 | 36.702 | 38.452 | 48.619 | 1.00 | 48.45 |

FIGURE 3AN

| A | B | C | D E | F | G | H | I | J |
|---|---|---|---|---|---|---|---|---|
| 4130 | O4* | ATP | A1000 | 36.838 | 39.812 | 48.897 | 1.00 | 48.02 |
| 4131 | C1* | ATP | A1000 | 37.801 | 40.399 | 48.075 | 1.00 | 51.30 |
| 4132 | C2* | ATP | A1000 | 38.364 | 39.349 | 47.132 | 1.00 | 56.06 |
| 4133 | O2* | ATP | A1000 | 37.709 | 39.459 | 45.885 | 1.00 | 53.71 |
| 4134 | C3* | ATP | A1000 | 37.962 | 38.092 | 47.863 | 1.00 | 56.21 |
| 4135 | O3* | ATP | A1000 | 37.576 | 37.178 | 46.929 | 1.00 | 56.41 |
| 4136 | N9 | ATP | A1000 | 38.870 | 40.760 | 48.977 | 1.00 | 48.97 |
| 4137 | C8 | ATP | A1000 | 39.164 | 40.209 | 50.155 | 1.00 | 46.56 |
| 4138 | N7 | ATP | A1000 | 40.236 | 40.937 | 50.642 | 1.00 | 47.18 |
| 4139 | C5 | ATP | A1000 | 40.553 | 41.923 | 49.802 | 1.00 | 46.85 |
| 4140 | C6 | ATP | A1000 | 41.495 | 42.912 | 49.749 | 1.00 | 45.05 |
| 4141 | N6 | ATP | A1000 | 42.491 | 43.015 | 50.606 | 1.00 | 51.47 |
| 4142 | C4 | ATP | A1000 | 39.721 | 41.807 | 48.758 | 1.00 | 44.98 |
| 4143 | N3 | ATP | A1000 | 39.840 | 42.616 | 47.754 | 1.00 | 40.18 |
| 4144 | C2 | ATP | A1000 | 40.730 | 43.613 | 47.652 | 1.00 | 40.86 |
| 4145 | N1 | ATP | A1000 | 41.527 | 43.736 | 48.735 | 1.00 | 37.92 |
| 4177 | O | HOH | Y 301 | 34.209 | -7.517 | 100.111 | 1.00 | 42.77 |
| 4178 | O | HOH | Y 302 | 52.030 | 44.683 | 51.996 | 1.00 | 37.34 |
| 4179 | O | HOH | Y 303 | 36.987 | 20.304 | 84.823 | 1.00 | 48.24 |
| 4180 | O | HOH | Y 304 | 24.445 | 37.848 | 61.354 | 1.00 | 30.63 |
| 4181 | O | HOH | Y 305 | 38.693 | 6.951 | 84.781 | 1.00 | 33.40 |
| 4182 | O | HOH | Y 306 | 43.619 | 28.688 | 43.907 | 1.00 | 36.33 |
| 4183 | O | HOH | Y 307 | 35.150 | 4.275 | 99.892 | 1.00 | 38.81 |
| 4184 | O | HOH | Y 308 | 34.293 | 39.454 | 56.291 | 1.00 | 26.79 |
| 4185 | O | HOH | Y 309 | 26.249 | 38.679 | 67.871 | 1.00 | 28.41 |
| 4186 | O | HOH | Y 310 | 37.152 | -3.870 | 86.285 | 1.00 | 44.21 |
| 4187 | O | HOH | Y 311 | 52.468 | 18.101 | 40.466 | 1.00 | 34.94 |
| 4188 | O | HOH | Y 312 | 58.705 | 41.579 | 36.068 | 1.00 | 42.08 |
| 4189 | O | HOH | Y 313 | 21.983 | -0.989 | 94.287 | 1.00 | 43.17 |
| 4190 | O | HOH | Y 314 | 50.636 | 25.308 | 51.909 | 1.00 | 29.96 |
| 4191 | O | HOH | Y 315 | 38.314 | 43.464 | 44.478 | 1.00 | 53.90 |
| 4192 | O | HOH | Y 316 | 58.592 | 38.555 | 28.508 | 1.00 | 46.60 |
| 4193 | O | HOH | Y 317 | 34.711 | 38.223 | 45.323 | 1.00 | 38.90 |
| 4194 | O | HOH | Y 318 | 51.004 | 34.502 | 28.290 | 1.00 | 43.71 |
| 4195 | O | HOH | Y 319 | 50.245 | 44.662 | 31.484 | 1.00 | 39.87 |
| 4196 | O | HOH | Y 320 | 53.203 | 28.844 | 30.705 | 1.00 | 35.11 |
| 4197 | O | HOH | Y 321 | 37.565 | 5.987 | 104.482 | 1.00 | 42.90 |
| 4198 | O | HOH | Y 322 | 51.412 | 38.707 | 25.922 | 1.00 | 46.40 |
| 4199 | O | HOH | Y 323 | 50.121 | -23.627 | 89.919 | 1.00 | 49.18 |
| 4200 | O | HOH | Y 324 | 54.265 | 41.237 | 40.221 | 1.00 | 38.57 |
| 4201 | O | HOH | Y 325 | 35.932 | 15.979 | 69.458 | 1.00 | 44.49 |
| 4202 | O | HOH | Y 327 | 40.167 | 40.451 | 29.178 | 1.00 | 43.85 |
| 4203 | O | HOH | Y 328 | 63.877 | 28.468 | 30.538 | 1.00 | 41.56 |
| 4204 | O | HOH | Y 329 | 62.331 | 40.960 | 56.402 | 1.00 | 46.79 |
| 4205 | O | HOH | Y 330 | 49.475 | 13.163 | 96.500 | 1.00 | 41.09 |
| 4206 | O | HOH | Y 331 | 46.704 | 12.338 | 89.706 | 1.00 | 32.58 |
| 4207 | O | HOH | Y 332 | 34.910 | 37.079 | 56.822 | 1.00 | 29.88 |
| 4208 | O | HOH | Y 333 | 66.529 | 22.709 | 35.322 | 1.00 | 38.73 |
| 4209 | O | HOH | Y 334 | 54.290 | 40.356 | 42.871 | 1.00 | 33.86 |
| 4210 | O | HOH | Y 335 | 39.125 | 35.580 | 29.291 | 1.00 | 52.12 |
| 4211 | O | HOH | Y 336 | 30.038 | 21.951 | 78.948 | 1.00 | 38.53 |
| 4212 | O | HOH | Y 337 | 39.032 | 40.142 | 27.076 | 1.00 | 46.77 |

FIGURE 3AO

| A | B | C | D | E | F | G | H | I | J |
|---|---|---|---|---|---|---|---|---|---|
| 4213 | O | HOH | Y | 338 | 27.063 | 12.328 | 81.741 | 1.00 | 49.23 |
| 4214 | O | HOH | Y | 339 | 43.495 | -1.978 | 101.845 | 1.00 | 29.87 |
| 4215 | O | HOH | Y | 340 | 24.042 | 11.453 | 87.471 | 1.00 | 41.90 |
| 4216 | O | HOH | Y | 341 | 28.532 | 21.817 | 105.465 | 1.00 | 51.38 |
| 4217 | O | HOH | Y | 342 | 34.250 | -2.816 | 87.557 | 1.00 | 40.16 |
| 4218 | O | HOH | Y | 343 | 61.321 | 37.753 | 51.409 | 1.00 | 42.73 |
| 4219 | O | HOH | Y | 344 | 36.839 | -8.065 | 88.494 | 1.00 | 47.43 |
| 4220 | O | HOH | Y | 345 | 36.931 | 51.353 | 67.108 | 1.00 | 43.87 |
| 4221 | O | HOH | Y | 346 | 32.133 | 3.426 | 74.670 | 1.00 | 41.40 |
| 4222 | O | HOH | Y | 347 | 35.239 | -3.830 | 103.044 | 1.00 | 32.29 |
| 4223 | O | HOH | Y | 348 | 29.414 | 4.943 | 100.046 | 1.00 | 41.59 |
| 4224 | O | HOH | Y | 349 | 24.239 | 20.789 | 98.495 | 1.00 | 55.55 |
| 4225 | O | HOH | Y | 350 | 56.249 | 24.229 | 27.459 | 1.00 | 35.32 |
| 4226 | O | HOH | Y | 351 | 42.039 | 36.733 | 27.828 | 1.00 | 31.77 |
| 4227 | O | HOH | Y | 352 | 49.598 | 14.602 | 89.944 | 1.00 | 39.22 |
| 4228 | O | HOH | Y | 353 | 53.086 | 45.810 | 55.315 | 1.00 | 46.66 |
| 4229 | O | HOH | Y | 354 | 56.134 | 28.666 | 55.481 | 1.00 | 37.89 |
| 4230 | O | HOH | Y | 355 | 63.607 | 21.585 | 51.318 | 1.00 | 45.92 |
| 4231 | O | HOH | Y | 356 | 47.007 | -0.656 | 101.802 | 1.00 | 39.67 |
| 4232 | O | HOH | Y | 357 | 56.849 | 42.289 | 30.051 | 1.00 | 43.93 |
| 4233 | O | HOH | Y | 358 | 50.297 | 45.047 | 58.166 | 1.00 | 37.20 |
| 4234 | O | HOH | Y | 359 | 28.541 | 41.183 | 57.319 | 1.00 | 46.64 |
| 4235 | O | HOH | Y | 360 | 61.669 | 23.736 | 51.056 | 1.00 | 46.15 |
| 4236 | O | HOH | Y | 361 | 46.431 | 16.691 | 103.110 | 1.00 | 35.98 |
| 4237 | O | HOH | Y | 362 | 43.512 | 8.970 | 105.775 | 1.00 | 36.32 |
| 4238 | O | HOH | Y | 363 | 62.088 | 25.972 | 23.786 | 1.00 | 38.78 |
| 4239 | O | HOH | Y | 364 | 64.287 | 31.187 | 20.702 | 1.00 | 44.19 |
| 4240 | O | HOH | Y | 365 | 34.618 | 30.621 | 63.970 | 1.00 | 40.96 |
| 4241 | O | HOH | Y | 366 | 25.281 | 41.511 | 59.290 | 1.00 | 44.80 |
| 4242 | O | HOH | Y | 367 | 45.275 | 20.695 | 97.308 | 1.00 | 46.67 |

FIGURE 3AP

| A | B | C | D | E | F | G | H | I | J |
|---|---|---|---|---|---|---|---|---|---|
| 2057 | N | ALA | B | 602 | 61.588 | -1.705 | 97.096 | 1.00 | 75.62 |
| 2058 | CA | ALA | B | 602 | 61.031 | -2.970 | 96.546 | 1.00 | 76.68 |
| 2059 | CB | ALA | B | 602 | 61.665 | -3.292 | 95.199 | 1.00 | 76.47 |
| 2060 | C | ALA | B | 602 | 61.337 | -4.080 | 97.519 | 1.00 | 77.44 |
| 2061 | O | ALA | B | 602 | 61.332 | -5.311 | 97.156 | 1.00 | 75.75 |
| 2062 | N | LYS | B | 603 | 61.635 | -3.605 | 98.744 | 1.00 | 77.75 |
| 2063 | CA | LYS | B | 603 | 62.173 | -4.417 | 99.861 | 1.00 | 77.56 |
| 2064 | CB | LYS | B | 603 | 63.425 | -3.748 | 100.411 | 1.00 | 78.96 |
| 2065 | CG | LYS | B | 603 | 63.212 | -2.282 | 100.938 | 1.00 | 78.12 |
| 2066 | CD | LYS | B | 603 | 62.779 | -2.211 | 102.422 | 1.00 | 78.99 |
| 2067 | CE | LYS | B | 603 | 63.952 | -2.034 | 103.426 | 1.00 | 79.93 |
| 2068 | NZ | LYS | B | 603 | 64.536 | -0.656 | 103.573 | 1.00 | 79.82 |
| 2069 | C | LYS | B | 603 | 61.103 | -4.418 | 100.921 | 1.00 | 76.81 |
| 2070 | O | LYS | B | 603 | 61.315 | -4.798 | 102.072 | 1.00 | 75.16 |
| 2071 | N | PHE | B | 604 | 59.938 | -3.975 | 100.457 | 1.00 | 76.03 |
| 2072 | CA | PHE | B | 604 | 58.711 | -3.929 | 101.207 | 1.00 | 74.92 |
| 2073 | CB | PHE | B | 604 | 58.102 | -2.575 | 100.991 | 1.00 | 76.05 |
| 2074 | CG | PHE | B | 604 | 58.700 | -1.538 | 101.857 | 1.00 | 78.39 |
| 2075 | CD1 | PHE | B | 604 | 58.564 | -1.631 | 103.231 | 1.00 | 79.39 |
| 2076 | CE1 | PHE | B | 604 | 59.115 | -0.671 | 104.059 | 1.00 | 84.10 |
| 2077 | CZ | PHE | B | 604 | 59.854 | 0.395 | 103.511 | 1.00 | 81.74 |
| 2078 | CE2 | PHE | B | 604 | 60.017 | 0.474 | 102.144 | 1.00 | 82.47 |
| 2079 | CD2 | PHE | B | 604 | 59.448 | -0.503 | 101.312 | 1.00 | 81.05 |
| 2080 | C | PHE | B | 604 | 57.783 | -5.006 | 100.707 | 1.00 | 73.54 |
| 2081 | O | PHE | B | 604 | 56.553 | -4.941 | 100.826 | 1.00 | 73.46 |
| 2082 | N | THR | B | 605 | 58.368 | -6.069 | 100.190 | 1.00 | 71.71 |
| 2083 | CA | THR | B | 605 | 57.496 | -7.068 | 99.640 | 1.00 | 68.96 |
| 2084 | CB | THR | B | 605 | 57.540 | -6.922 | 98.163 | 1.00 | 68.75 |
| 2085 | OG1 | THR | B | 605 | 57.203 | -8.191 | 97.632 | 1.00 | 71.34 |
| 2086 | CG2 | THR | B | 605 | 58.991 | -6.774 | 97.722 | 1.00 | 71.15 |
| 2087 | C | THR | B | 605 | 57.874 | -8.494 | 99.969 | 1.00 | 65.74 |
| 2088 | O | THR | B | 605 | 59.000 | -8.868 | 99.864 | 1.00 | 66.65 |
| 2089 | N | THR | B | 606 | 56.897 | -9.294 | 100.339 | 1.00 | 61.47 |
| 2090 | CA | THR | B | 606 | 57.083 | -10.702 | 100.542 | 1.00 | 56.89 |
| 2091 | CB | THR | B | 606 | 55.818 | -11.150 | 101.234 | 1.00 | 58.04 |
| 2092 | OG1 | THR | B | 606 | 55.636 | -10.407 | 102.470 | 1.00 | 53.91 |
| 2093 | CG2 | THR | B | 606 | 55.854 | -12.662 | 101.579 | 1.00 | 56.07 |
| 2094 | C | THR | B | 606 | 57.153 | -11.402 | 99.182 | 1.00 | 55.32 |
| 2095 | O | THR | B | 606 | 56.376 | -11.139 | 98.285 | 1.00 | 55.18 |
| 2096 | N | GLU | B | 607 | 58.053 | -12.330 | 99.008 | 1.00 | 52.87 |
| 2097 | CA | GLU | B | 607 | 58.113 | -13.077 | 97.771 | 1.00 | 48.83 |
| 2098 | CB | GLU | B | 607 | 59.550 | -13.585 | 97.546 | 1.00 | 50.19 |
| 2099 | CG | GLU | B | 607 | 59.720 | -14.650 | 96.488 | 1.00 | 49.52 |
| 2100 | CD | GLU | B | 607 | 59.828 | -14.069 | 95.132 | 1.00 | 53.13 |

FIGURE 3AQ

| A | B | C | D | E | F | G | H | I | J |
|---|---|---|---|---|---|---|---|---|---|
| 2101 | OE1 | GLU | B | 607 | 59.999 | -12.782 | 95.021 | 1.00 | 47.52 |
| 2102 | OE2 | GLU | B | 607 | 59.708 | -14.931 | 94.179 | 1.00 | 56.60 |
| 2103 | C | GLU | B | 607 | 57.128 | -14.194 | 97.907 | 1.00 | 47.66 |
| 2104 | O | GLU | B | 607 | 57.022 | -14.795 | 98.940 | 1.00 | 45.85 |
| 2105 | N | ILE | B | 608 | 56.391 | -14.548 | 96.865 | 1.00 | 47.65 |
| 2106 | CA | ILE | B | 608 | 55.448 | -15.608 | 97.148 | 1.00 | 47.68 |
| 2107 | CB | ILE | B | 608 | 54.064 | -15.132 | 96.825 | 1.00 | 48.07 |
| 2108 | CG1 | ILE | B | 608 | 53.550 | -14.230 | 97.980 | 1.00 | 49.31 |
| 2109 | CD1 | ILE | B | 608 | 52.448 | -13.233 | 97.562 | 1.00 | 50.75 |
| 2110 | CG2 | ILE | B | 608 | 53.146 | -16.282 | 96.537 | 1.00 | 42.03 |
| 2111 | C | ILE | B | 608 | 55.742 | -16.879 | 96.433 | 1.00 | 48.49 |
| 2112 | O | ILE | B | 608 | 56.251 | -16.848 | 95.356 | 1.00 | 47.91 |
| 2113 | N | HIS | B | 609 | 55.425 | -18.022 | 97.025 | 1.00 | 49.63 |
| 2114 | CA | HIS | B | 609 | 55.656 | -19.227 | 96.270 | 1.00 | 51.07 |
| 2115 | CB | HIS | B | 609 | 56.018 | -20.399 | 97.228 | 1.00 | 52.62 |
| 2116 | CG | HIS | B | 609 | 56.581 | -21.599 | 96.510 | 1.00 | 58.19 |
| 2117 | ND1 | HIS | B | 609 | 55.816 | -22.693 | 96.162 | 1.00 | 61.53 |
| 2118 | CE1 | HIS | B | 609 | 56.579 | -23.592 | 95.553 | 1.00 | 64.63 |
| 2119 | NE2 | HIS | B | 609 | 57.808 | -23.110 | 95.462 | 1.00 | 68.36 |
| 2120 | CD2 | HIS | B | 609 | 57.837 | -21.866 | 96.060 | 1.00 | 67.33 |
| 2121 | C | HIS | B | 609 | 54.553 | -19.610 | 95.259 | 1.00 | 49.78 |
| 2122 | O | HIS | B | 609 | 53.384 | -19.793 | 95.618 | 1.00 | 51.06 |
| 2123 | N | PRO | B | 610 | 54.961 | -19.951 | 94.060 | 1.00 | 49.31 |
| 2124 | CA | PRO | B | 610 | 54.043 | -20.289 | 92.937 | 1.00 | 48.79 |
| 2125 | CB | PRO | B | 610 | 54.978 | -20.868 | 91.902 | 1.00 | 47.24 |
| 2126 | CG | PRO | B | 610 | 56.241 | -20.130 | 92.245 | 1.00 | 45.60 |
| 2127 | CD | PRO | B | 610 | 56.362 | -20.127 | 93.691 | 1.00 | 48.27 |
| 2128 | C | PRO | B | 610 | 52.968 | -21.233 | 93.256 | 1.00 | 47.95 |
| 2129 | O | PRO | B | 610 | 51.831 | -21.007 | 92.869 | 1.00 | 49.54 |
| 2130 | N | SER | B | 611 | 53.307 | -22.313 | 93.907 | 1.00 | 48.59 |
| 2131 | CA | SER | B | 611 | 52.298 | -23.175 | 94.438 | 1.00 | 48.44 |
| 2132 | CB | SER | B | 611 | 52.899 | -24.417 | 95.162 | 1.00 | 51.57 |
| 2133 | OG | SER | B | 611 | 53.726 | -24.112 | 96.289 | 1.00 | 52.63 |
| 2134 | C | SER | B | 611 | 51.472 | -22.460 | 95.404 | 1.00 | 47.60 |
| 2135 | O | SER | B | 611 | 50.501 | -22.969 | 95.803 | 1.00 | 48.97 |
| 2136 | N | CYS | B | 612 | 51.820 | -21.290 | 95.872 | 1.00 | 46.75 |
| 2137 | CA | CYS | B | 612 | 50.813 | -20.743 | 96.749 | 1.00 | 48.06 |
| 2138 | CB | CYS | B | 612 | 51.361 | -19.740 | 97.818 | 1.00 | 47.86 |
| 2139 | SG | CYS | B | 612 | 52.389 | -20.799 | 98.813 | 1.00 | 51.39 |
| 2140 | C | CYS | B | 612 | 49.624 | -20.195 | 96.060 | 1.00 | 45.77 |
| 2141 | O | CYS | B | 612 | 48.614 | -19.972 | 96.685 | 1.00 | 45.07 |
| 2142 | N | VAL | B | 613 | 49.747 | -20.011 | 94.767 | 1.00 | 44.88 |
| 2143 | CA | VAL | B | 613 | 48.774 | -19.212 | 94.037 | 1.00 | 44.04 |
| 2144 | CB | VAL | B | 613 | 49.503 | -18.166 | 93.300 | 1.00 | 45.69 |
| 2145 | CG1 | VAL | B | 613 | 48.618 | -17.575 | 92.151 | 1.00 | 41.35 |
| 2146 | CG2 | VAL | B | 613 | 50.034 | -17.191 | 94.320 | 1.00 | 41.89 |
| 2147 | C | VAL | B | 613 | 47.999 | -19.928 | 93.015 | 1.00 | 42.53 |
| 2148 | O | VAL | B | 613 | 48.497 | -20.712 | 92.308 | 1.00 | 43.54 |
| 2149 | N | THR | B | 614 | 46.777 | -19.543 | 92.870 | 1.00 | 40.71 |
| 2150 | CA | THR | B | 614 | 45.947 | -20.229 | 91.985 | 1.00 | 41.54 |
| 2151 | CB | THR | B | 614 | 45.183 | -21.096 | 92.969 | 1.00 | 40.51 |
| 2152 | OG1 | THR | B | 614 | 45.217 | -22.498 | 92.671 | 1.00 | 48.61 |

FIGURE 3AR

| A | B | C | D | E | F | G | H | I | J |
|---|---|---|---|---|---|---|---|---|---|
| 2153 | CG2 | THR | B | 614 | 43.817 | -20.769 | 93.108 | 1.00 | 44.50 |
| 2154 | C | THR | B | 614 | 45.095 | -19.149 | 91.179 | 1.00 | 41.38 |
| 2155 | O | THR | B | 614 | 44.528 | -18.144 | 91.814 | 1.00 | 42.18 |
| 2156 | N | ARG | B | 615 | 44.943 | -19.369 | 89.853 | 1.00 | 38.93 |
| 2157 | CA | ARG | B | 615 | 44.168 | -18.494 | 88.956 | 1.00 | 36.43 |
| 2158 | CB | ARG | B | 615 | 44.933 | -18.179 | 87.724 | 1.00 | 36.87 |
| 2159 | CG | ARG | B | 615 | 46.293 | -17.663 | 87.956 | 1.00 | 35.71 |
| 2160 | CD | ARG | B | 615 | 47.125 | -17.512 | 86.727 | 1.00 | 38.53 |
| 2161 | NE | ARG | B | 615 | 47.289 | -18.840 | 86.152 | 1.00 | 38.81 |
| 2162 | CZ | ARG | B | 615 | 47.844 | -19.126 | 84.944 | 1.00 | 38.46 |
| 2163 | NH1 | ARG | B | 615 | 47.984 | -20.387 | 84.635 | 1.00 | 31.60 |
| 2164 | NH2 | ARG | B | 615 | 48.288 | -18.181 | 84.111 | 1.00 | 33.51 |
| 2165 | C | ARG | B | 615 | 42.893 | -19.117 | 88.530 | 1.00 | 37.76 |
| 2166 | O | ARG | B | 615 | 42.807 | -20.263 | 88.159 | 1.00 | 39.62 |
| 2167 | N | GLN | B | 616 | 41.827 | -18.383 | 88.576 | 1.00 | 38.21 |
| 2168 | CA | GLN | B | 616 | 40.604 | -18.954 | 88.262 | 1.00 | 37.39 |
| 2169 | CB | GLN | B | 616 | 39.752 | -18.618 | 89.472 | 1.00 | 39.47 |
| 2170 | CG | GLN | B | 616 | 39.837 | -19.563 | 90.688 | 1.00 | 43.49 |
| 2171 | CD | GLN | B | 616 | 39.636 | -18.814 | 92.022 | 1.00 | 50.53 |
| 2172 | OE1 | GLN | B | 616 | 40.185 | -17.701 | 92.256 | 1.00 | 48.97 |
| 2173 | NE2 | GLN | B | 616 | 38.866 | -19.425 | 92.903 | 1.00 | 57.89 |
| 2174 | C | GLN | B | 616 | 39.977 | -18.178 | 87.047 | 1.00 | 36.84 |
| 2175 | O | GLN | B | 616 | 38.992 | -18.598 | 86.463 | 1.00 | 32.04 |
| 2176 | N | LYS | B | 617 | 40.448 | -16.990 | 86.746 | 1.00 | 35.94 |
| 2177 | CA | LYS | B | 617 | 39.759 | -16.287 | 85.725 | 1.00 | 38.36 |
| 2178 | CB | LYS | B | 617 | 38.377 | -16.007 | 86.263 | 1.00 | 39.22 |
| 2179 | CG | LYS | B | 617 | 37.772 | -14.698 | 86.233 | 1.00 | 42.77 |
| 2180 | CD | LYS | B | 617 | 36.370 | -14.825 | 86.696 | 1.00 | 53.79 |
| 2181 | CE | LYS | B | 617 | 35.593 | -13.466 | 87.025 | 1.00 | 63.68 |
| 2182 | NZ | LYS | B | 617 | 35.717 | -12.927 | 88.489 | 1.00 | 63.21 |
| 2183 | C | LYS | B | 617 | 40.552 | -15.100 | 85.316 | 1.00 | 40.50 |
| 2184 | O | LYS | B | 617 | 41.225 | -14.556 | 86.140 | 1.00 | 42.28 |
| 2185 | N | VAL | B | 618 | 40.594 | -14.712 | 84.039 | 1.00 | 40.89 |
| 2186 | CA | VAL | B | 618 | 41.186 | -13.431 | 83.793 | 1.00 | 40.18 |
| 2187 | CB | VAL | B | 618 | 41.706 | -13.349 | 82.385 | 1.00 | 40.55 |
| 2188 | CG1 | VAL | B | 618 | 42.262 | -11.973 | 82.120 | 1.00 | 44.64 |
| 2189 | CG2 | VAL | B | 618 | 42.780 | -14.535 | 82.162 | 1.00 | 41.80 |
| 2190 | C | VAL | B | 618 | 40.213 | -12.346 | 83.975 | 1.00 | 38.00 |
| 2191 | O | VAL | B | 618 | 39.093 | -12.485 | 83.503 | 1.00 | 39.02 |
| 2192 | N | ILE | B | 619 | 40.614 | -11.229 | 84.559 | 1.00 | 38.05 |
| 2193 | CA | ILE | B | 619 | 39.694 | -10.134 | 84.823 | 1.00 | 39.66 |
| 2194 | CB | ILE | B | 619 | 39.608 | -9.832 | 86.309 | 1.00 | 40.93 |
| 2195 | CG1 | ILE | B | 619 | 40.991 | -9.612 | 86.979 | 1.00 | 38.06 |
| 2196 | CD1 | ILE | B | 619 | 40.786 | -9.252 | 88.632 | 1.00 | 36.23 |
| 2197 | CG2 | ILE | B | 619 | 38.943 | -11.004 | 87.102 | 1.00 | 40.94 |
| 2198 | C | ILE | B | 619 | 40.206 | -8.870 | 84.202 | 1.00 | 43.93 |
| 2199 | O | ILE | B | 619 | 39.560 | -7.812 | 84.237 | 1.00 | 42.87 |
| 2200 | N | GLY | B | 620 | 41.393 | -8.925 | 83.623 | 1.00 | 45.17 |
| 2201 | CA | GLY | B | 620 | 41.915 | -7.673 | 83.104 | 1.00 | 47.33 |
| 2202 | C | GLY | B | 620 | 43.224 | -8.092 | 82.429 | 1.00 | 50.85 |
| 2203 | O | GLY | B | 620 | 43.871 | -9.236 | 82.620 | 1.00 | 51.47 |
| 2204 | N | ALA | B | 621 | 43.595 | -7.160 | 81.572 | 1.00 | 51.35 |

FIGURE 3AS

| A | B | C | D | E | F | G | H | I | J |
|---|---|---|---|---|---|---|---|---|---|
| 2205 | CA | ALA | B | 621 | 44.760 | -7.184 | 80.745 | 1.00 | 53.88 |
| 2206 | CB | ALA | B | 621 | 44.426 | -7.688 | 79.316 | 1.00 | 54.10 |
| 2207 | C | ALA | B | 621 | 45.299 | -5.791 | 80.674 | 1.00 | 55.13 |
| 2208 | O | ALA | B | 621 | 44.828 | -4.959 | 79.886 | 1.00 | 57.99 |
| 2209 | N | GLY | B | 622 | 46.264 | -5.589 | 81.554 | 1.00 | 57.03 |
| 2210 | CA | GLY | B | 622 | 47.168 | -4.483 | 81.562 | 1.00 | 59.11 |
| 2211 | C | GLY | B | 622 | 48.209 | -4.562 | 80.477 | 1.00 | 58.66 |
| 2212 | O | GLY | B | 622 | 48.272 | -5.501 | 79.641 | 1.00 | 59.00 |
| 2213 | N | GLU | B | 623 | 49.057 | -3.532 | 80.510 | 1.00 | 59.69 |
| 2214 | CA | GLU | B | 623 | 50.174 | -3.401 | 79.539 | 1.00 | 60.06 |
| 2215 | CB | GLU | B | 623 | 50.715 | -1.953 | 79.435 | 1.00 | 61.65 |
| 2216 | CG | GLU | B | 623 | 51.576 | -1.387 | 80.577 | 1.00 | 66.11 |
| 2217 | CD | GLU | B | 623 | 52.456 | -0.197 | 80.080 | 1.00 | 77.25 |
| 2218 | OE1 | GLU | B | 623 | 52.149 | 0.983 | 80.464 | 1.00 | 79.02 |
| 2219 | OE2 | GLU | B | 623 | 53.437 | -0.432 | 79.272 | 1.00 | 79.70 |
| 2220 | C | GLU | B | 623 | 51.309 | -4.335 | 79.842 | 1.00 | 58.25 |
| 2221 | O | GLU | B | 623 | 52.235 | -4.436 | 79.070 | 1.00 | 60.16 |
| 2222 | N | PHE | B | 624 | 51.275 | -5.016 | 80.970 | 1.00 | 54.74 |
| 2223 | CA | PHE | B | 624 | 52.410 | -5.847 | 81.262 | 1.00 | 51.99 |
| 2224 | CB | PHE | B | 624 | 52.789 | -5.730 | 82.754 | 1.00 | 51.88 |
| 2225 | CG | PHE | B | 624 | 53.391 | -4.399 | 83.133 | 1.00 | 54.02 |
| 2226 | CD1 | PHE | B | 624 | 54.733 | -4.102 | 82.907 | 1.00 | 55.50 |
| 2227 | CE1 | PHE | B | 624 | 55.256 | -2.813 | 83.249 | 1.00 | 56.20 |
| 2228 | CZ | PHE | B | 624 | 54.422 | -1.780 | 83.816 | 1.00 | 56.45 |
| 2229 | CE2 | PHE | B | 624 | 53.062 | -2.046 | 84.037 | 1.00 | 52.77 |
| 2230 | CD2 | PHE | B | 624 | 52.556 | -3.379 | 83.686 | 1.00 | 56.55 |
| 2231 | C | PHE | B | 624 | 51.975 | -7.269 | 80.865 | 1.00 | 50.15 |
| 2232 | O | PHE | B | 624 | 52.725 | -8.128 | 80.468 | 1.00 | 50.83 |
| 2233 | N | GLY | B | 625 | 50.672 | -7.410 | 80.863 | 1.00 | 47.48 |
| 2234 | CA | GLY | B | 625 | 50.054 | -8.656 | 80.601 | 1.00 | 45.33 |
| 2235 | C | GLY | B | 625 | 48.716 | -8.751 | 81.302 | 1.00 | 43.78 |
| 2236 | O | GLY | B | 625 | 48.093 | -7.765 | 81.722 | 1.00 | 43.69 |
| 2237 | N | GLU | B | 626 | 48.326 | -10.005 | 81.484 | 1.00 | 44.33 |
| 2238 | CA | GLU | B | 626 | 47.015 | -10.291 | 82.001 | 1.00 | 43.81 |
| 2239 | CB | GLU | B | 626 | 46.732 | -11.745 | 81.695 | 1.00 | 44.48 |
| 2240 | CG | GLU | B | 626 | 47.155 | -12.117 | 80.292 | 1.00 | 51.57 |
| 2241 | CD | GLU | B | 626 | 45.953 | -12.312 | 79.404 | 1.00 | 61.26 |
| 2242 | OE1 | GLU | B | 626 | 45.469 | -11.265 | 78.940 | 1.00 | 69.20 |
| 2243 | OE2 | GLU | B | 626 | 45.429 | -13.467 | 79.241 | 1.00 | 64.36 |
| 2244 | C | GLU | B | 626 | 46.908 | -10.078 | 83.494 | 1.00 | 40.95 |
| 2245 | O | GLU | B | 626 | 47.921 | -10.120 | 84.202 | 1.00 | 41.04 |
| 2246 | N | VAL | B | 627 | 45.674 | -9.798 | 83.869 | 1.00 | 37.16 |
| 2247 | CA | VAL | B | 627 | 45.186 | -9.710 | 85.213 | 1.00 | 35.92 |
| 2248 | CB | VAL | B | 627 | 44.730 | -8.283 | 85.610 | 1.00 | 34.09 |
| 2249 | CG1 | VAL | B | 627 | 44.433 | -8.208 | 87.155 | 1.00 | 27.95 |
| 2250 | CG2 | VAL | B | 627 | 45.864 | -7.191 | 85.273 | 1.00 | 36.93 |
| 2251 | C | VAL | B | 627 | 44.123 | -10.796 | 85.471 | 1.00 | 35.59 |
| 2252 | O | VAL | B | 627 | 43.112 | -10.850 | 84.773 | 1.00 | 37.84 |
| 2253 | N | TYR | B | 628 | 44.407 | -11.644 | 86.441 | 1.00 | 31.13 |
| 2254 | CA | TYR | B | 628 | 43.597 | -12.753 | 86.884 | 1.00 | 31.63 |
| 2255 | CB | TYR | B | 628 | 44.497 | -14.055 | 87.021 | 1.00 | 30.96 |
| 2256 | CG | TYR | B | 628 | 45.250 | -14.532 | 85.752 | 1.00 | 30.76 |

FIGURE 3AT

| A | B | C | D | E | F | G | H | I | J |
|---|---|---|---|---|---|---|---|---|---|
| 2257 | CD1 | TYR | B | 628 | 46.561 | -14.097 | 85.486 | 1.00 | 28.48 |
| 2258 | CE1 | TYR | B | 628 | 47.279 | -14.488 | 84.434 | 1.00 | 30.85 |
| 2259 | CZ | TYR | B | 628 | 46.688 | -15.369 | 83.475 | 1.00 | 38.38 |
| 2260 | OH | TYR | B | 628 | 47.394 | -15.748 | 82.353 | 1.00 | 43.82 |
| 2261 | CE2 | TYR | B | 628 | 45.377 | -15.760 | 83.588 | 1.00 | 33.96 |
| 2262 | CD2 | TYR | B | 628 | 44.636 | -15.354 | 84.802 | 1.00 | 34.73 |
| 2263 | C | TYR | B | 628 | 43.038 | -12.555 | 88.305 | 1.00 | 33.38 |
| 2264 | O | TYR | B | 628 | 43.643 | -11.894 | 89.182 | 1.00 | 33.26 |
| 2265 | N | LYS | B | 629 | 41.975 | -13.240 | 88.574 | 1.00 | 33.61 |
| 2266 | CA | LYS | B | 629 | 41.460 | -13.260 | 89.864 | 1.00 | 36.43 |
| 2267 | CB | LYS | B | 629 | 39.965 | -13.117 | 89.816 | 1.00 | 34.99 |
| 2268 | CG | LYS | B | 629 | 39.239 | -14.031 | 90.690 | 1.00 | 42.88 |
| 2269 | CD | LYS | B | 629 | 39.362 | -13.567 | 92.036 | 1.00 | 47.09 |
| 2270 | CE | LYS | B | 629 | 39.418 | -14.774 | 92.959 | 1.00 | 51.42 |
| 2271 | NZ | LYS | B | 629 | 38.203 | -15.510 | 93.282 | 1.00 | 38.62 |
| 2272 | C | LYS | B | 629 | 41.838 | -14.646 | 90.264 | 1.00 | 38.05 |
| 2273 | O | LYS | B | 629 | 41.706 | -15.573 | 89.484 | 1.00 | 34.96 |
| 2274 | N | GLY | B | 630 | 42.248 | -14.773 | 91.520 | 1.00 | 39.79 |
| 2275 | CA | GLY | B | 630 | 42.714 | -16.017 | 92.012 | 1.00 | 40.62 |
| 2276 | C | GLY | B | 630 | 42.659 | -16.168 | 93.499 | 1.00 | 41.62 |
| 2277 | O | GLY | B | 630 | 41.952 | -15.455 | 94.134 | 1.00 | 42.67 |
| 2278 | N | MET | B | 631 | 43.414 | -17.122 | 94.046 | 1.00 | 42.11 |
| 2279 | CA | MET | B | 631 | 43.374 | -17.424 | 95.471 | 1.00 | 40.08 |
| 2280 | CB | MET | B | 631 | 42.675 | -18.782 | 95.697 | 1.00 | 39.40 |
| 2281 | CG | MET | B | 631 | 41.244 | -18.772 | 95.422 | 1.00 | 36.74 |
| 2282 | SD | MET | B | 631 | 40.271 | -17.481 | 96.157 | 1.00 | 46.24 |
| 2283 | CE | MET | B | 631 | 40.094 | -18.103 | 98.007 | 1.00 | 44.76 |
| 2284 | C | MET | B | 631 | 44.847 | -17.573 | 95.862 | 1.00 | 40.76 |
| 2285 | O | MET | B | 631 | 45.643 | -18.078 | 95.080 | 1.00 | 38.68 |
| 2286 | N | LEU | B | 632 | 45.205 | -17.167 | 97.064 | 1.00 | 41.51 |
| 2287 | CA | LEU | B | 632 | 46.542 | -17.311 | 97.497 | 1.00 | 43.33 |
| 2288 | CB | LEU | B | 632 | 47.248 | -15.967 | 97.744 | 1.00 | 43.33 |
| 2289 | CG | LEU | B | 632 | 48.602 | -15.982 | 98.533 | 1.00 | 39.74 |
| 2290 | CD1 | LEU | B | 632 | 49.835 | -16.156 | 97.728 | 1.00 | 38.69 |
| 2291 | CD2 | LEU | B | 632 | 48.819 | -14.657 | 99.169 | 1.00 | 41.35 |
| 2292 | C | LEU | B | 632 | 46.389 | -18.052 | 98.813 | 1.00 | 47.21 |
| 2293 | O | LEU | B | 632 | 45.547 | -17.737 | 99.630 | 1.00 | 46.45 |
| 2294 | N | ALA | B | 633 | 47.235 | -19.043 | 98.998 | 1.00 | 51.87 |
| 2295 | CA | ALA | B | 633 | 47.226 | -19.803 | 100.227 | 1.00 | 56.44 |
| 2296 | CB | ALA | B | 633 | 47.668 | -21.328 | 100.004 | 1.00 | 56.80 |
| 2297 | C | ALA | B | 633 | 48.165 | -19.045 | 101.124 | 1.00 | 57.40 |
| 2298 | O | ALA | B | 633 | 49.243 | -18.761 | 100.712 | 1.00 | 56.04 |
| 2299 | N | THR | B | 634 | 47.593 | -18.599 | 102.247 | 1.00 | 61.86 |
| 2300 | CA | THR | B | 634 | 48.165 | -17.932 | 103.448 | 1.00 | 65.92 |
| 2301 | CB | THR | B | 634 | 47.508 | -16.513 | 103.700 | 1.00 | 67.32 |
| 2302 | OG1 | THR | B | 634 | 46.250 | -16.420 | 102.996 | 1.00 | 67.54 |
| 2303 | CG2 | THR | B | 634 | 48.373 | -15.309 | 103.123 | 1.00 | 69.80 |
| 2304 | C | THR | B | 634 | 47.620 | -18.840 | 104.576 | 1.00 | 67.85 |
| 2305 | O | THR | B | 634 | 48.260 | -19.118 | 105.602 | 1.00 | 70.48 |
| 2306 | N | LYS | B | 639 | 44.627 | -20.684 | 106.044 | 1.00 | 68.69 |
| 2307 | CA | LYS | B | 639 | 43.550 | -20.394 | 105.027 | 1.00 | 66.79 |
| 2308 | CB | LYS | B | 639 | 42.454 | -19.415 | 105.557 | 1.00 | 67.15 |

FIGURE 3AU

| A | B | C | D | E | F | G | H | I | J |
|---|---|---|---|---|---|---|---|---|---|
| 2309 | CG | LYS | B | 639 | 42.933 | -18.018 | 106.081 | 1.00 | 68.24 |
| 2310 | CD | LYS | B | 639 | 41.772 | -17.136 | 106.688 | 1.00 | 74.03 |
| 2311 | CE | LYS | B | 639 | 41.759 | -17.148 | 108.280 | 1.00 | 79.83 |
| 2312 | NZ | LYS | B | 639 | 41.868 | -18.541 | 108.918 | 1.00 | 77.67 |
| 2313 | C | LYS | B | 639 | 44.048 | -20.001 | 103.622 | 1.00 | 65.00 |
| 2314 | O | LYS | B | 639 | 45.070 | -20.547 | 103.104 | 1.00 | 65.73 |
| 2315 | N | GLU | B | 640 | 43.302 | -19.082 | 103.006 | 1.00 | 60.87 |
| 2316 | CA | GLU | B | 640 | 43.491 | -18.779 | 101.612 | 1.00 | 57.13 |
| 2317 | CB | GLU | B | 640 | 42.992 | -19.919 | 100.768 | 1.00 | 58.15 |
| 2318 | CG | GLU | B | 640 | 41.495 | -19.957 | 100.494 | 1.00 | 60.04 |
| 2319 | CD | GLU | B | 640 | 41.096 | -20.995 | 99.392 | 1.00 | 64.28 |
| 2320 | OE1 | GLU | B | 640 | 39.891 | -21.294 | 99.310 | 1.00 | 63.14 |
| 2321 | OE2 | GLU | B | 640 | 41.957 | -21.522 | 98.604 | 1.00 | 61.98 |
| 2322 | C | GLU | B | 640 | 42.667 | -17.575 | 101.332 | 1.00 | 54.89 |
| 2323 | O | GLU | B | 640 | 41.528 | -17.402 | 101.881 | 1.00 | 53.30 |
| 2324 | N | VAL | B | 641 | 43.261 | -16.690 | 100.573 | 1.00 | 49.18 |
| 2325 | CA | VAL | B | 641 | 42.508 | -15.531 | 100.324 | 1.00 | 48.68 |
| 2326 | CB | VAL | B | 641 | 42.994 | -14.411 | 101.085 | 1.00 | 49.50 |
| 2327 | CG1 | VAL | B | 641 | 44.390 | -14.089 | 100.811 | 1.00 | 48.06 |
| 2328 | CG2 | VAL | B | 641 | 42.291 | -13.327 | 100.489 | 1.00 | 57.76 |
| 2329 | C | VAL | B | 641 | 42.394 | -15.118 | 98.866 | 1.00 | 45.71 |
| 2330 | O | VAL | B | 641 | 43.174 | -15.525 | 97.986 | 1.00 | 46.28 |
| 2331 | N | PRO | B | 642 | 41.310 | -14.483 | 98.553 | 1.00 | 43.57 |
| 2332 | CA | PRO | B | 642 | 41.105 | -14.052 | 97.166 | 1.00 | 40.99 |
| 2333 | CB | PRO | B | 642 | 39.607 | -13.620 | 97.182 | 1.00 | 40.42 |
| 2334 | CG | PRO | B | 642 | 39.389 | -13.154 | 98.678 | 1.00 | 41.18 |
| 2335 | CD | PRO | B | 642 | 40.063 | -14.358 | 99.351 | 1.00 | 42.33 |
| 2336 | C | PRO | B | 642 | 42.062 | -12.898 | 96.773 | 1.00 | 38.73 |
| 2337 | O | PRO | B | 642 | 42.234 | -12.022 | 97.550 | 1.00 | 38.87 |
| 2338 | N | VAL | B | 643 | 42.659 | -12.896 | 95.580 | 1.00 | 36.26 |
| 2339 | CA | VAL | B | 643 | 43.631 | -11.916 | 95.253 | 1.00 | 35.27 |
| 2340 | CB | VAL | B | 643 | 44.920 | -12.558 | 95.411 | 1.00 | 35.78 |
| 2341 | CG1 | VAL | B | 643 | 45.284 | -12.734 | 96.921 | 1.00 | 33.58 |
| 2342 | CG2 | VAL | B | 643 | 44.782 | -13.818 | 94.815 | 1.00 | 34.92 |
| 2343 | C | VAL | B | 643 | 43.508 | -11.546 | 93.775 | 1.00 | 36.64 |
| 2344 | O | VAL | B | 643 | 43.123 | -12.389 | 92.922 | 1.00 | 38.44 |
| 2345 | N | ALA | B | 644 | 43.893 | -10.326 | 93.428 | 1.00 | 33.63 |
| 2346 | CA | ALA | B | 644 | 44.132 | -10.046 | 91.975 | 1.00 | 33.25 |
| 2347 | CB | ALA | B | 644 | 43.934 | -8.580 | 91.626 | 1.00 | 29.05 |
| 2348 | C | ALA | B | 644 | 45.585 | -10.378 | 91.637 | 1.00 | 33.38 |
| 2349 | O | ALA | B | 644 | 46.510 | -10.129 | 92.483 | 1.00 | 34.78 |
| 2350 | N | ILE | B | 645 | 45.812 | -10.898 | 90.423 | 1.00 | 34.84 |
| 2351 | CA | ILE | B | 645 | 47.140 | -11.220 | 89.994 | 1.00 | 34.70 |
| 2352 | CB | ILE | B | 645 | 47.222 | -12.634 | 89.772 | 1.00 | 36.71 |
| 2353 | CG1 | ILE | B | 645 | 46.794 | -13.340 | 91.011 | 1.00 | 36.62 |
| 2354 | CD1 | ILE | B | 645 | 46.106 | -14.627 | 90.739 | 1.00 | 35.69 |
| 2355 | CG2 | ILE | B | 645 | 48.668 | -13.009 | 89.414 | 1.00 | 36.76 |
| 2356 | C | ILE | B | 645 | 47.509 | -10.663 | 88.716 | 1.00 | 35.66 |
| 2357 | O | ILE | B | 645 | 46.933 | -11.078 | 87.655 | 1.00 | 33.28 |
| 2358 | N | LYS | B | 646 | 48.576 | -9.822 | 88.775 | 1.00 | 37.62 |
| 2359 | CA | LYS | B | 646 | 49.100 | -9.156 | 87.627 | 1.00 | 39.51 |
| 2360 | CB | LYS | B | 646 | 49.392 | -7.713 | 87.934 | 1.00 | 40.50 |

FIGURE 3AV

| A | B | C | D | E | F | G | H | I | J |
|---|---|---|---|---|---|---|---|---|---|
| 2361 | CG | LYS | B | 646 | 48.112 | -6.902 | 88.103 | 1.00 | 43.92 |
| 2362 | CD | LYS | B | 646 | 48.459 | -5.427 | 88.516 | 1.00 | 51.47 |
| 2363 | CE | LYS | B | 646 | 48.982 | -4.629 | 87.354 | 1.00 | 57.30 |
| 2364 | NZ | LYS | B | 646 | 49.752 | -3.453 | 87.904 | 1.00 | 62.15 |
| 2365 | C | LYS | B | 646 | 50.303 | -9.865 | 87.182 | 1.00 | 42.10 |
| 2366 | O | LYS | B | 646 | 51.198 | -10.125 | 87.959 | 1.00 | 43.88 |
| 2367 | N | THR | B | 647 | 50.265 | -10.323 | 85.945 | 1.00 | 45.48 |
| 2368 | CA | THR | B | 647 | 51.429 | -10.990 | 85.290 | 1.00 | 46.92 |
| 2369 | CB | THR | B | 647 | 50.985 | -12.184 | 84.508 | 1.00 | 45.72 |
| 2370 | OG1 | THR | B | 647 | 49.855 | -11.807 | 83.714 | 1.00 | 49.53 |
| 2371 | CG2 | THR | B | 647 | 50.425 | -13.128 | 85.536 | 1.00 | 44.75 |
| 2372 | C | THR | B | 647 | 52.160 | -10.155 | 84.313 | 1.00 | 47.24 |
| 2373 | O | THR | B | 647 | 51.699 | -9.142 | 83.797 | 1.00 | 48.92 |
| 2374 | N | LEU | B | 648 | 53.351 | -10.596 | 84.070 | 1.00 | 48.96 |
| 2375 | CA | LEU | B | 648 | 54.249 | -9.855 | 83.227 | 1.00 | 50.53 |
| 2376 | CB | LEU | B | 648 | 55.590 | -9.732 | 83.968 | 1.00 | 49.36 |
| 2377 | CG | LEU | B | 648 | 56.542 | -8.585 | 83.642 | 1.00 | 48.99 |
| 2378 | CD1 | LEU | B | 648 | 58.040 | -8.996 | 83.579 | 1.00 | 48.58 |
| 2379 | CD2 | LEU | B | 648 | 56.116 | -7.850 | 82.381 | 1.00 | 43.45 |
| 2380 | C | LEU | B | 648 | 54.374 | -10.784 | 82.043 | 1.00 | 51.82 |
| 2381 | O | LEU | B | 648 | 54.927 | -11.893 | 82.196 | 1.00 | 52.19 |
| 2382 | N | ALA | B | 649 | 53.868 | -10.417 | 80.869 | 1.00 | 54.10 |
| 2383 | CA | ALA | B | 649 | 54.004 | -11.362 | 79.756 | 1.00 | 56.21 |
| 2384 | CB | ALA | B | 649 | 53.270 | -10.894 | 78.487 | 1.00 | 58.42 |
| 2385 | C | ALA | B | 649 | 55.446 | -11.687 | 79.395 | 1.00 | 56.49 |
| 2386 | O | ALA | B | 649 | 56.377 | -10.974 | 79.740 | 1.00 | 56.04 |
| 2387 | N | ALA | B | 650 | 55.630 | -12.811 | 78.718 | 1.00 | 56.23 |
| 2388 | CA | ALA | B | 650 | 56.941 | -13.049 | 78.140 | 1.00 | 56.52 |
| 2389 | CB | ALA | B | 650 | 57.027 | -14.433 | 77.525 | 1.00 | 57.04 |
| 2390 | C | ALA | B | 650 | 57.144 | -11.965 | 77.057 | 1.00 | 56.58 |
| 2391 | O | ALA | B | 650 | 56.155 | -11.510 | 76.413 | 1.00 | 56.42 |
| 2392 | N | GLY | B | 651 | 58.416 | -11.595 | 76.834 | 1.00 | 55.88 |
| 2393 | CA | GLY | B | 651 | 58.778 | -10.553 | 75.873 | 1.00 | 57.02 |
| 2394 | C | GLY | B | 651 | 59.312 | -9.445 | 76.746 | 1.00 | 57.57 |
| 2395 | O | GLY | B | 651 | 59.712 | -8.311 | 76.347 | 1.00 | 58.43 |
| 2396 | N | TYR | B | 652 | 59.366 | -9.788 | 78.022 | 1.00 | 58.43 |
| 2397 | CA | TYR | B | 652 | 59.573 | -8.682 | 78.940 | 1.00 | 57.59 |
| 2398 | CB | TYR | B | 652 | 59.435 | -9.019 | 80.478 | 1.00 | 54.77 |
| 2399 | CG | TYR | B | 652 | 60.213 | -10.134 | 81.202 | 1.00 | 56.20 |
| 2400 | CD1 | TYR | B | 652 | 59.693 | -11.415 | 81.380 | 1.00 | 57.11 |
| 2401 | CE1 | TYR | B | 652 | 60.384 | -12.382 | 82.148 | 1.00 | 54.44 |
| 2402 | CZ | TYR | B | 652 | 61.565 | -12.044 | 82.766 | 1.00 | 59.06 |
| 2403 | OH | TYR | B | 652 | 62.237 | -13.076 | 83.485 | 1.00 | 65.51 |
| 2404 | CE2 | TYR | B | 652 | 62.093 | -10.787 | 82.618 | 1.00 | 57.44 |
| 2405 | CD2 | TYR | B | 652 | 61.426 | -9.857 | 81.867 | 1.00 | 54.60 |
| 2406 | C | TYR | B | 652 | 60.713 | -7.765 | 78.455 | 1.00 | 57.13 |
| 2407 | O | TYR | B | 652 | 61.890 | -8.195 | 78.247 | 1.00 | 56.27 |
| 2408 | N | THR | B | 653 | 60.253 | -6.536 | 78.165 | 1.00 | 59.21 |
| 2409 | CA | THR | B | 653 | 61.056 | -5.309 | 77.938 | 1.00 | 61.19 |
| 2410 | CB | THR | B | 653 | 60.410 | -4.127 | 78.740 | 1.00 | 62.43 |
| 2411 | OG1 | THR | B | 653 | 58.961 | -3.939 | 78.394 | 1.00 | 63.91 |
| 2412 | CG2 | THR | B | 653 | 61.197 | -2.732 | 78.552 | 1.00 | 59.49 |

FIGURE 3AW

| A | B | C | D | E | F | G | H | I | J |
|---|---|---|---|---|---|---|---|---|---|
| 2413 | C | THR | B | 653 | 62.510 | -5.458 | 78.383 | 1.00 | 62.37 |
| 2414 | O | THR | B | 653 | 63.408 | -5.096 | 77.655 | 1.00 | 63.93 |
| 2415 | N | ALA | B | 654 | 62.748 | -6.047 | 79.537 | 1.00 | 65.18 |
| 2416 | CA | ALA | B | 654 | 64.118 | -6.339 | 80.065 | 1.00 | 66.92 |
| 2417 | CB | ALA | B | 654 | 65.181 | -6.632 | 78.995 | 1.00 | 68.35 |
| 2418 | C | ALA | B | 654 | 64.482 | -5.184 | 80.915 | 1.00 | 67.15 |
| 2419 | O | ALA | B | 654 | 65.452 | -5.259 | 81.675 | 1.00 | 68.11 |
| 2420 | N | LYS | B | 655 | 63.683 | -4.123 | 80.723 | 1.00 | 65.70 |
| 2421 | CA | LYS | B | 655 | 63.542 | -3.126 | 81.715 | 1.00 | 64.02 |
| 2422 | CB | LYS | B | 655 | 64.033 | -1.755 | 81.277 | 1.00 | 64.04 |
| 2423 | CG | LYS | B | 655 | 62.873 | -0.760 | 81.003 | 1.00 | 62.73 |
| 2424 | CD | LYS | B | 655 | 62.975 | 0.659 | 81.731 | 1.00 | 66.52 |
| 2425 | CE | LYS | B | 655 | 61.719 | 1.600 | 81.419 | 1.00 | 70.62 |
| 2426 | NZ | LYS | B | 655 | 61.431 | 3.073 | 82.018 | 1.00 | 71.15 |
| 2427 | C | LYS | B | 655 | 62.035 | -3.062 | 81.945 | 1.00 | 64.99 |
| 2428 | O | LYS | B | 655 | 61.594 | -2.189 | 82.707 | 1.00 | 65.05 |
| 2429 | N | ALA | B | 656 | 61.184 | -3.849 | 81.273 | 1.00 | 65.62 |
| 2430 | CA | ALA | B | 656 | 59.741 | -3.683 | 81.659 | 1.00 | 63.59 |
| 2431 | CB | ALA | B | 656 | 58.729 | -4.389 | 80.698 | 1.00 | 63.21 |
| 2432 | C | ALA | B | 656 | 59.776 | -4.378 | 83.002 | 1.00 | 63.77 |
| 2433 | O | ALA | B | 656 | 59.045 | -4.059 | 83.953 | 1.00 | 65.32 |
| 2434 | N | ALA | B | 657 | 60.688 | -5.343 | 83.081 | 1.00 | 62.81 |
| 2435 | CA | ALA | B | 657 | 60.896 | -5.994 | 84.326 | 1.00 | 61.44 |
| 2436 | CB | ALA | B | 657 | 62.153 | -6.830 | 84.259 | 1.00 | 62.87 |
| 2437 | C | ALA | B | 657 | 60.921 | -5.063 | 85.578 | 1.00 | 61.39 |
| 2438 | O | ALA | B | 657 | 60.315 | -5.374 | 86.615 | 1.00 | 60.78 |
| 2439 | N | VAL | B | 658 | 61.571 | -3.906 | 85.517 | 1.00 | 60.99 |
| 2440 | CA | VAL | B | 658 | 61.752 | -3.219 | 86.804 | 1.00 | 60.46 |
| 2441 | CB | VAL | B | 658 | 62.852 | -2.176 | 86.857 | 1.00 | 60.81 |
| 2442 | CG1 | VAL | B | 658 | 64.200 | -2.834 | 86.665 | 1.00 | 62.51 |
| 2443 | CG2 | VAL | B | 658 | 62.560 | -1.118 | 85.803 | 1.00 | 62.91 |
| 2444 | C | VAL | B | 658 | 60.583 | -2.403 | 87.005 | 1.00 | 59.81 |
| 2445 | O | VAL | B | 658 | 60.146 | -2.289 | 88.146 | 1.00 | 58.61 |
| 2446 | N | ASP | B | 659 | 60.080 | -1.838 | 85.890 | 1.00 | 58.44 |
| 2447 | CA | ASP | B | 659 | 58.911 | -0.960 | 85.994 | 1.00 | 57.85 |
| 2448 | CB | ASP | B | 659 | 58.611 | -0.274 | 84.666 | 1.00 | 58.73 |
| 2449 | CG | ASP | B | 659 | 59.082 | 1.150 | 84.657 | 1.00 | 62.54 |
| 2450 | OD1 | ASP | B | 659 | 59.986 | 1.499 | 83.839 | 1.00 | 65.80 |
| 2451 | OD2 | ASP | B | 659 | 58.612 | 1.992 | 85.486 | 1.00 | 70.42 |
| 2452 | C | ASP | B | 659 | 57.696 | -1.717 | 86.556 | 1.00 | 55.40 |
| 2453 | O | ASP | B | 659 | 56.889 | -1.170 | 87.285 | 1.00 | 54.47 |
| 2454 | N | PHE | B | 660 | 57.645 | -2.993 | 86.222 | 1.00 | 53.30 |
| 2455 | CA | PHE | B | 660 | 56.616 | -3.893 | 86.688 | 1.00 | 51.47 |
| 2456 | CB | PHE | B | 660 | 56.687 | -5.210 | 85.888 | 1.00 | 50.03 |
| 2457 | CG | PHE | B | 660 | 55.699 | -6.247 | 86.324 | 1.00 | 45.78 |
| 2458 | CD1 | PHE | B | 660 | 54.375 | -6.154 | 85.964 | 1.00 | 42.78 |
| 2459 | CE1 | PHE | B | 660 | 53.495 | -7.117 | 86.364 | 1.00 | 29.42 |
| 2460 | CZ | PHE | B | 660 | 53.919 | -8.122 | 87.106 | 1.00 | 35.70 |
| 2461 | CE2 | PHE | B | 660 | 55.234 | -8.230 | 87.541 | 1.00 | 34.32 |
| 2462 | CD2 | PHE | B | 660 | 56.092 | -7.299 | 87.134 | 1.00 | 41.88 |
| 2463 | C | PHE | B | 660 | 56.809 | -4.159 | 88.180 | 1.00 | 51.98 |
| 2464 | O | PHE | B | 660 | 55.970 | -3.826 | 88.979 | 1.00 | 53.32 |

FIGURE 3AX

| A | B | C | D | E | F | G | H | I | J |
|---|---|---|---|---|---|---|---|---|---|
| 2465 | N | LEU | B | 661 | 57.867 | -4.818 | 88.587 | 1.00 | 51.16 |
| 2466 | CA | LEU | B | 661 | 58.052 | -4.986 | 90.025 | 1.00 | 49.90 |
| 2467 | CB | LEU | B | 661 | 59.410 | -5.608 | 90.304 | 1.00 | 50.17 |
| 2468 | CG | LEU | B | 661 | 59.401 | -7.101 | 89.967 | 1.00 | 49.47 |
| 2469 | CD1 | LEU | B | 661 | 60.075 | -7.725 | 91.087 | 1.00 | 49.31 |
| 2470 | CD2 | LEU | B | 661 | 58.040 | -7.634 | 90.013 | 1.00 | 47.87 |
| 2471 | C | LEU | B | 661 | 58.084 | -3.654 | 90.722 | 1.00 | 48.85 |
| 2472 | O | LEU | B | 661 | 57.712 | -3.584 | 91.846 | 1.00 | 52.10 |
| 2473 | N | GLY | B | 662 | 58.555 | -2.595 | 90.098 | 1.00 | 46.78 |
| 2474 | CA | GLY | B | 662 | 58.683 | -1.340 | 90.803 | 1.00 | 44.02 |
| 2475 | C | GLY | B | 662 | 57.361 | -0.929 | 91.466 | 1.00 | 45.84 |
| 2476 | O | GLY | B | 662 | 57.336 | -0.347 | 92.600 | 1.00 | 45.76 |
| 2477 | N | GLU | B | 663 | 56.258 | -1.222 | 90.753 | 1.00 | 44.38 |
| 2478 | CA | GLU | B | 663 | 54.970 | -0.787 | 91.194 | 1.00 | 43.00 |
| 2479 | CB | GLU | B | 663 | 53.843 | -1.079 | 90.191 | 1.00 | 43.42 |
| 2480 | CG | GLU | B | 663 | 52.554 | -1.313 | 91.003 | 1.00 | 48.94 |
| 2481 | CD | GLU | B | 663 | 51.261 | -1.147 | 90.298 | 1.00 | 55.99 |
| 2482 | OE1 | GLU | B | 663 | 50.348 | -0.344 | 90.786 | 1.00 | 56.46 |
| 2483 | OE2 | GLU | B | 663 | 51.131 | -1.926 | 89.326 | 1.00 | 62.78 |
| 2484 | C | GLU | B | 663 | 54.735 | -1.449 | 92.490 | 1.00 | 40.69 |
| 2485 | O | GLU | B | 663 | 54.243 | -0.836 | 93.429 | 1.00 | 39.77 |
| 2486 | N | ALA | B | 664 | 55.147 | -2.699 | 92.549 | 1.00 | 41.23 |
| 2487 | CA | ALA | B | 664 | 54.964 | -3.521 | 93.768 | 1.00 | 42.51 |
| 2488 | CB | ALA | B | 664 | 55.361 | -4.924 | 93.525 | 1.00 | 40.07 |
| 2489 | C | ALA | B | 664 | 55.811 | -2.917 | 94.871 | 1.00 | 42.68 |
| 2490 | O | ALA | B | 664 | 55.438 | -2.924 | 96.042 | 1.00 | 43.36 |
| 2491 | N | GLY | B | 665 | 56.960 | -2.374 | 94.476 | 1.00 | 43.87 |
| 2492 | CA | GLY | B | 665 | 57.931 | -1.819 | 95.439 | 1.00 | 43.94 |
| 2493 | C | GLY | B | 665 | 57.330 | -0.667 | 96.169 | 1.00 | 43.52 |
| 2494 | O | GLY | B | 665 | 57.462 | -0.519 | 97.381 | 1.00 | 44.23 |
| 2495 | N | ILE | B | 666 | 56.629 | 0.158 | 95.425 | 1.00 | 42.33 |
| 2496 | CA | ILE | B | 666 | 55.965 | 1.280 | 96.055 | 1.00 | 42.70 |
| 2497 | CB | ILE | B | 666 | 55.513 | 2.167 | 94.932 | 1.00 | 43.27 |
| 2498 | CG1 | ILE | B | 666 | 56.724 | 2.800 | 94.203 | 1.00 | 40.47 |
| 2499 | CD1 | ILE | B | 666 | 56.305 | 3.460 | 92.869 | 1.00 | 45.35 |
| 2500 | CG2 | ILE | B | 666 | 54.692 | 3.137 | 95.468 | 1.00 | 42.19 |
| 2501 | C | ILE | B | 666 | 54.729 | 0.884 | 96.947 | 1.00 | 43.44 |
| 2502 | O | ILE | B | 666 | 54.624 | 1.234 | 98.167 | 1.00 | 43.04 |
| 2503 | N | MET | B | 667 | 53.817 | 0.140 | 96.328 | 1.00 | 42.32 |
| 2504 | CA | MET | B | 667 | 52.569 | -0.368 | 96.938 | 1.00 | 42.19 |
| 2505 | CB | MET | B | 667 | 51.932 | -1.230 | 95.817 | 1.00 | 41.53 |
| 2506 | CG | MET | B | 667 | 51.176 | -2.507 | 96.165 | 1.00 | 47.32 |
| 2507 | SD | MET | B | 667 | 49.731 | -2.572 | 94.829 | 1.00 | 52.61 |
| 2508 | CE | MET | B | 667 | 50.549 | -1.966 | 93.551 | 1.00 | 44.11 |
| 2509 | C | MET | B | 667 | 52.855 | -1.095 | 98.259 | 1.00 | 40.97 |
| 2510 | O | MET | B | 667 | 52.115 | -1.057 | 99.249 | 1.00 | 40.07 |
| 2511 | N | GLY | B | 668 | 53.973 | -1.762 | 98.310 | 1.00 | 41.23 |
| 2512 | CA | GLY | B | 668 | 54.340 | -2.512 | 99.534 | 1.00 | 40.60 |
| 2513 | C | GLY | B | 668 | 54.751 | -1.560 | 100.685 | 1.00 | 40.90 |
| 2514 | O | GLY | B | 668 | 54.848 | -1.869 | 101.852 | 1.00 | 40.12 |
| 2515 | N | GLN | B | 669 | 54.995 | -0.332 | 100.355 | 1.00 | 42.10 |
| 2516 | CA | GLN | B | 669 | 55.298 | 0.588 | 101.398 | 1.00 | 41.36 |

FIGURE 3AY

| A | B | C | D | E | F | G | H | I | J |
|---|---|---|---|---|---|---|---|---|---|
| 2517 | CB | GLN | B | 669 | 55.949 | 1.743 | 100.749 | 1.00 | 40.50 |
| 2518 | CG | GLN | B | 669 | 57.369 | 1.598 | 100.440 | 1.00 | 44.93 |
| 2519 | CD | GLN | B | 669 | 57.848 | 2.816 | 99.700 | 1.00 | 53.63 |
| 2520 | OE1 | GLN | B | 669 | 57.922 | 3.974 | 100.272 | 1.00 | 55.16 |
| 2521 | NE2 | GLN | B | 669 | 58.134 | 2.617 | 98.409 | 1.00 | 51.35 |
| 2522 | C | GLN | B | 669 | 53.996 | 1.102 | 102.075 | 1.00 | 43.35 |
| 2523 | O | GLN | B | 669 | 54.128 | 1.753 | 103.081 | 1.00 | 45.25 |
| 2524 | N | PHE | B | 670 | 52.769 | 0.833 | 101.553 | 1.00 | 41.08 |
| 2525 | CA | PHE | B | 670 | 51.612 | 1.398 | 102.134 | 1.00 | 37.80 |
| 2526 | CB | PHE | B | 670 | 50.688 | 2.045 | 101.056 | 1.00 | 37.43 |
| 2527 | CG | PHE | B | 670 | 51.446 | 2.912 | 100.086 | 1.00 | 36.83 |
| 2528 | CD1 | PHE | B | 670 | 51.220 | 2.868 | 98.724 | 1.00 | 36.12 |
| 2529 | CE1 | PHE | B | 670 | 51.971 | 3.676 | 97.852 | 1.00 | 41.89 |
| 2530 | CZ | PHE | B | 670 | 52.941 | 4.539 | 98.359 | 1.00 | 43.63 |
| 2531 | CE2 | PHE | B | 670 | 53.078 | 4.636 | 99.746 | 1.00 | 39.81 |
| 2532 | CD2 | PHE | B | 670 | 52.356 | 3.822 | 100.563 | 1.00 | 34.13 |
| 2533 | C | PHE | B | 670 | 50.888 | 0.359 | 102.865 | 1.00 | 35.75 |
| 2534 | O | PHE | B | 670 | 51.117 | -0.756 | 102.607 | 1.00 | 31.50 |
| 2535 | N | SER | B | 671 | 50.178 | 0.774 | 103.923 | 1.00 | 35.37 |
| 2536 | CA | SER | B | 671 | 49.179 | -0.001 | 104.556 | 1.00 | 35.63 |
| 2537 | CB | SER | B | 671 | 49.795 | -0.920 | 105.584 | 1.00 | 37.05 |
| 2538 | OG | SER | B | 671 | 48.754 | -1.432 | 106.452 | 1.00 | 35.05 |
| 2539 | C | SER | B | 671 | 48.009 | 0.915 | 105.119 | 1.00 | 35.05 |
| 2540 | O | SER | B | 671 | 48.061 | 1.604 | 106.184 | 1.00 | 36.76 |
| 2541 | N | HIS | B | 672 | 46.930 | 0.915 | 104.391 | 1.00 | 33.56 |
| 2542 | CA | HIS | B | 672 | 45.871 | 1.856 | 104.659 | 1.00 | 34.12 |
| 2543 | CB | HIS | B | 672 | 46.232 | 3.243 | 103.989 | 1.00 | 32.36 |
| 2544 | CG | HIS | B | 672 | 45.251 | 4.288 | 104.307 | 1.00 | 33.02 |
| 2545 | ND1 | HIS | B | 672 | 44.080 | 4.461 | 103.586 | 1.00 | 33.28 |
| 2546 | CE1 | HIS | B | 672 | 43.406 | 5.471 | 104.112 | 1.00 | 34.10 |
| 2547 | NE2 | HIS | B | 672 | 44.044 | 5.886 | 105.198 | 1.00 | 38.41 |
| 2548 | CD2 | HIS | B | 672 | 45.198 | 5.161 | 105.333 | 1.00 | 38.63 |
| 2549 | C | HIS | B | 672 | 44.633 | 1.308 | 104.017 | 1.00 | 33.03 |
| 2550 | O | HIS | B | 672 | 44.733 | 0.644 | 102.951 | 1.00 | 33.41 |
| 2551 | N | HIS | B | 673 | 43.502 | 1.611 | 104.635 | 1.00 | 30.53 |
| 2552 | CA | HIS | B | 673 | 42.230 | 1.095 | 104.299 | 1.00 | 31.97 |
| 2553 | CB | HIS | B | 673 | 41.296 | 1.817 | 105.206 | 1.00 | 30.58 |
| 2554 | CG | HIS | B | 673 | 39.877 | 1.451 | 105.083 | 1.00 | 37.08 |
| 2555 | ND1 | HIS | B | 673 | 39.369 | 0.217 | 105.415 | 1.00 | 42.49 |
| 2556 | CE1 | HIS | B | 673 | 38.051 | 0.245 | 105.241 | 1.00 | 43.15 |
| 2557 | NE2 | HIS | B | 673 | 37.690 | 1.458 | 104.828 | 1.00 | 31.71 |
| 2558 | CD2 | HIS | B | 673 | 38.814 | 2.217 | 104.721 | 1.00 | 39.22 |
| 2559 | C | HIS | B | 673 | 41.832 | 1.498 | 102.843 | 1.00 | 33.87 |
| 2560 | O | HIS | B | 673 | 40.989 | 0.910 | 102.229 | 1.00 | 34.38 |
| 2561 | N | ASN | B | 674 | 42.323 | 2.594 | 102.363 | 1.00 | 33.75 |
| 2562 | CA | ASN | B | 674 | 41.797 | 3.014 | 101.126 | 1.00 | 32.88 |
| 2563 | CB | ASN | B | 674 | 41.166 | 4.384 | 101.219 | 1.00 | 30.97 |
| 2564 | CG | ASN | B | 674 | 39.921 | 4.412 | 102.092 | 1.00 | 31.43 |
| 2565 | OD1 | ASN | B | 674 | 38.806 | 3.959 | 101.636 | 1.00 | 30.88 |
| 2566 | ND2 | ASN | B | 674 | 40.022 | 5.112 | 103.273 | 1.00 | 20.74 |
| 2567 | C | ASN | B | 674 | 42.854 | 2.913 | 100.080 | 1.00 | 31.69 |
| 2568 | O | ASN | B | 674 | 42.730 | 3.587 | 99.082 | 1.00 | 30.93 |

FIGURE 3AZ

| A | B | C | D | E | F | G | H | I | J |
|---|---|---|---|---|---|---|---|---|---|
| 2569 | N | ILE | B | 675 | 43.861 | 2.055 | 100.334 | 1.00 | 31.51 |
| 2570 | CA | ILE | B | 675 | 44.993 | 1.813 | 99.460 | 1.00 | 30.93 |
| 2571 | CB | ILE | B | 675 | 46.273 | 2.205 | 100.110 | 1.00 | 31.44 |
| 2572 | CG1 | ILE | B | 675 | 46.250 | 3.687 | 100.454 | 1.00 | 28.51 |
| 2573 | CD1 | ILE | B | 675 | 46.340 | 4.549 | 99.164 | 1.00 | 31.74 |
| 2574 | CG2 | ILE | B | 675 | 47.486 | 2.026 | 99.005 | 1.00 | 22.20 |
| 2575 | C | ILE | B | 675 | 45.052 | 0.297 | 99.215 | 1.00 | 34.26 |
| 2576 | O | ILE | B | 675 | 44.924 | -0.515 | 100.144 | 1.00 | 36.44 |
| 2577 | N | ILE | B | 676 | 45.186 | -0.100 | 97.964 | 1.00 | 34.31 |
| 2578 | CA | ILE | B | 676 | 44.977 | -1.451 | 97.663 | 1.00 | 34.35 |
| 2579 | CB | ILE | B | 676 | 44.919 | -1.703 | 96.111 | 1.00 | 35.23 |
| 2580 | CG1 | ILE | B | 676 | 44.509 | -3.132 | 95.837 | 1.00 | 35.18 |
| 2581 | CD1 | ILE | B | 676 | 42.941 | -3.264 | 96.042 | 1.00 | 39.25 |
| 2582 | CG2 | ILE | B | 676 | 46.229 | -1.573 | 95.495 | 1.00 | 35.77 |
| 2583 | C | ILE | B | 676 | 46.143 | -2.067 | 98.326 | 1.00 | 34.50 |
| 2584 | O | ILE | B | 676 | 47.226 | -1.536 | 98.234 | 1.00 | 33.39 |
| 2585 | N | ARG | B | 677 | 45.933 | -3.239 | 98.897 | 1.00 | 33.92 |
| 2586 | CA | ARG | B | 677 | 46.961 | -3.942 | 99.559 | 1.00 | 33.57 |
| 2587 | CB | ARG | B | 677 | 46.317 | -4.719 | 100.700 | 1.00 | 32.83 |
| 2588 | CG | ARG | B | 677 | 47.392 | -5.572 | 101.445 | 1.00 | 35.49 |
| 2589 | CD | ARG | B | 677 | 46.901 | -6.224 | 102.708 | 1.00 | 47.46 |
| 2590 | NE | ARG | B | 677 | 45.887 | -7.206 | 102.394 | 1.00 | 52.58 |
| 2591 | CZ | ARG | B | 677 | 44.635 | -7.100 | 102.814 | 1.00 | 59.96 |
| 2592 | NH1 | ARG | B | 677 | 44.304 | -6.024 | 103.587 | 1.00 | 55.86 |
| 2593 | NH2 | ARG | B | 677 | 43.742 | -8.063 | 102.463 | 1.00 | 56.27 |
| 2594 | C | ARG | B | 677 | 47.797 | -4.926 | 98.720 | 1.00 | 34.17 |
| 2595 | O | ARG | B | 677 | 47.229 | -5.704 | 97.993 | 1.00 | 36.51 |
| 2596 | N | LEU | B | 678 | 49.115 | -4.899 | 98.837 | 1.00 | 33.13 |
| 2597 | CA | LEU | B | 678 | 50.033 | -5.811 | 98.197 | 1.00 | 37.40 |
| 2598 | CB | LEU | B | 678 | 51.435 | -5.236 | 98.159 | 1.00 | 36.36 |
| 2599 | CG | LEU | B | 678 | 52.397 | -6.185 | 97.415 | 1.00 | 42.53 |
| 2600 | CD1 | LEU | B | 678 | 51.911 | -6.418 | 95.980 | 1.00 | 35.69 |
| 2601 | CD2 | LEU | B | 678 | 53.852 | -5.640 | 97.304 | 1.00 | 41.94 |
| 2602 | C | LEU | B | 678 | 50.171 | -7.067 | 99.042 | 1.00 | 39.09 |
| 2603 | O | LEU | B | 678 | 50.517 | -6.970 | 100.188 | 1.00 | 40.71 |
| 2604 | N | GLU | B | 679 | 49.836 | -8.226 | 98.507 | 1.00 | 41.09 |
| 2605 | CA | GLU | B | 679 | 49.976 | -9.417 | 99.253 | 1.00 | 42.38 |
| 2606 | CB | GLU | B | 679 | 49.026 | -10.474 | 98.789 | 1.00 | 41.41 |
| 2607 | CG | GLU | B | 679 | 47.562 | -10.172 | 99.081 | 1.00 | 45.00 |
| 2608 | CD | GLU | B | 679 | 47.179 | -10.261 | 100.578 | 1.00 | 51.76 |
| 2609 | OE1 | GLU | B | 679 | 47.778 | -11.040 | 101.316 | 1.00 | 52.41 |
| 2610 | OE2 | GLU | B | 679 | 46.290 | -9.498 | 101.008 | 1.00 | 55.14 |
| 2611 | C | GLU | B | 679 | 51.363 | -9.866 | 99.118 | 1.00 | 42.27 |
| 2612 | O | GLU | B | 679 | 51.912 | -10.278 | 100.108 | 1.00 | 44.77 |
| 2613 | N | GLY | B | 680 | 51.973 | -9.623 | 97.972 | 1.00 | 41.28 |
| 2614 | CA | GLY | B | 680 | 53.256 | -10.180 | 97.623 | 1.00 | 41.26 |
| 2615 | C | GLY | B | 680 | 53.582 | -10.240 | 96.127 | 1.00 | 42.91 |
| 2616 | O | GLY | B | 680 | 52.890 | -9.669 | 95.349 | 1.00 | 42.87 |
| 2617 | N | VAL | B | 681 | 54.656 | -10.893 | 95.716 | 1.00 | 44.63 |
| 2618 | CA | VAL | B | 681 | 55.060 | -10.858 | 94.316 | 1.00 | 47.33 |
| 2619 | CB | VAL | B | 681 | 56.171 | -9.792 | 93.916 | 1.00 | 47.94 |
| 2620 | CG1 | VAL | B | 681 | 55.769 | -8.411 | 94.202 | 1.00 | 48.45 |
| 2621 | CG2 | VAL | B | 681 | 57.459 | -10.075 | 94.630 | 1.00 | 47.53 |
| 2622 | C | VAL | B | 681 | 55.811 | -12.121 | 94.003 | 1.00 | 49.45 |

FIGURE 3BA

| A | B | C | D | E | F | G | H | I | J |
|---|---|---|---|---|---|---|---|---|---|
| 2623 | O | VAL | B | 681 | 56.375 | -12.823 | 94.891 | 1.00 | 48.56 |
| 2624 | N | ILE | B | 682 | 55.785 | -12.422 | 92.707 | 1.00 | 50.88 |
| 2625 | CA | ILE | B | 682 | 56.648 | -13.445 | 92.194 | 1.00 | 52.35 |
| 2626 | CB | ILE | B | 682 | 56.040 | -14.781 | 92.219 | 1.00 | 52.57 |
| 2627 | CG1 | ILE | B | 682 | 54.614 | -14.850 | 91.771 | 1.00 | 54.23 |
| 2628 | CD1 | ILE | B | 682 | 53.863 | -16.059 | 92.607 | 1.00 | 42.89 |
| 2629 | CG2 | ILE | B | 682 | 55.622 | -14.986 | 93.632 | 1.00 | 48.84 |
| 2630 | C | ILE | B | 682 | 57.528 | -13.017 | 91.033 | 1.00 | 54.22 |
| 2631 | O | ILE | B | 682 | 57.085 | -12.426 | 89.997 | 1.00 | 54.69 |
| 2632 | N | SER | B | 683 | 58.806 | -13.061 | 91.420 | 1.00 | 56.54 |
| 2633 | CA | SER | B | 683 | 60.026 | -12.729 | 90.672 | 1.00 | 59.27 |
| 2634 | CB | SER | B | 683 | 60.835 | -11.648 | 91.417 | 1.00 | 57.57 |
| 2635 | OG | SER | B | 683 | 61.114 | -12.079 | 92.783 | 1.00 | 64.03 |
| 2636 | C | SER | B | 683 | 60.691 | -14.088 | 90.824 | 1.00 | 60.75 |
| 2637 | O | SER | B | 683 | 60.093 | -15.011 | 91.285 | 1.00 | 61.98 |
| 2638 | N | ALA | B | 684 | 61.921 | -14.287 | 90.467 | 1.00 | 64.16 |
| 2639 | CA | ALA | B | 684 | 62.404 | -15.660 | 90.662 | 1.00 | 65.44 |
| 2640 | CB | ALA | B | 684 | 62.426 | -16.045 | 92.155 | 1.00 | 65.45 |
| 2641 | C | ALA | B | 684 | 61.607 | -16.690 | 89.844 | 1.00 | 65.59 |
| 2642 | O | ALA | B | 684 | 62.156 | -17.667 | 89.411 | 1.00 | 66.62 |
| 2643 | N | TYR | B | 685 | 60.320 | -16.489 | 89.629 | 1.00 | 65.92 |
| 2644 | CA | TYR | B | 685 | 59.566 | -17.433 | 88.808 | 1.00 | 65.61 |
| 2645 | CB | TYR | B | 685 | 58.513 | -18.132 | 89.646 | 1.00 | 66.23 |
| 2646 | CG | TYR | B | 685 | 59.148 | -19.196 | 90.468 | 1.00 | 69.68 |
| 2647 | CD1 | TYR | B | 685 | 59.519 | -18.961 | 91.769 | 1.00 | 67.64 |
| 2648 | CE1 | TYR | B | 685 | 60.131 | -19.935 | 92.519 | 1.00 | 71.61 |
| 2649 | CZ | TYR | B | 685 | 60.433 | -21.157 | 91.970 | 1.00 | 74.46 |
| 2650 | OH | TYR | B | 685 | 61.042 | -22.113 | 92.750 | 1.00 | 75.04 |
| 2651 | CE2 | TYR | B | 685 | 60.081 | -21.448 | 90.663 | 1.00 | 75.00 |
| 2652 | CD2 | TYR | B | 685 | 59.446 | -20.453 | 89.905 | 1.00 | 75.26 |
| 2653 | C | TYR | B | 685 | 58.964 | -16.788 | 87.581 | 1.00 | 65.25 |
| 2654 | O | TYR | B | 685 | 58.899 | -15.527 | 87.499 | 1.00 | 66.17 |
| 2655 | N | ALA | B | 686 | 58.551 | -17.617 | 86.612 | 1.00 | 63.68 |
| 2656 | CA | ALA | B | 686 | 58.036 | -17.091 | 85.334 | 1.00 | 62.32 |
| 2657 | CB | ALA | B | 686 | 58.506 | -17.805 | 84.124 | 1.00 | 63.30 |
| 2658 | C | ALA | B | 686 | 56.596 | -17.082 | 85.432 | 1.00 | 62.05 |
| 2659 | O | ALA | B | 686 | 56.007 | -18.119 | 85.775 | 1.00 | 63.53 |
| 2660 | N | PRO | B | 687 | 56.081 | -16.278 | 84.593 | 1.00 | 60.53 |
| 2661 | CA | PRO | B | 687 | 55.343 | -15.047 | 84.649 | 1.00 | 58.99 |
| 2662 | CB | PRO | B | 687 | 53.882 | -15.447 | 84.418 | 1.00 | 58.56 |
| 2663 | CG | PRO | B | 687 | 53.888 | -16.897 | 84.821 | 1.00 | 60.26 |
| 2664 | CD | PRO | B | 687 | 55.173 | -17.326 | 84.077 | 1.00 | 61.17 |
| 2665 | C | PRO | B | 687 | 55.589 | -14.602 | 86.037 | 1.00 | 56.90 |
| 2666 | O | PRO | B | 687 | 55.308 | -15.358 | 86.974 | 1.00 | 56.82 |
| 2667 | N | MET | B | 688 | 56.186 | -13.428 | 86.143 | 1.00 | 55.27 |
| 2668 | CA | MET | B | 688 | 56.320 | -12.750 | 87.404 | 1.00 | 54.44 |
| 2669 | CB | MET | B | 688 | 57.223 | -11.566 | 87.255 | 1.00 | 55.33 |
| 2670 | CG | MET | B | 688 | 58.596 | -11.932 | 86.692 | 1.00 | 55.74 |
| 2671 | SD | MET | B | 688 | 59.901 | -11.043 | 87.530 | 1.00 | 60.68 |
| 2672 | CE | MET | B | 688 | 60.394 | -9.447 | 86.370 | 1.00 | 57.44 |
| 2673 | C | MET | B | 688 | 54.924 | -12.281 | 87.695 | 1.00 | 53.73 |
| 2674 | O | MET | B | 688 | 54.115 | -11.957 | 86.766 | 1.00 | 55.62 |
| 2675 | N | MET | B | 689 | 54.593 | -12.326 | 88.964 | 1.00 | 49.82 |
| 2676 | CA | MET | B | 689 | 53.314 | -11.945 | 89.372 | 1.00 | 45.50 |

FIGURE 3BB

| A | B | C | D | E | F | G | H | I | J |
|---|---|---|---|---|---|---|---|---|---|
| 2677 | CB | MET | B | 689 | 52.726 | -13.198 | 89.919 | 1.00 | 46.09 |
| 2678 | CG | MET | B | 689 | 52.209 | -14.107 | 88.832 | 1.00 | 42.85 |
| 2679 | SD | MET | B | 689 | 51.622 | -15.683 | 89.528 | 1.00 | 50.11 |
| 2680 | CE | MET | B | 689 | 50.901 | -16.233 | 88.146 | 1.00 | 42.03 |
| 2681 | C | MET | B | 689 | 53.460 | -10.876 | 90.439 | 1.00 | 44.44 |
| 2682 | O | MET | B | 689 | 54.468 | -10.868 | 91.193 | 1.00 | 43.66 |
| 2683 | N | ILE | B | 690 | 52.546 | -9.929 | 90.420 | 1.00 | 40.55 |
| 2684 | CA | ILE | B | 690 | 52.358 | -8.991 | 91.483 | 1.00 | 39.05 |
| 2685 | CB | ILE | B | 690 | 52.225 | -7.585 | 90.904 | 1.00 | 41.79 |
| 2686 | CG1 | ILE | B | 690 | 53.596 | -6.955 | 90.607 | 1.00 | 40.50 |
| 2687 | CD1 | ILE | B | 690 | 53.501 | -5.528 | 89.890 | 1.00 | 37.73 |
| 2688 | CG2 | ILE | B | 690 | 51.421 | -6.707 | 91.895 | 1.00 | 38.75 |
| 2689 | C | ILE | B | 690 | 50.932 | -9.386 | 91.986 | 1.00 | 38.72 |
| 2690 | O | ILE | B | 690 | 49.971 | -9.343 | 91.192 | 1.00 | 36.41 |
| 2691 | N | ILE | B | 691 | 50.807 | -9.788 | 93.255 | 1.00 | 38.28 |
| 2692 | CA | ILE | B | 691 | 49.587 | -10.296 | 93.856 | 1.00 | 37.73 |
| 2693 | CB | ILE | B | 691 | 49.904 | -11.537 | 94.642 | 1.00 | 37.57 |
| 2694 | CG1 | ILE | B | 691 | 50.662 | -12.539 | 93.759 | 1.00 | 43.22 |
| 2695 | CD1 | ILE | B | 691 | 49.780 | -13.030 | 92.551 | 1.00 | 43.78 |
| 2696 | CG2 | ILE | B | 691 | 48.666 | -12.175 | 95.178 | 1.00 | 33.95 |
| 2697 | C | ILE | B | 691 | 48.965 | -9.298 | 94.809 | 1.00 | 37.68 |
| 2698 | O | ILE | B | 691 | 49.621 | -8.935 | 95.803 | 1.00 | 38.31 |
| 2699 | N | THR | B | 692 | 47.707 | -8.901 | 94.597 | 1.00 | 36.61 |
| 2700 | CA | THR | B | 692 | 47.089 | -7.867 | 95.484 | 1.00 | 35.83 |
| 2701 | CB | THR | B | 692 | 46.777 | -6.579 | 94.767 | 1.00 | 34.36 |
| 2702 | OG1 | THR | B | 692 | 46.064 | -6.922 | 93.582 | 1.00 | 36.12 |
| 2703 | CG2 | THR | B | 692 | 48.064 | -5.799 | 94.178 | 1.00 | 32.38 |
| 2704 | C | THR | B | 692 | 45.788 | -8.406 | 96.022 | 1.00 | 36.80 |
| 2705 | O | THR | B | 692 | 45.333 | -9.470 | 95.601 | 1.00 | 38.54 |
| 2706 | N | GLU | B | 693 | 45.145 | -7.663 | 96.924 | 1.00 | 37.13 |
| 2707 | CA | GLU | B | 693 | 43.857 | -8.165 | 97.503 | 1.00 | 36.04 |
| 2708 | CB | GLU | B | 693 | 43.424 | -7.317 | 98.719 | 1.00 | 33.77 |
| 2709 | CG | GLU | B | 693 | 43.251 | -5.824 | 98.385 | 1.00 | 36.54 |
| 2710 | CD | GLU | B | 693 | 42.731 | -4.903 | 99.522 | 1.00 | 37.60 |
| 2711 | OE1 | GLU | B | 693 | 43.250 | -3.736 | 99.716 | 1.00 | 38.54 |
| 2712 | OE2 | GLU | B | 693 | 41.720 | -5.266 | 100.137 | 1.00 | 42.02 |
| 2713 | C | GLU | B | 693 | 42.821 | -8.028 | 96.364 | 1.00 | 35.07 |
| 2714 | O | GLU | B | 693 | 42.890 | -7.067 | 95.588 | 1.00 | 35.55 |
| 2715 | N | TYR | B | 694 | 41.845 | -8.911 | 96.272 | 1.00 | 32.10 |
| 2716 | CA | TYR | B | 694 | 40.970 | -8.809 | 95.150 | 1.00 | 28.28 |
| 2717 | CB | TYR | B | 694 | 40.440 | -10.153 | 94.874 | 1.00 | 28.39 |
| 2718 | CG | TYR | B | 694 | 39.351 | -10.217 | 93.769 | 1.00 | 32.24 |
| 2719 | CD1 | TYR | B | 694 | 39.617 | -9.921 | 92.416 | 1.00 | 28.95 |
| 2720 | CE1 | TYR | B | 694 | 38.566 | -10.081 | 91.432 | 1.00 | 33.82 |
| 2721 | CZ | TYR | B | 694 | 37.375 | -10.533 | 91.790 | 1.00 | 31.62 |
| 2722 | OH | TYR | B | 694 | 36.297 | -10.655 | 90.899 | 1.00 | 37.93 |
| 2723 | CE2 | TYR | B | 694 | 37.108 | -10.758 | 93.113 | 1.00 | 35.35 |
| 2724 | CD2 | TYR | B | 694 | 38.076 | -10.619 | 94.080 | 1.00 | 35.75 |
| 2725 | C | TYR | B | 694 | 39.814 | -7.896 | 95.538 | 1.00 | 28.69 |
| 2726 | O | TYR | B | 694 | 39.243 | -8.023 | 96.662 | 1.00 | 28.77 |
| 2727 | N | MET | B | 695 | 39.475 | -6.996 | 94.627 | 1.00 | 25.99 |
| 2728 | CA | MET | B | 695 | 38.480 | -6.015 | 94.790 | 1.00 | 28.69 |

FIGURE 3BC

| A | B | C | D | E | F | G | H | I | J |
|---|---|---|---|---|---|---|---|---|---|
| 2729 | CB | MET | B | 695 | 39.057 | -4.593 | 94.582 | 1.00 | 27.01 |
| 2730 | CG | MET | B | 695 | 40.089 | -4.121 | 95.806 | 1.00 | 26.26 |
| 2731 | SD | MET | B | 695 | 39.137 | -4.002 | 97.332 | 1.00 | 29.69 |
| 2732 | CE | MET | B | 695 | 38.140 | -2.317 | 96.950 | 1.00 | 19.49 |
| 2733 | C | MET | B | 695 | 37.337 | -6.451 | 93.887 | 1.00 | 30.89 |
| 2734 | O | MET | B | 695 | 37.371 | -6.254 | 92.716 | 1.00 | 35.87 |
| 2735 | N | GLU | B | 696 | 36.406 | -7.188 | 94.437 | 1.00 | 31.23 |
| 2736 | CA | GLU | B | 696 | 35.369 | -7.846 | 93.720 | 1.00 | 32.82 |
| 2737 | CB | GLU | B | 696 | 34.419 | -8.666 | 94.666 | 1.00 | 30.79 |
| 2738 | CG | GLU | B | 696 | 33.717 | -7.643 | 95.469 | 1.00 | 38.13 |
| 2739 | CD | GLU | B | 696 | 33.271 | -8.107 | 96.846 | 1.00 | 48.34 |
| 2740 | OE1 | GLU | B | 696 | 32.877 | -9.291 | 96.897 | 1.00 | 61.33 |
| 2741 | OE2 | GLU | B | 696 | 33.160 | -7.330 | 97.803 | 1.00 | 43.84 |
| 2742 | C | GLU | B | 696 | 34.529 | -7.028 | 92.836 | 1.00 | 32.02 |
| 2743 | O | GLU | B | 696 | 33.781 | -7.625 | 92.021 | 1.00 | 31.01 |
| 2744 | N | ASN | B | 697 | 34.505 | -5.694 | 92.943 | 1.00 | 33.21 |
| 2745 | CA | ASN | B | 697 | 33.694 | -4.999 | 91.904 | 1.00 | 31.07 |
| 2746 | CB | ASN | B | 697 | 32.725 | -4.026 | 92.537 | 1.00 | 30.83 |
| 2747 | CG | ASN | B | 697 | 31.440 | -4.657 | 92.940 | 1.00 | 34.34 |
| 2748 | OD1 | ASN | B | 697 | 30.947 | -5.594 | 92.243 | 1.00 | 34.99 |
| 2749 | ND2 | ASN | B | 697 | 30.834 | -4.156 | 94.055 | 1.00 | 28.78 |
| 2750 | C | ASN | B | 697 | 34.630 | -4.265 | 90.926 | 1.00 | 31.59 |
| 2751 | O | ASN | B | 697 | 34.193 | -3.413 | 90.103 | 1.00 | 31.69 |
| 2752 | N | GLY | B | 698 | 35.910 | -4.526 | 90.990 | 1.00 | 29.27 |
| 2753 | CA | GLY | B | 698 | 36.768 | -3.815 | 90.060 | 1.00 | 29.77 |
| 2754 | C | GLY | B | 698 | 36.882 | -2.261 | 90.054 | 1.00 | 29.16 |
| 2755 | O | GLY | B | 698 | 36.746 | -1.550 | 91.056 | 1.00 | 31.76 |
| 2756 | N | ALA | B | 699 | 37.160 | -1.773 | 88.888 | 1.00 | 27.39 |
| 2757 | CA | ALA | B | 699 | 37.387 | -0.402 | 88.524 | 1.00 | 26.35 |
| 2758 | CB | ALA | B | 699 | 37.888 | -0.293 | 87.086 | 1.00 | 25.30 |
| 2759 | C | ALA | B | 699 | 36.179 | 0.215 | 88.629 | 1.00 | 27.91 |
| 2760 | O | ALA | B | 699 | 35.168 | -0.299 | 88.130 | 1.00 | 30.28 |
| 2761 | N | LEU | B | 700 | 36.280 | 1.357 | 89.268 | 1.00 | 29.27 |
| 2762 | CA | LEU | B | 700 | 35.121 | 2.026 | 89.707 | 1.00 | 32.33 |
| 2763 | CB | LEU | B | 700 | 35.450 | 3.069 | 90.838 | 1.00 | 29.30 |
| 2764 | CG | LEU | B | 700 | 34.459 | 4.089 | 91.301 | 1.00 | 31.76 |
| 2765 | CD1 | LEU | B | 700 | 33.464 | 3.627 | 92.353 | 1.00 | 30.61 |
| 2766 | CD2 | LEU | B | 700 | 35.145 | 5.322 | 91.920 | 1.00 | 28.14 |
| 2767 | C | LEU | B | 700 | 34.449 | 2.671 | 88.617 | 1.00 | 30.67 |
| 2768 | O | LEU | B | 700 | 33.279 | 2.926 | 88.812 | 1.00 | 32.59 |
| 2769 | N | ASP | B | 701 | 35.175 | 3.092 | 87.584 | 1.00 | 28.67 |
| 2770 | CA | ASP | B | 701 | 34.475 | 3.801 | 86.542 | 1.00 | 33.44 |
| 2771 | CB | ASP | B | 701 | 35.382 | 4.505 | 85.575 | 1.00 | 33.00 |
| 2772 | CG | ASP | B | 701 | 36.230 | 3.542 | 84.702 | 1.00 | 38.53 |
| 2773 | OD1 | ASP | B | 701 | 36.810 | 2.573 | 85.221 | 1.00 | 37.75 |
| 2774 | OD2 | ASP | B | 701 | 36.395 | 3.751 | 83.440 | 1.00 | 40.32 |
| 2775 | C | ASP | B | 701 | 33.529 | 2.791 | 85.837 | 1.00 | 33.01 |
| 2776 | O | ASP | B | 701 | 32.301 | 3.048 | 85.715 | 1.00 | 32.42 |
| 2777 | N | LYS | B | 702 | 34.074 | 1.635 | 85.538 | 1.00 | 30.90 |
| 2778 | CA | LYS | B | 702 | 33.249 | 0.568 | 84.960 | 1.00 | 35.12 |
| 2779 | CB | LYS | B | 702 | 34.186 | -0.548 | 84.449 | 1.00 | 37.13 |
| 2780 | CG | LYS | B | 702 | 33.542 | -1.537 | 83.686 | 1.00 | 47.55 |

FIGURE 3BD

| A | B | C | D | E | F | G | H | I | J |
|---|---|---|---|---|---|---|---|---|---|
| 2781 | CD  | LYS | B | 702 | 34.296 | -2.821 | 83.631 | 1.00 | 60.43 |
| 2782 | CE  | LYS | B | 702 | 33.493 | -3.758 | 82.740 | 1.00 | 63.91 |
| 2783 | NZ  | LYS | B | 702 | 34.151 | -5.137 | 82.655 | 1.00 | 69.98 |
| 2784 | C   | LYS | B | 702 | 32.158 |  0.088 | 85.872 | 1.00 | 35.34 |
| 2785 | O   | LYS | B | 702 | 31.006 | -0.038 | 85.504 | 1.00 | 36.22 |
| 2786 | N   | PHE | B | 703 | 32.421 | -0.020 | 87.179 | 1.00 | 37.97 |
| 2787 | CA  | PHE | B | 703 | 31.403 | -0.517 | 88.060 | 1.00 | 34.72 |
| 2788 | CB  | PHE | B | 703 | 31.980 | -0.605 | 89.436 | 1.00 | 35.11 |
| 2789 | CG  | PHE | B | 703 | 30.985 | -0.877 | 90.473 | 1.00 | 29.25 |
| 2790 | CD1 | PHE | B | 703 | 30.252 | -2.115 | 90.505 | 1.00 | 27.25 |
| 2791 | CE1 | PHE | B | 703 | 29.389 | -2.361 | 91.525 | 1.00 | 29.92 |
| 2792 | CZ  | PHE | B | 703 | 29.256 | -1.467 | 92.569 | 1.00 | 29.83 |
| 2793 | CE2 | PHE | B | 703 | 29.913 | -0.313 | 92.538 | 1.00 | 29.77 |
| 2794 | CD2 | PHE | B | 703 | 30.785 |  0.001 | 91.443 | 1.00 | 30.63 |
| 2795 | C   | PHE | B | 703 | 30.265 |  0.452 | 88.121 | 1.00 | 36.80 |
| 2796 | O   | PHE | B | 703 | 29.032 |  0.086 | 88.137 | 1.00 | 37.46 |
| 2797 | N   | LEU | B | 704 | 30.622 |  1.724 | 88.157 | 1.00 | 36.09 |
| 2798 | CA  | LEU | B | 704 | 29.567 |  2.730 | 88.283 | 1.00 | 35.58 |
| 2799 | CB  | LEU | B | 704 | 30.162 |  4.112 | 88.554 | 1.00 | 36.04 |
| 2800 | CG  | LEU | B | 704 | 30.722 |  4.526 | 89.921 | 1.00 | 39.33 |
| 2801 | CD1 | LEU | B | 704 | 31.453 |  5.870 | 89.856 | 1.00 | 39.49 |
| 2802 | CD2 | LEU | B | 704 | 29.689 |  4.488 | 91.097 | 1.00 | 39.49 |
| 2803 | C   | LEU | B | 704 | 28.723 |  2.859 | 87.005 | 1.00 | 35.48 |
| 2804 | O   | LEU | B | 704 | 27.545 |  3.304 | 87.050 | 1.00 | 36.13 |
| 2805 | N   | ARG | B | 705 | 29.342 |  2.607 | 85.865 | 1.00 | 36.71 |
| 2806 | CA  | ARG | B | 705 | 28.645 |  2.652 | 84.601 | 1.00 | 37.41 |
| 2807 | CB  | ARG | B | 705 | 29.599 |  2.330 | 83.433 | 1.00 | 37.84 |
| 2808 | CG  | ARG | B | 705 | 30.260 |  3.590 | 82.802 | 1.00 | 34.77 |
| 2809 | CD  | ARG | B | 705 | 30.660 |  3.455 | 81.367 | 1.00 | 41.95 |
| 2810 | NE  | ARG | B | 705 | 31.988 |  2.810 | 81.271 | 1.00 | 42.52 |
| 2811 | CZ  | ARG | B | 705 | 33.068 |  3.374 | 81.792 | 1.00 | 45.05 |
| 2812 | NH1 | ARG | B | 705 | 34.261 |  2.852 | 81.678 | 1.00 | 42.04 |
| 2813 | NH2 | ARG | B | 705 | 32.913 |  4.565 | 82.399 | 1.00 | 40.02 |
| 2814 | C   | ARG | B | 705 | 27.609 |  1.598 | 84.550 | 1.00 | 40.12 |
| 2815 | O   | ARG | B | 705 | 26.733 |  1.639 | 83.716 | 1.00 | 43.46 |
| 2816 | N   | GLU | B | 706 | 27.773 |  0.561 | 85.322 | 1.00 | 41.24 |
| 2817 | CA  | GLU | B | 706 | 26.916 | -0.555 | 85.216 | 1.00 | 43.79 |
| 2818 | CB  | GLU | B | 706 | 27.684 | -1.832 | 85.558 | 1.00 | 46.45 |
| 2819 | CG  | GLU | B | 706 | 28.385 | -2.583 | 84.416 | 1.00 | 53.31 |
| 2820 | CD  | GLU | B | 706 | 29.070 | -3.871 | 85.011 | 1.00 | 65.10 |
| 2821 | OE1 | GLU | B | 706 | 28.273 | -4.757 | 85.532 | 1.00 | 68.07 |
| 2822 | OE2 | GLU | B | 706 | 30.368 | -4.034 | 84.995 | 1.00 | 63.05 |
| 2823 | C   | GLU | B | 706 | 25.852 | -0.364 | 86.216 | 1.00 | 43.47 |
| 2824 | O   | GLU | B | 706 | 24.864 | -1.051 | 86.164 | 1.00 | 45.43 |
| 2825 | N   | LYS | B | 707 | 26.029 |  0.565 | 87.117 | 1.00 | 43.14 |
| 2826 | CA  | LYS | B | 707 | 25.013 |  0.851 | 88.098 | 1.00 | 44.44 |
| 2827 | CB  | LYS | B | 707 | 25.584 |  0.449 | 89.490 | 1.00 | 46.43 |
| 2828 | CG  | LYS | B | 707 | 26.172 | -1.029 | 89.491 | 1.00 | 44.84 |
| 2829 | CD  | LYS | B | 707 | 25.573 | -1.880 | 90.569 | 1.00 | 43.24 |
| 2830 | CE  | LYS | B | 707 | 25.352 | -3.405 | 90.147 | 1.00 | 48.65 |
| 2831 | NZ  | LYS | B | 707 | 24.010 | -3.911 | 90.629 | 1.00 | 46.05 |
| 2832 | C   | LYS | B | 707 | 24.448 |  2.319 | 88.048 | 1.00 | 43.63 |

FIGURE 3BE

| A | B | C | D | E | F | G | H | I | J |
|---|---|---|---|---|---|---|---|---|---|
| 2833 | O | LYS | B | 707 | 23.968 | 2.911 | 89.012 | 1.00 | 43.30 |
| 2834 | N | ASP | B | 708 | 24.510 | 2.886 | 86.899 | 1.00 | 43.40 |
| 2835 | CA | ASP | B | 708 | 24.061 | 4.208 | 86.688 | 1.00 | 45.41 |
| 2836 | CB | ASP | B | 708 | 23.816 | 4.329 | 85.214 | 1.00 | 45.17 |
| 2837 | CG | ASP | B | 708 | 23.571 | 5.756 | 84.769 | 1.00 | 51.04 |
| 2838 | OD1 | ASP | B | 708 | 23.369 | 5.861 | 83.513 | 1.00 | 56.65 |
| 2839 | OD2 | ASP | B | 708 | 23.578 | 6.789 | 85.536 | 1.00 | 50.26 |
| 2840 | C | ASP | B | 708 | 22.776 | 4.514 | 87.400 | 1.00 | 46.40 |
| 2841 | O | ASP | B | 708 | 21.809 | 3.760 | 87.256 | 1.00 | 48.89 |
| 2842 | N | GLY | B | 709 | 22.748 | 5.610 | 88.155 | 1.00 | 45.59 |
| 2843 | CA | GLY | B | 709 | 21.516 | 6.076 | 88.791 | 1.00 | 45.68 |
| 2844 | C | GLY | B | 709 | 21.043 | 5.454 | 90.056 | 1.00 | 45.97 |
| 2845 | O | GLY | B | 709 | 20.134 | 5.987 | 90.790 | 1.00 | 45.98 |
| 2846 | N | GLU | B | 710 | 21.713 | 4.355 | 90.402 | 1.00 | 46.33 |
| 2847 | CA | GLU | B | 710 | 21.266 | 3.524 | 91.498 | 1.00 | 44.07 |
| 2848 | CB | GLU | B | 710 | 21.639 | 2.091 | 91.156 | 1.00 | 43.37 |
| 2849 | CG | GLU | B | 710 | 21.240 | 1.530 | 89.788 | 1.00 | 45.17 |
| 2850 | CD | GLU | B | 710 | 21.407 | 0.012 | 89.910 | 1.00 | 50.33 |
| 2851 | OE1 | GLU | B | 710 | 21.591 | -0.451 | 91.103 | 1.00 | 57.24 |
| 2852 | OE2 | GLU | B | 710 | 21.522 | -0.675 | 88.894 | 1.00 | 45.95 |
| 2853 | C | GLU | B | 710 | 21.845 | 3.640 | 92.888 | 1.00 | 45.39 |
| 2854 | O | GLU | B | 710 | 21.521 | 2.760 | 93.718 | 1.00 | 47.34 |
| 2855 | N | PHE | B | 711 | 22.760 | 4.543 | 93.196 | 1.00 | 43.13 |
| 2856 | CA | PHE | B | 711 | 23.200 | 4.589 | 94.566 | 1.00 | 40.55 |
| 2857 | CB | PHE | B | 711 | 24.679 | 4.658 | 94.597 | 1.00 | 39.03 |
| 2858 | CG | PHE | B | 711 | 25.276 | 3.409 | 94.246 | 1.00 | 42.05 |
| 2859 | CD1 | PHE | B | 711 | 26.050 | 3.281 | 93.108 | 1.00 | 38.47 |
| 2860 | CE1 | PHE | B | 711 | 26.599 | 2.064 | 92.802 | 1.00 | 39.65 |
| 2861 | CZ | PHE | B | 711 | 26.275 | 0.880 | 93.622 | 1.00 | 41.38 |
| 2862 | CE2 | PHE | B | 711 | 25.452 | 1.062 | 94.740 | 1.00 | 34.06 |
| 2863 | CD2 | PHE | B | 711 | 24.989 | 2.245 | 95.050 | 1.00 | 37.46 |
| 2864 | C | PHE | B | 711 | 22.626 | 5.863 | 95.009 | 1.00 | 40.79 |
| 2865 | O | PHE | B | 711 | 22.154 | 6.588 | 94.204 | 1.00 | 41.46 |
| 2866 | N | SER | B | 712 | 22.638 | 6.126 | 96.287 | 1.00 | 42.27 |
| 2867 | CA | SER | B | 712 | 22.217 | 7.392 | 96.828 | 1.00 | 43.06 |
| 2868 | CB | SER | B | 712 | 22.065 | 7.169 | 98.297 | 1.00 | 41.23 |
| 2869 | OG | SER | B | 712 | 23.405 | 7.227 | 98.787 | 1.00 | 49.09 |
| 2870 | C | SER | B | 712 | 23.457 | 8.292 | 96.753 | 1.00 | 43.66 |
| 2871 | O | SER | B | 712 | 24.613 | 7.773 | 96.636 | 1.00 | 45.02 |
| 2872 | N | VAL | B | 713 | 23.235 | 9.574 | 96.953 | 1.00 | 42.17 |
| 2873 | CA | VAL | B | 713 | 24.207 | 10.574 | 96.853 | 1.00 | 42.95 |
| 2874 | CB | VAL | B | 713 | 23.524 | 11.961 | 97.062 | 1.00 | 44.89 |
| 2875 | CG1 | VAL | B | 713 | 24.513 | 13.096 | 97.189 | 1.00 | 44.06 |
| 2876 | CG2 | VAL | B | 713 | 22.675 | 12.272 | 95.826 | 1.00 | 48.34 |
| 2877 | C | VAL | B | 713 | 25.151 | 10.328 | 97.995 | 1.00 | 43.30 |
| 2878 | O | VAL | B | 713 | 26.361 | 10.633 | 97.881 | 1.00 | 41.24 |
| 2879 | N | LEU | B | 714 | 24.607 | 9.742 | 99.082 | 1.00 | 42.36 |
| 2880 | CA | LEU | B | 714 | 25.412 | 9.441 | 100.294 | 1.00 | 42.34 |
| 2881 | CB | LEU | B | 714 | 24.549 | 8.997 | 101.456 | 1.00 | 41.80 |
| 2882 | CG | LEU | B | 714 | 24.175 | 10.104 | 102.419 | 1.00 | 45.27 |
| 2883 | CD1 | LEU | B | 714 | 23.237 | 9.593 | 103.631 | 1.00 | 45.36 |
| 2884 | CD2 | LEU | B | 714 | 25.513 | 10.577 | 102.995 | 1.00 | 43.80 |

FIGURE 3BF

| A | B | C | D | E | F | G | H | I | J |
|---|---|---|---|---|---|---|---|---|---|
| 2885 | C | LEU | B | 714 | 26.436 | 8.393 | 99.951 | 1.00 | 40.57 |
| 2886 | O | LEU | B | 714 | 27.671 | 8.526 | 100.117 | 1.00 | 40.01 |
| 2887 | N | GLN | B | 715 | 25.900 | 7.402 | 99.314 | 1.00 | 40.78 |
| 2888 | CA | GLN | B | 715 | 26.755 | 6.362 | 98.870 | 1.00 | 40.81 |
| 2889 | CB | GLN | B | 715 | 25.933 | 5.288 | 98.183 | 1.00 | 40.42 |
| 2890 | CG | GLN | B | 715 | 25.177 | 4.515 | 99.255 | 1.00 | 40.01 |
| 2891 | CD | GLN | B | 715 | 24.070 | 3.635 | 98.723 | 1.00 | 44.67 |
| 2892 | OE1 | GLN | B | 715 | 23.548 | 3.831 | 97.622 | 1.00 | 44.92 |
| 2893 | NE2 | GLN | B | 715 | 23.716 | 2.651 | 99.517 | 1.00 | 48.08 |
| 2894 | C | GLN | B | 715 | 27.860 | 6.935 | 98.036 | 1.00 | 39.80 |
| 2895 | O | GLN | B | 715 | 29.054 | 6.675 | 98.339 | 1.00 | 42.92 |
| 2896 | N | LEU | B | 716 | 27.532 | 7.760 | 97.064 | 1.00 | 36.73 |
| 2897 | CA | LEU | B | 716 | 28.556 | 8.274 | 96.227 | 1.00 | 35.84 |
| 2898 | CB | LEU | B | 716 | 27.903 | 9.036 | 95.104 | 1.00 | 37.36 |
| 2899 | CG | LEU | B | 716 | 27.084 | 8.148 | 94.217 | 1.00 | 36.58 |
| 2900 | CD1 | LEU | B | 716 | 26.356 | 9.177 | 93.311 | 1.00 | 46.24 |
| 2901 | CD2 | LEU | B | 716 | 27.996 | 7.350 | 93.371 | 1.00 | 37.81 |
| 2902 | C | LEU | B | 716 | 29.573 | 9.163 | 96.975 | 1.00 | 36.89 |
| 2903 | O | LEU | B | 716 | 30.819 | 9.095 | 96.782 | 1.00 | 36.93 |
| 2904 | N | VAL | B | 717 | 29.051 | 10.026 | 97.831 | 1.00 | 37.35 |
| 2905 | CA | VAL | B | 717 | 29.898 | 10.905 | 98.613 | 1.00 | 36.10 |
| 2906 | CB | VAL | B | 717 | 28.967 | 11.708 | 99.387 | 1.00 | 37.20 |
| 2907 | CG1 | VAL | B | 717 | 29.667 | 12.776 | 100.344 | 1.00 | 33.48 |
| 2908 | CG2 | VAL | B | 717 | 28.088 | 12.401 | 98.375 | 1.00 | 38.82 |
| 2909 | C | VAL | B | 717 | 30.870 | 10.002 | 99.410 | 1.00 | 38.05 |
| 2910 | O | VAL | B | 717 | 32.154 | 10.206 | 99.454 | 1.00 | 37.55 |
| 2911 | N | GLY | B | 718 | 30.264 | 8.952 | 99.981 | 1.00 | 36.80 |
| 2912 | CA | GLY | B | 718 | 31.042 | 8.022 | 100.772 | 1.00 | 33.97 |
| 2913 | C | GLY | B | 718 | 32.163 | 7.457 | 100.020 | 1.00 | 34.81 |
| 2914 | O | GLY | B | 718 | 33.349 | 7.436 | 100.512 | 1.00 | 37.01 |
| 2915 | N | MET | B | 719 | 31.892 | 7.099 | 98.779 | 1.00 | 34.31 |
| 2916 | CA | MET | B | 719 | 33.019 | 6.609 | 97.959 | 1.00 | 31.67 |
| 2917 | CB | MET | B | 719 | 32.491 | 6.176 | 96.577 | 1.00 | 32.74 |
| 2918 | CG | MET | B | 719 | 31.662 | 4.841 | 96.825 | 1.00 | 35.62 |
| 2919 | SD | MET | B | 719 | 30.875 | 4.103 | 95.295 | 1.00 | 55.32 |
| 2920 | CE | MET | B | 719 | 30.945 | 5.495 | 94.494 | 1.00 | 42.34 |
| 2921 | C | MET | B | 719 | 34.081 | 7.610 | 97.784 | 1.00 | 30.03 |
| 2922 | O | MET | B | 719 | 35.279 | 7.293 | 97.765 | 1.00 | 32.08 |
| 2923 | N | LEU | B | 720 | 33.687 | 8.847 | 97.618 | 1.00 | 30.17 |
| 2924 | CA | LEU | B | 720 | 34.667 | 9.890 | 97.346 | 1.00 | 33.37 |
| 2925 | CB | LEU | B | 720 | 33.986 | 11.242 | 96.935 | 1.00 | 32.33 |
| 2926 | CG | LEU | B | 720 | 33.343 | 11.032 | 95.575 | 1.00 | 38.69 |
| 2927 | CD1 | LEU | B | 720 | 32.375 | 12.150 | 95.300 | 1.00 | 38.75 |
| 2928 | CD2 | LEU | B | 720 | 34.427 | 10.867 | 94.495 | 1.00 | 35.80 |
| 2929 | C | LEU | B | 720 | 35.489 | 10.109 | 98.597 | 1.00 | 32.85 |
| 2930 | O | LEU | B | 720 | 36.671 | 10.336 | 98.518 | 1.00 | 31.06 |
| 2931 | N | ARG | B | 721 | 34.809 | 10.018 | 99.755 | 1.00 | 34.48 |
| 2932 | CA | ARG | B | 721 | 35.496 | 10.144 | 100.996 | 1.00 | 33.62 |
| 2933 | CB | ARG | B | 721 | 34.472 | 10.122 | 102.146 | 1.00 | 35.11 |
| 2934 | CG | ARG | B | 721 | 35.051 | 10.679 | 103.478 | 1.00 | 34.63 |
| 2935 | CD | ARG | B | 721 | 35.575 | 9.494 | 104.326 | 1.00 | 39.88 |
| 2936 | NE | ARG | B | 721 | 36.004 | 9.899 | 105.636 | 1.00 | 43.02 |

FIGURE 3BG

| A | B | C | D | E | F | G | H | I | J |
|---|---|---|---|---|---|---|---|---|---|
| 2937 | CZ | ARG | B | 721 | 36.937 | 9.323 | 106.397 | 1.00 | 45.17 |
| 2938 | NH1 | ARG | B | 721 | 37.612 | 8.271 | 105.961 | 1.00 | 40.58 |
| 2939 | NH2 | ARG | B | 721 | 37.213 | 9.851 | 107.611 | 1.00 | 38.32 |
| 2940 | C | ARG | B | 721 | 36.678 | 9.202 | 101.170 | 1.00 | 31.50 |
| 2941 | O | ARG | B | 721 | 37.783 | 9.594 | 101.591 | 1.00 | 32.33 |
| 2942 | N | GLY | B | 722 | 36.429 | 7.940 | 100.919 | 1.00 | 30.70 |
| 2943 | CA | GLY | B | 722 | 37.450 | 6.885 | 100.918 | 1.00 | 24.89 |
| 2944 | C | GLY | B | 722 | 38.535 | 7.253 | 99.976 | 1.00 | 26.45 |
| 2945 | O | GLY | B | 722 | 39.751 | 7.161 | 100.307 | 1.00 | 27.04 |
| 2946 | N | ILE | B | 723 | 38.180 | 7.638 | 98.764 | 1.00 | 24.68 |
| 2947 | CA | ILE | B | 723 | 39.285 | 7.928 | 97.861 | 1.00 | 25.69 |
| 2948 | CB | ILE | B | 723 | 38.728 | 8.341 | 96.509 | 1.00 | 25.40 |
| 2949 | CG1 | ILE | B | 723 | 38.089 | 7.129 | 95.744 | 1.00 | 23.38 |
| 2950 | CD1 | ILE | B | 723 | 36.956 | 7.550 | 94.656 | 1.00 | 17.00 |
| 2951 | CG2 | ILE | B | 723 | 39.915 | 8.818 | 95.562 | 1.00 | 25.42 |
| 2952 | C | ILE | B | 723 | 40.040 | 9.056 | 98.437 | 1.00 | 27.97 |
| 2953 | O | ILE | B | 723 | 41.273 | 9.063 | 98.412 | 1.00 | 29.92 |
| 2954 | N | ALA | B | 724 | 39.321 | 10.112 | 98.878 | 1.00 | 27.72 |
| 2955 | CA | ALA | B | 724 | 40.055 | 11.203 | 99.382 | 1.00 | 31.14 |
| 2956 | CB | ALA | B | 724 | 39.092 | 12.388 | 99.837 | 1.00 | 30.09 |
| 2957 | C | ALA | B | 724 | 40.994 | 10.756 | 100.578 | 1.00 | 32.43 |
| 2958 | O | ALA | B | 724 | 42.102 | 11.293 | 100.707 | 1.00 | 36.23 |
| 2959 | N | ALA | B | 725 | 40.599 | 9.778 | 101.386 | 1.00 | 32.15 |
| 2960 | CA | ALA | B | 725 | 41.367 | 9.437 | 102.613 | 1.00 | 33.49 |
| 2961 | CB | ALA | B | 725 | 40.465 | 8.568 | 103.649 | 1.00 | 31.16 |
| 2962 | C | ALA | B | 725 | 42.563 | 8.658 | 102.180 | 1.00 | 33.06 |
| 2963 | O | ALA | B | 725 | 43.630 | 8.759 | 102.838 | 1.00 | 36.69 |
| 2964 | N | GLY | B | 726 | 42.407 | 7.837 | 101.134 | 1.00 | 29.85 |
| 2965 | CA | GLY | B | 726 | 43.519 | 7.036 | 100.688 | 1.00 | 26.93 |
| 2966 | C | GLY | B | 726 | 44.531 | 8.080 | 100.151 | 1.00 | 31.48 |
| 2967 | O | GLY | B | 726 | 45.699 | 7.946 | 100.370 | 1.00 | 28.56 |
| 2968 | N | MET | B | 727 | 44.033 | 9.136 | 99.451 | 1.00 | 32.07 |
| 2969 | CA | MET | B | 727 | 44.899 | 10.121 | 98.846 | 1.00 | 33.27 |
| 2970 | CB | MET | B | 727 | 44.051 | 10.999 | 97.853 | 1.00 | 33.40 |
| 2971 | CG | MET | B | 727 | 43.815 | 10.423 | 96.365 | 1.00 | 31.54 |
| 2972 | SD | MET | B | 727 | 45.180 | 9.612 | 95.806 | 1.00 | 35.66 |
| 2973 | CE | MET | B | 727 | 46.441 | 10.934 | 95.492 | 1.00 | 31.92 |
| 2974 | C | MET | B | 727 | 45.618 | 10.984 | 100.018 | 1.00 | 33.03 |
| 2975 | O | MET | B | 727 | 46.780 | 11.331 | 99.892 | 1.00 | 31.10 |
| 2976 | N | LYS | B | 728 | 44.889 | 11.344 | 101.078 | 1.00 | 33.25 |
| 2977 | CA | LYS | B | 728 | 45.494 | 12.060 | 102.185 | 1.00 | 35.83 |
| 2978 | CB | LYS | B | 728 | 44.516 | 12.292 | 103.204 | 1.00 | 36.03 |
| 2979 | CG | LYS | B | 728 | 45.095 | 12.999 | 104.451 | 1.00 | 41.39 |
| 2980 | CD | LYS | B | 728 | 44.169 | 12.657 | 105.549 | 1.00 | 49.57 |
| 2981 | CE | LYS | B | 728 | 44.504 | 13.360 | 106.868 | 1.00 | 58.31 |
| 2982 | NZ | LYS | B | 728 | 44.561 | 12.303 | 107.986 | 1.00 | 63.45 |
| 2983 | C | LYS | B | 728 | 46.658 | 11.233 | 102.743 | 1.00 | 38.33 |
| 2984 | O | LYS | B | 728 | 47.792 | 11.753 | 103.065 | 1.00 | 39.63 |
| 2985 | N | TYR | B | 729 | 46.494 | 9.922 | 102.617 | 1.00 | 36.94 |
| 2986 | CA | TYR | B | 729 | 47.452 | 9.075 | 103.219 | 1.00 | 36.82 |
| 2987 | CB | TYR | B | 729 | 46.858 | 7.693 | 103.663 | 1.00 | 34.05 |
| 2988 | CG | TYR | B | 729 | 47.899 | 6.657 | 103.835 | 1.00 | 34.37 |

FIGURE 3BH

| A | B | C | D | E | F | G | H | I | J |
|---|---|---|---|---|---|---|---|---|---|
| 2989 | CD1 | TYR | B | 729 | 48.409 | 6.323 | 105.122 | 1.00 | 31.09 |
| 2990 | CE1 | TYR | B | 729 | 49.368 | 5.343 | 105.286 | 1.00 | 25.86 |
| 2991 | CZ | TYR | B | 729 | 49.864 | 4.733 | 104.160 | 1.00 | 32.58 |
| 2992 | OH | TYR | B | 729 | 50.764 | 3.772 | 104.302 | 1.00 | 30.28 |
| 2993 | CE2 | TYR | B | 729 | 49.369 | 5.022 | 102.863 | 1.00 | 28.90 |
| 2994 | CD2 | TYR | B | 729 | 48.343 | 5.918 | 102.735 | 1.00 | 28.62 |
| 2995 | C | TYR | B | 729 | 48.625 | 9.040 | 102.348 | 1.00 | 38.24 |
| 2996 | O | TYR | B | 729 | 49.760 | 9.011 | 102.837 | 1.00 | 40.23 |
| 2997 | N | LEU | B | 730 | 48.419 | 9.012 | 101.057 | 1.00 | 37.36 |
| 2998 | CA | LEU | B | 730 | 49.598 | 8.971 | 100.182 | 1.00 | 38.39 |
| 2999 | CB | LEU | B | 730 | 49.161 | 8.801 | 98.691 | 1.00 | 38.07 |
| 3000 | CG | LEU | B | 730 | 49.096 | 7.274 | 98.506 | 1.00 | 40.77 |
| 3001 | CD1 | LEU | B | 730 | 48.033 | 6.879 | 97.535 | 1.00 | 46.74 |
| 3002 | CD2 | LEU | B | 730 | 50.540 | 6.625 | 98.141 | 1.00 | 40.15 |
| 3003 | C | LEU | B | 730 | 50.415 | 10.239 | 100.271 | 1.00 | 36.79 |
| 3004 | O | LEU | B | 730 | 51.565 | 10.238 | 100.325 | 1.00 | 35.87 |
| 3005 | N | ALA | B | 731 | 49.753 | 11.330 | 100.211 | 1.00 | 38.07 |
| 3006 | CA | ALA | B | 731 | 50.421 | 12.597 | 100.382 | 1.00 | 41.33 |
| 3007 | CB | ALA | B | 731 | 49.377 | 13.802 | 100.342 | 1.00 | 35.88 |
| 3008 | C | ALA | B | 731 | 51.191 | 12.559 | 101.743 | 1.00 | 41.93 |
| 3009 | O | ALA | B | 731 | 52.353 | 12.861 | 101.784 | 1.00 | 41.92 |
| 3010 | N | ASN | B | 732 | 50.556 | 12.176 | 102.837 | 1.00 | 43.62 |
| 3011 | CA | ASN | B | 732 | 51.340 | 12.240 | 104.035 | 1.00 | 45.24 |
| 3012 | CB | ASN | B | 732 | 50.558 | 11.897 | 105.275 | 1.00 | 45.55 |
| 3013 | CG | ASN | B | 732 | 49.605 | 12.947 | 105.613 | 1.00 | 45.67 |
| 3014 | OD1 | ASN | B | 732 | 49.792 | 14.047 | 105.114 | 1.00 | 45.78 |
| 3015 | ND2 | ASN | B | 732 | 48.503 | 12.620 | 106.390 | 1.00 | 42.26 |
| 3016 | C | ASN | B | 732 | 52.439 | 11.247 | 103.945 | 1.00 | 46.19 |
| 3017 | O | ASN | B | 732 | 53.250 | 11.259 | 104.809 | 1.00 | 48.18 |
| 3018 | N | MET | B | 733 | 52.475 | 10.319 | 102.986 | 1.00 | 45.55 |
| 3019 | CA | MET | B | 733 | 53.611 | 9.396 | 102.967 | 1.00 | 42.71 |
| 3020 | CB | MET | B | 733 | 53.181 | 8.051 | 102.457 | 1.00 | 43.29 |
| 3021 | CG | MET | B | 733 | 52.418 | 7.229 | 103.469 | 1.00 | 44.11 |
| 3022 | SD | MET | B | 733 | 53.390 | 6.662 | 104.809 | 1.00 | 45.37 |
| 3023 | CE | MET | B | 733 | 54.537 | 5.722 | 104.067 | 1.00 | 43.23 |
| 3024 | C | MET | B | 733 | 54.473 | 10.030 | 101.973 | 1.00 | 43.07 |
| 3025 | O | MET | B | 733 | 55.449 | 9.447 | 101.489 | 1.00 | 39.67 |
| 3026 | N | ASN | B | 734 | 54.114 | 11.288 | 101.639 | 1.00 | 45.47 |
| 3027 | CA | ASN | B | 734 | 54.895 | 11.978 | 100.620 | 1.00 | 45.76 |
| 3028 | CB | ASN | B | 734 | 56.293 | 12.036 | 101.146 | 1.00 | 48.02 |
| 3029 | CG | ASN | B | 734 | 56.917 | 13.372 | 100.855 | 1.00 | 55.08 |
| 3030 | OD1 | ASN | B | 734 | 57.998 | 13.441 | 100.227 | 1.00 | 57.65 |
| 3031 | ND2 | ASN | B | 734 | 56.191 | 14.466 | 101.227 | 1.00 | 57.16 |
| 3032 | C | ASN | B | 734 | 55.017 | 11.329 | 99.233 | 1.00 | 44.84 |
| 3033 | O | ASN | B | 734 | 56.122 | 11.359 | 98.598 | 1.00 | 45.91 |
| 3034 | N | TYR | B | 735 | 53.933 | 10.733 | 98.723 | 1.00 | 43.14 |
| 3035 | CA | TYR | B | 735 | 53.846 | 10.348 | 97.298 | 1.00 | 39.99 |
| 3036 | CB | TYR | B | 735 | 53.511 | 8.904 | 97.196 | 1.00 | 42.06 |
| 3037 | CG | TYR | B | 735 | 54.612 | 7.939 | 97.303 | 1.00 | 39.82 |
| 3038 | CD1 | TYR | B | 735 | 55.073 | 7.272 | 96.195 | 1.00 | 40.71 |
| 3039 | CE1 | TYR | B | 735 | 56.143 | 6.364 | 96.327 | 1.00 | 49.17 |
| 3040 | CZ | TYR | B | 735 | 56.659 | 6.076 | 97.610 | 1.00 | 49.26 |

FIGURE 3BI

| A | B | C | D | E | F | G | H | I | J |
|---|---|---|---|---|---|---|---|---|---|
| 3041 | OH | TYR | B | 735 | 57.681 | 5.174 | 97.808 | 1.00 | 53.69 |
| 3042 | CE2 | TYR | B | 735 | 56.180 | 6.710 | 98.706 | 1.00 | 46.44 |
| 3043 | CD2 | TYR | B | 735 | 55.118 | 7.596 | 98.563 | 1.00 | 44.21 |
| 3044 | C | TYR | B | 735 | 52.766 | 11.131 | 96.513 | 1.00 | 40.01 |
| 3045 | O | TYR | B | 735 | 51.681 | 11.403 | 97.063 | 1.00 | 38.30 |
| 3046 | N | VAL | B | 736 | 53.084 | 11.534 | 95.242 | 1.00 | 39.05 |
| 3047 | CA | VAL | B | 736 | 52.155 | 12.135 | 94.317 | 1.00 | 37.57 |
| 3048 | CB | VAL | B | 736 | 52.978 | 12.826 | 93.220 | 1.00 | 40.62 |
| 3049 | CG1 | VAL | B | 736 | 52.210 | 13.815 | 92.384 | 1.00 | 40.34 |
| 3050 | CG2 | VAL | B | 736 | 54.164 | 13.336 | 93.780 | 1.00 | 46.41 |
| 3051 | C | VAL | B | 736 | 51.824 | 10.887 | 93.435 | 1.00 | 37.17 |
| 3052 | O | VAL | B | 736 | 52.735 | 10.241 | 92.930 | 1.00 | 29.75 |
| 3053 | N | HIS | B | 737 | 50.539 | 10.633 | 93.185 | 1.00 | 37.35 |
| 3054 | CA | HIS | B | 737 | 50.106 | 9.466 | 92.371 | 1.00 | 37.48 |
| 3055 | CB | HIS | B | 737 | 48.645 | 9.217 | 92.703 | 1.00 | 37.46 |
| 3056 | CG | HIS | B | 737 | 48.149 | 7.922 | 92.212 | 1.00 | 38.36 |
| 3057 | ND1 | HIS | B | 737 | 47.788 | 7.709 | 90.894 | 1.00 | 33.89 |
| 3058 | CE1 | HIS | B | 737 | 47.448 | 6.446 | 90.753 | 1.00 | 38.45 |
| 3059 | NE2 | HIS | B | 737 | 47.527 | 5.845 | 91.941 | 1.00 | 38.58 |
| 3060 | CD2 | HIS | B | 737 | 48.022 | 6.737 | 92.850 | 1.00 | 36.23 |
| 3061 | C | HIS | B | 737 | 50.310 | 9.689 | 90.885 | 1.00 | 37.35 |
| 3062 | O | HIS | B | 737 | 50.900 | 8.930 | 90.179 | 1.00 | 37.49 |
| 3063 | N | ARG | B | 738 | 49.921 | 10.862 | 90.420 | 1.00 | 41.12 |
| 3064 | CA | ARG | B | 738 | 50.156 | 11.215 | 89.025 | 1.00 | 41.82 |
| 3065 | CB | ARG | B | 738 | 51.548 | 10.752 | 88.576 | 1.00 | 42.45 |
| 3066 | CG | ARG | B | 738 | 52.900 | 11.362 | 89.171 | 1.00 | 43.81 |
| 3067 | CD | ARG | B | 738 | 53.934 | 12.099 | 88.306 | 1.00 | 50.41 |
| 3068 | NE | ARG | B | 738 | 54.475 | 11.640 | 87.014 | 1.00 | 59.49 |
| 3069 | CZ | ARG | B | 738 | 55.049 | 10.452 | 86.751 | 1.00 | 66.23 |
| 3070 | NH1 | ARG | B | 738 | 55.115 | 9.499 | 87.671 | 1.00 | 66.49 |
| 3071 | NH2 | ARG | B | 738 | 55.533 | 10.202 | 85.535 | 1.00 | 66.53 |
| 3072 | C | ARG | B | 738 | 49.061 | 10.581 | 88.104 | 1.00 | 42.10 |
| 3073 | O | ARG | B | 738 | 48.853 | 11.056 | 87.025 | 1.00 | 42.38 |
| 3074 | N | ASP | B | 739 | 48.304 | 9.578 | 88.572 | 1.00 | 40.65 |
| 3075 | CA | ASP | B | 739 | 47.402 | 8.839 | 87.683 | 1.00 | 37.25 |
| 3076 | CB | ASP | B | 739 | 48.098 | 7.585 | 87.132 | 1.00 | 36.50 |
| 3077 | CG | ASP | B | 739 | 47.447 | 7.043 | 85.859 | 1.00 | 39.77 |
| 3078 | OD1 | ASP | B | 739 | 46.714 | 7.845 | 85.259 | 1.00 | 35.07 |
| 3079 | OD2 | ASP | B | 739 | 47.588 | 5.843 | 85.423 | 1.00 | 38.97 |
| 3080 | C | ASP | B | 739 | 46.159 | 8.470 | 88.383 | 1.00 | 33.96 |
| 3081 | O | ASP | B | 739 | 45.641 | 7.385 | 88.230 | 1.00 | 33.13 |
| 3082 | N | LEU | B | 740 | 45.612 | 9.440 | 89.054 | 1.00 | 32.76 |
| 3083 | CA | LEU | B | 740 | 44.385 | 9.304 | 89.792 | 1.00 | 32.28 |
| 3084 | CB | LEU | B | 740 | 44.218 | 10.378 | 90.903 | 1.00 | 28.90 |
| 3085 | CG | LEU | B | 740 | 42.918 | 10.273 | 91.633 | 1.00 | 31.41 |
| 3086 | CD1 | LEU | B | 740 | 42.750 | 8.844 | 92.335 | 1.00 | 29.24 |
| 3087 | CD2 | LEU | B | 740 | 42.714 | 11.301 | 92.751 | 1.00 | 31.09 |
| 3088 | C | LEU | B | 740 | 43.230 | 9.487 | 88.854 | 1.00 | 33.40 |
| 3089 | O | LEU | B | 740 | 42.972 | 10.631 | 88.367 | 1.00 | 32.41 |
| 3090 | N | ALA | B | 741 | 42.375 | 8.464 | 88.851 | 1.00 | 32.10 |
| 3091 | CA | ALA | B | 741 | 41.256 | 8.492 | 87.939 | 1.00 | 31.90 |
| 3092 | CB | ALA | B | 741 | 41.795 | 8.228 | 86.473 | 1.00 | 25.99 |

FIGURE 3BJ

| A | B | C | D | E | F | G | H | I | J |
|---|---|---|---|---|---|---|---|---|---|
| 3093 | C | ALA | B | 741 | 40.361 | 7.405 | 88.402 | 1.00 | 30.39 |
| 3094 | O | ALA | B | 741 | 40.849 | 6.468 | 89.090 | 1.00 | 32.43 |
| 3095 | N | ALA | B | 742 | 39.091 | 7.450 | 87.997 | 1.00 | 30.00 |
| 3096 | CA | ALA | B | 742 | 38.230 | 6.405 | 88.434 | 1.00 | 28.92 |
| 3097 | CB | ALA | B | 742 | 36.771 | 6.688 | 88.146 | 1.00 | 32.43 |
| 3098 | C | ALA | B | 742 | 38.702 | 5.046 | 87.904 | 1.00 | 31.77 |
| 3099 | O | ALA | B | 742 | 38.551 | 4.078 | 88.607 | 1.00 | 30.25 |
| 3100 | N | ARG | B | 743 | 39.282 | 4.907 | 86.696 | 1.00 | 31.71 |
| 3101 | CA | ARG | B | 743 | 39.685 | 3.568 | 86.348 | 1.00 | 32.57 |
| 3102 | CB | ARG | B | 743 | 40.311 | 3.530 | 84.893 | 1.00 | 30.75 |
| 3103 | CG | ARG | B | 743 | 41.249 | 4.519 | 84.625 | 1.00 | 29.61 |
| 3104 | CD | ARG | B | 743 | 42.260 | 4.076 | 83.465 | 1.00 | 43.52 |
| 3105 | NE | ARG | B | 743 | 43.297 | 5.113 | 83.400 | 1.00 | 45.54 |
| 3106 | CZ | ARG | B | 743 | 42.950 | 6.342 | 83.147 | 1.00 | 45.33 |
| 3107 | NH1 | ARG | B | 743 | 41.651 | 6.558 | 82.868 | 1.00 | 38.16 |
| 3108 | NH2 | ARG | B | 743 | 43.844 | 7.305 | 83.199 | 1.00 | 38.31 |
| 3109 | C | ARG | B | 743 | 40.697 | 3.045 | 87.291 | 1.00 | 32.35 |
| 3110 | O | ARG | B | 743 | 41.122 | 1.917 | 87.211 | 1.00 | 33.13 |
| 3111 | N | ASN | B | 744 | 41.306 | 3.909 | 88.055 | 1.00 | 33.51 |
| 3112 | CA | ASN | B | 744 | 42.357 | 3.337 | 88.857 | 1.00 | 32.87 |
| 3113 | CB | ASN | B | 744 | 43.651 | 4.144 | 88.701 | 1.00 | 33.36 |
| 3114 | CG | ASN | B | 744 | 44.393 | 3.813 | 87.400 | 1.00 | 34.78 |
| 3115 | OD1 | ASN | B | 744 | 44.062 | 2.792 | 86.820 | 1.00 | 48.21 |
| 3116 | ND2 | ASN | B | 744 | 45.248 | 4.718 | 86.851 | 1.00 | 31.64 |
| 3117 | C | ASN | B | 744 | 41.888 | 3.251 | 90.300 | 1.00 | 34.12 |
| 3118 | O | ASN | B | 744 | 42.689 | 3.242 | 91.157 | 1.00 | 36.14 |
| 3119 | N | ILE | B | 745 | 40.592 | 3.314 | 90.558 | 1.00 | 32.33 |
| 3120 | CA | ILE | B | 745 | 40.098 | 3.112 | 91.861 | 1.00 | 31.92 |
| 3121 | CB | ILE | B | 745 | 39.154 | 4.230 | 92.239 | 1.00 | 31.00 |
| 3122 | CG1 | ILE | B | 745 | 39.824 | 5.704 | 92.215 | 1.00 | 32.78 |
| 3123 | CD1 | ILE | B | 745 | 41.204 | 5.701 | 92.993 | 1.00 | 32.89 |
| 3124 | CG2 | ILE | B | 745 | 38.602 | 3.943 | 93.507 | 1.00 | 25.39 |
| 3125 | C | ILE | B | 745 | 39.347 | 1.767 | 91.809 | 1.00 | 32.48 |
| 3126 | O | ILE | B | 745 | 38.592 | 1.602 | 90.864 | 1.00 | 32.62 |
| 3127 | N | LEU | B | 746 | 39.593 | 0.833 | 92.752 | 1.00 | 29.93 |
| 3128 | CA | LEU | B | 746 | 38.994 | -0.526 | 92.790 | 1.00 | 28.79 |
| 3129 | CB | LEU | B | 746 | 40.047 | -1.578 | 93.158 | 1.00 | 27.96 |
| 3130 | CG | LEU | B | 746 | 41.188 | -1.793 | 92.142 | 1.00 | 27.80 |
| 3131 | CD1 | LEU | B | 746 | 42.431 | -2.746 | 92.482 | 1.00 | 36.80 |
| 3132 | CD2 | LEU | B | 746 | 40.582 | -2.251 | 90.857 | 1.00 | 32.27 |
| 3133 | C | LEU | B | 746 | 37.941 | -0.457 | 93.907 | 1.00 | 31.64 |
| 3134 | O | LEU | B | 746 | 38.176 | 0.242 | 94.933 | 1.00 | 32.71 |
| 3135 | N | VAL | B | 747 | 36.752 | -1.061 | 93.727 | 1.00 | 32.95 |
| 3136 | CA | VAL | B | 747 | 35.729 | -0.956 | 94.751 | 1.00 | 33.60 |
| 3137 | CB | VAL | B | 747 | 34.337 | -0.627 | 94.211 | 1.00 | 35.06 |
| 3138 | CG1 | VAL | B | 747 | 33.569 | 0.153 | 95.190 | 1.00 | 32.73 |
| 3139 | CG2 | VAL | B | 747 | 34.311 | -0.145 | 92.802 | 1.00 | 36.08 |
| 3140 | C | VAL | B | 747 | 35.379 | -2.348 | 95.139 | 1.00 | 32.18 |
| 3141 | O | VAL | B | 747 | 35.438 | -3.132 | 94.271 | 1.00 | 32.47 |
| 3142 | N | ASN | B | 748 | 34.809 | -2.569 | 96.331 | 1.00 | 31.01 |
| 3143 | CA | ASN | B | 748 | 34.300 | -3.873 | 96.670 | 1.00 | 32.11 |
| 3144 | CB | ASN | B | 748 | 35.076 | -4.503 | 97.805 | 1.00 | 29.71 |

FIGURE 3BK

| A | B | C | D | E | F | G | H | I | J |
|---|---|---|---|---|---|---|---|---|---|
| 3145 | CG | ASN | B | 748 | 34.872 | -3.789 | 99.093 | 1.00 | 30.19 |
| 3146 | OD1 | ASN | B | 748 | 34.002 | -2.965 | 99.154 | 1.00 | 29.21 |
| 3147 | ND2 | ASN | B | 748 | 35.724 | -4.051 | 100.145 | 1.00 | 27.55 |
| 3148 | C | ASN | B | 748 | 32.782 | -3.847 | 96.880 | 1.00 | 32.91 |
| 3149 | O | ASN | B | 748 | 32.137 | -2.821 | 96.558 | 1.00 | 34.46 |
| 3150 | N | SER | B | 749 | 32.200 | -4.931 | 97.392 | 1.00 | 31.86 |
| 3151 | CA | SER | B | 749 | 30.779 | -4.924 | 97.589 | 1.00 | 32.16 |
| 3152 | CB | SER | B | 749 | 30.203 | -6.341 | 97.762 | 1.00 | 33.15 |
| 3153 | OG | SER | B | 749 | 30.792 | -7.147 | 98.772 | 1.00 | 33.73 |
| 3154 | C | SER | B | 749 | 30.390 | -4.108 | 98.724 | 1.00 | 33.33 |
| 3155 | O | SER | B | 749 | 29.213 | -3.877 | 98.965 | 1.00 | 31.39 |
| 3156 | N | ASN | B | 750 | 31.368 | -3.666 | 99.517 | 1.00 | 34.87 |
| 3157 | CA | ASN | B | 750 | 30.972 | -2.694 | 100.547 | 1.00 | 35.09 |
| 3158 | CB | ASN | B | 750 | 31.781 | -2.859 | 101.809 | 1.00 | 37.06 |
| 3159 | CG | ASN | B | 750 | 31.421 | -4.146 | 102.582 | 1.00 | 41.91 |
| 3160 | OD1 | ASN | B | 750 | 30.278 | -4.661 | 102.549 | 1.00 | 38.82 |
| 3161 | ND2 | ASN | B | 750 | 32.424 | -4.652 | 103.275 | 1.00 | 46.14 |
| 3162 | C | ASN | B | 750 | 31.082 | -1.295 | 100.025 | 1.00 | 34.62 |
| 3163 | O | ASN | B | 750 | 30.760 | -0.354 | 100.737 | 1.00 | 36.26 |
| 3164 | N | LEU | B | 751 | 31.385 | -1.151 | 98.738 | 1.00 | 31.97 |
| 3165 | CA | LEU | B | 751 | 31.511 | 0.150 | 98.134 | 1.00 | 33.21 |
| 3166 | CB | LEU | B | 751 | 30.275 | 1.085 | 98.379 | 1.00 | 33.30 |
| 3167 | CG | LEU | B | 751 | 28.944 | 0.583 | 97.933 | 1.00 | 29.08 |
| 3168 | CD1 | LEU | B | 751 | 27.770 | 1.538 | 97.936 | 1.00 | 34.22 |
| 3169 | CD2 | LEU | B | 751 | 29.187 | 0.432 | 96.569 | 1.00 | 25.04 |
| 3170 | C | LEU | B | 751 | 32.774 | 0.820 | 98.675 | 1.00 | 31.97 |
| 3171 | O | LEU | B | 751 | 32.932 | 1.949 | 98.482 | 1.00 | 32.37 |
| 3172 | N | VAL | B | 752 | 33.673 | 0.112 | 99.330 | 1.00 | 31.80 |
| 3173 | CA | VAL | B | 752 | 34.884 | 0.756 | 99.838 | 1.00 | 32.23 |
| 3174 | CB | VAL | B | 752 | 35.557 | -0.206 | 100.847 | 1.00 | 34.25 |
| 3175 | CG1 | VAL | B | 752 | 36.916 | 0.159 | 101.117 | 1.00 | 28.08 |
| 3176 | CG2 | VAL | B | 752 | 34.701 | -0.310 | 102.072 | 1.00 | 27.86 |
| 3177 | C | VAL | B | 752 | 35.761 | 0.974 | 98.604 | 1.00 | 34.48 |
| 3178 | O | VAL | B | 752 | 35.900 | 0.035 | 97.753 | 1.00 | 33.89 |
| 3179 | N | CYS | B | 753 | 36.345 | 2.183 | 98.450 | 1.00 | 34.53 |
| 3180 | CA | CYS | B | 753 | 37.139 | 2.463 | 97.238 | 1.00 | 33.46 |
| 3181 | CB | CYS | B | 753 | 36.667 | 3.795 | 96.590 | 1.00 | 32.57 |
| 3182 | SG | CYS | B | 753 | 35.024 | 3.589 | 95.866 | 1.00 | 33.85 |
| 3183 | C | CYS | B | 753 | 38.595 | 2.504 | 97.641 | 1.00 | 32.87 |
| 3184 | O | CYS | B | 753 | 38.918 | 2.994 | 98.661 | 1.00 | 33.65 |
| 3185 | N | LYS | B | 754 | 39.490 | 2.019 | 96.815 | 1.00 | 31.25 |
| 3186 | CA | LYS | B | 754 | 40.879 | 2.069 | 97.142 | 1.00 | 28.59 |
| 3187 | CB | LYS | B | 754 | 41.393 | 0.682 | 97.601 | 1.00 | 28.62 |
| 3188 | CG | LYS | B | 754 | 40.612 | 0.009 | 98.777 | 1.00 | 25.26 |
| 3189 | CD | LYS | B | 754 | 41.255 | -1.359 | 99.092 | 1.00 | 26.47 |
| 3190 | CE | LYS | B | 754 | 40.451 | -2.186 | 100.084 | 1.00 | 31.42 |
| 3191 | NZ | LYS | B | 754 | 41.028 | -2.117 | 101.467 | 1.00 | 36.53 |
| 3192 | C | LYS | B | 754 | 41.659 | 2.488 | 95.931 | 1.00 | 29.63 |
| 3193 | O | LYS | B | 754 | 41.451 | 1.951 | 94.764 | 1.00 | 29.44 |
| 3194 | N | VAL | B | 755 | 42.643 | 3.336 | 96.190 | 1.00 | 28.68 |
| 3195 | CA | VAL | B | 755 | 43.512 | 3.819 | 95.158 | 1.00 | 30.76 |
| 3196 | CB | VAL | B | 755 | 44.484 | 4.852 | 95.681 | 1.00 | 29.87 |

FIGURE 3BL

| A | B | C | D | E | F | G | H | I | J |
|---|---|---|---|---|---|---|---|---|---|
| 3197 | CG1 | VAL | B | 755 | 45.380 | 5.460 | 94.520 | 1.00 | 26.20 |
| 3198 | CG2 | VAL | B | 755 | 43.750 | 5.907 | 96.257 | 1.00 | 28.72 |
| 3199 | C | VAL | B | 755 | 44.391 | 2.708 | 94.759 | 1.00 | 31.83 |
| 3200 | O | VAL | B | 755 | 44.894 | 2.059 | 95.618 | 1.00 | 30.86 |
| 3201 | N | SER | B | 756 | 44.722 | 2.641 | 93.486 | 1.00 | 33.08 |
| 3202 | CA | SER | B | 756 | 45.431 | 1.545 | 92.914 | 1.00 | 36.43 |
| 3203 | CB | SER | B | 756 | 44.472 | 0.481 | 92.259 | 1.00 | 37.70 |
| 3204 | OG | SER | B | 756 | 45.281 | -0.617 | 91.571 | 1.00 | 40.69 |
| 3205 | C | SER | B | 756 | 46.368 | 2.061 | 91.849 | 1.00 | 37.72 |
| 3206 | O | SER | B | 756 | 46.466 | 3.263 | 91.576 | 1.00 | 37.99 |
| 3207 | N | ASP | B | 757 | 46.978 | 1.130 | 91.147 | 1.00 | 38.48 |
| 3208 | CA | ASP | B | 757 | 47.861 | 1.499 | 90.074 | 1.00 | 41.72 |
| 3209 | CB | ASP | B | 757 | 47.023 | 1.917 | 88.888 | 1.00 | 41.39 |
| 3210 | CG | ASP | B | 757 | 47.849 | 1.913 | 87.574 | 1.00 | 50.91 |
| 3211 | OD1 | ASP | B | 757 | 47.211 | 2.091 | 86.487 | 1.00 | 51.60 |
| 3212 | OD2 | ASP | B | 757 | 49.141 | 1.757 | 87.558 | 1.00 | 52.69 |
| 3213 | C | ASP | B | 757 | 49.001 | 2.490 | 90.467 | 1.00 | 41.65 |
| 3214 | O | ASP | B | 757 | 48.943 | 3.671 | 90.267 | 1.00 | 41.11 |
| 3215 | N | PHE | B | 758 | 50.076 | 1.995 | 91.048 | 1.00 | 43.52 |
| 3216 | CA | PHE | B | 758 | 51.087 | 2.948 | 91.493 | 1.00 | 44.14 |
| 3217 | CB | PHE | B | 758 | 51.525 | 2.631 | 92.952 | 1.00 | 43.50 |
| 3218 | CG | PHE | B | 758 | 50.456 | 2.888 | 93.920 | 1.00 | 38.35 |
| 3219 | CD1 | PHE | B | 758 | 50.308 | 4.177 | 94.499 | 1.00 | 33.03 |
| 3220 | CE1 | PHE | B | 758 | 49.233 | 4.488 | 95.392 | 1.00 | 33.75 |
| 3221 | CZ | PHE | B | 758 | 48.282 | 3.458 | 95.734 | 1.00 | 35.68 |
| 3222 | CE2 | PHE | B | 758 | 48.419 | 2.141 | 95.050 | 1.00 | 35.33 |
| 3223 | CD2 | PHE | B | 758 | 49.531 | 1.901 | 94.184 | 1.00 | 37.29 |
| 3224 | C | PHE | B | 758 | 52.199 | 3.247 | 90.454 | 1.00 | 45.65 |
| 3225 | O | PHE | B | 758 | 53.160 | 4.088 | 90.646 | 1.00 | 46.52 |
| 3226 | N | GLY | B | 759 | 51.903 | 2.709 | 89.282 | 1.00 | 46.03 |
| 3227 | CA | GLY | B | 759 | 52.617 | 2.856 | 88.048 | 1.00 | 47.12 |
| 3228 | C | GLY | B | 759 | 53.353 | 4.173 | 87.857 | 1.00 | 50.02 |
| 3229 | O | GLY | B | 759 | 54.588 | 4.163 | 87.553 | 1.00 | 53.05 |
| 3230 | N | LEU | B | 760 | 52.664 | 5.294 | 87.911 | 1.00 | 46.21 |
| 3231 | CA | LEU | B | 760 | 53.371 | 6.532 | 87.683 | 1.00 | 47.41 |
| 3232 | CB | LEU | B | 760 | 52.504 | 7.502 | 86.833 | 1.00 | 46.97 |
| 3233 | CG | LEU | B | 760 | 52.025 | 7.054 | 85.450 | 1.00 | 52.65 |
| 3234 | CD1 | LEU | B | 760 | 51.187 | 8.062 | 84.659 | 1.00 | 51.82 |
| 3235 | CD2 | LEU | B | 760 | 53.252 | 6.691 | 84.637 | 1.00 | 51.03 |
| 3236 | C | LEU | B | 760 | 53.628 | 7.284 | 88.974 | 1.00 | 47.35 |
| 3237 | O | LEU | B | 760 | 53.755 | 8.468 | 88.928 | 1.00 | 47.23 |
| 3238 | N | SER | B | 761 | 53.643 | 6.672 | 90.144 | 1.00 | 48.54 |
| 3239 | CA | SER | B | 761 | 53.583 | 7.610 | 91.262 | 1.00 | 49.64 |
| 3240 | CB | SER | B | 761 | 52.674 | 7.066 | 92.329 | 1.00 | 47.14 |
| 3241 | OG | SER | B | 761 | 53.142 | 5.812 | 92.428 | 1.00 | 48.99 |
| 3242 | C | SER | B | 761 | 54.965 | 7.803 | 91.813 | 1.00 | 50.77 |
| 3243 | O | SER | B | 761 | 55.814 | 6.895 | 91.672 | 1.00 | 51.89 |
| 3244 | N | ARG | B | 762 | 55.227 | 8.947 | 92.427 | 1.00 | 50.64 |
| 3245 | CA | ARG | B | 762 | 56.576 | 9.132 | 92.940 | 1.00 | 51.02 |
| 3246 | CB | ARG | B | 762 | 57.561 | 9.689 | 91.897 | 1.00 | 52.96 |
| 3247 | CG | ARG | B | 762 | 57.051 | 10.548 | 90.775 | 1.00 | 55.70 |
| 3248 | CD | ARG | B | 762 | 57.559 | 10.114 | 89.374 | 1.00 | 67.92 |

FIGURE 3BM

| A | B | C | D | E | F | G | H | I | J |
|---|---|---|---|---|---|---|---|---|---|
| 3249 | NE | ARG | B | 762 | 57.115 | 8.769 | 88.974 | 1.00 | 75.81 |
| 3250 | CZ | ARG | B | 762 | 57.530 | 8.088 | 87.860 | 1.00 | 79.84 |
| 3251 | NH1 | ARG | B | 762 | 57.034 | 6.858 | 87.589 | 1.00 | 77.74 |
| 3252 | NH2 | ARG | B | 762 | 58.432 | 8.624 | 87.030 | 1.00 | 79.01 |
| 3253 | C | ARG | B | 762 | 56.692 | 9.874 | 94.202 | 1.00 | 50.69 |
| 3254 | O | ARG | B | 762 | 55.762 | 10.587 | 94.600 | 1.00 | 50.50 |
| 3255 | N | VAL | B | 763 | 57.834 | 9.667 | 94.879 | 1.00 | 52.25 |
| 3256 | CA | VAL | B | 763 | 58.143 | 10.438 | 96.111 | 1.00 | 53.91 |
| 3257 | CB | VAL | B | 763 | 59.438 | 9.932 | 96.770 | 1.00 | 56.45 |
| 3258 | CG1 | VAL | B | 763 | 59.822 | 10.769 | 98.058 | 1.00 | 53.41 |
| 3259 | CG2 | VAL | B | 763 | 59.293 | 8.431 | 97.046 | 1.00 | 53.98 |
| 3260 | C | VAL | B | 763 | 58.323 | 11.921 | 95.757 | 1.00 | 52.61 |
| 3261 | O | VAL | B | 763 | 58.998 | 12.205 | 94.849 | 1.00 | 52.54 |
| 3262 | N | ALA | B | 764 | 57.680 | 12.818 | 96.460 | 1.00 | 53.25 |
| 3263 | CA | ALA | B | 764 | 57.640 | 14.215 | 96.083 | 1.00 | 55.20 |
| 3264 | CB | ALA | B | 764 | 56.842 | 15.013 | 97.079 | 1.00 | 55.95 |
| 3265 | C | ALA | B | 764 | 58.997 | 14.901 | 95.822 | 1.00 | 58.47 |
| 3266 | O | ALA | B | 764 | 60.011 | 14.667 | 96.486 | 1.00 | 58.95 |
| 3267 | N | ALA | B | 778 | 52.512 | 8.707 | 77.650 | 1.00 | 63.16 |
| 3268 | CA | ALA | B | 778 | 53.274 | 9.379 | 78.726 | 1.00 | 64.24 |
| 3269 | CB | ALA | B | 778 | 54.203 | 10.520 | 78.164 | 1.00 | 63.79 |
| 3270 | C | ALA | B | 778 | 52.320 | 9.882 | 79.851 | 1.00 | 63.12 |
| 3271 | O | ALA | B | 778 | 52.320 | 9.355 | 80.966 | 1.00 | 63.11 |
| 3272 | N | ILE | B | 779 | 51.472 | 10.863 | 79.572 | 1.00 | 61.82 |
| 3273 | CA | ILE | B | 779 | 50.565 | 11.342 | 80.639 | 1.00 | 59.71 |
| 3274 | CB | ILE | B | 779 | 51.075 | 12.717 | 81.033 | 1.00 | 60.71 |
| 3275 | CG1 | ILE | B | 779 | 52.166 | 12.503 | 82.090 | 1.00 | 62.19 |
| 3276 | CD1 | ILE | B | 779 | 53.432 | 13.193 | 81.727 | 1.00 | 66.21 |
| 3277 | CG2 | ILE | B | 779 | 49.943 | 13.685 | 81.434 | 1.00 | 62.88 |
| 3278 | C | ILE | B | 779 | 49.010 | 11.248 | 80.435 | 1.00 | 57.07 |
| 3279 | O | ILE | B | 779 | 48.552 | 11.065 | 79.280 | 1.00 | 55.98 |
| 3280 | N | PRO | B | 780 | 48.228 | 11.201 | 81.549 | 1.00 | 54.65 |
| 3281 | CA | PRO | B | 780 | 46.770 | 11.559 | 81.509 | 1.00 | 52.75 |
| 3282 | CB | PRO | B | 780 | 46.321 | 11.448 | 82.969 | 1.00 | 53.47 |
| 3283 | CG | PRO | B | 780 | 47.247 | 10.442 | 83.543 | 1.00 | 51.28 |
| 3284 | CD | PRO | B | 780 | 48.603 | 10.801 | 82.915 | 1.00 | 54.55 |
| 3285 | C | PRO | B | 780 | 46.610 | 12.952 | 81.191 | 1.00 | 50.88 |
| 3286 | O | PRO | B | 780 | 46.988 | 13.770 | 82.008 | 1.00 | 56.60 |
| 3287 | N | ILE | B | 781 | 46.112 | 13.222 | 80.017 | 1.00 | 46.48 |
| 3288 | CA | ILE | B | 781 | 45.849 | 14.560 | 79.767 | 1.00 | 43.01 |
| 3289 | CB | ILE | B | 781 | 45.897 | 14.790 | 78.286 | 1.00 | 41.97 |
| 3290 | CG1 | ILE | B | 781 | 47.316 | 15.269 | 78.013 | 1.00 | 45.31 |
| 3291 | CD1 | ILE | B | 781 | 48.308 | 14.194 | 77.831 | 1.00 | 50.28 |
| 3292 | CG2 | ILE | B | 781 | 45.107 | 15.941 | 77.979 | 1.00 | 38.03 |
| 3293 | C | ILE | B | 781 | 44.611 | 15.023 | 80.581 | 1.00 | 40.95 |
| 3294 | O | ILE | B | 781 | 44.748 | 15.814 | 81.489 | 1.00 | 40.34 |
| 3295 | N | ARG | B | 782 | 43.460 | 14.431 | 80.284 | 1.00 | 41.60 |
| 3296 | CA | ARG | B | 782 | 42.166 | 14.646 | 80.837 | 1.00 | 38.55 |
| 3297 | CB | ARG | B | 782 | 41.127 | 13.968 | 79.858 | 1.00 | 40.91 |
| 3298 | CG | ARG | B | 782 | 40.395 | 12.734 | 80.126 | 1.00 | 39.72 |
| 3299 | CD | ARG | B | 782 | 40.142 | 12.040 | 78.779 | 1.00 | 44.03 |
| 3300 | NE | ARG | B | 782 | 38.977 | 12.556 | 78.126 | 1.00 | 50.70 |

FIGURE 3BN

| A | B | C | D | E | F | G | H | I | J |
|---|---|---|---|---|---|---|---|---|---|
| 3301 | CZ | ARG | B | 782 | 38.978 | 13.000 | 76.853 | 1.00 | 52.30 |
| 3302 | NH1 | ARG | B | 782 | 37.828 | 13.451 | 76.324 | 1.00 | 46.70 |
| 3303 | NH2 | ARG | B | 782 | 40.126 | 13.022 | 76.153 | 1.00 | 44.94 |
| 3304 | C | ARG | B | 782 | 42.033 | 14.486 | 82.369 | 1.00 | 36.84 |
| 3305 | O | ARG | B | 782 | 41.124 | 15.127 | 82.932 | 1.00 | 37.92 |
| 3306 | N | TRP | B | 783 | 42.986 | 13.873 | 83.062 | 1.00 | 35.41 |
| 3307 | CA | TRP | B | 783 | 42.931 | 13.863 | 84.548 | 1.00 | 36.23 |
| 3308 | CB | TRP | B | 783 | 43.045 | 12.446 | 85.168 | 1.00 | 35.36 |
| 3309 | CG | TRP | B | 783 | 41.939 | 11.580 | 84.894 | 1.00 | 34.89 |
| 3310 | CD1 | TRP | B | 783 | 40.959 | 11.347 | 85.728 | 1.00 | 34.55 |
| 3311 | NE1 | TRP | B | 783 | 40.032 | 10.518 | 85.152 | 1.00 | 35.15 |
| 3312 | CE2 | TRP | B | 783 | 40.417 | 10.196 | 83.889 | 1.00 | 28.35 |
| 3313 | CD2 | TRP | B | 783 | 41.611 | 10.885 | 83.662 | 1.00 | 29.59 |
| 3314 | CE3 | TRP | B | 783 | 42.243 | 10.720 | 82.424 | 1.00 | 33.66 |
| 3315 | CZ3 | TRP | B | 783 | 41.642 | 9.873 | 81.461 | 1.00 | 39.20 |
| 3316 | CH2 | TRP | B | 783 | 40.386 | 9.270 | 81.697 | 1.00 | 30.32 |
| 3317 | CZ2 | TRP | B | 783 | 39.750 | 9.394 | 82.892 | 1.00 | 26.79 |
| 3318 | C | TRP | B | 783 | 44.019 | 14.767 | 85.182 | 1.00 | 37.26 |
| 3319 | O | TRP | B | 783 | 44.078 | 14.934 | 86.462 | 1.00 | 32.75 |
| 3320 | N | THR | B | 784 | 44.868 | 15.335 | 84.294 | 1.00 | 38.13 |
| 3321 | CA | THR | B | 784 | 46.074 | 16.069 | 84.782 | 1.00 | 38.14 |
| 3322 | CB | THR | B | 784 | 47.220 | 15.822 | 83.921 | 1.00 | 38.22 |
| 3323 | OG1 | THR | B | 784 | 47.407 | 14.394 | 83.791 | 1.00 | 32.84 |
| 3324 | CG2 | THR | B | 784 | 48.499 | 16.365 | 84.574 | 1.00 | 27.62 |
| 3325 | C | THR | B | 784 | 45.959 | 17.558 | 84.819 | 1.00 | 42.12 |
| 3326 | O | THR | B | 784 | 45.451 | 18.183 | 83.855 | 1.00 | 44.07 |
| 3327 | N | ALA | B | 785 | 46.415 | 18.118 | 85.944 | 1.00 | 42.78 |
| 3328 | CA | ALA | B | 785 | 46.490 | 19.525 | 86.209 | 1.00 | 42.20 |
| 3329 | CB | ALA | B | 785 | 47.126 | 19.714 | 87.503 | 1.00 | 41.73 |
| 3330 | C | ALA | B | 785 | 47.330 | 20.250 | 85.152 | 1.00 | 42.59 |
| 3331 | O | ALA | B | 785 | 48.358 | 19.707 | 84.633 | 1.00 | 41.88 |
| 3332 | N | PRO | B | 786 | 46.867 | 21.443 | 84.823 | 1.00 | 41.88 |
| 3333 | CA | PRO | B | 786 | 47.509 | 22.281 | 83.783 | 1.00 | 43.28 |
| 3334 | CB | PRO | B | 786 | 46.514 | 23.437 | 83.610 | 1.00 | 42.82 |
| 3335 | CG | PRO | B | 786 | 45.682 | 23.472 | 84.854 | 1.00 | 38.60 |
| 3336 | CD | PRO | B | 786 | 45.625 | 22.022 | 85.316 | 1.00 | 40.34 |
| 3337 | C | PRO | B | 786 | 48.937 | 22.647 | 84.199 | 1.00 | 44.36 |
| 3338 | O | PRO | B | 786 | 49.876 | 22.335 | 83.415 | 1.00 | 43.75 |
| 3339 | N | GLU | B | 787 | 49.161 | 23.067 | 85.458 | 1.00 | 47.66 |
| 3340 | CA | GLU | B | 787 | 50.585 | 23.216 | 85.879 | 1.00 | 48.56 |
| 3341 | CB | GLU | B | 787 | 50.799 | 23.521 | 87.366 | 1.00 | 50.25 |
| 3342 | CG | GLU | B | 787 | 50.506 | 22.415 | 88.438 | 1.00 | 47.77 |
| 3343 | CD | GLU | B | 787 | 49.055 | 22.343 | 88.835 | 1.00 | 45.14 |
| 3344 | OE1 | GLU | B | 787 | 48.239 | 23.053 | 88.217 | 1.00 | 47.89 |
| 3345 | OE2 | GLU | B | 787 | 48.675 | 21.581 | 89.750 | 1.00 | 48.40 |
| 3346 | C | GLU | B | 787 | 51.413 | 22.011 | 85.524 | 1.00 | 48.85 |
| 3347 | O | GLU | B | 787 | 52.601 | 22.103 | 85.448 | 1.00 | 49.02 |
| 3348 | N | ALA | B | 788 | 50.810 | 20.871 | 85.240 | 1.00 | 50.59 |
| 3349 | CA | ALA | B | 788 | 51.630 | 19.703 | 85.119 | 1.00 | 52.43 |
| 3350 | CB | ALA | B | 788 | 51.138 | 18.650 | 85.984 | 1.00 | 53.63 |
| 3351 | C | ALA | B | 788 | 51.881 | 19.205 | 83.771 | 1.00 | 54.39 |
| 3352 | O | ALA | B | 788 | 52.825 | 18.429 | 83.538 | 1.00 | 53.44 |

FIGURE 3BO

| A | B | C | D | E | F | G | H | I | J |
|---|---|---|---|---|---|---|---|---|---|
| 3353 | N | ILE | B | 789 | 51.076 | 19.709 | 82.848 | 1.00 | 58.49 |
| 3354 | CA | ILE | B | 789 | 51.180 | 19.309 | 81.466 | 1.00 | 60.06 |
| 3355 | CB | ILE | B | 789 | 49.791 | 19.422 | 80.879 | 1.00 | 60.19 |
| 3356 | CG1 | ILE | B | 789 | 49.005 | 18.288 | 81.542 | 1.00 | 57.40 |
| 3357 | CD1 | ILE | B | 789 | 47.545 | 18.338 | 81.498 | 1.00 | 52.54 |
| 3358 | CG2 | ILE | B | 789 | 49.888 | 19.223 | 79.405 | 1.00 | 60.76 |
| 3359 | C | ILE | B | 789 | 52.175 | 20.260 | 80.860 | 1.00 | 61.11 |
| 3360 | O | ILE | B | 789 | 53.217 | 19.903 | 80.277 | 1.00 | 61.28 |
| 3361 | N | SER | B | 790 | 51.775 | 21.498 | 81.090 | 1.00 | 63.37 |
| 3362 | CA | SER | B | 790 | 52.455 | 22.746 | 80.870 | 1.00 | 65.13 |
| 3363 | CB | SER | B | 790 | 51.887 | 23.687 | 81.908 | 1.00 | 64.75 |
| 3364 | OG | SER | B | 790 | 52.132 | 22.945 | 83.109 | 1.00 | 72.95 |
| 3365 | C | SER | B | 790 | 53.883 | 22.498 | 81.324 | 1.00 | 65.49 |
| 3366 | O | SER | B | 790 | 54.721 | 22.181 | 80.519 | 1.00 | 65.88 |
| 3367 | N | TYR | B | 791 | 54.080 | 22.534 | 82.650 | 1.00 | 67.60 |
| 3368 | CA | TYR | B | 791 | 55.356 | 22.655 | 83.371 | 1.00 | 67.61 |
| 3369 | CB | TYR | B | 791 | 55.133 | 23.658 | 84.492 | 1.00 | 67.72 |
| 3370 | CG | TYR | B | 791 | 54.527 | 24.979 | 84.072 | 1.00 | 69.06 |
| 3371 | CD1 | TYR | B | 791 | 53.373 | 25.468 | 84.681 | 1.00 | 73.54 |
| 3372 | CE1 | TYR | B | 791 | 52.811 | 26.729 | 84.343 | 1.00 | 77.27 |
| 3373 | CZ | TYR | B | 791 | 53.434 | 27.536 | 83.361 | 1.00 | 78.11 |
| 3374 | OH | TYR | B | 791 | 52.888 | 28.779 | 83.031 | 1.00 | 74.15 |
| 3375 | CE2 | TYR | B | 791 | 54.617 | 27.080 | 82.777 | 1.00 | 76.67 |
| 3376 | CD2 | TYR | B | 791 | 55.167 | 25.794 | 83.142 | 1.00 | 74.63 |
| 3377 | C | TYR | B | 791 | 55.841 | 21.341 | 83.987 | 1.00 | 67.44 |
| 3378 | O | TYR | B | 791 | 56.991 | 21.177 | 84.471 | 1.00 | 66.78 |
| 3379 | N | ARG | B | 792 | 54.955 | 20.377 | 83.993 | 1.00 | 66.21 |
| 3380 | CA | ARG | B | 792 | 55.418 | 19.098 | 84.530 | 1.00 | 65.39 |
| 3381 | CB | ARG | B | 792 | 56.655 | 18.642 | 83.811 | 1.00 | 65.99 |
| 3382 | CG | ARG | B | 792 | 56.702 | 17.131 | 83.750 | 1.00 | 72.90 |
| 3383 | CD | ARG | B | 792 | 57.978 | 16.532 | 83.158 | 1.00 | 81.61 |
| 3384 | NE | ARG | B | 792 | 58.984 | 17.572 | 83.010 | 1.00 | 88.48 |
| 3385 | CZ | ARG | B | 792 | 60.191 | 17.394 | 82.478 | 1.00 | 91.91 |
| 3386 | NH1 | ARG | B | 792 | 60.980 | 18.468 | 82.408 | 1.00 | 92.54 |
| 3387 | NH2 | ARG | B | 792 | 60.592 | 16.196 | 82.009 | 1.00 | 89.53 |
| 3388 | C | ARG | B | 792 | 55.624 | 19.127 | 86.033 | 1.00 | 61.73 |
| 3389 | O | ARG | B | 792 | 56.452 | 18.430 | 86.557 | 1.00 | 61.41 |
| 3390 | N | ALA | B | 793 | 54.792 | 19.903 | 86.722 | 1.00 | 58.85 |
| 3391 | CA | ALA | B | 793 | 54.853 | 20.039 | 88.179 | 1.00 | 56.36 |
| 3392 | CB | ALA | B | 793 | 54.957 | 21.543 | 88.590 | 1.00 | 55.91 |
| 3393 | C | ALA | B | 793 | 53.713 | 19.275 | 88.952 | 1.00 | 55.37 |
| 3394 | O | ALA | B | 793 | 52.576 | 19.774 | 89.157 | 1.00 | 53.05 |
| 3395 | N | PHE | B | 794 | 54.087 | 18.085 | 89.403 | 1.00 | 53.01 |
| 3396 | CA | PHE | B | 794 | 53.197 | 17.141 | 90.066 | 1.00 | 52.23 |
| 3397 | CB | PHE | B | 794 | 53.621 | 15.682 | 89.718 | 1.00 | 51.93 |
| 3398 | CG | PHE | B | 794 | 53.400 | 15.338 | 88.275 | 1.00 | 52.20 |
| 3399 | CD1 | PHE | B | 794 | 52.102 | 15.265 | 87.761 | 1.00 | 55.84 |
| 3400 | CE1 | PHE | B | 794 | 51.857 | 14.993 | 86.368 | 1.00 | 57.33 |
| 3401 | CZ | PHE | B | 794 | 52.972 | 14.849 | 85.527 | 1.00 | 57.10 |
| 3402 | CE2 | PHE | B | 794 | 54.271 | 14.956 | 86.076 | 1.00 | 51.98 |
| 3403 | CD2 | PHE | B | 794 | 54.461 | 15.189 | 87.425 | 1.00 | 50.42 |
| 3404 | C | PHE | B | 794 | 53.311 | 17.374 | 91.542 | 1.00 | 50.46 |

FIGURE 3BP

| A | B | C | D | E | F | G | H | I | J |
|---|---|---|---|---|---|---|---|---|---|
| 3405 | O | PHE | B | 794 | 54.347 | 17.425 | 92.050 | 1.00 | 51.33 |
| 3406 | N | THR | B | 795 | 52.221 | 17.321 | 92.249 | 1.00 | 49.78 |
| 3407 | CA | THR | B | 795 | 52.232 | 17.820 | 93.561 | 1.00 | 47.81 |
| 3408 | CB | THR | B | 795 | 52.007 | 19.294 | 93.227 | 1.00 | 48.89 |
| 3409 | OG1 | THR | B | 795 | 53.044 | 20.092 | 93.792 | 1.00 | 53.29 |
| 3410 | CG2 | THR | B | 795 | 50.667 | 19.849 | 93.729 | 1.00 | 46.81 |
| 3411 | C | THR | B | 795 | 50.983 | 17.224 | 94.222 | 1.00 | 46.44 |
| 3412 | O | THR | B | 795 | 50.005 | 16.921 | 93.564 | 1.00 | 45.65 |
| 3413 | N | SER | B | 796 | 50.946 | 17.050 | 95.504 | 1.00 | 42.66 |
| 3414 | CA | SER | B | 796 | 49.646 | 16.708 | 95.943 | 1.00 | 42.64 |
| 3415 | CB | SER | B | 796 | 49.536 | 16.690 | 97.500 | 1.00 | 42.15 |
| 3416 | OG | SER | B | 796 | 50.321 | 15.565 | 97.792 | 1.00 | 41.91 |
| 3417 | C | SER | B | 796 | 48.526 | 17.544 | 95.328 | 1.00 | 41.72 |
| 3418 | O | SER | B | 796 | 47.377 | 17.048 | 95.157 | 1.00 | 41.30 |
| 3419 | N | ALA | B | 797 | 48.784 | 18.819 | 95.079 | 1.00 | 40.89 |
| 3420 | CA | ALA | B | 797 | 47.663 | 19.681 | 94.615 | 1.00 | 40.50 |
| 3421 | CB | ALA | B | 797 | 48.022 | 21.114 | 94.671 | 1.00 | 39.74 |
| 3422 | C | ALA | B | 797 | 47.280 | 19.305 | 93.173 | 1.00 | 39.17 |
| 3423 | O | ALA | B | 797 | 46.128 | 19.595 | 92.751 | 1.00 | 38.84 |
| 3424 | N | SER | B | 798 | 48.263 | 18.720 | 92.489 | 1.00 | 34.53 |
| 3425 | CA | SER | B | 798 | 48.225 | 18.096 | 91.130 | 1.00 | 37.20 |
| 3426 | CB | SER | B | 798 | 49.628 | 17.544 | 91.024 | 1.00 | 36.03 |
| 3427 | OG | SER | B | 798 | 50.147 | 17.397 | 89.784 | 1.00 | 39.62 |
| 3428 | C | SER | B | 798 | 47.230 | 16.905 | 91.257 | 1.00 | 37.26 |
| 3429 | O | SER | B | 798 | 46.155 | 16.860 | 90.659 | 1.00 | 39.61 |
| 3430 | N | ASP | B | 799 | 47.482 | 16.037 | 92.210 | 1.00 | 38.19 |
| 3431 | CA | ASP | B | 799 | 46.573 | 14.920 | 92.473 | 1.00 | 37.01 |
| 3432 | CB | ASP | B | 799 | 47.107 | 14.077 | 93.579 | 1.00 | 35.52 |
| 3433 | CG | ASP | B | 799 | 48.139 | 13.180 | 93.147 | 1.00 | 34.06 |
| 3434 | OD1 | ASP | B | 799 | 48.373 | 13.014 | 91.930 | 1.00 | 35.46 |
| 3435 | OD2 | ASP | B | 799 | 48.888 | 12.613 | 93.969 | 1.00 | 38.80 |
| 3436 | C | ASP | B | 799 | 45.199 | 15.458 | 92.855 | 1.00 | 35.89 |
| 3437 | O | ASP | B | 799 | 44.175 | 14.779 | 92.609 | 1.00 | 37.05 |
| 3438 | N | VAL | B | 800 | 45.142 | 16.620 | 93.477 | 1.00 | 35.26 |
| 3439 | CA | VAL | B | 800 | 43.822 | 17.145 | 93.947 | 1.00 | 32.94 |
| 3440 | CB | VAL | B | 800 | 43.940 | 18.266 | 95.019 | 1.00 | 34.11 |
| 3441 | CG1 | VAL | B | 800 | 42.646 | 19.149 | 95.117 | 1.00 | 22.48 |
| 3442 | CG2 | VAL | B | 800 | 44.469 | 17.699 | 96.515 | 1.00 | 28.48 |
| 3443 | C | VAL | B | 800 | 42.950 | 17.561 | 92.768 | 1.00 | 34.34 |
| 3444 | O | VAL | B | 800 | 41.709 | 17.445 | 92.760 | 1.00 | 35.47 |
| 3445 | N | TRP | B | 801 | 43.636 | 18.049 | 91.764 | 1.00 | 34.34 |
| 3446 | CA | TRP | B | 801 | 43.044 | 18.275 | 90.477 | 1.00 | 35.48 |
| 3447 | CB | TRP | B | 801 | 44.091 | 18.901 | 89.507 | 1.00 | 35.00 |
| 3448 | CG | TRP | B | 801 | 43.459 | 19.177 | 88.157 | 1.00 | 40.40 |
| 3449 | CD1 | TRP | B | 801 | 43.141 | 18.226 | 87.174 | 1.00 | 38.90 |
| 3450 | NE1 | TRP | B | 801 | 42.553 | 18.884 | 86.133 | 1.00 | 39.62 |
| 3451 | CE2 | TRP | B | 801 | 42.424 | 20.212 | 86.419 | 1.00 | 34.39 |
| 3452 | CD2 | TRP | B | 801 | 43.007 | 20.444 | 87.642 | 1.00 | 34.20 |
| 3453 | CE3 | TRP | B | 801 | 43.005 | 21.746 | 88.138 | 1.00 | 38.91 |
| 3454 | CZ3 | TRP | B | 801 | 42.445 | 22.736 | 87.399 | 1.00 | 36.57 |
| 3455 | CH2 | TRP | B | 801 | 41.952 | 22.492 | 86.152 | 1.00 | 36.98 |
| 3456 | CZ2 | TRP | B | 801 | 41.885 | 21.221 | 85.652 | 1.00 | 38.72 |

FIGURE 3BQ

| A | B | C | D | E | F | G | H | I | J |
|---|---|---|---|---|---|---|---|---|---|
| 3457 | C | TRP | B | 801 | 42.351 | 16.959 | 89.962 | 1.00 | 33.13 |
| 3458 | O | TRP | B | 801 | 41.094 | 16.871 | 89.763 | 1.00 | 32.82 |
| 3459 | N | SER | B | 802 | 43.167 | 15.932 | 89.804 | 1.00 | 33.07 |
| 3460 | CA | SER | B | 802 | 42.670 | 14.644 | 89.377 | 1.00 | 30.99 |
| 3461 | CB | SER | B | 802 | 43.764 | 13.696 | 89.596 | 1.00 | 32.92 |
| 3462 | OG | SER | B | 802 | 44.915 | 13.966 | 88.873 | 1.00 | 25.93 |
| 3463 | C | SER | B | 802 | 41.511 | 14.199 | 90.191 | 1.00 | 32.70 |
| 3464 | O | SER | B | 802 | 40.470 | 13.693 | 89.697 | 1.00 | 33.27 |
| 3465 | N | PHE | B | 803 | 41.612 | 14.494 | 91.467 | 1.00 | 30.29 |
| 3466 | CA | PHE | B | 803 | 40.592 | 14.026 | 92.333 | 1.00 | 29.47 |
| 3467 | CB | PHE | B | 803 | 40.976 | 14.324 | 93.828 | 1.00 | 27.73 |
| 3468 | CG | PHE | B | 803 | 39.873 | 14.000 | 94.769 | 1.00 | 29.18 |
| 3469 | CD1 | PHE | B | 803 | 39.025 | 15.007 | 95.261 | 1.00 | 23.67 |
| 3470 | CE1 | PHE | B | 803 | 38.016 | 14.683 | 96.177 | 1.00 | 32.92 |
| 3471 | CZ | PHE | B | 803 | 37.764 | 13.282 | 96.514 | 1.00 | 31.89 |
| 3472 | CE2 | PHE | B | 803 | 38.619 | 12.258 | 95.929 | 1.00 | 28.18 |
| 3473 | CD2 | PHE | B | 803 | 39.656 | 12.633 | 95.129 | 1.00 | 30.46 |
| 3474 | C | PHE | B | 803 | 39.283 | 14.713 | 92.014 | 1.00 | 29.62 |
| 3475 | O | PHE | B | 803 | 38.185 | 14.221 | 92.288 | 1.00 | 29.50 |
| 3476 | N | GLY | B | 804 | 39.385 | 15.925 | 91.508 | 1.00 | 31.66 |
| 3477 | CA | GLY | B | 804 | 38.192 | 16.682 | 91.178 | 1.00 | 32.09 |
| 3478 | C | GLY | B | 804 | 37.595 | 15.997 | 89.930 | 1.00 | 31.91 |
| 3479 | O | GLY | B | 804 | 36.344 | 15.792 | 89.811 | 1.00 | 32.78 |
| 3480 | N | ILE | B | 805 | 38.471 | 15.468 | 89.086 | 1.00 | 31.21 |
| 3481 | CA | ILE | B | 805 | 37.922 | 14.809 | 87.937 | 1.00 | 30.79 |
| 3482 | CB | ILE | B | 805 | 39.019 | 14.336 | 86.958 | 1.00 | 31.83 |
| 3483 | CG1 | ILE | B | 805 | 39.901 | 15.503 | 86.501 | 1.00 | 29.56 |
| 3484 | CD1 | ILE | B | 805 | 39.060 | 16.699 | 85.638 | 1.00 | 28.04 |
| 3485 | CG2 | ILE | B | 805 | 38.273 | 13.590 | 85.789 | 1.00 | 30.62 |
| 3486 | C | ILE | B | 805 | 37.187 | 13.531 | 88.399 | 1.00 | 30.39 |
| 3487 | O | ILE | B | 805 | 36.137 | 13.167 | 87.862 | 1.00 | 30.88 |
| 3488 | N | VAL | B | 806 | 37.856 | 12.771 | 89.253 | 1.00 | 30.81 |
| 3489 | CA | VAL | B | 806 | 37.335 | 11.519 | 89.853 | 1.00 | 28.37 |
| 3490 | CB | VAL | B | 806 | 38.295 | 10.897 | 90.978 | 1.00 | 29.63 |
| 3491 | CG1 | VAL | B | 806 | 37.674 | 9.730 | 91.601 | 1.00 | 21.00 |
| 3492 | CG2 | VAL | B | 806 | 39.518 | 10.536 | 90.425 | 1.00 | 22.65 |
| 3493 | C | VAL | B | 806 | 36.055 | 11.924 | 90.505 | 1.00 | 29.32 |
| 3494 | O | VAL | B | 806 | 35.066 | 11.258 | 90.312 | 1.00 | 32.00 |
| 3495 | N | MET | B | 807 | 36.006 | 12.981 | 91.282 | 1.00 | 28.61 |
| 3496 | CA | MET | B | 807 | 34.635 | 13.320 | 91.782 | 1.00 | 30.01 |
| 3497 | CB | MET | B | 807 | 34.544 | 14.686 | 92.556 | 1.00 | 27.73 |
| 3498 | CG | MET | B | 807 | 35.490 | 14.830 | 93.746 | 1.00 | 29.47 |
| 3499 | SD | MET | B | 807 | 35.350 | 16.540 | 94.517 | 1.00 | 35.02 |
| 3500 | CE | MET | B | 807 | 33.929 | 16.536 | 95.089 | 1.00 | 33.26 |
| 3501 | C | MET | B | 807 | 33.615 | 13.403 | 90.606 | 1.00 | 30.22 |
| 3502 | O | MET | B | 807 | 32.442 | 13.037 | 90.717 | 1.00 | 30.29 |
| 3503 | N | TRP | B | 808 | 34.040 | 13.980 | 89.473 | 1.00 | 31.44 |
| 3504 | CA | TRP | B | 808 | 33.026 | 14.215 | 88.453 | 1.00 | 28.58 |
| 3505 | CB | TRP | B | 808 | 33.626 | 15.123 | 87.374 | 1.00 | 30.92 |
| 3506 | CG | TRP | B | 808 | 32.681 | 15.593 | 86.292 | 1.00 | 26.01 |
| 3507 | CD1 | TRP | B | 808 | 31.826 | 16.670 | 86.368 | 1.00 | 25.96 |
| 3508 | NE1 | TRP | B | 808 | 31.178 | 16.794 | 85.186 | 1.00 | 34.62 |

FIGURE 3BR

| A | B | C | D | E | F | G | H | I | J |
|---|---|---|---|---|---|---|---|---|---|
| 3509 | CE2 | TRP | B | 808 | 31.566 | 15.779 | 84.355 | 1.00 | 32.11 |
| 3510 | CD2 | TRP | B | 808 | 32.468 | 14.980 | 85.061 | 1.00 | 28.97 |
| 3511 | CE3 | TRP | B | 808 | 33.064 | 13.909 | 84.398 | 1.00 | 28.52 |
| 3512 | CZ3 | TRP | B | 808 | 32.709 | 13.687 | 83.032 | 1.00 | 32.24 |
| 3513 | CH2 | TRP | B | 808 | 31.725 | 14.446 | 82.425 | 1.00 | 35.24 |
| 3514 | CZ2 | TRP | B | 808 | 31.185 | 15.521 | 83.050 | 1.00 | 31.09 |
| 3515 | C | TRP | B | 808 | 32.712 | 12.873 | 87.869 | 1.00 | 28.00 |
| 3516 | O | TRP | B | 808 | 31.577 | 12.568 | 87.668 | 1.00 | 31.29 |
| 3517 | N | GLU | B | 809 | 33.684 | 12.013 | 87.650 | 1.00 | 27.30 |
| 3518 | CA | GLU | B | 809 | 33.330 | 10.714 | 87.110 | 1.00 | 28.51 |
| 3519 | CB | GLU | B | 809 | 34.555 | 9.884 | 86.910 | 1.00 | 30.85 |
| 3520 | CG | GLU | B | 809 | 35.617 | 10.432 | 86.024 | 1.00 | 25.12 |
| 3521 | CD | GLU | B | 809 | 36.813 | 9.571 | 86.014 | 1.00 | 28.19 |
| 3522 | OE1 | GLU | B | 809 | 36.849 | 8.704 | 85.133 | 1.00 | 32.40 |
| 3523 | OE2 | GLU | B | 809 | 37.778 | 9.798 | 86.791 | 1.00 | 31.60 |
| 3524 | C | GLU | B | 809 | 32.435 | 9.919 | 88.019 | 1.00 | 30.07 |
| 3525 | O | GLU | B | 809 | 31.575 | 9.111 | 87.555 | 1.00 | 33.66 |
| 3526 | N | VAL | B | 810 | 32.507 | 10.201 | 89.289 | 1.00 | 30.06 |
| 3527 | CA | VAL | B | 810 | 31.716 | 9.434 | 90.205 | 1.00 | 29.76 |
| 3528 | CB | VAL | B | 810 | 32.255 | 9.428 | 91.665 | 1.00 | 30.24 |
| 3529 | CG1 | VAL | B | 810 | 31.095 | 9.097 | 92.609 | 1.00 | 24.88 |
| 3530 | CG2 | VAL | B | 810 | 33.391 | 8.481 | 91.834 | 1.00 | 25.13 |
| 3531 | C | VAL | B | 810 | 30.346 | 10.058 | 90.287 | 1.00 | 30.62 |
| 3532 | O | VAL | B | 810 | 29.381 | 9.349 | 90.313 | 1.00 | 27.09 |
| 3533 | N | MET | B | 811 | 30.247 | 11.393 | 90.308 | 1.00 | 32.39 |
| 3534 | CA | MET | B | 811 | 28.889 | 11.928 | 90.411 | 1.00 | 34.71 |
| 3535 | CB | MET | B | 811 | 28.900 | 13.402 | 90.899 | 1.00 | 35.87 |
| 3536 | CG | MET | B | 811 | 29.590 | 13.624 | 92.224 | 1.00 | 38.06 |
| 3537 | SD | MET | B | 811 | 28.965 | 12.583 | 93.435 | 1.00 | 43.12 |
| 3538 | CE | MET | B | 811 | 27.111 | 12.868 | 93.575 | 1.00 | 35.71 |
| 3539 | C | MET | B | 811 | 28.162 | 11.746 | 89.043 | 1.00 | 33.74 |
| 3540 | O | MET | B | 811 | 27.022 | 11.928 | 88.905 | 1.00 | 36.24 |
| 3541 | N | THR | B | 812 | 28.845 | 11.231 | 88.066 | 1.00 | 35.66 |
| 3542 | CA | THR | B | 812 | 28.304 | 11.132 | 86.752 | 1.00 | 35.64 |
| 3543 | CB | THR | B | 812 | 29.319 | 11.867 | 85.953 | 1.00 | 37.45 |
| 3544 | OG1 | THR | B | 812 | 28.697 | 12.834 | 85.169 | 1.00 | 38.86 |
| 3545 | CG2 | THR | B | 812 | 30.251 | 11.113 | 85.174 | 1.00 | 23.27 |
| 3546 | C | THR | B | 812 | 28.173 | 9.753 | 86.352 | 1.00 | 37.54 |
| 3547 | O | THR | B | 812 | 27.786 | 9.432 | 85.230 | 1.00 | 38.76 |
| 3548 | N | TYR | B | 813 | 28.448 | 8.869 | 87.286 | 1.00 | 37.57 |
| 3549 | CA | TYR | B | 813 | 28.363 | 7.432 | 86.943 | 1.00 | 34.78 |
| 3550 | CB | TYR | B | 813 | 26.962 | 6.945 | 86.721 | 1.00 | 34.82 |
| 3551 | CG | TYR | B | 813 | 26.132 | 6.832 | 88.076 | 1.00 | 34.63 |
| 3552 | CD1 | TYR | B | 813 | 25.269 | 7.812 | 88.444 | 1.00 | 29.08 |
| 3553 | CE1 | TYR | B | 813 | 24.637 | 7.762 | 89.559 | 1.00 | 29.89 |
| 3554 | CZ | TYR | B | 813 | 24.749 | 6.694 | 90.445 | 1.00 | 35.16 |
| 3555 | OH | TYR | B | 813 | 23.994 | 6.732 | 91.691 | 1.00 | 33.13 |
| 3556 | CE2 | TYR | B | 813 | 25.605 | 5.638 | 90.112 | 1.00 | 31.34 |
| 3557 | CD2 | TYR | B | 813 | 26.330 | 5.766 | 88.953 | 1.00 | 30.20 |
| 3558 | C | TYR | B | 813 | 29.301 | 6.978 | 85.923 | 1.00 | 34.15 |
| 3559 | O | TYR | B | 813 | 28.981 | 6.116 | 85.162 | 1.00 | 35.41 |
| 3560 | N | GLY | B | 814 | 30.513 | 7.539 | 85.891 | 1.00 | 33.63 |

FIGURE 3BS

| A | B | C | D | E | F | G | H | I | J |
|---|---|---|---|---|---|---|---|---|---|
| 3561 | CA | GLY | B | 814 | 31.485 | 6.912 | 85.013 | 1.00 | 33.04 |
| 3562 | C | GLY | B | 814 | 31.465 | 7.503 | 83.656 | 1.00 | 33.66 |
| 3563 | O | GLY | B | 814 | 31.929 | 6.919 | 82.671 | 1.00 | 29.15 |
| 3564 | N | GLU | B | 815 | 30.913 | 8.688 | 83.576 | 1.00 | 34.73 |
| 3565 | CA | GLU | B | 815 | 31.053 | 9.319 | 82.301 | 1.00 | 37.09 |
| 3566 | CB | GLU | B | 815 | 30.177 | 10.491 | 82.237 | 1.00 | 38.02 |
| 3567 | CG | GLU | B | 815 | 30.303 | 11.378 | 80.999 | 1.00 | 40.70 |
| 3568 | CD | GLU | B | 815 | 29.679 | 10.720 | 79.825 | 1.00 | 39.58 |
| 3569 | OE1 | GLU | B | 815 | 30.404 | 10.091 | 79.087 | 1.00 | 37.45 |
| 3570 | OE2 | GLU | B | 815 | 28.456 | 10.675 | 79.743 | 1.00 | 43.36 |
| 3571 | C | GLU | B | 815 | 32.498 | 9.735 | 82.095 | 1.00 | 38.19 |
| 3572 | O | GLU | B | 815 | 33.212 | 10.124 | 83.020 | 1.00 | 38.65 |
| 3573 | N | ARG | B | 816 | 32.930 | 9.543 | 80.863 | 1.00 | 37.01 |
| 3574 | CA | ARG | B | 816 | 34.213 | 9.930 | 80.391 | 1.00 | 38.78 |
| 3575 | CB | ARG | B | 816 | 34.352 | 9.446 | 78.966 | 1.00 | 38.98 |
| 3576 | CG | ARG | B | 816 | 35.424 | 10.059 | 78.162 | 1.00 | 42.28 |
| 3577 | CD | ARG | B | 816 | 36.087 | 9.017 | 77.341 | 1.00 | 52.01 |
| 3578 | NE | ARG | B | 816 | 37.532 | 9.132 | 77.360 | 1.00 | 54.71 |
| 3579 | CZ | ARG | B | 816 | 38.138 | 9.580 | 76.306 | 1.00 | 59.21 |
| 3580 | NH1 | ARG | B | 816 | 37.353 | 9.900 | 75.305 | 1.00 | 68.31 |
| 3581 | NH2 | ARG | B | 816 | 39.446 | 9.779 | 76.226 | 1.00 | 56.49 |
| 3582 | C | ARG | B | 816 | 34.381 | 11.410 | 80.467 | 1.00 | 38.72 |
| 3583 | O | ARG | B | 816 | 33.687 | 12.139 | 79.791 | 1.00 | 39.78 |
| 3584 | N | PRO | B | 817 | 35.330 | 11.824 | 81.298 | 1.00 | 37.40 |
| 3585 | CA | PRO | B | 817 | 35.684 | 13.217 | 81.461 | 1.00 | 37.95 |
| 3586 | CB | PRO | B | 817 | 36.997 | 13.136 | 82.256 | 1.00 | 37.05 |
| 3587 | CG | PRO | B | 817 | 36.763 | 11.888 | 83.183 | 1.00 | 38.15 |
| 3588 | CD | PRO | B | 817 | 36.171 | 10.927 | 82.136 | 1.00 | 38.41 |
| 3589 | C | PRO | B | 817 | 35.788 | 13.947 | 80.089 | 1.00 | 38.69 |
| 3590 | O | PRO | B | 817 | 36.495 | 13.433 | 79.252 | 1.00 | 36.60 |
| 3591 | N | TYR | B | 818 | 35.057 | 15.066 | 79.844 | 1.00 | 38.82 |
| 3592 | CA | TYR | B | 818 | 35.210 | 15.759 | 78.539 | 1.00 | 39.23 |
| 3593 | CB | TYR | B | 818 | 36.663 | 16.068 | 78.236 | 1.00 | 38.09 |
| 3594 | CG | TYR | B | 818 | 37.266 | 16.821 | 79.315 | 1.00 | 39.70 |
| 3595 | CD1 | TYR | B | 818 | 36.909 | 18.157 | 79.532 | 1.00 | 34.79 |
| 3596 | CE1 | TYR | B | 818 | 37.443 | 18.905 | 80.645 | 1.00 | 34.86 |
| 3597 | CZ | TYR | B | 818 | 38.325 | 18.209 | 81.532 | 1.00 | 37.76 |
| 3598 | OH | TYR | B | 818 | 38.860 | 18.893 | 82.603 | 1.00 | 39.95 |
| 3599 | CE2 | TYR | B | 818 | 38.653 | 16.824 | 81.335 | 1.00 | 33.51 |
| 3600 | CD2 | TYR | B | 818 | 38.098 | 16.158 | 80.229 | 1.00 | 36.26 |
| 3601 | C | TYR | B | 818 | 34.667 | 14.938 | 77.424 | 1.00 | 38.80 |
| 3602 | O | TYR | B | 818 | 34.928 | 15.202 | 76.270 | 1.00 | 39.89 |
| 3603 | N | TRP | B | 819 | 33.846 | 13.989 | 77.763 | 1.00 | 38.70 |
| 3604 | CA | TRP | B | 819 | 33.188 | 13.270 | 76.700 | 1.00 | 39.85 |
| 3605 | CB | TRP | B | 819 | 32.069 | 14.135 | 76.151 | 1.00 | 38.03 |
| 3606 | CG | TRP | B | 819 | 31.456 | 14.694 | 77.287 | 1.00 | 36.05 |
| 3607 | CD1 | TRP | B | 819 | 30.606 | 14.112 | 78.042 | 1.00 | 30.08 |
| 3608 | NE1 | TRP | B | 819 | 30.225 | 14.945 | 79.039 | 1.00 | 25.80 |
| 3609 | CE2 | TRP | B | 819 | 30.803 | 16.169 | 78.851 | 1.00 | 30.10 |
| 3610 | CD2 | TRP | B | 819 | 31.604 | 16.053 | 77.781 | 1.00 | 36.77 |
| 3611 | CE3 | TRP | B | 819 | 32.310 | 17.173 | 77.346 | 1.00 | 33.18 |
| 3612 | CZ3 | TRP | B | 819 | 32.236 | 18.266 | 77.979 | 1.00 | 31.31 |

FIGURE 3BT

| A | B | C | D | E | F | G | H | I | J |
|---|---|---|---|---|---|---|---|---|---|
| 3613 | CH2 | TRP | B | 819 | 31.410 | 18.424 | 79.081 | 1.00 | 35.76 |
| 3614 | CZ2 | TRP | B | 819 | 30.670 | 17.374 | 79.552 | 1.00 | 36.26 |
| 3615 | C | TRP | B | 819 | 34.172 | 12.981 | 75.636 | 1.00 | 39.50 |
| 3616 | O | TRP | B | 819 | 35.257 | 12.601 | 75.950 | 1.00 | 42.24 |
| 3617 | N | GLU | B | 820 | 33.837 | 13.251 | 74.389 | 1.00 | 39.99 |
| 3618 | CA | GLU | B | 820 | 34.742 | 12.918 | 73.254 | 1.00 | 40.61 |
| 3619 | CB | GLU | B | 820 | 33.941 | 12.178 | 72.114 | 1.00 | 41.25 |
| 3620 | CG | GLU | B | 820 | 33.263 | 10.859 | 72.529 | 1.00 | 40.27 |
| 3621 | CD | GLU | B | 820 | 32.030 | 11.030 | 73.446 | 1.00 | 45.99 |
| 3622 | OE1 | GLU | B | 820 | 31.875 | 10.407 | 74.529 | 1.00 | 48.82 |
| 3623 | OE2 | GLU | B | 820 | 31.163 | 11.766 | 73.086 | 1.00 | 36.20 |
| 3624 | C | GLU | B | 820 | 35.708 | 14.020 | 72.749 | 1.00 | 40.02 |
| 3625 | O | GLU | B | 820 | 36.216 | 13.972 | 71.706 | 1.00 | 39.30 |
| 3626 | N | LEU | B | 821 | 35.944 | 15.037 | 73.516 | 1.00 | 42.32 |
| 3627 | CA | LEU | B | 821 | 36.969 | 16.002 | 73.125 | 1.00 | 45.66 |
| 3628 | CB | LEU | B | 821 | 37.212 | 16.973 | 74.283 | 1.00 | 45.63 |
| 3629 | CG | LEU | B | 821 | 36.273 | 18.189 | 74.253 | 1.00 | 50.25 |
| 3630 | CD1 | LEU | B | 821 | 34.848 | 17.908 | 73.740 | 1.00 | 53.81 |
| 3631 | CD2 | LEU | B | 821 | 36.254 | 18.988 | 75.530 | 1.00 | 46.51 |
| 3632 | C | LEU | B | 821 | 38.234 | 15.199 | 72.892 | 1.00 | 45.45 |
| 3633 | O | LEU | B | 821 | 38.302 | 14.137 | 73.411 | 1.00 | 45.58 |
| 3634 | N | SER | B | 822 | 39.183 | 15.665 | 72.097 | 1.00 | 45.03 |
| 3635 | CA | SER | B | 822 | 40.462 | 14.994 | 71.975 | 1.00 | 47.64 |
| 3636 | CB | SER | B | 822 | 41.264 | 15.426 | 70.738 | 1.00 | 47.83 |
| 3637 | OG | SER | B | 822 | 41.442 | 16.836 | 70.727 | 1.00 | 44.19 |
| 3638 | C | SER | B | 822 | 41.291 | 15.448 | 73.115 | 1.00 | 48.61 |
| 3639 | O | SER | B | 822 | 40.974 | 16.431 | 73.769 | 1.00 | 48.62 |
| 3640 | N | ASN | B | 823 | 42.405 | 14.776 | 73.341 | 1.00 | 50.08 |
| 3641 | CA | ASN | B | 823 | 43.325 | 15.385 | 74.319 | 1.00 | 53.14 |
| 3642 | CB | ASN | B | 823 | 44.484 | 14.436 | 74.614 | 1.00 | 53.45 |
| 3643 | CG | ASN | B | 823 | 43.996 | 13.177 | 75.311 | 1.00 | 57.25 |
| 3644 | OD1 | ASN | B | 823 | 42.979 | 13.236 | 76.090 | 1.00 | 56.44 |
| 3645 | ND2 | ASN | B | 823 | 44.642 | 12.035 | 75.027 | 1.00 | 50.82 |
| 3646 | C | ASN | B | 823 | 43.669 | 16.895 | 74.071 | 1.00 | 52.98 |
| 3647 | O | ASN | B | 823 | 43.354 | 17.756 | 74.937 | 1.00 | 53.13 |
| 3648 | N | HIS | B | 824 | 44.132 | 17.237 | 72.858 | 1.00 | 54.65 |
| 3649 | CA | HIS | B | 824 | 44.478 | 18.636 | 72.459 | 1.00 | 54.79 |
| 3650 | CB | HIS | B | 824 | 45.032 | 18.740 | 70.973 | 1.00 | 58.59 |
| 3651 | CG | HIS | B | 824 | 44.129 | 19.419 | 69.940 | 1.00 | 67.70 |
| 3652 | ND1 | HIS | B | 824 | 43.609 | 20.705 | 70.072 | 1.00 | 73.79 |
| 3653 | CE1 | HIS | B | 824 | 42.888 | 21.017 | 69.000 | 1.00 | 75.94 |
| 3654 | CE1 | HIS | B | 824 | 42.761 | 20.940 | 69.073 | 1.00 | 75.87 |
| 3655 | NE2 | HIS | B | 824 | 42.935 | 19.999 | 68.157 | 1.00 | 76.47 |
| 3656 | CD2 | HIS | B | 824 | 43.718 | 18.994 | 68.703 | 1.00 | 75.66 |
| 3657 | C | HIS | B | 824 | 43.306 | 19.509 | 72.778 | 1.00 | 52.56 |
| 3658 | O | HIS | B | 824 | 43.424 | 20.588 | 73.463 | 1.00 | 49.91 |
| 3659 | N | GLU | B | 825 | 42.128 | 19.027 | 72.387 | 1.00 | 50.66 |
| 3660 | CA | GLU | B | 825 | 40.942 | 19.831 | 72.718 | 1.00 | 50.31 |
| 3661 | CB | GLU | B | 825 | 39.699 | 19.255 | 72.086 | 1.00 | 52.70 |
| 3662 | CG | GLU | B | 825 | 39.956 | 18.712 | 70.695 | 1.00 | 55.19 |
| 3663 | CD | GLU | B | 825 | 38.704 | 18.188 | 70.065 | 1.00 | 60.55 |
| 3664 | OE1 | GLU | B | 825 | 38.480 | 16.987 | 70.221 | 1.00 | 63.97 |

FIGURE 3BU

| A | B | C | D | E | F | G | H | I | J |
|---|---|---|---|---|---|---|---|---|---|
| 3665 | OE2 | GLU | B | 825 | 37.946 | 18.964 | 69.435 | 1.00 | 63.96 |
| 3666 | C | GLU | B | 825 | 40.747 | 20.079 | 74.206 | 1.00 | 49.70 |
| 3667 | O | GLU | B | 825 | 40.538 | 21.250 | 74.669 | 1.00 | 48.88 |
| 3668 | N | VAL | B | 826 | 40.903 | 19.012 | 74.976 | 1.00 | 47.68 |
| 3669 | CA | VAL | B | 826 | 40.825 | 19.160 | 76.439 | 1.00 | 46.21 |
| 3670 | CB | VAL | B | 826 | 41.173 | 17.756 | 77.124 | 1.00 | 47.64 |
| 3671 | CG1 | VAL | B | 826 | 41.421 | 17.900 | 78.686 | 1.00 | 46.13 |
| 3672 | CG2 | VAL | B | 826 | 40.130 | 16.592 | 76.663 | 1.00 | 38.86 |
| 3673 | C | VAL | B | 826 | 41.762 | 20.239 | 76.958 | 1.00 | 46.74 |
| 3674 | O | VAL | B | 826 | 41.363 | 21.236 | 77.651 | 1.00 | 46.61 |
| 3675 | N | MET | B | 827 | 43.023 | 20.076 | 76.582 | 1.00 | 47.29 |
| 3676 | CA | MET | B | 827 | 44.025 | 21.031 | 77.016 | 1.00 | 48.46 |
| 3677 | CB | MET | B | 827 | 45.429 | 20.635 | 76.593 | 1.00 | 49.16 |
| 3678 | CG | MET | B | 827 | 46.036 | 19.261 | 77.139 | 1.00 | 48.31 |
| 3679 | SD | MET | B | 827 | 47.464 | 18.772 | 76.174 | 1.00 | 56.19 |
| 3680 | CE | MET | B | 827 | 48.223 | 20.801 | 76.241 | 1.00 | 53.80 |
| 3681 | C | MET | B | 827 | 43.641 | 22.449 | 76.548 | 1.00 | 50.31 |
| 3682 | O | MET | B | 827 | 43.675 | 23.355 | 77.381 | 1.00 | 51.02 |
| 3683 | N | ALA | B | 828 | 43.175 | 22.647 | 75.280 | 1.00 | 50.45 |
| 3684 | CA | ALA | B | 828 | 42.812 | 23.992 | 74.874 | 1.00 | 48.64 |
| 3685 | CB | ALA | B | 828 | 42.467 | 24.087 | 73.404 | 1.00 | 49.40 |
| 3686 | C | ALA | B | 828 | 41.656 | 24.425 | 75.727 | 1.00 | 47.69 |
| 3687 | O | ALA | B | 828 | 41.688 | 25.516 | 76.302 | 1.00 | 45.93 |
| 3688 | N | ALA | B | 829 | 40.622 | 23.600 | 75.859 | 1.00 | 48.34 |
| 3689 | CA | ALA | B | 829 | 39.500 | 24.095 | 76.706 | 1.00 | 49.28 |
| 3690 | CB | ALA | B | 829 | 38.454 | 23.025 | 76.877 | 1.00 | 48.53 |
| 3691 | C | ALA | B | 829 | 39.974 | 24.564 | 78.107 | 1.00 | 50.69 |
| 3692 | O | ALA | B | 829 | 39.428 | 25.519 | 78.706 | 1.00 | 52.39 |
| 3693 | N | ILE | B | 830 | 40.902 | 23.804 | 78.674 | 1.00 | 51.92 |
| 3694 | CA | ILE | B | 830 | 41.427 | 24.108 | 79.998 | 1.00 | 54.05 |
| 3695 | CB | ILE | B | 830 | 42.400 | 22.914 | 80.456 | 1.00 | 54.22 |
| 3696 | CG1 | ILE | B | 830 | 41.635 | 21.788 | 81.139 | 1.00 | 55.56 |
| 3697 | CD1 | ILE | B | 830 | 40.775 | 22.243 | 82.301 | 1.00 | 56.62 |
| 3698 | CG2 | ILE | B | 830 | 43.521 | 23.378 | 81.390 | 1.00 | 52.02 |
| 3699 | C | ILE | B | 830 | 42.152 | 25.485 | 79.957 | 1.00 | 54.79 |
| 3700 | O | ILE | B | 830 | 41.872 | 26.417 | 80.751 | 1.00 | 54.16 |
| 3701 | N | ASN | B | 831 | 43.068 | 25.588 | 79.006 | 1.00 | 55.43 |
| 3702 | CA | ASN | B | 831 | 43.834 | 26.818 | 78.871 | 1.00 | 57.64 |
| 3703 | CB | ASN | B | 831 | 44.900 | 26.698 | 77.762 | 1.00 | 57.97 |
| 3704 | CG | ASN | B | 831 | 46.082 | 25.749 | 78.170 | 1.00 | 61.45 |
| 3705 | OD1 | ASN | B | 831 | 46.313 | 25.407 | 79.388 | 1.00 | 63.42 |
| 3706 | ND2 | ASN | B | 831 | 46.803 | 25.283 | 77.160 | 1.00 | 61.97 |
| 3707 | C | ASN | B | 831 | 42.869 | 28.013 | 78.776 | 1.00 | 56.48 |
| 3708 | O | ASN | B | 831 | 43.088 | 29.055 | 79.374 | 1.00 | 57.73 |
| 3709 | N | ASP | B | 832 | 41.729 | 27.833 | 78.136 | 1.00 | 55.50 |
| 3710 | CA | ASP | B | 832 | 40.747 | 28.879 | 78.162 | 1.00 | 54.22 |
| 3711 | CB | ASP | B | 832 | 39.824 | 28.726 | 76.982 | 1.00 | 56.03 |
| 3712 | CG | ASP | B | 832 | 40.475 | 29.240 | 75.659 | 1.00 | 62.62 |
| 3713 | OD1 | ASP | B | 832 | 40.519 | 30.491 | 75.432 | 1.00 | 65.21 |
| 3714 | OD2 | ASP | B | 832 | 41.001 | 28.469 | 74.822 | 1.00 | 63.16 |
| 3715 | C | ASP | B | 832 | 39.956 | 28.914 | 79.478 | 1.00 | 53.83 |
| 3716 | O | ASP | B | 832 | 39.026 | 29.722 | 79.634 | 1.00 | 49.78 |

FIGURE 3BV

| A | B | C | D | E | F | G | H | I | J |
|---|---|---|---|---|---|---|---|---|---|
| 3717 | N | GLY | B | 833 | 40.258 | 28.009 | 80.431 | 1.00 | 52.62 |
| 3718 | CA | GLY | B | 833 | 39.487 | 28.103 | 81.674 | 1.00 | 52.59 |
| 3719 | C | GLY | B | 833 | 38.078 | 27.498 | 81.698 | 1.00 | 51.69 |
| 3720 | O | GLY | B | 833 | 37.252 | 27.863 | 82.546 | 1.00 | 53.45 |
| 3721 | N | PHE | B | 834 | 37.795 | 26.621 | 80.730 | 1.00 | 50.06 |
| 3722 | CA | PHE | B | 834 | 36.587 | 25.786 | 80.701 | 1.00 | 49.17 |
| 3723 | CB | PHE | B | 834 | 36.577 | 24.912 | 79.451 | 1.00 | 46.71 |
| 3724 | CG | PHE | B | 834 | 35.397 | 23.934 | 79.392 | 1.00 | 49.59 |
| 3725 | CD1 | PHE | B | 834 | 35.538 | 22.592 | 79.676 | 1.00 | 48.43 |
| 3726 | CE1 | PHE | B | 834 | 34.451 | 21.720 | 79.632 | 1.00 | 49.88 |
| 3727 | CZ | PHE | B | 834 | 33.226 | 22.210 | 79.315 | 1.00 | 47.84 |
| 3728 | CE2 | PHE | B | 834 | 33.106 | 23.517 | 78.977 | 1.00 | 49.60 |
| 3729 | CD2 | PHE | B | 834 | 34.149 | 24.351 | 78.999 | 1.00 | 49.93 |
| 3730 | C | PHE | B | 834 | 36.831 | 24.753 | 81.816 | 1.00 | 47.10 |
| 3731 | O | PHE | B | 834 | 37.960 | 24.368 | 82.076 | 1.00 | 46.20 |
| 3732 | N | ARG | B | 835 | 35.745 | 24.346 | 82.462 | 1.00 | 43.32 |
| 3733 | CA | ARG | B | 835 | 35.681 | 23.378 | 83.528 | 1.00 | 41.36 |
| 3734 | CB | ARG | B | 835 | 35.414 | 23.993 | 84.921 | 1.00 | 40.95 |
| 3735 | CG | ARG | B | 835 | 36.467 | 24.942 | 85.518 | 1.00 | 39.62 |
| 3736 | CD | ARG | B | 835 | 37.837 | 24.358 | 85.418 | 1.00 | 38.69 |
| 3737 | NE | ARG | B | 835 | 38.881 | 25.042 | 86.088 | 1.00 | 44.32 |
| 3738 | CZ | ARG | B | 835 | 39.934 | 25.489 | 85.438 | 1.00 | 50.44 |
| 3739 | NH1 | ARG | B | 835 | 40.938 | 26.049 | 86.127 | 1.00 | 43.02 |
| 3740 | NH2 | ARG | B | 835 | 39.981 | 25.329 | 84.088 | 1.00 | 44.62 |
| 3741 | C | ARG | B | 835 | 34.440 | 22.546 | 83.165 | 1.00 | 40.49 |
| 3742 | O | ARG | B | 835 | 33.483 | 23.057 | 82.604 | 1.00 | 41.54 |
| 3743 | N | LEU | B | 836 | 34.469 | 21.271 | 83.482 | 1.00 | 37.93 |
| 3744 | CA | LEU | B | 836 | 33.425 | 20.396 | 83.233 | 1.00 | 36.15 |
| 3745 | CB | LEU | B | 836 | 33.838 | 18.994 | 83.815 | 1.00 | 37.66 |
| 3746 | CG | LEU | B | 836 | 35.116 | 18.323 | 83.267 | 1.00 | 35.29 |
| 3747 | CD1 | LEU | B | 836 | 35.499 | 17.005 | 83.929 | 1.00 | 33.23 |
| 3748 | CD2 | LEU | B | 836 | 34.789 | 18.074 | 81.815 | 1.00 | 38.91 |
| 3749 | C | LEU | B | 836 | 32.232 | 20.956 | 83.981 | 1.00 | 36.97 |
| 3750 | O | LEU | B | 836 | 32.432 | 21.572 | 85.028 | 1.00 | 36.64 |
| 3751 | N | PRO | B | 837 | 30.999 | 20.719 | 83.525 | 1.00 | 34.28 |
| 3752 | CA | PRO | B | 837 | 29.824 | 21.275 | 84.187 | 1.00 | 34.92 |
| 3753 | CB | PRO | B | 837 | 28.789 | 21.273 | 83.072 | 1.00 | 34.34 |
| 3754 | CG | PRO | B | 837 | 29.449 | 20.600 | 81.871 | 1.00 | 39.22 |
| 3755 | CD | PRO | B | 837 | 30.650 | 19.919 | 82.344 | 1.00 | 35.63 |
| 3756 | C | PRO | B | 837 | 29.206 | 20.394 | 85.301 | 1.00 | 36.66 |
| 3757 | O | PRO | B | 837 | 29.462 | 19.205 | 85.411 | 1.00 | 34.31 |
| 3758 | N | THR | B | 838 | 28.308 | 20.910 | 86.081 | 1.00 | 37.44 |
| 3759 | CA | THR | B | 838 | 27.996 | 20.063 | 87.170 | 1.00 | 41.30 |
| 3760 | CB | THR | B | 838 | 27.125 | 20.677 | 88.173 | 1.00 | 42.22 |
| 3761 | OG1 | THR | B | 838 | 26.152 | 19.670 | 88.570 | 1.00 | 45.09 |
| 3762 | CG2 | THR | B | 838 | 26.224 | 21.773 | 87.502 | 1.00 | 44.87 |
| 3763 | C | THR | B | 838 | 27.248 | 18.908 | 86.572 | 1.00 | 43.03 |
| 3764 | O | THR | B | 838 | 26.534 | 19.021 | 85.578 | 1.00 | 44.86 |
| 3765 | N | PRO | B | 839 | 27.366 | 17.803 | 87.218 | 1.00 | 41.53 |
| 3766 | CA | PRO | B | 839 | 26.726 | 16.604 | 86.740 | 1.00 | 43.52 |
| 3767 | CB | PRO | B | 839 | 27.395 | 15.497 | 87.609 | 1.00 | 40.76 |
| 3768 | CG | PRO | B | 839 | 28.609 | 16.173 | 88.078 | 1.00 | 42.05 |

FIGURE 3BW

| A | B | C | D | E | F | G | H | I | J |
|---|---|---|---|---|---|---|---|---|---|
| 3769 | CD | PRO | B | 839 | 28.056 | 17.580 | 88.467 | 1.00 | 42.30 |
| 3770 | C | PRO | B | 839 | 25.278 | 16.789 | 87.071 | 1.00 | 44.34 |
| 3771 | O | PRO | B | 839 | 24.955 | 17.610 | 87.915 | 1.00 | 46.72 |
| 3772 | N | ALA | B | 840 | 24.416 | 16.004 | 86.466 | 1.00 | 46.17 |
| 3773 | CA | ALA | B | 840 | 22.989 | 16.149 | 86.701 | 1.00 | 46.30 |
| 3774 | CB | ALA | B | 840 | 22.229 | 15.193 | 85.735 | 1.00 | 46.61 |
| 3775 | C | ALA | B | 840 | 22.791 | 15.690 | 88.100 | 1.00 | 47.32 |
| 3776 | O | ALA | B | 840 | 23.359 | 14.659 | 88.452 | 1.00 | 48.03 |
| 3777 | N | ASP | B | 841 | 21.963 | 16.400 | 88.859 | 1.00 | 47.66 |
| 3778 | CA | ASP | B | 841 | 21.685 | 16.142 | 90.292 | 1.00 | 48.16 |
| 3779 | CB | ASP | B | 841 | 20.927 | 14.837 | 90.420 | 1.00 | 50.16 |
| 3780 | CG | ASP | B | 841 | 19.492 | 14.998 | 89.877 | 1.00 | 56.15 |
| 3781 | OD1 | ASP | B | 841 | 18.696 | 13.990 | 89.914 | 1.00 | 57.77 |
| 3782 | OD2 | ASP | B | 841 | 19.120 | 16.143 | 89.372 | 1.00 | 56.22 |
| 3783 | C | ASP | B | 841 | 22.863 | 16.166 | 91.204 | 1.00 | 47.22 |
| 3784 | O | ASP | B | 841 | 22.887 | 15.601 | 92.244 | 1.00 | 48.47 |
| 3785 | N | CYS | B | 842 | 23.875 | 16.886 | 90.866 | 1.00 | 45.42 |
| 3786 | CA | CYS | B | 842 | 24.882 | 16.890 | 91.830 | 1.00 | 42.29 |
| 3787 | CB | CYS | B | 842 | 26.202 | 17.117 | 91.137 | 1.00 | 42.38 |
| 3788 | SG | CYS | B | 842 | 27.632 | 17.081 | 92.149 | 1.00 | 39.32 |
| 3789 | C | CYS | B | 842 | 24.617 | 17.957 | 92.802 | 1.00 | 43.32 |
| 3790 | O | CYS | B | 842 | 24.280 | 19.092 | 92.452 | 1.00 | 45.03 |
| 3791 | N | PRO | B | 843 | 24.714 | 17.602 | 94.064 | 1.00 | 43.72 |
| 3792 | CA | PRO | B | 843 | 24.628 | 18.589 | 95.111 | 1.00 | 42.14 |
| 3793 | CB | PRO | B | 843 | 24.991 | 17.794 | 96.325 | 1.00 | 44.83 |
| 3794 | CG | PRO | B | 843 | 24.594 | 16.246 | 95.888 | 1.00 | 42.62 |
| 3795 | CD | PRO | B | 843 | 24.689 | 16.198 | 94.536 | 1.00 | 40.73 |
| 3796 | C | PRO | B | 843 | 25.658 | 19.593 | 94.858 | 1.00 | 42.60 |
| 3797 | O | PRO | B | 843 | 26.804 | 19.223 | 94.460 | 1.00 | 43.32 |
| 3798 | N | SER | B | 844 | 25.288 | 20.847 | 95.134 | 1.00 | 40.74 |
| 3799 | CA | SER | B | 844 | 26.138 | 22.019 | 94.922 | 1.00 | 41.10 |
| 3800 | CB | SER | B | 844 | 25.378 | 23.281 | 95.359 | 1.00 | 45.78 |
| 3801 | OG | SER | B | 844 | 24.007 | 22.921 | 95.667 | 1.00 | 47.77 |
| 3802 | C | SER | B | 844 | 27.363 | 22.044 | 95.753 | 1.00 | 39.64 |
| 3803 | O | SER | B | 844 | 28.384 | 22.625 | 95.348 | 1.00 | 40.26 |
| 3804 | N | ALA | B | 845 | 27.313 | 21.508 | 96.965 | 1.00 | 37.83 |
| 3805 | CA | ALA | B | 845 | 28.582 | 21.420 | 97.650 | 1.00 | 36.40 |
| 3806 | CB | ALA | B | 845 | 28.347 | 21.151 | 99.043 | 1.00 | 39.16 |
| 3807 | C | ALA | B | 845 | 29.485 | 20.414 | 97.041 | 1.00 | 36.50 |
| 3808 | O | ALA | B | 845 | 30.717 | 20.568 | 96.981 | 1.00 | 40.92 |
| 3809 | N | ILE | B | 846 | 28.983 | 19.393 | 96.448 | 1.00 | 37.49 |
| 3810 | CA | ILE | B | 846 | 29.931 | 18.505 | 95.824 | 1.00 | 38.19 |
| 3811 | CB | ILE | B | 846 | 29.123 | 17.228 | 95.389 | 1.00 | 38.40 |
| 3812 | CG1 | ILE | B | 846 | 28.802 | 16.375 | 96.633 | 1.00 | 41.00 |
| 3813 | CD1 | ILE | B | 846 | 30.056 | 16.440 | 97.794 | 1.00 | 34.53 |
| 3814 | CG2 | ILE | B | 846 | 29.935 | 16.381 | 94.424 | 1.00 | 38.32 |
| 3815 | C | ILE | B | 846 | 30.488 | 19.261 | 94.613 | 1.00 | 39.49 |
| 3816 | O | ILE | B | 846 | 31.719 | 19.363 | 94.292 | 1.00 | 37.89 |
| 3817 | N | TYR | B | 847 | 29.540 | 19.759 | 93.833 | 1.00 | 42.21 |
| 3818 | CA | TYR | B | 847 | 30.006 | 20.529 | 92.653 | 1.00 | 42.74 |
| 3819 | CB | TYR | B | 847 | 28.846 | 21.081 | 91.802 | 1.00 | 43.60 |
| 3820 | CG | TYR | B | 847 | 29.434 | 21.686 | 90.506 | 1.00 | 46.75 |

FIGURE 3BX

| A | B | C | D | E | F | G | H | I | J |
|---|---|---|---|---|---|---|---|---|---|
| 3821 | CD1 | TYR | B | 847 | 29.238 | 23.035 | 90.142 | 1.00 | 40.15 |
| 3822 | CE1 | TYR | B | 847 | 29.804 | 23.528 | 88.926 | 1.00 | 48.32 |
| 3823 | CZ | TYR | B | 847 | 30.561 | 22.684 | 88.120 | 1.00 | 44.77 |
| 3824 | OH | TYR | B | 847 | 31.151 | 23.079 | 86.988 | 1.00 | 40.40 |
| 3825 | CE2 | TYR | B | 847 | 30.776 | 21.358 | 88.509 | 1.00 | 44.70 |
| 3826 | CD2 | TYR | B | 847 | 30.234 | 20.893 | 89.685 | 1.00 | 47.08 |
| 3827 | C | TYR | B | 847 | 30.858 | 21.662 | 93.143 | 1.00 | 40.26 |
| 3828 | O | TYR | B | 847 | 31.963 | 21.877 | 92.659 | 1.00 | 40.34 |
| 3829 | N | GLN | B | 848 | 30.451 | 22.340 | 94.207 | 1.00 | 41.30 |
| 3830 | CA | GLN | B | 848 | 31.418 | 23.410 | 94.664 | 1.00 | 43.37 |
| 3831 | CB | GLN | B | 848 | 30.823 | 24.320 | 95.701 | 1.00 | 45.07 |
| 3832 | CG | GLN | B | 848 | 31.676 | 25.537 | 96.106 | 1.00 | 51.95 |
| 3833 | CD | GLN | B | 848 | 31.283 | 26.899 | 95.372 | 1.00 | 63.54 |
| 3834 | OE1 | GLN | B | 848 | 30.417 | 26.923 | 94.412 | 1.00 | 64.88 |
| 3835 | NE2 | GLN | B | 848 | 31.976 | 28.042 | 95.806 | 1.00 | 60.42 |
| 3836 | C | GLN | B | 848 | 32.850 | 22.934 | 94.967 | 1.00 | 41.04 |
| 3837 | O | GLN | B | 848 | 33.897 | 23.527 | 94.527 | 1.00 | 41.33 |
| 3838 | N | LEU | B | 849 | 32.915 | 21.786 | 95.608 | 1.00 | 38.01 |
| 3839 | CA | LEU | B | 849 | 34.208 | 21.204 | 95.905 | 1.00 | 35.47 |
| 3840 | CB | LEU | B | 849 | 33.889 | 20.040 | 96.868 | 1.00 | 36.49 |
| 3841 | CG | LEU | B | 849 | 35.120 | 19.349 | 97.222 | 1.00 | 36.62 |
| 3842 | CD1 | LEU | B | 849 | 36.078 | 20.393 | 97.866 | 1.00 | 32.52 |
| 3843 | CD2 | LEU | B | 849 | 34.708 | 18.241 | 98.241 | 1.00 | 43.70 |
| 3844 | C | LEU | B | 849 | 34.946 | 20.716 | 94.708 | 1.00 | 35.06 |
| 3845 | O | LEU | B | 849 | 36.200 | 20.891 | 94.564 | 1.00 | 34.28 |
| 3846 | N | MET | B | 850 | 34.223 | 20.003 | 93.821 | 1.00 | 35.02 |
| 3847 | CA | MET | B | 850 | 34.861 | 19.681 | 92.512 | 1.00 | 36.09 |
| 3848 | CB | MET | B | 850 | 33.703 | 19.134 | 91.632 | 1.00 | 37.35 |
| 3849 | CG | MET | B | 850 | 33.905 | 18.476 | 90.380 | 1.00 | 32.97 |
| 3850 | SD | MET | B | 850 | 32.372 | 17.871 | 89.923 | 1.00 | 36.02 |
| 3851 | CE | MET | B | 850 | 31.755 | 17.245 | 91.136 | 1.00 | 32.09 |
| 3852 | C | MET | B | 850 | 35.487 | 21.062 | 92.000 | 1.00 | 36.72 |
| 3853 | O | MET | B | 850 | 36.645 | 21.219 | 91.693 | 1.00 | 38.32 |
| 3854 | N | MET | B | 851 | 34.747 | 22.126 | 91.975 | 1.00 | 37.60 |
| 3855 | CA | MET | B | 851 | 35.408 | 23.296 | 91.429 | 1.00 | 38.96 |
| 3856 | CB | MET | B | 851 | 34.424 | 24.425 | 91.381 | 1.00 | 38.34 |
| 3857 | CG | MET | B | 851 | 33.322 | 24.168 | 90.395 | 1.00 | 38.17 |
| 3858 | SD | MET | B | 851 | 33.760 | 24.269 | 88.645 | 1.00 | 45.90 |
| 3859 | CE | MET | B | 851 | 34.669 | 25.672 | 88.676 | 1.00 | 46.07 |
| 3860 | C | MET | B | 851 | 36.688 | 23.732 | 92.181 | 1.00 | 41.53 |
| 3861 | O | MET | B | 851 | 37.765 | 24.106 | 91.542 | 1.00 | 43.20 |
| 3862 | N | GLN | B | 852 | 36.617 | 23.715 | 93.495 | 1.00 | 38.35 |
| 3863 | CA | GLN | B | 852 | 37.772 | 24.172 | 94.206 | 1.00 | 39.33 |
| 3864 | CB | GLN | B | 852 | 37.474 | 24.264 | 95.703 | 1.00 | 42.34 |
| 3865 | CG | GLN | B | 852 | 36.356 | 25.195 | 96.036 | 1.00 | 45.28 |
| 3866 | CD | GLN | B | 852 | 35.754 | 24.863 | 97.391 | 1.00 | 62.60 |
| 3867 | OE1 | GLN | B | 852 | 34.797 | 25.545 | 97.871 | 1.00 | 68.59 |
| 3868 | NE2 | GLN | B | 852 | 36.292 | 23.806 | 98.030 | 1.00 | 69.44 |
| 3869 | C | GLN | B | 852 | 38.834 | 23.236 | 93.879 | 1.00 | 40.26 |
| 3870 | O | GLN | B | 852 | 39.939 | 23.631 | 93.706 | 1.00 | 41.90 |
| 3871 | N | CYS | B | 853 | 38.590 | 21.960 | 93.648 | 1.00 | 40.71 |
| 3872 | CA | CYS | B | 853 | 39.835 | 21.254 | 93.263 | 1.00 | 39.23 |

FIGURE 3BY

| A | B | C | D | E | F | G | H | I | J |
|---|---|---|---|---|---|---|---|---|---|
| 3873 | CB | CYS | B | 853 | 39.782 | 19.711 | 93.273 | 1.00 | 39.20 |
| 3874 | SG | CYS | B | 853 | 38.918 | 18.954 | 94.690 | 1.00 | 40.47 |
| 3875 | C | CYS | B | 853 | 40.318 | 21.686 | 91.913 | 1.00 | 40.72 |
| 3876 | O | CYS | B | 853 | 41.421 | 21.347 | 91.564 | 1.00 | 38.66 |
| 3877 | N | TRP | B | 854 | 39.519 | 22.366 | 91.092 | 1.00 | 41.68 |
| 3878 | CA | TRP | B | 854 | 40.111 | 22.647 | 89.772 | 1.00 | 44.18 |
| 3879 | CB | TRP | B | 854 | 39.031 | 22.457 | 88.667 | 1.00 | 44.45 |
| 3880 | CG | TRP | B | 854 | 38.618 | 21.114 | 88.501 | 1.00 | 41.82 |
| 3881 | CD1 | TRP | B | 854 | 39.368 | 19.980 | 88.704 | 1.00 | 41.87 |
| 3882 | NE1 | TRP | B | 854 | 38.602 | 18.866 | 88.449 | 1.00 | 35.93 |
| 3883 | CE2 | TRP | B | 854 | 37.352 | 19.263 | 88.140 | 1.00 | 32.47 |
| 3884 | CD2 | TRP | B | 854 | 37.333 | 20.687 | 88.167 | 1.00 | 38.06 |
| 3885 | CE3 | TRP | B | 854 | 36.138 | 21.359 | 87.897 | 1.00 | 32.76 |
| 3886 | CZ3 | TRP | B | 854 | 35.127 | 20.665 | 87.536 | 1.00 | 29.91 |
| 3887 | CH2 | TRP | B | 854 | 35.159 | 19.211 | 87.528 | 1.00 | 36.45 |
| 3888 | CZ2 | TRP | B | 854 | 36.282 | 18.524 | 87.789 | 1.00 | 32.15 |
| 3889 | C | TRP | B | 854 | 40.722 | 24.083 | 89.583 | 1.00 | 45.26 |
| 3890 | O | TRP | B | 854 | 41.080 | 24.493 | 88.441 | 1.00 | 43.51 |
| 3891 | N | GLN | B | 855 | 40.727 | 24.844 | 90.675 | 1.00 | 45.68 |
| 3892 | CA | GLN | B | 855 | 41.226 | 26.182 | 90.651 | 1.00 | 46.55 |
| 3893 | CB | GLN | B | 855 | 41.379 | 26.724 | 92.049 | 1.00 | 48.28 |
| 3894 | CG | GLN | B | 855 | 40.053 | 26.999 | 92.625 | 1.00 | 50.56 |
| 3895 | CD | GLN | B | 855 | 40.145 | 28.208 | 93.423 | 1.00 | 60.72 |
| 3896 | OE1 | GLN | B | 855 | 40.024 | 28.135 | 94.670 | 1.00 | 58.07 |
| 3897 | NE2 | GLN | B | 855 | 40.408 | 29.384 | 92.729 | 1.00 | 61.21 |
| 3898 | C | GLN | B | 855 | 42.519 | 26.130 | 90.037 | 1.00 | 45.75 |
| 3899 | O | GLN | B | 855 | 43.278 | 25.307 | 90.342 | 1.00 | 42.80 |
| 3900 | N | GLN | B | 856 | 42.710 | 27.051 | 89.106 | 1.00 | 47.78 |
| 3901 | CA | GLN | B | 856 | 43.924 | 27.243 | 88.368 | 1.00 | 47.38 |
| 3902 | CB | GLN | B | 856 | 43.729 | 28.485 | 87.470 | 1.00 | 49.87 |
| 3903 | CG | GLN | B | 856 | 44.834 | 28.698 | 86.488 | 1.00 | 49.20 |
| 3904 | CD | GLN | B | 856 | 44.839 | 27.597 | 85.453 | 1.00 | 59.89 |
| 3905 | OE1 | GLN | B | 856 | 43.788 | 26.947 | 85.185 | 1.00 | 61.37 |
| 3906 | NE2 | GLN | B | 856 | 46.017 | 27.356 | 84.866 | 1.00 | 60.84 |
| 3907 | C | GLN | B | 856 | 45.065 | 27.456 | 89.331 | 1.00 | 46.71 |
| 3908 | O | GLN | B | 856 | 46.106 | 26.883 | 89.154 | 1.00 | 44.54 |
| 3909 | N | GLU | B | 857 | 44.892 | 28.308 | 90.331 | 1.00 | 48.11 |
| 3910 | CA | GLU | B | 857 | 45.984 | 28.408 | 91.341 | 1.00 | 51.65 |
| 3911 | CB | GLU | B | 857 | 45.768 | 29.578 | 92.387 | 1.00 | 52.14 |
| 3912 | CG | GLU | B | 857 | 46.166 | 30.915 | 91.710 | 1.00 | 62.33 |
| 3913 | CD | GLU | B | 857 | 45.832 | 32.252 | 92.398 | 1.00 | 71.26 |
| 3914 | OE1 | GLU | B | 857 | 45.616 | 32.369 | 93.641 | 1.00 | 76.69 |
| 3915 | OE2 | GLU | B | 857 | 45.828 | 33.239 | 91.631 | 1.00 | 75.04 |
| 3916 | C | GLU | B | 857 | 46.160 | 27.138 | 92.117 | 1.00 | 49.78 |
| 3917 | O | GLU | B | 857 | 45.368 | 26.874 | 93.003 | 1.00 | 50.77 |
| 3918 | N | ARG | B | 858 | 47.167 | 26.345 | 91.823 | 1.00 | 48.84 |
| 3919 | CA | ARG | B | 858 | 47.332 | 25.179 | 92.679 | 1.00 | 48.89 |
| 3920 | CB | ARG | B | 858 | 48.631 | 24.421 | 92.402 | 1.00 | 48.75 |
| 3921 | CG | ARG | B | 858 | 49.933 | 24.995 | 92.988 | 1.00 | 46.77 |
| 3922 | CD | ARG | B | 858 | 51.166 | 24.444 | 92.169 | 1.00 | 55.09 |
| 3923 | NE | ARG | B | 858 | 52.374 | 24.183 | 92.946 | 1.00 | 66.77 |
| 3924 | CZ | ARG | B | 858 | 53.580 | 24.706 | 92.706 | 1.00 | 70.86 |

FIGURE 3BZ

| A | B | C | D | E | F | G | H | I | J |
|---|---|---|---|---|---|---|---|---|---|
| 3925 | NH1 | ARG | B | 858 | 53.804 | 25.519 | 91.672 | 1.00 | 68.19 |
| 3926 | NH2 | ARG | B | 858 | 54.588 | 24.373 | 93.510 | 1.00 | 75.23 |
| 3927 | C | ARG | B | 858 | 47.192 | 25.455 | 94.211 | 1.00 | 49.58 |
| 3928 | O | ARG | B | 858 | 46.606 | 24.640 | 94.922 | 1.00 | 47.02 |
| 3929 | N | ALA | B | 859 | 47.743 | 26.584 | 94.704 | 1.00 | 49.56 |
| 3930 | CA | ALA | B | 859 | 47.766 | 26.775 | 96.131 | 1.00 | 49.75 |
| 3931 | CB | ALA | B | 859 | 48.584 | 27.954 | 96.533 | 1.00 | 51.56 |
| 3932 | C | ALA | B | 859 | 46.364 | 26.871 | 96.691 | 1.00 | 49.92 |
| 3933 | O | ALA | B | 859 | 46.123 | 26.666 | 97.946 | 1.00 | 47.88 |
| 3934 | N | ALA | B | 860 | 45.410 | 27.081 | 95.789 | 1.00 | 47.89 |
| 3935 | CA | ALA | B | 860 | 44.084 | 27.368 | 96.360 | 1.00 | 46.93 |
| 3936 | CB | ALA | B | 860 | 43.377 | 28.492 | 95.576 | 1.00 | 48.07 |
| 3937 | C | ALA | B | 860 | 43.240 | 26.131 | 96.356 | 1.00 | 45.49 |
| 3938 | O | ALA | B | 860 | 42.064 | 26.182 | 96.738 | 1.00 | 43.79 |
| 3939 | N | ARG | B | 861 | 43.808 | 25.041 | 95.824 | 1.00 | 45.18 |
| 3940 | CA | ARG | B | 861 | 43.069 | 23.742 | 95.850 | 1.00 | 45.03 |
| 3941 | CB | ARG | B | 861 | 43.616 | 22.678 | 94.889 | 1.00 | 45.11 |
| 3942 | CG | ARG | B | 861 | 43.572 | 23.172 | 93.351 | 1.00 | 46.90 |
| 3943 | CD | ARG | B | 861 | 44.345 | 22.261 | 92.433 | 1.00 | 44.77 |
| 3944 | NE | ARG | B | 861 | 44.743 | 22.970 | 91.264 | 1.00 | 38.07 |
| 3945 | CZ | ARG | B | 861 | 45.809 | 22.714 | 90.575 | 1.00 | 41.87 |
| 3946 | NH1 | ARG | B | 861 | 46.592 | 21.700 | 90.905 | 1.00 | 38.56 |
| 3947 | NH2 | ARG | B | 861 | 46.150 | 23.523 | 89.537 | 1.00 | 43.27 |
| 3948 | C | ARG | B | 861 | 43.130 | 23.309 | 97.271 | 1.00 | 45.07 |
| 3949 | O | ARG | B | 861 | 44.103 | 23.626 | 98.032 | 1.00 | 44.45 |
| 3950 | N | PRO | B | 862 | 42.026 | 22.694 | 97.660 | 1.00 | 43.87 |
| 3951 | CA | PRO | B | 862 | 41.895 | 22.193 | 98.984 | 1.00 | 43.84 |
| 3952 | CB | PRO | B | 862 | 40.554 | 21.463 | 98.980 | 1.00 | 44.25 |
| 3953 | CG | PRO | B | 862 | 39.896 | 21.841 | 97.717 | 1.00 | 41.03 |
| 3954 | CD | PRO | B | 862 | 40.829 | 22.473 | 96.845 | 1.00 | 44.03 |
| 3955 | C | PRO | B | 862 | 42.931 | 21.188 | 99.086 | 1.00 | 43.12 |
| 3956 | O | PRO | B | 862 | 43.244 | 20.570 | 98.142 | 1.00 | 42.37 |
| 3957 | N | LYS | B | 863 | 43.431 | 21.006 | 100.274 | 1.00 | 43.78 |
| 3958 | CA | LYS | B | 863 | 44.308 | 19.872 | 100.517 | 1.00 | 44.01 |
| 3959 | CB | LYS | B | 863 | 45.168 | 20.223 | 101.764 | 1.00 | 44.71 |
| 3960 | CG | LYS | B | 863 | 46.523 | 20.788 | 101.339 | 1.00 | 51.54 |
| 3961 | CD | LYS | B | 863 | 46.460 | 22.176 | 100.652 | 1.00 | 56.44 |
| 3962 | CE | LYS | B | 863 | 47.864 | 22.699 | 100.246 | 1.00 | 61.29 |
| 3963 | NZ | LYS | B | 863 | 49.033 | 21.667 | 100.373 | 1.00 | 67.02 |
| 3964 | C | LYS | B | 863 | 43.545 | 18.527 | 100.706 | 1.00 | 39.71 |
| 3965 | O | LYS | B | 863 | 42.327 | 18.497 | 101.170 | 1.00 | 38.33 |
| 3966 | N | PHE | B | 864 | 44.230 | 17.402 | 100.460 | 1.00 | 36.76 |
| 3967 | CA | PHE | B | 864 | 43.420 | 16.152 | 100.759 | 1.00 | 38.90 |
| 3968 | CB | PHE | B | 864 | 44.140 | 14.817 | 100.429 | 1.00 | 37.94 |
| 3969 | CG | PHE | B | 864 | 44.178 | 14.527 | 98.922 | 1.00 | 33.91 |
| 3970 | CD1 | PHE | B | 864 | 45.375 | 14.533 | 98.233 | 1.00 | 29.69 |
| 3971 | CE1 | PHE | B | 864 | 45.459 | 14.319 | 96.835 | 1.00 | 34.24 |
| 3972 | CZ | PHE | B | 864 | 44.247 | 14.052 | 96.097 | 1.00 | 34.64 |
| 3973 | CE2 | PHE | B | 864 | 43.040 | 14.039 | 96.796 | 1.00 | 34.40 |
| 3974 | CD2 | PHE | B | 864 | 43.011 | 14.281 | 98.235 | 1.00 | 33.00 |
| 3975 | C | PHE | B | 864 | 42.796 | 16.097 | 102.134 | 1.00 | 39.31 |
| 3976 | O | PHE | B | 864 | 41.644 | 15.610 | 102.340 | 1.00 | 42.22 |

FIGURE 3CA

| A | B | C | D | E | F | G | H | I | J |
|---|---|---|---|---|---|---|---|---|---|
| 3977 | N | ALA | B | 865 | 43.535 | 16.632 | 103.081 | 1.00 | 38.65 |
| 3978 | CA | ALA | B | 865 | 43.021 | 16.590 | 104.387 | 1.00 | 41.81 |
| 3979 | CB | ALA | B | 865 | 44.179 | 16.905 | 105.512 | 1.00 | 42.20 |
| 3980 | C | ALA | B | 865 | 41.864 | 17.534 | 104.488 | 1.00 | 41.60 |
| 3981 | O | ALA | B | 865 | 40.936 | 17.255 | 105.218 | 1.00 | 41.67 |
| 3982 | N | ASP | B | 866 | 41.882 | 18.696 | 103.846 | 1.00 | 42.39 |
| 3983 | CA | ASP | B | 866 | 40.590 | 19.411 | 104.022 | 1.00 | 44.31 |
| 3984 | CB | ASP | B | 866 | 40.540 | 20.833 | 103.439 | 1.00 | 44.90 |
| 3985 | CG | ASP | B | 866 | 41.770 | 21.613 | 103.675 | 1.00 | 50.05 |
| 3986 | OD1 | ASP | B | 866 | 42.078 | 21.770 | 104.884 | 1.00 | 55.78 |
| 3987 | OD2 | ASP | B | 866 | 42.487 | 22.082 | 102.707 | 1.00 | 49.26 |
| 3988 | C | ASP | B | 866 | 39.398 | 18.607 | 103.357 | 1.00 | 43.11 |
| 3989 | O | ASP | B | 866 | 38.289 | 18.577 | 103.908 | 1.00 | 40.88 |
| 3990 | N | ILE | B | 867 | 39.687 | 17.950 | 102.214 | 1.00 | 41.48 |
| 3991 | CA | ILE | B | 867 | 38.644 | 17.260 | 101.454 | 1.00 | 39.52 |
| 3992 | CB | ILE | B | 867 | 39.235 | 16.640 | 100.175 | 1.00 | 39.26 |
| 3993 | CG1 | ILE | B | 867 | 39.557 | 17.782 | 99.199 | 1.00 | 37.38 |
| 3994 | CD1 | ILE | B | 867 | 40.457 | 17.388 | 97.911 | 1.00 | 34.65 |
| 3995 | CG2 | ILE | B | 867 | 38.265 | 15.618 | 99.527 | 1.00 | 30.26 |
| 3996 | C | ILE | B | 867 | 38.010 | 16.203 | 102.272 | 1.00 | 39.36 |
| 3997 | O | ILE | B | 867 | 36.787 | 16.055 | 102.304 | 1.00 | 37.24 |
| 3998 | N | VAL | B | 868 | 38.841 | 15.458 | 102.980 | 1.00 | 40.82 |
| 3999 | CA | VAL | B | 868 | 38.200 | 14.447 | 103.809 | 1.00 | 40.27 |
| 4000 | CB | VAL | B | 868 | 39.269 | 13.491 | 104.586 | 1.00 | 43.83 |
| 4001 | CG1 | VAL | B | 868 | 38.560 | 12.555 | 105.520 | 1.00 | 38.82 |
| 4002 | CG2 | VAL | B | 868 | 40.125 | 12.770 | 103.646 | 1.00 | 39.45 |
| 4003 | C | VAL | B | 868 | 37.345 | 15.129 | 104.808 | 1.00 | 40.69 |
| 4004 | O | VAL | B | 868 | 36.193 | 14.723 | 105.003 | 1.00 | 41.29 |
| 4005 | N | SER | B | 869 | 37.826 | 16.169 | 105.485 | 1.00 | 41.17 |
| 4006 | CA | SER | B | 869 | 36.879 | 16.666 | 106.516 | 1.00 | 44.54 |
| 4007 | CB | SER | B | 869 | 37.479 | 17.651 | 107.541 | 1.00 | 46.64 |
| 4008 | OG | SER | B | 869 | 38.536 | 18.378 | 106.941 | 1.00 | 50.61 |
| 4009 | C | SER | B | 869 | 35.713 | 17.290 | 105.912 | 1.00 | 44.10 |
| 4010 | O | SER | B | 869 | 34.559 | 17.140 | 106.449 | 1.00 | 45.09 |
| 4011 | N | ILE | B | 870 | 35.941 | 17.977 | 104.771 | 1.00 | 43.54 |
| 4012 | CA | ILE | B | 870 | 34.744 | 18.495 | 104.139 | 1.00 | 42.08 |
| 4013 | CB | ILE | B | 870 | 34.755 | 19.950 | 103.300 | 1.00 | 43.22 |
| 4014 | CG1 | ILE | B | 870 | 33.586 | 19.999 | 102.312 | 1.00 | 41.61 |
| 4015 | CD1 | ILE | B | 870 | 33.949 | 19.365 | 101.176 | 1.00 | 41.32 |
| 4016 | CG2 | ILE | B | 870 | 36.033 | 20.464 | 102.635 | 1.00 | 40.07 |
| 4017 | C | ILE | B | 870 | 33.864 | 17.382 | 103.682 | 1.00 | 41.89 |
| 4018 | O | ILE | B | 870 | 32.658 | 17.458 | 103.793 | 1.00 | 41.51 |
| 4019 | N | LEU | B | 871 | 34.404 | 16.281 | 103.192 | 1.00 | 42.27 |
| 4020 | CA | LEU | B | 871 | 33.374 | 15.249 | 102.861 | 1.00 | 42.82 |
| 4021 | CB | LEU | B | 871 | 33.923 | 14.113 | 101.973 | 1.00 | 40.18 |
| 4022 | CG | LEU | B | 871 | 34.172 | 14.656 | 100.580 | 1.00 | 43.50 |
| 4023 | CD1 | LEU | B | 871 | 34.974 | 13.645 | 99.846 | 1.00 | 42.97 |
| 4024 | CD2 | LEU | B | 871 | 32.952 | 15.032 | 99.820 | 1.00 | 30.76 |
| 4025 | C | LEU | B | 871 | 32.699 | 14.672 | 104.115 | 1.00 | 41.38 |
| 4026 | O | LEU | B | 871 | 31.528 | 14.182 | 104.128 | 1.00 | 43.91 |
| 4027 | N | ASP | B | 872 | 33.394 | 14.658 | 105.207 | 1.00 | 41.15 |
| 4028 | CA | ASP | B | 872 | 32.653 | 14.052 | 106.384 | 1.00 | 41.49 |

FIGURE 3CB

| A | B | C | D | E | F | G | H | I | J |
|---|---|---|---|---|---|---|---|---|---|
| 4029 | CB | ASP | B | 872 | 33.673 | 13.713 | 107.437 | 1.00 | 39.80 |
| 4030 | CG | ASP | B | 872 | 34.462 | 12.401 | 107.107 | 1.00 | 45.40 |
| 4031 | OD1 | ASP | B | 872 | 33.894 | 11.494 | 106.424 | 1.00 | 51.78 |
| 4032 | OD2 | ASP | B | 872 | 35.617 | 12.127 | 107.556 | 1.00 | 52.74 |
| 4033 | C | ASP | B | 872 | 31.402 | 14.875 | 106.910 | 1.00 | 43.24 |
| 4034 | O | ASP | B | 872 | 30.268 | 14.269 | 107.347 | 1.00 | 42.17 |
| 4035 | N | LYS | B | 873 | 31.557 | 16.226 | 106.813 | 1.00 | 42.48 |
| 4036 | CA | LYS | B | 873 | 30.499 | 17.147 | 107.252 | 1.00 | 45.45 |
| 4037 | CB | LYS | B | 873 | 30.925 | 18.620 | 107.369 | 1.00 | 46.52 |
| 4038 | CG | LYS | B | 873 | 32.038 | 18.846 | 108.362 | 1.00 | 52.07 |
| 4039 | CD | LYS | B | 873 | 32.946 | 20.036 | 107.986 | 1.00 | 60.03 |
| 4040 | CE | LYS | B | 873 | 33.740 | 20.457 | 109.190 | 1.00 | 66.29 |
| 4041 | NZ | LYS | B | 873 | 34.221 | 19.164 | 109.838 | 1.00 | 72.68 |
| 4042 | C | LYS | B | 873 | 29.324 | 17.049 | 106.377 | 1.00 | 47.08 |
| 4043 | O | LYS | B | 873 | 28.196 | 17.131 | 106.833 | 1.00 | 48.85 |
| 4044 | N | LEU | B | 874 | 29.503 | 16.815 | 105.094 | 1.00 | 46.56 |
| 4045 | CA | LEU | B | 874 | 28.235 | 16.640 | 104.425 | 1.00 | 45.19 |
| 4046 | CB | LEU | B | 874 | 28.375 | 16.817 | 102.875 | 1.00 | 46.34 |
| 4047 | CG | LEU | B | 874 | 29.232 | 18.022 | 102.434 | 1.00 | 48.30 |
| 4048 | CD1 | LEU | B | 874 | 29.940 | 17.832 | 101.164 | 1.00 | 45.32 |
| 4049 | CD2 | LEU | B | 874 | 28.475 | 19.386 | 102.439 | 1.00 | 51.85 |
| 4050 | C | LEU | B | 874 | 27.677 | 15.295 | 104.767 | 1.00 | 46.11 |
| 4051 | O | LEU | B | 874 | 26.433 | 15.095 | 104.797 | 1.00 | 42.90 |
| 4052 | N | ILE | B | 875 | 28.568 | 14.289 | 104.846 | 1.00 | 48.45 |
| 4053 | CA | ILE | B | 875 | 28.076 | 12.933 | 105.024 | 1.00 | 49.62 |
| 4054 | CB | ILE | B | 875 | 29.276 | 11.927 | 105.013 | 1.00 | 50.00 |
| 4055 | CG1 | ILE | B | 875 | 29.557 | 11.427 | 103.630 | 1.00 | 49.38 |
| 4056 | CD1 | ILE | B | 875 | 30.973 | 10.853 | 103.455 | 1.00 | 50.85 |
| 4057 | CG2 | ILE | B | 875 | 29.010 | 10.708 | 105.957 | 1.00 | 48.28 |
| 4058 | C | ILE | B | 875 | 27.452 | 13.055 | 106.397 | 1.00 | 52.40 |
| 4059 | O | ILE | B | 875 | 26.435 | 12.478 | 106.683 | 1.00 | 52.10 |
| 4060 | N | ARG | B | 876 | 28.026 | 13.876 | 107.267 | 1.00 | 55.97 |
| 4061 | CA | ARG | B | 876 | 27.371 | 13.957 | 108.590 | 1.00 | 59.43 |
| 4062 | CB | ARG | B | 876 | 28.395 | 14.347 | 109.636 | 1.00 | 60.00 |
| 4063 | CG | ARG | B | 876 | 28.796 | 13.204 | 110.592 | 1.00 | 61.19 |
| 4064 | CD | ARG | B | 876 | 29.309 | 11.888 | 110.037 | 1.00 | 67.05 |
| 4065 | NE | ARG | B | 876 | 30.770 | 11.823 | 110.044 | 1.00 | 76.99 |
| 4066 | CZ | ARG | B | 876 | 31.568 | 11.708 | 111.116 | 1.00 | 79.95 |
| 4067 | NH1 | ARG | B | 876 | 32.887 | 11.691 | 110.939 | 1.00 | 81.01 |
| 4068 | NH2 | ARG | B | 876 | 31.067 | 11.609 | 112.335 | 1.00 | 79.88 |
| 4069 | C | ARG | B | 876 | 26.149 | 14.868 | 108.667 | 1.00 | 61.31 |
| 4070 | O | ARG | B | 876 | 25.336 | 14.774 | 109.576 | 1.00 | 63.40 |
| 4071 | N | ALA | B | 877 | 25.990 | 15.796 | 107.728 | 1.00 | 61.95 |
| 4072 | CA | ALA | B | 877 | 24.782 | 16.639 | 107.724 | 1.00 | 60.39 |
| 4073 | CB | ALA | B | 877 | 25.142 | 18.071 | 108.099 | 1.00 | 61.56 |
| 4074 | C | ALA | B | 877 | 24.104 | 16.542 | 106.334 | 1.00 | 60.30 |
| 4075 | O | ALA | B | 877 | 24.050 | 17.450 | 105.548 | 1.00 | 59.22 |
| 4076 | N | PRO | B | 878 | 23.522 | 15.391 | 106.110 | 1.00 | 60.43 |
| 4077 | CA | PRO | B | 878 | 23.006 | 14.995 | 104.833 | 1.00 | 60.78 |
| 4078 | CB | PRO | B | 878 | 22.159 | 13.749 | 105.162 | 1.00 | 60.53 |
| 4079 | CG | PRO | B | 878 | 22.572 | 13.309 | 106.396 | 1.00 | 59.55 |
| 4080 | CD | PRO | B | 878 | 23.223 | 14.408 | 107.159 | 1.00 | 61.36 |

FIGURE 3CC

| A | B | C | D | E | F | G | H | I | J |
|---|---|---|---|---|---|---|---|---|---|
| 4081 | C | PRO | B | 878 | 22.093 | 16.025 | 104.243 | 1.00 | 60.68 |
| 4082 | O | PRO | B | 878 | 21.843 | 15.907 | 103.015 | 1.00 | 60.12 |
| 4083 | N | ASP | B | 879 | 21.492 | 16.871 | 105.081 | 1.00 | 59.38 |
| 4084 | CA | ASP | B | 879 | 20.644 | 17.925 | 104.532 | 1.00 | 59.16 |
| 4085 | CB | ASP | B | 879 | 19.959 | 18.741 | 105.618 | 1.00 | 59.04 |
| 4086 | CG | ASP | B | 879 | 18.427 | 18.579 | 105.571 | 1.00 | 66.19 |
| 4087 | OD1 | ASP | B | 879 | 17.726 | 19.586 | 105.290 | 1.00 | 72.48 |
| 4088 | OD2 | ASP | B | 879 | 17.829 | 17.463 | 105.707 | 1.00 | 71.81 |
| 4089 | C | ASP | B | 879 | 21.462 | 18.826 | 103.603 | 1.00 | 57.43 |
| 4090 | O | ASP | B | 879 | 20.981 | 19.301 | 102.590 | 1.00 | 57.64 |
| 4091 | N | SER | B | 880 | 22.716 | 19.032 | 103.975 | 1.00 | 56.33 |
| 4092 | CA | SER | B | 880 | 23.644 | 19.836 | 103.267 | 1.00 | 54.79 |
| 4093 | CB | SER | B | 880 | 24.929 | 19.797 | 104.005 | 1.00 | 55.24 |
| 4094 | OG | SER | B | 880 | 25.622 | 18.605 | 103.690 | 1.00 | 55.50 |
| 4095 | C | SER | B | 880 | 23.879 | 19.301 | 101.868 | 1.00 | 54.99 |
| 4096 | O | SER | B | 880 | 24.507 | 19.979 | 101.077 | 1.00 | 53.72 |
| 4097 | N | LEU | B | 881 | 23.348 | 18.113 | 101.566 | 1.00 | 55.55 |
| 4098 | CA | LEU | B | 881 | 23.478 | 17.516 | 100.243 | 1.00 | 56.64 |
| 4099 | CB | LEU | B | 881 | 23.957 | 16.066 | 100.370 | 1.00 | 55.16 |
| 4100 | CG | LEU | B | 881 | 25.385 | 16.073 | 100.877 | 1.00 | 47.41 |
| 4101 | CD1 | LEU | B | 881 | 25.879 | 14.711 | 101.097 | 1.00 | 44.25 |
| 4102 | CD2 | LEU | B | 881 | 26.234 | 16.645 | 99.827 | 1.00 | 38.61 |
| 4103 | C | LEU | B | 881 | 22.260 | 17.570 | 99.338 | 1.00 | 60.26 |
| 4104 | O | LEU | B | 881 | 22.311 | 17.141 | 98.189 | 1.00 | 61.01 |
| 4105 | N | ALA | B | 882 | 21.141 | 18.068 | 99.839 | 1.00 | 64.54 |
| 4106 | CA | ALA | B | 882 | 19.923 | 18.077 | 99.007 | 1.00 | 66.81 |
| 4107 | CB | ALA | B | 882 | 18.619 | 18.004 | 99.875 | 1.00 | 66.76 |
| 4108 | C | ALA | B | 882 | 19.875 | 19.245 | 98.028 | 1.00 | 68.16 |
| 4109 | O | ALA | B | 882 | 19.531 | 19.064 | 96.866 | 1.00 | 69.24 |
| 4110 | N | ALA | B | 883 | 20.126 | 20.446 | 98.515 | 1.00 | 68.60 |
| 4111 | CA | ALA | B | 883 | 20.325 | 21.591 | 97.630 | 1.00 | 69.28 |
| 4112 | CB | ALA | B | 883 | 20.372 | 22.901 | 98.461 | 1.00 | 69.49 |
| 4113 | C | ALA | B | 883 | 21.685 | 21.361 | 96.886 | 1.00 | 69.14 |
| 4114 | O | ALA | B | 883 | 21.818 | 21.511 | 95.652 | 1.00 | 68.44 |
| 4146 | O1A | ATP | B1001 | | 46.712 | -3.440 | 86.953 | 1.00 | 89.49 |
| 4147 | PA | ATP | B1001 | | 45.850 | -2.328 | 86.523 | 1.00 | 84.33 |
| 4148 | O2A | ATP | B1001 | | 45.971 | -1.113 | 87.512 | 1.00 | 78.95 |
| 4149 | O3A | ATP | B1001 | | 46.316 | -2.240 | 84.993 | 1.00 | 89.69 |
| 4150 | PB | ATP | B1001 | | 47.730 | -1.566 | 84.575 | 1.00 | 98.93 |
| 4151 | O1B | ATP | B1001 | | 48.070 | -2.089 | 83.230 | 1.00 | 99.05 |
| 4152 | O2B | ATP | B1001 | | 48.948 | -1.908 | 85.490 | 1.00 | 95.56 |
| 4153 | O3B | ATP | B1001 | | 47.340 | 0.025 | 84.490 | 1.00 | 97.61 |
| 4154 | PG | ATP | B1001 | | 45.810 | 0.614 | 84.344 | 1.00 | 101.51 |
| 4155 | O3G | ATP | B1001 | | 45.916 | 2.031 | 83.685 | 1.00 | 97.15 |
| 4156 | O2G | ATP | B1001 | | 45.159 | 0.728 | 85.746 | 1.00 | 95.81 |
| 4157 | O1G | ATP | B1001 | | 44.985 | -0.323 | 83.475 | 1.00 | 99.53 |
| 4158 | O5* | ATP | B1001 | | 44.345 | -2.779 | 86.226 | 1.00 | 81.43 |
| 4159 | C5* | ATP | B1001 | | 44.056 | -3.806 | 85.310 | 1.00 | 76.05 |
| 4160 | C4* | ATP | B1001 | | 42.586 | -4.122 | 85.531 | 1.00 | 72.65 |
| 4161 | O4* | ATP | B1001 | | 42.294 | -5.396 | 86.149 | 1.00 | 66.71 |
| 4162 | C1* | ATP | B1001 | | 41.362 | -5.132 | 87.170 | 1.00 | 60.60 |
| 4163 | C2* | ATP | B1001 | | 40.769 | -3.740 | 86.836 | 1.00 | 62.85 |

FIGURE 3CD

| A | B | C | D E | F | G | H | I | J |
|---|---|---|---|---|---|---|---|---|
| 4164 | O2* | ATP | B1001 | 40.111 | -3.694 | 85.576 | 1.00 | 60.83 |
| 4165 | C3* | ATP | B1001 | 42.005 | -3.004 | 86.424 | 1.00 | 67.86 |
| 4166 | O3* | ATP | B1001 | 41.724 | -1.884 | 85.612 | 1.00 | 68.16 |
| 4167 | N9 | ATP | B1001 | 42.167 | -5.202 | 88.434 | 1.00 | 53.63 |
| 4168 | C8 | ATP | B1001 | 43.500 | -4.813 | 88.655 | 1.00 | 53.17 |
| 4169 | N7 | ATP | B1001 | 43.833 | -5.108 | 89.970 | 1.00 | 50.95 |
| 4170 | C5 | ATP | B1001 | 42.701 | -5.612 | 90.619 | 1.00 | 46.80 |
| 4171 | C6 | ATP | B1001 | 42.436 | -6.005 | 91.949 | 1.00 | 44.40 |
| 4172 | N6 | ATP | B1001 | 43.185 | -5.600 | 93.067 | 1.00 | 37.97 |
| 4173 | C4 | ATP | B1001 | 41.684 | -5.687 | 89.652 | 1.00 | 48.42 |
| 4174 | N3 | ATP | B1001 | 40.432 | -6.108 | 89.965 | 1.00 | 44.97 |
| 4175 | C2 | ATP | B1001 | 40.181 | -6.529 | 91.253 | 1.00 | 46.46 |
| 4176 | N1 | ATP | B1001 | 41.180 | -6.522 | 92.179 | 1.00 | 41.31 |

… # FIGURE 4
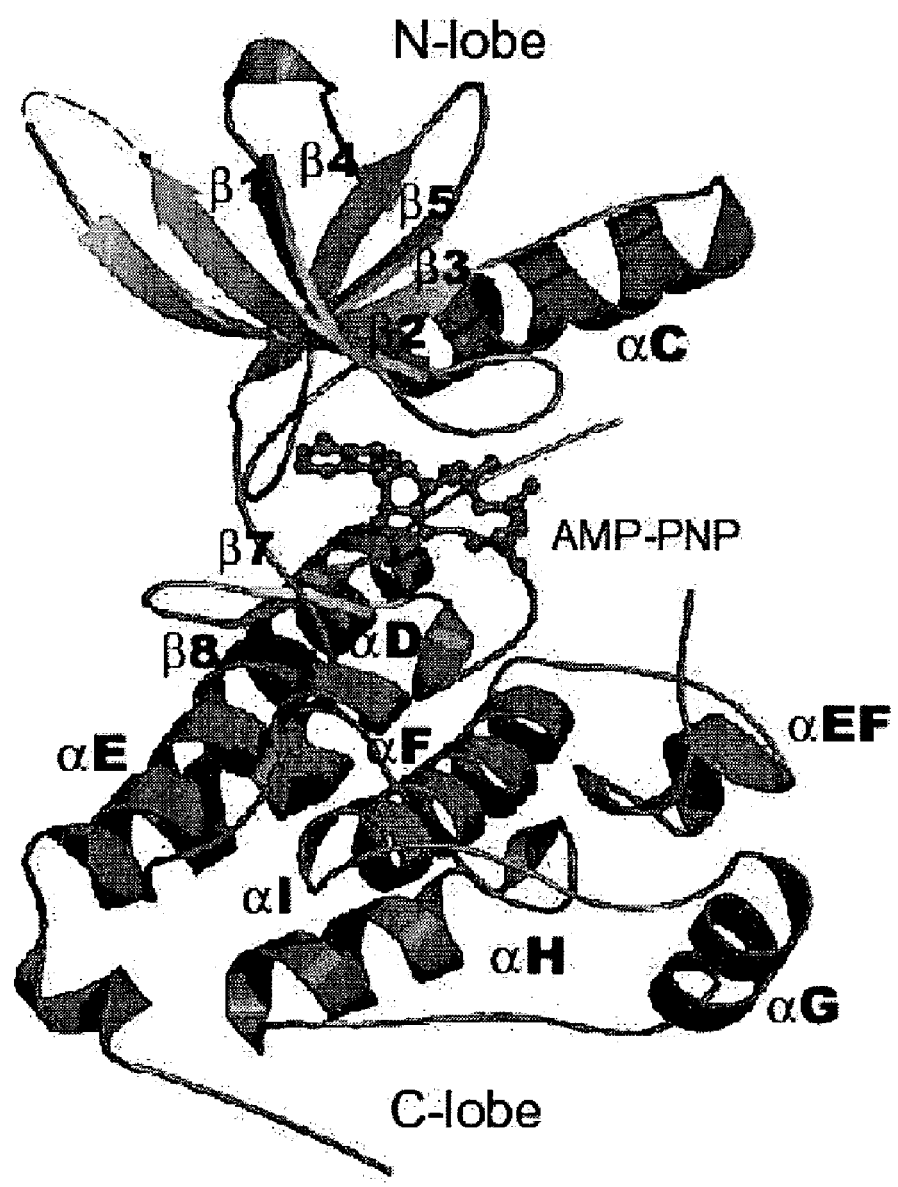

US 7,326,552 B1

WILD-TYPE KINASE DOMAIN OF HUMAN EPHRIN RECEPTOR A2 (EPHA2) AND CRYSTALLIZATION THEREOF

RELATED APPLICATION

This application claims the benefit of U.S. Provisional Application No. 60/390,356, filed Jun. 21, 2002, which is incorporated herein by reference.

FIELD OF THE INVENTION

The present invention relates to Ephrin receptor A2 ("EPHA2") and more specifically to EPHA2 in crystalline form, methods of forming crystals comprising EPHA2, methods of using crystals comprising EPHA2, a crystal structure of EPHA2, and methods of using the crystal structure.

BACKGROUND OF THE INVENTION

The most dangerous forms of cancer comprise malignant cells that metastasize to distant sites in a body. Metastatic cells have the property of being able to break away from a primary tumor, translocate to distant sites, and colonize distant and foreign microenvironments. Cancer cell metastasis requires cellular capacity to 1) detach from a primary tumor, 2) migrate and invade through local tissues, 3) translocate to distant sites in the body (via lymph or blood), 4) colonize a foreign site, and 5) grow and survive in this foreign environment. All of these behaviors are linked to cell adhesions.

Cell adhesions control the physical interactions of cells with their microenvironment. Cell adhesions also initiate signals that dictate tumor cell growth, death, and differentiation. At the cellular level, metastatic cells have overcome restraints upon cell growth and migration that result from physical linkages and signals conveyed by cell-cell contacts. Malignant cells often have increased interactions with surrounding extracellular matrix (ECM) proteins that provide linkages and signals that promote several aspects of metastasis.

Protein tyrosine phosphorylation is believed to regulate a balance between cell-cell and cell-ECM adhesions in epithelial cells. Elevated tyrosine kinase activity weakens cell-cell contacts and promotes ECM adhesions. Alteration in levels of tyrosine phosphorylation is believed to be important for tumor cell invasiveness. Tyrosine phosphorylation is controlled by cell membrane tyrosine kinases, and increased expression of tyrosine kinases is known to occur in metastatic cancer cells. It is therefore desirable to have compounds that selectively inhibit tyrosine kinases, particularly those tyrosine kinases that are involved in malignant cell growth.

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three dimensional structure coordinates. Various methods for preparing crystalline proteins are known in the art.

Once protein crystals are produced, crystallographic data can be generated using the crystals to provide useful structural information that assists the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues in the binding pocket, one may design new ligands that will interact favorably with the protein. With such structural information, available computational methods may be used to predict how strong the ligand binding interaction will be. Such methods help in the design of inhibitors that bind strongly, as well as selectively to the protein.

SUMMARY OF THE INVENTION

The present invention is directed to crystals comprising EPHA2 and particularly crystals comprising EPHA2 that have sufficient size and quality to obtain useful information about the structural properties of EPHA2 and molecules or complexes that may associate with EPHA2.

In one embodiment, a composition is provided that comprises a protein in crystalline form wherein at least a portion of the protein has 55%, 65%, 75%, 85%, 90%, 95%, 97%, 99% or greater identity with residues 572-976, 596-900, or 605-883 of SEQ. ID No. 1.

In one variation, the protein has activity characteristic of EPHA2. For example, the protein may optionally be inhibited by inhibitors of wild type EPHA2. The protein crystal may also diffract X-rays for a determination of structure coordinates to a resolution having a value of 4 Å, 3.5 Å, 3.0 Å or less.

In one variation, the protein crystal has a crystal lattice in a $P3_221$ space group. The protein crystal may also have a crystal lattice having unit cell dimensions, +/−5%, of a=72.12 Å, b=72.12 Å and c=241.62 Å.

The present invention is also directed to crystallizing EPHA2. The present invention is also directed to the conditions useful for crystallizing EPHA2. It should be recognized that a wide variety of crystallization methods can be used in combination with the crystallization conditions to form crystals comprising EPHA2 including, but not limited to, vapor diffusion, batch, dialysis, and other methods of contacting the protein solution for the purpose of crystallization.

The present invention is also directed to crystallizing EPHA2. The present invention is also directed to the conditions useful for crystallizing EPHA2. It should be recognized that a wide variety of crystallization methods can be used in combination with the crystallization conditions to form crystals comprising EPHA2 including, but not limited to, vapor diffusion, batch, dialysis, and other methods of contacting the protein solution for the purpose of crystallization.

In one embodiment, a method is provided for forming crystals of a protein comprising: forming a crystallization volume comprising: a protein wherein at least a portion of the protein has 55%, 65%, 75%, 85%, 90%, 95% 97%, 99% or greater identity with residues 572-976, 596-900, or 605-883 of, SEQ. ID No. 1; and storing the crystallization volume under conditions suitable for crystal formation.

In one variation, the crystallization volume comprises the protein in a concentration between 1 mg/ml and 50 mg/ml, and 5-50% w/v of precipitant wherein the precipitant comprises one or more members of the group consisting of PEG MME 2K, PEG 1K, PEG 2K and PEG 3K, and wherein the crystallization volume has a pH between pH 4 and pH 7.

The method may optionally further comprise forming a protein crystal that has a crystal lattice in a $P3_221$ space group. The method also optionally further comprises forming a protein crystal that has a crystal lattice having unit cell dimensions, +/−5%, of a=72.12 Å, b=72.12 Åand c=241.62 Å. The invention also relates to protein crystals formed by these methods.

The present invention is also directed to a composition comprising an isolated protein that comprises or consists of one or more of the protein sequence(s) of EPHA2 taught herein for crystallizing EPHA2. The present invention is also directed to a composition comprising an isolated nucleic acid molecule that comprises or consists of the nucleotides for expressing the protein sequence of EPHA2 taught herein for crystallizing EPHA2.

The present invention is also directed to an expression vector that may be used to express the isolated proteins taught herein for crystallizing EPHA2.

The present invention is also directed to an expression vector that may be used to express the isolated proteins taught herein for crystallizing EPHA2. In one variation, the expression vector comprises a promoter that promotes expression of the isolated protein.

The present invention is also directed to a cell line transformed or transfected by an isolated nucleic acid molecule or expression vector of the present invention.

The present invention is also directed to structure coordinates for EPHA2 as well as structure coordinates that are comparatively similar to these structure coordinates. It is noted that these comparatively similar structure coordinates may encompass proteins with similar sequences and/or structures. For example, machine-readable data storage media is provided having data storage material encoded with machine-readable data that comprises structure coordinates that are comparatively similar to the structure coordinates of EPHA2. The present invention is also directed to a machine readable data storage medium having data storage material encoded with machine readable data, which, when read by an appropriate machine, can display a three dimensional representation of all or a portion of a structure of EPHA2 or a model that is comparatively similar to the structure of all or a portion of EPHA2.

Various embodiments of machine readable data storage medium are provided that comprise data storage material encoded with machine readable data. The machine readable data comprises: structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1. The amino acids being overlayed and compared need not to be identical when the RMSD calculation is performed on alpha carbons and main chain atoms but the amino acids being overlayed and compared must have identical side chains when the RMSD calculation is performed on all non-hydrogen atoms.

For example, in one embodiment where the comparison is based on the 4 Angstrom set of amino acid residues (Column 1) and is based on superimposing alpha-carbon atoms (Column 2), the structure coordinates may have a root mean square deviation equal to or less than 0.21 when compared to the structure coordinates of FIG. 3.

TABLE 1

| AA RESIDUES TO USE TO PERFORM RMSD COMPARISON | PORTION OF EACH AA RESIDUE USED TO PERFORM RMSD COMPARISON | RMSD VALUE LESS THAN OR EQUAL TO | | |
|---|---|---|---|---|
| Table 3 (4 Angstrom set) | alpha-carbon atoms[1] | 0.21 | 0.16 | 0.11 |
|  | main-chain atoms[1] | 0.25 | 0.20 | 0.13 |
|  | all non-hydrogen[2] | 0.44 | 0.33 | 0.22 |
| Table 4 (7 Angstrom set) | alpha-carbon atoms[1] | 0.21 | 0.16 | 0.11 |
|  | main-chain atoms[1] | 0.22 | 0.16 | 0.11 |
|  | all non-hydrogen[2] | 0.43 | 0.33 | 0.22 |
| Table 5 (10 Angstrom set) | alpha-carbon atoms[1] | 0.19 | 0.15 | 0.10 |
|  | main-chain atoms[1] | 0.21 | 0.16 | 0.11 |
|  | all non-hydrogen[2] | 0.40 | 0.30 | 0.20 |
| 572-976, 596-900, or 605-883 of SEQ. ID No. 1 | alpha-carbon atoms[1] | 0.28 | 0.21 | 0.14 |
|  | main-chain atoms[1] | 0.29 | 0.20 | 0.15 |
|  | all non-hydrogen[2] | 0.41 | 0.30 | 0.20 |

[1]the RMSD computed between the atoms of all amino acids that are common to both the target and the reference in the aligned and superposed structure. The amino acids need not to be identical.
[2]the RMSD computed only between identical amino acids, which are common to both the target and the reference in the aligned and superposed structure.

The present invention is also directed to a three-dimensional structure of all or a portion of EPHA2. This three-dimensional structure may be used to identify binding sites, to provide mutants having desirable binding properties, and ultimately, to design, characterize, or identify ligands capable of interacting with EPHA2. Ligands that interact with EPHA2 may be any type of atom, compound, protein or chemical group that binds to or otherwise associates with the protein. Examples of types of ligands include natural substrates for EPHA2, inhibitors of EPHA2, and heavy atoms. The inhibitors of EPHA2 may optionally be used as drugs to treat therapeutic indications by modifying the in vivo activity of EPHA2.

In various embodiments, methods are provided for displaying a three dimensional representation of a structure of a protein comprising:

taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing a three dimensional representation of a structure based on the structure coordinates; and displaying the three dimensional representation.

The present invention is also directed to a method for solving a three-dimensional crystal structure of a target protein using the structure of EPHA2.

In various embodiments, computational methods are provided comprising: taking machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

computing phases based on the structural coordinates;

computing an electron density map based on the computed phases; and determining a three-dimensional crystal structure based on the computed electron density map.

In various embodiments, computational methods are provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

These methods may optionally further comprise determining a three-dimensional crystal structure based upon the computed three-dimensional electron density map.

The present invention is also directed to using a crystal structure of EPHA2, in particular the structure coordinates of EPHA2 and the surface contour defined by them, in methods for screening, designing, or optimizing molecules or other chemical entities that interact with and preferably inhibit EPHA2.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of EPHA2 and/or its structure coordinates to evaluate the ability of entities to associate with EPHA2. The entities may be any entity that may function as a ligand and thus may be any type of atom, compound, protein (such as antibodies) or chemical group that can bind to or otherwise associate with a protein.

In various embodiments, methods are provided for evaluating a potential of an entity to associate with a protein comprising:

creating a computer model of a protein structure using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

performing a fitting operation between the entity and the computer model; and analyzing results of the fitting operation to quantify an association between the entity and the model.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein; and contacting the entity with a protein wherein at least a portion of the protein has 55%, 65%, 75%, 85%, 90%, 95%, 97%, 99% or greater identity with residues 572-976, 596-900, or 605-883 of SEQ. ID No. 1.

In other embodiments, methods are provided for identifying entities that can associate with a protein comprising:

generating a three-dimensional structure of a protein using structure coordinates that comprise structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and employing the three-dimensional structure to design or select an entity that can associate with the protein.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein; and contacting the entity with a protein wherein at least a portion of the protein has 55%, 65%, 75%, 85%, 90%, 95%, 97%, 99% or greater identity with residues 572-976, 596-900, or 605-883 of SEQ. ID No. 1.

In other embodiments, methods are provided for identifying entities that can associate with a protein comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and employing the computer model to design or select an entity that can associate with the protein.

In other embodiments, methods are provided for evaluating the ability of an entity to associate with a protein, the method comprising:

constructing a computer model defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; and selecting an entity to be evaluated by a method selected from the group consisting of (i) assembling molecular fragments into the entity, (ii) selecting an entity from a small molecule database, (iii) do novo ligand design of the entity, and (iv) modifying a known ligand for EPHA2, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In other embodiments, methods are provided for evaluating the ability of an entity to associate with a protein, the method comprising:

computing a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1); and selecting an entity to be evaluated by a method selected from the group consisting of (i) assembling molecular fragments into the entity, (ii) selecting an entity from a small molecule database, (iii) de novo ligand design of the entity, and (iv) modifying a known ligand for EPHA2, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In regard to each of these embodiments, the protein may optionally have activity characteristic of EPHA2. For example, the protein may optionally be inhibited by inhibitors of wild type EPHA2.

In another embodiment, a method is provided for identifying an entity that associates with a protein comprising: taking structure coordinates from diffraction data obtained from a crystal of a protein wherein at least a portion of the protein has 55%, 65%, 75%, 85%, 90%, 95%, 97%, 99% or greater identity with residues 572-976, 596-900, or 605-883 of SEQ. ID No. 1; and performing rational drug design using a three dimensional structure that is based on the obtained structure coordinates.

The protein crystals may optionally have a crystal lattice with a $P3_221$ space group and unit cell dimensions, +/−5%, of a=72.12 Å, b=72.12 Å and c=241.62 Å.

The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may optionally further comprise contacting cells expressing the protein with the one or more entities and detecting a change in a phenotype of the cells when a particular entity is present.

BRIEF DESCRIPTION OF THE FIGURES

FIG. 1-1A illustrates SEQ. ID Nos. 1, 2, and 3 referred to in this application.

FIG. 3 lists the atomic structure coordinates for EPHA2 (reference numbers in Col. E corresponding to the residue numbering for SEQ ID NO: 1) as derived by X-ray crystallography from a crystal that comprises the protein which is present as a dimer. Drawing sheets 3-3AO of FIG. 3 list the structure coordinates of chain A; drawing sheets 3AP-3CD of FIG. 3 list the structure coordinates of chain B. The following abbreviations are used in FIG. 3: "X, Y, Z" crystallographically define the atomic position of the element measured: "B" is a thermal factor that measures movement of the atom around its atomic center; "Occ" is an occupancy factor that refers to the fraction of the molecules in which each atom occupies the position specified by the coordinates (a value of "1" indicates that each atom has the same conformation, i.e. the same position, in all molecules of the crystal).

FIG. 4 illustrates a ribbon diagram overview of the structure of EPHA2, highlighting the secondary structural elements of the protein.

DETAILED DESCRIPTION OF THE INVENTION

Figure 2:
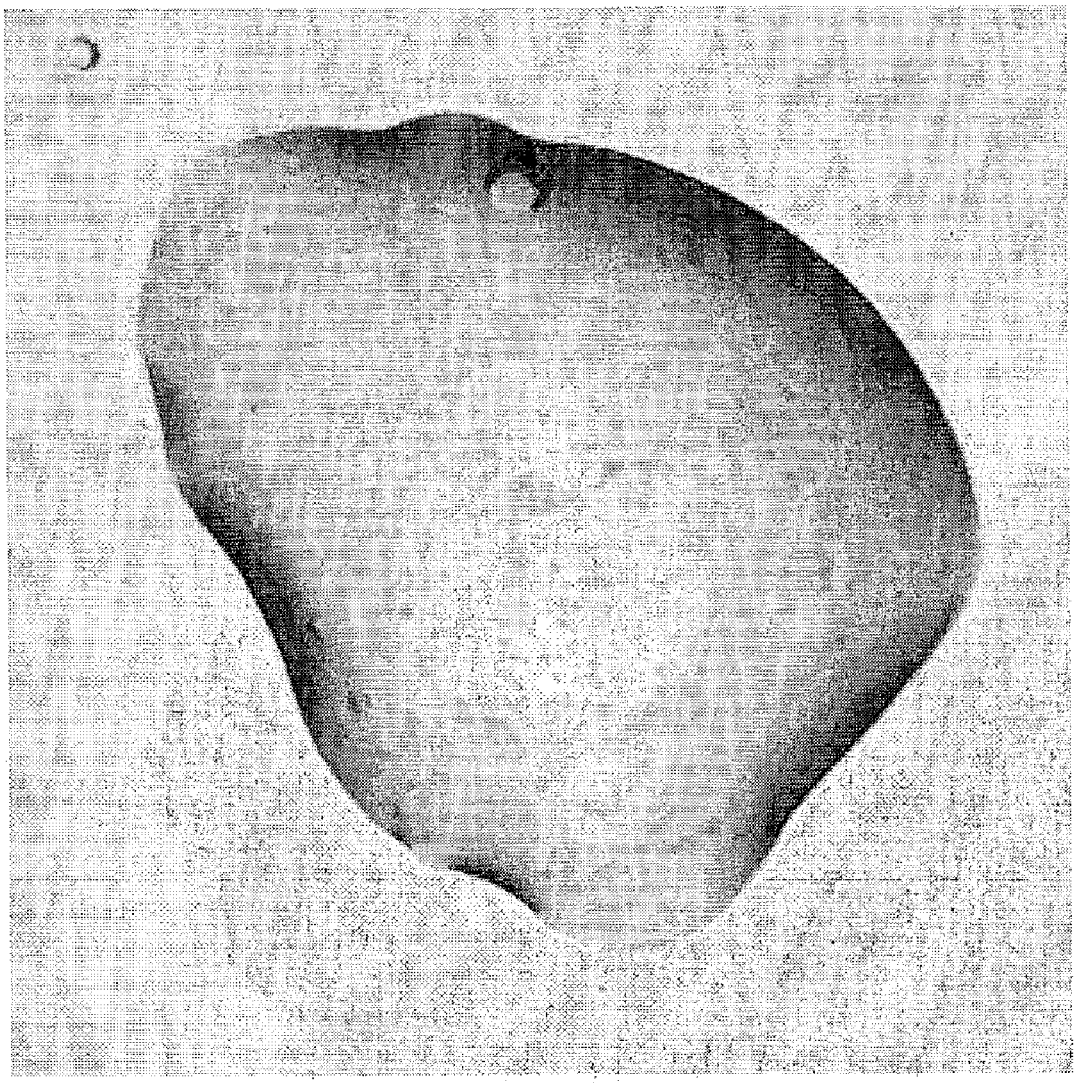
FIG. 2 illustrates a crystal of an EPHA2-AMP-PNP complex.

The present invention relates to one of the Eph family of tyrosine kinases known as EPHA2. More specifically, present invention relates to EPHA2 in crystalline form, methods of forming crystals comprising EPHA2, methods of using crystals comprising EPHA2, a crystal structure of EPIA2, and methods of using the crystal structure.

In describing protein structure and function herein, reference is made to amino acids comprising the protein. The amino acids may also be referred to by their conventional abbreviations; A=Ala=Alanine; T=Thr Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

1. EPHA2

The wild type form of EPHA2 is a 130 kDa receptor tyrosine kinase that is expressed on adult epithelia. EPHA2 is one of at least 14 currently known members of the Eph family of tyrosine kinases known as Ephrin receptors.

EPHA2 is a transmembrane receptor tyrosine kinase with a cell-bound ligand. EPHA2 expression has been found to be altered in many malignant carcinomas, including melanoma, lung, breast, colon, and prostrate tumors. Additionally, the distribution and/or phosphorylation of EPHA2 is altered in metastatic cells. Moreover, cells that have been transformed to over express EPHA2 demonstrate malignant growth, and stimulation of EPHA2 is sufficient to confer malignant growth and invasiveness.

It should be understood that the methods and compositions provided herein relating to EPHA2 are not intended to be limited to wild type EPHA2 but instead are also directed to fragments and variants of EPHA2 as described herein.

In one embodiment, EPHA2 comprises the wild-type form of full length EPHA2, set forth herein as SEQ. ID No. 1. (GenBank Accession Number NP 004422; Lindberg, R. A. and Hunter, T., "cDNA cloning and characterization of eck, an epithelial cell receptor protein-tyrosine kinase in the eph/elk family of protein kinases", *Mol. Cell. Biol.* 10 (12), 6316-6324, 1990).

In another embodiment, EPHA2 comprises residues 572-976 of SEQ. ID No. 1 which comprises the kinase domain of wild-type EPHA2.

In another embodiment, EPHA2 comprises residues 596-900 of SEQ. ID No. 1 which also comprises the kinase domain of wild-type EPHA2.

In another embodiment, EPHA2 comprises of SEQ. ID No. 3 which comprises the portion of the kinase domain of wild-type EPHA2 that are represented in both the first and second sets of structure coordinates shown in FIG. 3 (reference numbers in Col. E of FIG. 3 refer to residue numbering for SEQ ID NO: 1).

It should be recognized that the invention may be readily extended to various variants of wild-type EPHA2 and variants of fragments thereof. In another embodiment, EPHA2 comprises a sequence that has at least 65% identity, preferably at least 70%, 80%, 90%, 95% or higher identity with any one of the above sequences (e.g., all of SEQ. ID No. 1 or residues 572-976, 596-900, or 605-883 of SEQ. ID No. 1).

It is also noted that the above sequences of EPHA2 is also intended to encompass isoforms, mutants and fusion proteins of these sequences. Preferred fusion proteins are exemplified by SEQ. ID No. 3 which includes an N-terminal poly-histidine (His$_6$) region that may be used to facilitate purification of the protein.

With the crystal structure provided herein, where amino acid residues are positioned in the structure are now known. As a result, the impact of different substitutions can be more easily predicted and understood.

For example, based on the crystal structure, applicants have determined that EPHA2 amino acids in Table 2 are within 4 Angstroms of and therefore close enough to interact with AMP-PNP. Applicants have also determined that the amino acids of Table 3 are within 7 Angstroms of bound AMP-PNP and therefore are also close enough to interact with that substrate or analogs thereof. Further it has been determined that the amino acids of Table 4 are within 10 Angstroms of the bound AMP-PNP. One or either of these sets of amino acids is preferably conserved in a variant of EPHA2. Hence, EPHA2 may optionally comprise a sequence that has at least 65% identity, preferably at least 70%, 80%, 90%, 95% or higher identity with any one of the above sequences (e.g., all of SEQ. ID No. 1 or residues 572-976, 596-900, or 605-883 of SEQ. ID No. 1) where at least the residues shown in Tables 2, 3, and/or 4 are conserved with the exception of 0, 1, 2, 3, or 4 residues. It should be recognized that one might optionally also vary some of the binding site residues in order to determine the effect such changes have on structure or activity.

TABLE 2

ATP binding site residues within 4 Angstroms of the AMP-PNP binding site (SEQ ID NO: 1).

| | | |
|---|---|---|
| ILE 619 | VAL 627 | GLU 693 |
| GLY 620 | ALA 644 | TYR 694 |
| ALA 621 | LYS 646 | MET 695 |
| GLY 622 | THR 692 | LEU 746 |
| GLU 623 | | |

TABLE 3

ATP binding site residues within 7 Angstroms of the AMP-PNP binding site (SEQ ID No. 1).

| | | |
|---|---|---|
| ILE 619 | ALA 644 | ASN 697 |
| GLY 620 | ILE 645 | GLY 698 |
| ALA 621 | LYS 646 | ALA 699 |
| GLY 622 | GLU 663 | LYS 702 |
| GLU 623 | ILE 676 | ARG 743 |
| PHE 624 | ARG 677 | ASN 744 |
| GLY 625 | THR 692 | LEU 746 |
| VAL 627 | GLU 693 | VAL 747 |
| TYR 628 | TYR 694 | SER 756 |
| LYS 629 | MET 695 | ASP 757 |
| VAL 643 | GLU 696 | |

TABLE 4

ATP binding site residues within 10 Angstroms of the AMP-PNP binding site (SEQ ID No. 1).

| | | |
|---|---|---|
| LYS 617 | PHE 660 | LYS 702 |
| VAL 618 | GLU 663 | PHE 703 |
| ILE 619 | MET 667 | ARG 705 |
| GLY 620 | ILE 675 | GLU 706 |
| ALA 621 | ILE 676 | ASP 739 |
| GLY 622 | ARG 677 | ALA 741 |
| GLU 623 | LEU 678 | ALA 742 |
| PHE 624 | GLU 679 | ARG 743 |
| GLY 625 | ILE 690 | ASN 744 |
| GLU 626 | ILE 691 | ILE 745 |
| VAL 627 | THR 692 | LEU 746 |
| TYR 628 | GLU 693 | VAL 747 |
| LYS 629 | TYR 694 | ASN 748 |
| GLY 630 | MET 695 | SER 749 |
| PRO 642 | GLU 696 | LYS 754 |
| VAL 643 | ASN 697 | VAL 755 |
| ALA 644 | GLY 698 | SER 756 |
| ILE 645 | ALA 699 | ASP 757 |
| LYS 646 | LEU 700 | PHE 758 |
| THR 647 | ASP 701 | GLY 759 |
| LYS 778 | | |

With the benefit of the crystal structure and guidance provided by Tables 2, 3, and 4, a wide variety of EPHA2 variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of EPHA2.

Variants of EPHA2 may be insertional variants in which one or more amino acid residues are introduced into a predetermined site in the EPHA2 sequence. For instance, insertional variants can be fusions of heterologous proteins or polypeptides to the amino or carboxyl terminus of the subunits.

Variants of EPHA2 also, may be substitutional variants in which at least one residue has been removed and a different residue inserted in its place. Non-natural amino acids (i.e. amino acids not normally found in native proteins), as well as isosteric analogs (amino acid or otherwise) may optionally be employed in substitutional variants. Examples of suitable substitutions are well known in the art, such as the Glu→Asp, Ser→Cys, Cys→Ser, and His→Ala for example.

Another class of variants is deletional variants, which are characterized by the removal of one or more amino acid residues from the EPHA2 sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; O-methylisourea, 2,4-pentanedione; and transaminaseN:talyzed reaction with glyoxylate, and N-hydroxysuccinamide esters of polyethylene glycol or other bulky substitutions.

Arginyl residues may be modified by reaction with a number of reagents, including phenylglyoxal, 2,3-butanedione, 1,2-cyclohexanedione, and ninhydrin. Modification of arginine residues requires that the reaction be performed in alkaline conditions because of the high $pK_a$, of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming 0-acetyl tyrosyl species and 3-nitro derivatives, respectively. Tyrgsyl residues may also be iodinated using $^{125}I$ or $^{131}I$ to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins: Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding EPHA2 may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for there affect on a variety of different properties including, for example, solubility, crystallizability and a modification to the protein's structure and activity.

In one variation, the variant and/or fragment of wild-type EPHA2 is functional in the sense that the resulting protein is capable of associating with at least one same chemical entity that is also capable of selectively associating with a protein comprising the kinase domain of wild-type EPHA2 (e.g., residues 596-900 of SEQ. ID No. 1) since this common associative ability evidences that at least a portion of the native structure has been conserved.

It is noted the activity of the native protein need not necessarily be, conserved. Rather, amino acid substitutions, additions or deletions that interfere with native activity but which do not significantly alter the three-dimensional structure of the domain are specifically contemplated by the invention. Crystals comprising such variants of EPHA2, and the atomic structure coordinates obtained there from, can be used to identify compounds that bind to the native domain. These compounds may affect the activity or the native domain.

Amino acid substitutions, deletions and additions that do not significantly interfere with the three-dimensional structure of EPHA2 will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

It should be understood that the protein; may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of EPHA2 will be apparent to: those having skills in the art, particularly in view of the three dimensional structure of EPHA2 provided herein.

2. Cloning Expression and Purification of EPHA2

The gene encoding EPHA2 can be isolated from RNA, cDNA or cDNA libraries. In this case, the portion of the gene encoding residues 596-900 was isolated and is shown as SEQ. I.D. No. 2.

Construction of expression vectors and recombinant proteins from the DNA sequence, encoding EPHA2 may be performed by various methods well known in the art. For example, these techniques may be performed according to Sambrook et al., Molecular Cloning-A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of EPHA2. Example 1 provides one such expression system.

Once expressed, purification steps are employed to produce EPHA2 in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography, (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

EPHA2 may optionally be affinity labeled during cloning, preferably with a poly-histidine ($His_6$) region, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization & Crystals Comprising EPHA2

One aspect of the present invention relates to methods for forming crystals comprising EPHA2 as well as crystals comprising ELPHA2.

In one embodiment, a method for forming crystals comprising EPHA2 is provided comprising forming a crystallization volume comprising EPHA2, precipitant, optionally a buffer, optionally a monovalent or divalent salt and optionally an organic solvent; and storing the crystallization volume under conditions suitable for crystal formation.

In another embodiment, a method for forming crystals comprising EPHA2 is provided comprising forming a crystallization volume comprising EPHA2, precipitants selected from the group comprising ethylene glycol, polyethylene glycol or ammonium salt (or mixtures thereof), optionally a buffer, optionally a monovalent or divalent salt and optionally an organic solvent; and storing the crystallization volume under conditions suitable for crystal formation.

In yet another embodiment, a method for forming crystals comprising EPHA2 is provided comprising forming a crystallization volume comprising EPHA2 in solution comprising the components shown in Table 5; and storing the crystallization volume under conditions suitable for crystal formation.

TABLE 5

| Precipitant |
| --- |
| 5-50% w/v comprising one or more of PEG MME 2K, PEG 1K, PEG 2K and PEG 3K |
| pH |
| pH 4-7. Buffers that may be used include, but are not limited to imidazole, acetate, hepes, citrate, and combinations thereof. |
| Protein Concentration |
| 1 mg/ml-50 mg/ml |
| Temperature |
| 4° C.-25° C. |

In yet another embodiment, a method for forming crystals comprising EPHA2 is provided comprising forming a crystallization volume comprising EPHA2; introducing crystals comprising EPHA2 as nucleation sites, and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro and/or macro seeding of crystals may also be performed to facilitate crystallization.

It should be understood that forming crystals comprising EPHA2 and crystals comprising EPHA2 according to the invention are not intended to be limited to the wild-type, full length EPHA2 shown in SEQ. ID No. 1 and to fragments comprising residues 572-976, 596-900, or 605-883 of SEQ. ID No. 1. Rather, it should be recognized that the invention may be extended to various other fragments and variants of wild-type EPHA2 as described above.

It should also be understood that forming crystals comprising EPHA2 and crystals comprising EPHA2 according to the invention may be such that EPHA2 is complexed with one or more ligands. The ligand used to form the complex may be any ligand capable of binding to EPHA2. In one variation, the ligand is an natural substrate. In another variation, the ligand is an inhibitor.

In one particular variation, the ligand binds to the ATP binding site of the protein. Examples of such ligands include, but are not limited to, small molecule inhibitors of EPHA2 as well as ATP, non-hydrolyzable ATP analogs and suicide substrates. Non-hydrolyzable ATP analogs useful in the crystallizable compositions of this invention include AMP-PCH$_2$P, AMP-PNP, AMP-PSP and AMP where the oxygen linking the second and third phosphates of the ATP analogs is replaced by $CH_2$, $S(ATP\gamma S)$ and, NH, respectively. An example of a suicidal substrate is 5'-(p-fluorosulfonyl benzoyl) adenosine (FSBA). Preferably, the crystallizable compositions of this invention comprise AMP-PNP as the substrate.

Optionally, the EPHA2 complex may further comprise divalent cations, especially magnesium or manganese cations, which may be introduced in any suitable manner. For example, the cations may be introduced by incubating the desired ligand with a suitable metal salt such as $MgCl_2$ prior to incubation with the EPHA2 protein.

In one particular embodiment, EPHA2 crystals have a crystal lattice in the P3$_2$21 space group. EPHA2 crystals may also optionally have unit cell dimensions, +1-5%, of a=72.12 Å, b=72.12 Åand c=241.62 Å.

EPHA2 crystals also preferably are capable of diffracting X-rays for determination of atomic coordinates to a resolution having a value of 4 Å, 3 Å, 2.5 Å, 2 Å or less.

Crystals comprising EPHA2 may be formed by a variety of different methods known in the art. For example, crystallizations may be performed by batch, dialysis, and vapor diffusion (sitting drop and hanging drop) methods. A detailed description of basic protein crystallization setups may be found in McRee, D. and David. P., *Practical Protein Crystallography* 2$^{nd}$ Ed. (1999), Academic Press Inc. Further descriptions regarding performing crystallization experiments are provided in Stevens, et al. (2000) *Curr. Opin. Struct. Biol.*: 10(5):558-63, and U.S. Pat. Nos. 6,296,673, 5,419,278, and 5,096,676.

In one variation, crystals comprising EPHA2 are formed by mixing substantially pure EPHA2 with an aqueous buffer containing a precipitant at a concentration just below a concentration necessary to precipitate the protein. One suitable precipitant for crystallizing EPHA2 is polyethylene glycol (PEG), which combines some of the characteristics of the salts and other organic precipitants (see, for example, Ward et al., *J. Mol. Biol.* 98:161, 1975, and McPherson, *J. Biol. Chem.* 251:6300, 1976.

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to tbese methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of an EPHA2-AMP-PNP complex were obtained. In order to accomplish this, systematic broad screen crystallization trials were performed on an EPHA2-AMP-PNP complex using the sitting drop technique. In each experiment, a 100 nL mixture of EPHA2-AMP-PNP complex and precipitant was placed on a platform positioned over a well containing 100 µL of the precipitating solution. Precipitate and crystal formation was detected in the sitting drops. Fine screening was then carried out for those crystallization conditions that appeared to produce precipitate and/or crystal in the drops.

Based on the crystallization experiments that were performed, a thorough understanding of how different crystallization conditions affect EPHA2 crystallization was obtained. Based on this understanding, a series of crystallization conditions were identified that may be used to form crystals comprising EPHA2. These conditions are summarized in Table 5. A particular example of crystallization conditions that may be used to form crystals diffraction quality crystals of the EPHA2-AMP-PNP complex is detailed in Example 2. FIG. 2 illustrates crystals of the EPHA2-AMP-PNP complex formed using the crystallization conditions provided in Table 5.

One skilled in the art will recognize that the crystallization conditions provided in Table 5 and Example 2 can be varied and still yield protein crystals comprising EPHA2. For example, it is noted that variations on the crystallization conditions described herein can be readily determined by taking the conditions provided in Table 5 and performing fine screens around those conditions by varying the type and concentration of the components in order to determine additional suitable conditions for crystallizing EPHA2, variants of EPHA2, and ligand complexes thereof.

Crystals comprising EPHA2 have a wide range of uses. For example, now that crystals comprising EPHA2 have been produced, it is noted that crystallizations may be performed using such crystals as a nucleation site within a concentrated protein solution. According to this variation, a concentrated protein solution is prepared and a crystalline material (microcrystals) is used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising EPFA2 according to the present invention, the crystals so formed can be used by this crystallization technique to initiate crystal growth of other EPHA2 comprising crystals, including EPHA2 complexed to other ligands.

As will be described herein in greater detail, crystals may also be used to perform X-ray or neutron diffraction analysis in order to determine the three-dimensional structure of EPHA2 and, in particular, to assist in the identification of its active site. Knowledge of the binding site region allows rational design and construction of ligands including inhibitors. Crystallization and structural determination of EPHA2 mutants having altered bioactivity allows the evaluation of whether such changes are caused by general structure deformation or by side chain alterations at the substitution site.

4. X-Ray Data Collection and Structure Determination

Crystals comprising EPHA2 may be obtained as described above in Section 3. As described herein, these crystals may then be used to perform x-ray data collection and for structure determination.

In one embodiment, described in Example 2, crystals of an EPHA2-AMP-PNP complex were obtained where EPHA2 has the sequence of residues shown in SEQ. ID No. 3. These particular crystals were used to determine the three dimensional structure of EPHA2. However, it is noted that other crystals comprising EPHA2 including different EPHA2 variants, fragments, and complexes thereof may also be used.

Diffraction data was collected from cryocooled crystals (100K) of the EPHA2-AMP-PNP complex at the Advanced Light Source beam line 5.0.3 using an ADSC CCD detector. The diffraction pattern of the EPHA2-AMP-PNP complex displayed symmetry consistent with space group $P3_221$, with unit cell dimensions a=b=72.12 Å and c=241.62 Å. Data were collected and integrated to 2.3 Å with MOSFLM and scaled with SCALA (CCP4 Study Weekend (eds. Sawyer, L., Isaacs; N. & Bailey, S.) 56-62 (SERC Daresbury Laboratory, England) (1993).

All crystallographic calculations were performed using the CCP4 program package (Collaborative Computational Project, N. The CCP4 Suite: Programs for Protein Crystallography. Acta Cryst. D50, 760-763 (1994)). The initial phases for EPHA2 were obtained by the molecular replacement method using the program AMORE. The coordinates of murine EPHB2 kinase domain (PDB code 1JPA) were used as a search model (72% identity) for the solution of the EPHA2-AMP-PNP structure. The highest solution from the translational function was subjected to a rigid body rotation followed by refinement against the maximum likelihood method as implemented in REFMAC(CCP4). Rigid body refinement and torsional dynamics refinement was followed by multiple rounds of manual building with Xfit (McRee, D. E. XtalView/Xfit-A versatile program for manipulating atomic coordinates and electron density *J. Struct. Biol.* 125, 156-65 (1999)) and/or ARP_WARP map improvement (Perrakis, A., Morris, R. J. & Lamzin, V. S. Automated protein model building combined with iterative structure refinement). All stages of model refinement were carried with bulk solvent correction and anisotropic scaling. The data collection and data refinement statistics are given in Table 6.

TABLE 6

| Crystal data | |
| --- | --- |
| Ligand | AMP-PNP |
| Space group | $P3_221$ |
| Unit cell dimensions | a = b = 72.12 |
| | c = 241.62 |
| Data collection | EPHA2-AMP-PNP |
| X-ray source | B1 5.0.3 |
| Wavelength [Å] | 1.0 |
| Resolution [Å] | 63-2.3 |
| Observations (unique) | 35,483 |
| Redundancy | 4.1 |
| Completeness overall (outer shell) | 95% (78%) |
| I/σ(I) overall (outer shell) | 11.5 (2.0) |
| $R_{symm}$[1] overall (outer shell) | 0.057 (0.485) |
| Refinement | |
| Reflections used | 30,484 |
| R-factor | 23.5% |
| $R_{free}$ | 29.3% |

TABLE 6-continued

| r.m.s bonds | 0.03 |
| --- | --- |
| r.m.s angles | 3.11 |

[1] $R_{symm} = \Sigma_{hkl}\Sigma_i |I(hkl)_i - \langle I(hkl)\rangle| / \Sigma_{hkl}\Sigma_i \langle I(hkl)_i\rangle$ over I observations of a reflection hkl Each unit cell comprised two EPHA2-AMP-PNP-$(Mg^{2+})_2$ complexes. Structure coordinates were determined for each of the two complexes and the resultant two sets of structure coordinates from the refinement are presented in FIG. 3.

It is noted that the sequence of the structure coordinates of chain A and chain B presented in FIG. 3 differ in some regards from the sequence shown in SEQ. ID No. 1.

For some residues, the electron density obtained was insufficient to identify the side chain. As a result, the side chains of these residues were truncated such that a different amino acid is reported. Tables 6 and 7 summarize the differences between SEQ. ID No. 1 and the truncated residues of chain A and chain B, appearing in drawing sheets 3-3AO and 3AP-3CP of FIG. 3, respectively.

TABLE 7

Truncated Residues in The Structure Coordinates of Chain A (FIG. 3) (SEQ ID NO: 1).

| T605-A605 | K633-A633 | T634-A634 |
| --- | --- | --- |
| K638-A638 | K639-A639 | L760-A760 |
| K793-A793 | K828-A828 | R858-A858 |
| R876-A876 | F887-A887 | |

TABLE 8

Truncated Residues in The Structure Coordinates of Chain A (FIG. 3) (SEQ ID NO: 1).

| L602-A602 | K633-A633 | K649-A649 |
| --- | --- | --- |
| E654-A654 | Q656-A656 | R657-A657 |
| K684-A684 | K686-A686 | L764-A764 |
| K778-A778 | K793-A793 | K828-A828 |
| M840-A840 | R860-A860 | K882-A882 |
| T883-A883 | | |

It is also noted that structure coordinates are not reported for some residues because the electron density obtained was insufficient to identify the position of these residues. For chain A, structure coordinates for residues 596-604, 635-637, 761-777 and 888-895 are not reported. For chain B, structure coordinates for residues 596-601, 635-638, 765-777, 884-895 are not reported.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket as used herein refers to a region of the protein that, as a result of its shape, favorably associates with a ligand These variations in coordinates may be generated because of mathematical manipulations of the EPHA2 structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that bound to the active site binding pocket of EPHA2 would also be expected to bind to another binding pocket whose structure coordinates defined a shape that fell within the acceptable error.

Various computational methods may be used to determine whether a particular protein or a portion thereof (referred to here as the "target protein"), typically the binding pocket, has a high degree of three-dimensional spatial similarity to another protein (referred to here as the "reference protein") against which the target protein is being compared.

The process of comparing a target protein structure to a reference protein structure may generally be divided into three steps: 1) defining the equivalent residues and/or atoms for the target and reference proteins, 2) performing a fitting operation between the proteins; and 3) analyzing the results. These steps are described in more detail below. All structure comparisons reported herein and the structure comparisons claimed are intended to be based on the particular comparison procedure described below.

Equivalent residues or atoms can be determined based upon an alignment of primary sequences of the proteins, an alignment of their structural domains or as a combination of both. Sequence alignments generally implement the dynamic programming algorithm of Needleman and Wunsch [*J. Mol. Biol.* 48: 442-453, 1970]. For the purpose of this invention the sequence alignment was performed using the publicly available software program MOE (Chemical Computing Group Inc.) package version 2002.3, as described in the accompanying User's Manual. When using the MOE program, alignment was performed in the sequence editor window using the ALIGN option utilizing the following program parameters: Initial pairwise Build-up: ON, Substitution Matrix: Blosum62, Round Robin: ON, Gap Start: 7, Gap Extend: 1, Iterative Refinement: ON, Build-up: TREE-BASED, Secondary Structure: NONE, Structural Alignment: ENABLED, Gap Start: 1 Gap Extend: 0.1

Once aligned, a rigid body fitting operation is performed where the structure for the target protein is translated and rotated to obtain an optimum fit relative to the structure of the reference protein. The fitting operation uses an algorithm that computes the optimum translation and rotation to be applied to the moving structure, such that the root mean square deviation of the fit over the specified pairs of equivalent atoms is an absolute minimum. For the purpose of fitting operations made herein, the publicly available software program MOE (Chemical Computing Group Inc.) v. 2002.3 was used.

The results from this process are typically reported as an RMSD value between two sets of atoms. The term "root mean square deviation" means the square root of the arithmetic mean of the squares of deviations. It is a way to express the deviation or variation from a trend or object. As used herein, an RMSD value refers to a calculated value based on variations in the atomic coordinates of a reference protein from the atomic coordinates of a reference protein or portions of thereof. The structure coordinates for EPHA2, provided in FIG. 3, are used as the reference protein in these calculations.

The same set of atoms was used for initial fitting of the structures and for computing root mean square deviation values. For example, if a root mean square deviation (RMSD) between Cα atoms of two proteins is needed, the proteins in question should be superposed only on the Cα atoms and not on any other set of atoms. Similarly, if an RMSD calculation for all atoms is required, the superposition of two structures should be performed on all atoms.

Based on a review of protein structures deposited in the Protein Databank (PDB), 1JPA was identified as having the smallest RMSD values relative to the structure coordinates provided herein. Table 9 below provides a series of RMSD values that were calculated by the above described process using the structure coordinates in FIG. 3 as the reference protein and the structure coordinates from PDB code: 1JPA (Human EPHB2, neural kinase) as the target protein.

TABLE 9

| AA RESIDUES USED TO PERFORM RMSD COMPARISON WITH PDB:1JPA | PORTION OF EACH AA RESIDUE USED TO PERFORM RMSD COMPARISON WITH PDB:1JPA | RMSD [Å] |
|---|---|---|
| Table 3 (4 Angstrom set) | alpha-carbon atoms[1] | 0.42 |
| | main-chain atoms[1] | 0.51 |
| | all non-hydrogen[2] | 0.87 |
| Table 4 (7 Angstrom set) | alpha-carbon atoms[1] | 0.41 |
| | main-chain atoms[1] | 0.44 |
| | all non-hydrogen[2] | 0.87 |
| Table 5 (10 Angstrom set) | alpha-carbon atoms[1] | 0.38 |
| | main-chain atoms[1] | 0.42 |
| | all non-hydrogen[2] | 0.79 |
| 605-883 of SEQ. ID No. 1 | alpha-carbon atoms[1] | 0.55 |
| | main-chain atoms[1] | 0.57 |
| | all non-hydrogen[2] | 0.82 |

[1]the RMSD computed between the atoms of all amino acids that are common to both the target and the reference in the aligned and superposed structure. The amino acids need not to be identical.
[2]the RMSD computed only between identical amino acids, which are common to both the target and the reference in the aligned and superposed structure.

It is noted that mutants and variants of EPHA2 as well as other proteins likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation (RMSD) equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

As noted, there are many different ways to express the surface contours of the EPHA2 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation equal to or less than a given RMSD value specified in Columns 3, 4 or 5 of Table 1 when the coordinates used to compute the surface contour are compared to the structure coordinates of FIG. 3, wherein (a) the root mean square deviation is calculated by the calculation method set forth herein, (b) the portion of amino acid residues associated with the given RMSD value in Table 1 (specified in Column 2 of Table 1) are superimposed according to the RMSD calculation, and (c) the root mean square deviation is calculated based only on those amino acid residues present in both the protein being modeled and the portion of the protein associated with the given RMSD in Table 1 (specified in Column 1 of Table 1).

5. EPHA2-AMP-PNP Structure

The present invention is also directed to a three-dimensional crystal structure of EPHA2. This crystal structure may be used to identify binding sites, to provide mutants having desirable binding properties, and ultimately, to design, characterize, or identify ligands that interact with EPHA2.

The three-dimensional crystal structure of EPHA2 may be generated, as is known in the art, from the structure coordinates shown in FIG. 3 and similar such coordinates.

The refined crystal structure of EPHA2-AMP-PNP determined according to the present invention contains amino acids residues 605-887 as numbered according to SEQ. ID No. 1 (based on the coordinates of chain A), one bound AMP-PNP molecule, and two $Mg^{2+}$ ions. A total of 66 water molecules were included.

FIG. 4 illustrates a ribbon diagram overview of the structure of EPHA2, highlighting the secondary structural elements of the protein. As can be seen, the structure exhibits bilobal architecture typical of protein kinase catalytic domains. The smaller N-terminal lobe contains a five-stranded anti-parallel α-sheet (β1-β5) and an α-helix (αC). The larger C-temminal lobe consists of eight α-helices (αD-αJ). The C-terminal lobe contains functionally important loop regions: the glycine-rich nucleotide binding loop, the catalytic loop and the activation loop (A-loop) involved in polypeptide substrate binding. The nucleotide ligands bind in a cleft between the two lobes.

Kinases show considerable variability in the relative orientation of the N and C lobes, in the position and orientation of the αC, and in the conformation of the activation loop. This relative orientation of the N- and C-terminal lobes is important in kinase function. A catalytically active conformation is generally a closed structure in which the two lobes clamp together bringing conserved residues into catalytically optimal-positions. In particular, in the active conformation, the αC helix becomes parallel with the cleft between the lobes and makes tertiary contacts with the C-lobe. In the inactive conformation observed in several unphosphorylated kinase structures the two lobes are spaced apart at a much higher angle and the αC helix is rotated away from the C-lobe.

The conformation of the EPHA2 kinase is similar to the unphosphorylated, auto-inhibited structure of the murine EPHB2 kinase domain (the r.m.s. deviation between 267 Cα atoms of the two structures is 1.2 Å). The lobes of the EPHA2 are in the open conformation and the activation loop is disordered.

Figure 5A:
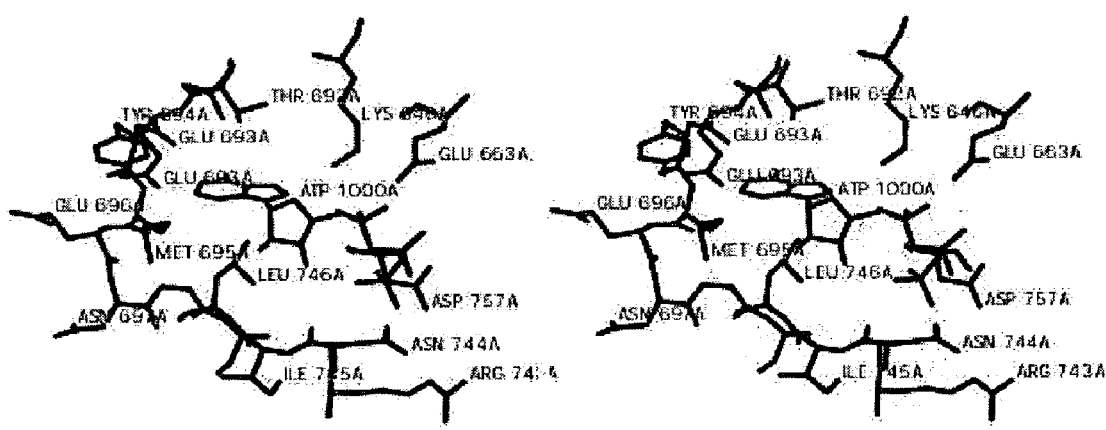
FIG. 5A illustrates AMP-PNP bound in the active site of EPHA2 based on the determined crystal structure for the molecule in the asymmetric unit corresponding to the structure coordinates of chain A shown in drawing sheets 3-3AO of FIG. 3.

FIG. 5A illustrates AMP-PNP bound in the active site of EPHA2 based on the determined crystal structure for the molecule in the asymmetric unit corresponding to the structure coordinates of chain A shown in drawing sheets 3-3AP of FIG. 3. As can be seen, the salt bridge between conserved K646 and E663 is not maintained in the structure.

Figure 5B:
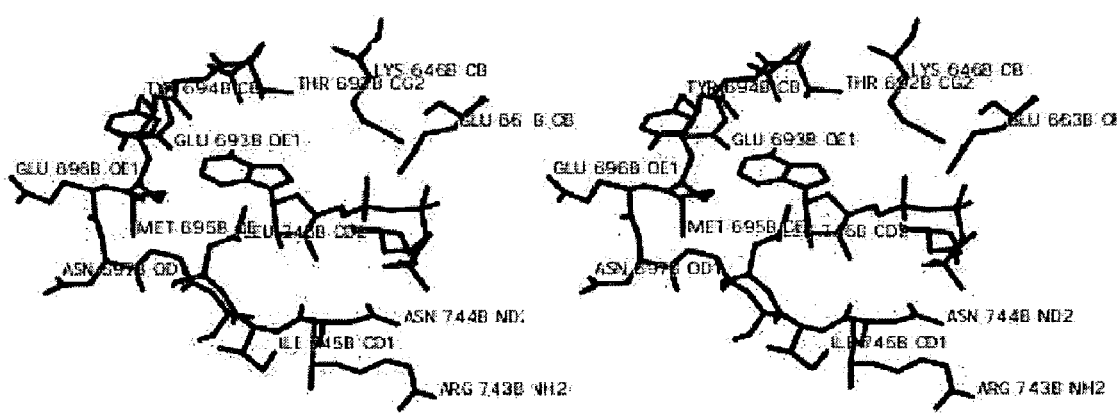
FIG. 5B illustrates AMP-PNP bound in the active site of EPHA2 based on the determined crystal structure for the molecule in the asymmetric unit corresponding to the structure coordinates of chain B shown in drawing sheets 3AP-3CD of FIG. 3.

FIG. 5B illustrates AMP-PNP bound in the active site of EPHA2 based on the determined crystal structure for the molecule in the asymmetric unit corresponding to the structure coordinates of chain B shown in drawing sheets 3AO-3CD of FIG. 3. As can be seen, the salt bridge between conserved K646 and E663 is maintained in the structure.

The previously solved structure of the EPHB2 kinase domain suggested a novel mode of autoinhibition resulting from the juxtamembrane region interacting with the αC helix and kinking it. Surprisingly, despite the absence of the juxtamembrane region, the structure of human EPHA2 displays a similar bent conformation of the αC helix (11 and 14 degrees, for EPHA2 and EPHB2, respectively). This suggests that the αC helix in the EPH kinase domains may have evolved an inherent structural flexibility that facilitates the autoinhibition of the kinase.

6. EPHA2 Binding Pocket and Ligand Interaction

The term "binding site" or "binding pocket", as the terms are used herein, refers to a region of a protein that, as a result of its shape, favorably associates with a ligand or substrate. The term "EPHA2-like binding pocket" refers to a portion of a molecule or molecular complex whose shape is sufficiently similar to the EPHA2 binding pockets as to bind common ligands. This commonality of shape may be quantitatively defined by a root mean square deviation (rmsd) from the structure coordinates of the backbone atoms of the amino acids that make up the binding pockets in EPHA2 (as set forth in FIG. 3).

The "active site binding pockets" or "active site" of EPHA2 refers to the area on the surface of EPHA2 where the substrate binds. FIGS. 5A and 5B illustrate AMP-PNP bound in the active site of EPHA2 based on the determined crystal structure of the present invention. As can be seen, AMP-PNP binds in a cleft between the two lobes and is coordinated by residues on the N-terminal lobe. Residues in the C-terminal lobe coordinate substrate binding and catalysis.

The ATP binding site of protein kinases is the most common target for the design of small molecule inhibitors. As shown in FIGS. 5A and 5B, the bound AMP-PNP interacts with the EPHA2 both directly and through water mediated contacts. The key structural differences in kinase ATP sites are clustered around the ribose ring and the N7 atom of the adenine base. The area adjacent to N7 has been utilized in the past to confer specificity to some of the most selective kinase inhibitors. This region forms a hydrophobic pocket bordered by the residue T692 in EPHA2. The size and shape of the pocket varies amongst kinases. In EPHA2, the side chain of T692 forms a hydrogen bond to the amino group of ATP.

As previously stated, the ATP binding site of protein kinases is a primary target for the design of small molecule inhibitors. The ATP binding site appears well conserved among protein kinases and involves residues protruding from the β1-β2-β3 sheet, helix C, the loop region linking β5 and the C-lobe, and the catalytic loop. The structure of the ATP binding pocket in the EPHA2-AMP-PNP complex shows considerable sequence variability with other kinases, which is reflective of diversity among kinase sub-families. The ATP binding cleft shows subtle differences in ATP site architecture that may be explored to confer specificity of inhibition. The position of the bound AMP-PNP is similar, but not identical, to other structures.

In resolving the crystal structure of EPHA2 in complex with AMP-PNP, applicants determined that EPHA2 amino acids in Table 2 (above) are within 4 Angstroms of and therefore close enough to interact with AMP-PNP. Applicants have also determined that the amino acids of Table 3 (above) are within 7 Angstroms of bound AMP-PNP and therefore are also close enough to interact with that substrate or analogs thereof. Further it has been determined that the amino acids of Table 4 (above) are within 10 Angstroms of the bound AMP-PNP. The 4, 7, and/or 10 Angstroms sets of amino acids are preferably conserved in variants of EPHA2. While it is desirable to largely conserve these residues, it should be recognized however that variants may also involve varying 1, 2, 3, 4 or more of the residues set forth in Tables 2, 3, and 4 in order to evaluate the roles these amino acids play in the binding pocket.

With the knowledge of the EPHA2 crystal structure provided herein, Applicants define an EPHA2 binding pocket as a binding pocket where the relative positioning of the 4, 7, and/or 10 Angstroms sets of amino acids are substantially conserved. Again, it is noted that it may be desirable to form variants where 1, 2, 3, 4 or more of the residues set forth in Tables 2, 3, and 4 are varied in order to evaluate the roles these amino acids play in the binding pocket. Accordingly, any set of structure coordinates for a protein from any source having a root mean square deviation of non-hydrogen atoms of less than 2 Å when superimposed on the non-hydrogen atom positions of the corresponding atomic coordinates of either chain A or chain B for the 4, 7, and/or 10 Angstroms sets of amino acids shall be considered identical. As noted previously, the root mean square deviation is intended to be limited to only those non-hydrogen atoms of amino acid residues that are common to both the protein fragments represented in FIG. 3 and the protein whose structure coordinates are being compared to the coordinates shown in FIG. 3 since the sequence of the protein may be varied somewhat.

Accordingly, in one embodiment, the invention relates to data, computer readable media comprising data, and uses of the data where the data comprises the structure coordinates of either chain A or chain B shown in FIG. 3 or structure coordinates having a root mean square deviation of non-hydrogen atoms of less than 2 Å when superimposed on the non-hydrogen atom positions of the corresponding atomic coordinates of either chain A or chain B in FIG. 3 for the 4, 7, and/or 10 Angstroms sets of amino acids.

Again, it is noted that the root mean square deviation is intended to be limited to only those non-hydrogen atoms of amino acid residues that are common to both the protein fragment represented in one or more of the tables and the protein whose structure coordinates are being compared to the coordinates shown in FIG. 3.

As noted above, there are many different ways to express the surface contours of the EPHA2 structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on non-hydrogen atoms in the structure coordinates of FIG. 3 that are present in residues shown in Tables 2, 3, and/or 4.

Optionally, the root mean square deviation of non-hydrogen atoms is less than 1.5 Å, 1 Å, 0.5 Å, or less.

It will be readily apparent to those of skill in the art that the numbering of amino acids in other isoforms of EPHA2 may be different than that set forth for EPHA2. Corresponding amino acids in other isoforms of EPHA2 are easily identified by visual inspection of the amino acid sequences or by using commercially available homology software programs, as further described below.

7. System for Displaying the Three Dimensional Structure of EPHA2

The present invention is also directed to machine-readable data storage media having data storage material encoded with machine-readable data that comprises structure coordinates for EIPHA2. The present invention is also directed to a machine readable data storage media having data storage material encoded with machine readable data, which, when read by an appropriate machine, can display a three dimensional representation of a structure of EPHA2.

All or a portion of the EPHA2 coordinate data shown in FIG. 3, when used in conjunction with a computer programmed with software to translate those coordinates into the three-dimensional structure of EPHA2 may be used for a variety of purposes, especially for purposes relating to drug discovery. Software for generating three-dimensional graphical representations are known and commercially available. The ready use of the coordinate data requires that it be stored in a computer-readable format. Thus, in accordance with the present invention, data capable of being displayed as the three-dimensional structure of EPHA2 and/or portions thereof and/or their structurally similar variants may be stored in a machine-readable storage medium, which is capable of displaying a graphical three-dimensional representation of the structure.

For example, in various embodiments, a computer is provided for producing a three-dimensional representation of at least an EPHA2-like binding pocket, the computer comprising:

machine readable data storage medium comprising a data storage material encoded with machine-readable data, the machine readable data comprising structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1;

a working memory for storing instructions for processing the machine-readable data;

a central-processing unit coupled to the working memory and to the machine-readable data storage medium, for processing the machine-readable data into the three-dimensional representation; and an output hardware coupled to the central processing unit, for receiving the three dimensional representation.

Another embodiment of this invention provides a machine-readable data storage medium, comprising a data storage material encoded with machine readable data which, when used by a machine programmed with instructions for using said data, displays a graphical three-dimensional representation comprising EPHA2 or a portion or variant thereof.

In various variations, the machine readable data comprises data for representing a protein based on structure coordinates where the structure coordinates have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1.

According to another embodiment, the machine-readable data storage medium comprises a data storage material encoded with a first set of machine readable data which comprises the Fourier transform of structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other EPHA2-like enzymes, and isoforms of EPHA2.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
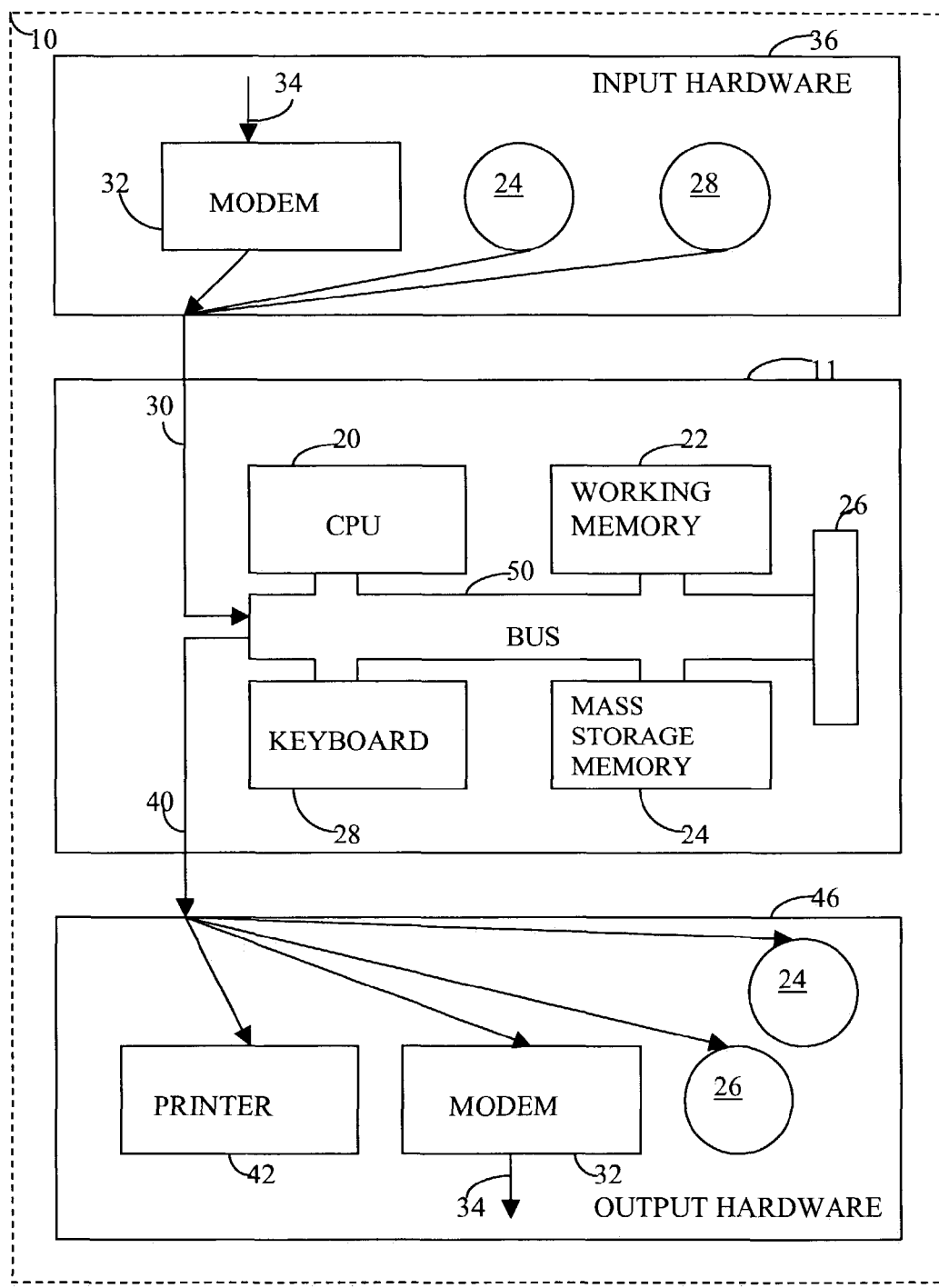
FIG. 6 illustrates a system that may be used to carry out instructions for displaying a crystal structure of EPHA2 encoded on a storage medium.

FIG. 6 illustrates an example of a computer system that may be used in combination with storage media according to the present invention. As illustrated, the computer system 11 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices may, similarly implement output hardware 46, coupled to computer 11 by output lines 40. By way of example, output hardware 46 may include CRT display terminal 26 for displaying a graphical representation of a binding pocket of this invention using a program such as MOE as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22, and determines the sequence of data processing steps. A number of programs may be used to process the machine-readable data of this invention. Such programs are discussed in reference to using the three dimensional structure of EPHA2 described herein.

The storage medium encoded with machine-readable data according to the present invention can be any conventional data storage device known in the art. For example, the storage medium can be a conventional floppy diskette or hard disk. The storage medium can also be an optically readable data storage medium, such as a CD-ROM or a DVD-ROM, or a rewritable medium such as a magneto-optical disk that is optically readable and magneto-optically writable.

8. Uses of the Three Dimensional Structure of EPHA2

The three-dimensional crystal structure of the present invention may be used to identify EPHA2 binding sites, be used as a molecular replacement model to solve the structure of unknown crystallized proteins, to design mutants having desirable binding properties, and ultimately, to design, characterize, identify entities capable of interacting with EPHA2 and other structurally similar proteins as well as other uses that would be recognized by one of ordinary skill in the art. Such entities may be chemical entities or proteins. The term "chemical entity", as used herein, refers to chemical compounds, complexes of at least two chemical compounds, and fragments of such compounds.

The EPHA2 structure coordinates provided herein are useful for screening and identifying drugs that inhibit EPHA2 and other structurally similar proteins. For example, the structure encoded by the data may be computationally evaluated for its ability to associate with putative substrates or ligands. Such compounds that associate with EPHA2 may inhibit EPHA2, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with EPHA2 or a fragment or variant thereof by using all or a portion of the structure coordinates provided in FIG. 3 or functional equivalents thereof. A method is also provided for evaluating the potential of an entity to associate with EPHA2 or a fragment or variant thereof by using structure coordinates similar to all or a portion of the structure coordinates provided in FIG. 3 or functional equivalents thereof.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 2, 3 and 4 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising an EPHA2-like binding pocket. One embodiment of the method comprises: using all or a portion of the structure coordinates provided herein to generate a three-dimensional structure of an EPHA2-like binding pocket; employing the three-dimensional structure to design or select a potential ligand; synthesizing the potential ligand; and contacting the synthesized potential ligand with a protein comprising an EPHA2-like binding pocket to determine the ability of the potential ligand to interact with protein. According to this method, the structure coordinates used may have a root mean square deviation equal to or less than the RMSD values specified in Columns 3, 4 or 5 of Table 1 when compared to the structure coordinates of FIG. 3 according to the RMSD calculation method set forth herein, provided that the portion of amino acid residues specified in Column 2 of Table 1 of each set of structure coordinates are superimposed and the root mean square deviation is calculated based only on those amino acid residues in the structure coordinates that are also present in the portion of the protein specified in Column 1 of Table 1. The portion of the protein structure used optionally comprises all of the amino acids listed in Tables 2, 3, and/or 4 that are present.

As noted previously, the three-dimensional structure of an EPHA2-like binding pocket need not be generated directly from structure coordinates. Rather, a computer model can be formed that defines a surface contour that is the same or similar to the surface contour defined by the structure coordinates.

A method is also provided for evaluating the ability of an entity, such as a compound or a protein to associate with an EPHA2-like binding pocket, the method comprising: constructing a computer model of a binding pocket defined by structure coordinates that have a root mean square deviation equal to or less than the RMSD value specified in Columns 3, 4 or 5 of Table 1 when compared to the structure coordinates of FIG. 3, the root mean square deviation being calculated such that the portion of amino acid residues specified in Column 2 of Table 1 of each set of structure coordinates are superimposed and the root mean square deviation is based only on those amino acid residues in the structure coordinates that are also present in the portion of the protein specified in specified in Column 1 of Table 1; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for EPHA2, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the said binding pocket.

The computer model of a binding pocket used in this embodiment need not be generated directly from structure coordinates. Rather, a computer model can be formed that defines a surface contour that is the same or similar to the surface contour defined by the structure coordinates.

Also according to the method, the method may further include synthesizing the entity; and contacting a protein having an EPHA2-like binding pocket with the synthesized entity.

With the structure provided herein, the present invention for the first time permits the use of molecular design techniques to identify, select or design potential inhibitors of EPHA2, based on the structure of an EPHA2-like binding pocket. Such a predictive model is valuable in light of the high costs associated with the preparation and testing of the many diverse compounds that may possibly bind to the EPHA2 protein.

According to this invention, a potential EPHA2 inhibitor may now be evaluated for its ability to bind an EPHA2-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of an EPHA2-like binding pocket may be computationally evaluated using a series of steps in which chemical entities or fragments are screened and selected for their ability to associate with the EPHA2-like binding pockets.

One skilled in the art may use one of several methods to screen entities (whether chemical or protein) for their ability to associate with an EPHA2-like binding pocket. This process may begin by visual inspection of, for example, an EPHA2-like binding pocket on a computer screen based on the EPHA2 structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK; MCSS (A. Miranker et al., "Functionality. Maps of Binding Sites: A Multiple Copy Simultaneous Search Method." Proteins: Structure, Function and Genetics, 11, pp. 29-34 (1991)). MCSS is available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)). AUTODOCK is available from Scripps Research Institute, La Jolla, Calif.; & DOCK (I. D. Kuntz et al., "A Geometric Approach to Macromolecule-Ligand Interactions", J. Mol. Biol., 161, pp. 269-288 (1982)). DOCK is available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of EPHA2. This may then be followed by manual model building using software such as MOE, QUANTA or Sybyl [Tripos Associates, St. Louis, Mo].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)). CAVEAT is available from the University of California, Berkeley, Calif.; 3D Database systems such as ISIS (MDL Information Systems, San Leandro, Calif.). This area is reviewed in Y. C. Martin, "3D. Database Searching in Drug Design", J. Med. Chem., 35, pp. 2.145-2154 (1992); HOOK (M. B. Eisen et al, "HOOK: A Program for Finding Novel Molecular Architectures that Satisfy the Chemical and Steric Requirements of a Macromolecule Binding Site", Proteins: Struct., Funct., Genet., 19, pp. 199-221 (1994). HOOK is available from Molecular Simulations, San Diego, Calif.

Instead of proceeding to build an inhibitor of an EPHA2-like binding pocket in a step-wise fashion one fragment or entity at a time as described above, inhibitory or other EPHA2 binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61-78 (1992)). LUDI is available from Molecular Simulations Incorporated, San Diego, Calif.; LEGEND (Y. Nishibata et al., Tetrahedron, 47, p. 8985 (1991)). LEGEND is available from Molecular Simulations Incorporated, San Diego, Calif.; LEAPFROG (available from Tripos Associates, St. Louis, Mo.); & SPROUT (V. Gillet et al, "SPROUT: A Program for Structure Generation)", J. Comput. Aided Mol. Design, 7, pp. 127-153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once an entity has been designed or selected, for example, by the above methods, the efficiency with which that entity may bind to an EPHA2 binding pocket may be tested and optimized by computational evaluation. For example, an effective EPHA2 binding pocket inhibitor preferably demonstrates a relatively small difference in energy between its bound and free states (i.e., a small deformation energy of binding). Thus, the most efficient EPHA2 binding pocket inhibitors should preferably be designed with deformation energy of binding of not greater than about 10 kcal/mole, more preferably, not greater than 7 kcal/mole. EPHA2 binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to an EPHA2 binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. COPYRGT.1995); AMBER, version 4.1 (P. A. Kollman, University of California at San Francisco, COPYRGT 1995); QUANTA/CHARMM (Molecular Simulations, Inc., San Diego, Calif. COPYRGT.1995); Insight II/Discover (Molecular Simulations, Inc., San Diego, Calif. COPYRGT.1995); DelPhi (Molecular Simulations, Inc., San Diego, Calif. COPYRGT.1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to an EPHA2 binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate: with an EPHA2-like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the EPHA2 provided by this invention (and set forth in FIG. 3) can be used to determine the structure of another crystallized molecule or molecular complex more quickly and efficiently than attempting an ab initio structure determination. One particular use includes use with other structurally similar proteins. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of EPHA2 according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of EPHA2 can be resolved by this method.

In one embodiment, the method of molecular replacement is utilized to obtain structural information about the present invention and any other EPHA2-like molecule. The structure coordinates of EPHA2, as provided by this invention, are particularly useful in solving the structure of other isoforms of EPHA2 or EPHA2 complexes.

The structure coordinates of EPHA2 as provided by this invention are useful in solving the structure of EPHA2 variants that have amino acid substitutions, additions and/or deletions (referred to collectively as "EPHA2 mutants", as compared to naturally occurring EPHA2). These EPHA2 mutants may optionally be crystallized in co-complex with a ligand, such as an inhibitor, substrate analogue or a suicide substrate. The crystal structures of a series of such complexes may then be solved by molecular replacement and compared with that of EPHA2. Potential sites for modification within the various binding sites of the enzyme may thus be identified. This information provides an additional tool for determining the most efficient binding interactions such as, for example, increased hydrophobic interactions, between EPHA2 and a ligand. It is noted that the ligand may be the protein's natural ligand or may be a potential agonist or antagonist of a protein.

All of the complexes referred to above may be studied using well-known X-ray diffraction techniques and may be refined versus 1.5-3 Åresolution X-ray data to an R value of about 0.22 or less using computer software, such as X-PLOR [Yale University, COPYRIGHT.1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known EPHA2 inhibitors, and more importantly, to design new EPHA2 inhibitors.

The structure coordinates described above may also be used to derive the dihedral angles, phi and psi, that define the conformation of the amino acids in the protein backbone. As will be understood by those skilled in the art, the $phi_n$ angle refers to the rotation around the bond between the alpha-carbon and the nitrogen, and the $psi_n$ angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of EPHA2

Crystals, crystallization conditions and the diffraction pattern of EPHA2 that can be generated from the crystals also have a range of uses. One particular use relates to screening entities that are not known ligands of EPHA2 for their ability to bind to EPHA2. For example, with the availability of crystallization conditions, crystals and diffraction patterns of EPHA2 provided according to the present invention, it is possible to take a crystal of EPHA2; expose the crystal to one or more entities that may be a ligand of EPHA2; and determine whether a ligand/EPHA2 complex is formed. The crystals of EPHA2 may be exposed to potential ligands by various methods, including but not limited to, soaking a crystal in a solution of one or more potential ligands or co-crystallizing EPHA2 in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/EPHA2 complex(es) may be used to design new ligands that bind tighter, bind more specifically, have better biological activity or have better safety profile than known ligands.

In one embodiment, a method is provided for identifying a ligand that binds to EPHA2 comprising: (a) attempting to crystallize a protein that comprises a sequence wherein at least a portion of the sequence has 55%, 65%, 75%, 85%, 90%, 95%, 97%, 99% or greater identity with SEQ. ID No. 3 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to EPHA2 comprising: soaking a crystal of a protein wherein at least a portion of the protein has 55%, 65%, 75%, 85%, 90%, 95%, 97%, 99% or greater identity with SEQ. ID No. 3 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-EPHA2 complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of EPHA2

This example describes the expression of EPHA2. It should be noted that a variety of other expression systems and hosts are also suitable for the expression of EPHA2, as would be readily appreciated by one of skill in the art.

The portion of the gene encoding residues 596-900 (from SEQ. ID No. 1) which correspond to the catalytic domains of human EPHA2 was isolated from cDNA libraries lung/spleen/HeLa by PCR and cloned into the BamH I site of pFastbacHTb (Gibco-BRL). This DNA sequence is presented in FIG. 1 as SEQ. ID No. 2.

Expression in this vector generated a fusion of the kinase domain with a cleavable (rTev) N-terminal 6x-histidine tag residues, the amino acid sequence of which is shown in FIG. 1 as SEQ. ID. 3. Recombinant baculoviruses incorporating the kinase cDNA constructs were generated by transposition using the Bac-to-Bac system (Gibco-BRL). High-titer viral stocks were generated by infection of *Spodoptera frugiperda* Sf9 cells and the expression of recombinant protein was carried out by infection of *Trichoplusia ni* Hi5 cells (Gibco-BRL) in 5L Wave Bioreactors (Wave Biotech). Recombinant proteins were isolated from cellular extracts by passage over ProBond (InVitrogen) resin. It is noted that the polyhistidine tags may optionally be removed by treatment with rTEV protease (InVitrogen). However, in this instance, the polyhistidine tag was not removed. The EPHA2 protein purity as determined on denaturing SDS-PAGE gel was 90-95%. EPHA2 was not phosphorylated during the isolation and purification procedures as confirmed by mass spectrometry. EPHA2 was concentrated to a final concentration of 6.1 mg/ml and stored at 4° C. in a buffer containing 50 mM TRIS-HCl pH 7.6, 250 mM NaCl, 1 mM EDTA and 1 mM DTT.

Example 2

Crystallization of EPHA2-AMP-PNP complex

This example describes the crystallization of EPHA2-AMP-PNP complex. It is noted that the precise crystallization conditions used may be further varied, for example by performing a fine screen based on these crystallization conditions.

EPHA2 protein samples were incubated with 2 mM AMP-PNP and 4 mM $MgCl_2$ before setting crystallization trials. Crystals were obtained after an extensive and broad screen of conditions, followed by optimization. Table 5 summarizes effective crystallization conditions that were identified.

Diffraction quality crystals were grown as in 100 nL sitting droplets using the vapor diffusion method. 50 nL comprising the EPHA2-AMP-PNP complex (6.1 mg/ml) was mixed with 50 nL from a reservoir solution (100 μL) comprising 0.1M Citrate/Acetate pH=5.0 and 24% PEG MME 2K. The resulting solution was incubated over a period of one week at 20° C.

Crystals typically appeared after 8-24 hours and grew to a maximum size within 48 hours. Single crystals were separated from their parent cluster and transferred, briefly, into a cryoprotecting solution containing the reservoir solution supplemented with 20% v/v ethylene glycol. Crystals were then flash frozen by immersion in liquid nitrogen and then stored under liquid nitrogen. A crystal of EPHA2-AMP-PNP complex produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, papers, and books cited in this application are incorporated herein in their entirety.

We claim:

1. A composition comprising a protein-ligand complex in crystalline form wherein the protein of the complex consists of SEQ ID NO: 3, wherein said protein is in complex with an ATP-binding site ligand, and wherein the protein crystal has a crystal lattice in a $P3_221$ space group and unit cell dimensions, ±5% of a=72.12 Å, b=72.12 Å and c=241.62 Å.

2. A composition according to claim 1 wherein there are two molecules of the protein-ligand complex per asymmetric unit of the crystal.

3. A composition according to claim 1 wherein the crystal diffracts X-rays for a determination of structure coordinates to a resolution higher than 3.0 Angstroms.

4. A method for forming a crystal of a protein-ligand complex comprising: forming a crystallization volume comprising a precipitant solution and a protein-ligand complex, wherein the protein of the complex consists of SEQ ID NO:3 and is in complex with an ATP-binding site ligand, storing the crystallization volume under conditions suitable for crystal formation of the protein-ligand complex such that a crystal of the protein-ligand complex is formed, wherein the crystal has a crystal lattice in a $P3_221$ space group and unit cell dimensions, ±5% of a=72.12 Å, b=72.12 Å and c=241.62 Å.

5. The method according to claim 4 wherein there are two molecules of the protein-ligand complex per asymmetric unit of the crystal.

6. A method according to claim 4 wherein the crystal diffracts X-rays for a determination of structure coordinates to a resolution higher than 3.0 Angstroms.

7. A method according to claim 4, the method further comprising:
   diffracting the protein ligand crystal to produce a diffraction pattern; and
   solving the structure of the protein from the diffraction pattern.

8. A method according to claim 7, the method further comprising:
   performing rational drug design using the solved structure; and
   identifying an entity that associates with the protein.

9. A method according to claim 8 wherein there are two molecules of the protein-ligand complex per asymmetric unit of the crystal.

10. A method according to claim 8, the method further comprising:
    selecting one or more entities based on the rational drug design; and
    contacting the selected entities with the protein.

11. A method according to claim 10, the method her comprising measuring an activity of the protein when contacted with the one or more entities.

12. A method according to claim 11, the method further comprising:
    comparing activity of the protein in a presence of and in the absence of the one or more entities, and
    selecting entities where activity of the protein changes depending whether a particular entity is present.

13. An isolated non-crystalline protein consisting of residues 596-900 of SEQ ID NO: 1.

14. A non-crystalline protein consisting of SEQ ID NO:3.

15. A non-crystalline protein comprising SEQ ID NO: 3.

* * * * *

SEQUENCE LISTING

```
<160> NUMBER OF SEQ ID NOS: 3

<210> SEQ ID NO 1
<211> LENGTH: 976
<212> TYPE: PRT
<213> ORGANISM: Homo sapiens
<220> FEATURE:
<221> NAME/KEY: Amino acid sequence for full length human wild type
      EPHA2
<222> LOCATION: (1)..(976)
<223> OTHER INFORMATION:
<220> FEATURE:
<221> NAME/KEY: Amino acid sequence for full length human wild type
      EPHA2
<222> LOCATION: (1)..(976)
<223> OTHER INFORMATION: SEQ. ID. No. 1 encodes for residues 596-900
<300> PUBLICATION INFORMATION:
<308> DATABASE ACCESSION NUMBER: GenBank Accession No. M59371
```

-continued

```
<309> DATABASE ENTRY DATE: 1994-11-21
<313> RELEVANT RESIDUES: (1)..(976)

<400> SEQUENCE: 1
```

| | | | | | | | | | | | | | | | |
|---|---|---|---|---|---|---|---|---|---|---|---|---|---|---|---|
| Met | Glu | Leu | Gln | Ala | Ala | Arg | Ala | Cys | Phe | Ala | Leu | Leu | Trp | Gly | Cys |
| 1 | | | | 5 | | | | | 10 | | | | | 15 | |
| Ala | Leu | Ala | Ala | Ala | Ala | Ala | Gln | Gly | Lys | Glu | Val | Val | Leu | Leu | |
| | | | 20 | | | | | 25 | | | | | 30 | | |
| Asp | Phe | Ala | Ala | Ala | Gly | Gly | Glu | Leu | Gly | Trp | Leu | Thr | His | Pro | Tyr |
| | | | 35 | | | | | 40 | | | | | 45 | | |
| Gly | Lys | Gly | Trp | Asp | Leu | Met | Gln | Asn | Ile | Met | Asn | Asp | Met | Pro | Ile |
| 50 | | | | | 55 | | | | | 60 | | | | | |
| Tyr | Met | Tyr | Ser | Val | Cys | Asn | Val | Met | Ser | Gly | Asp | Gln | Asp | Asn | Trp |
| 65 | | | | 70 | | | | | 75 | | | | | 80 | |
| Leu | Arg | Thr | Asn | Trp | Val | Tyr | Arg | Gly | Glu | Ala | Glu | Arg | Asn | Asn | Phe |
| | | | | 85 | | | | | 90 | | | | | 95 | |
| Glu | Leu | Asn | Phe | Thr | Val | Arg | Asp | Cys | Asn | Ser | Phe | Pro | Gly | Gly | Ala |
| | | | | 100 | | | | | 105 | | | | | 110 | |
| Ser | Ser | Cys | Lys | Glu | Thr | Phe | Asn | Leu | Tyr | Tyr | Ala | Glu | Ser | Asp | Leu |
| | | | 115 | | | | | 120 | | | | | 125 | | |
| Asp | Tyr | Gly | Thr | Asn | Phe | Gln | Lys | Arg | Leu | Phe | Thr | Lys | Ile | Asp | Thr |
| | | 130 | | | | | 135 | | | | | 140 | | | |
| Ile | Ala | Pro | Asp | Glu | Ile | Thr | Val | Ser | Ser | Asp | Phe | Glu | Ala | Arg | His |
| 145 | | | | | 150 | | | | | 155 | | | | | 160 |
| Val | Lys | Leu | Asn | Val | Glu | Glu | Arg | Ser | Val | Gly | Pro | Leu | Thr | Arg | Lys |
| | | | | 165 | | | | | 170 | | | | | 175 | |
| Gly | Phe | Tyr | Leu | Ala | Phe | Gln | Asp | Ile | Gly | Ala | Cys | Val | Ala | Leu | Leu |
| | | | 180 | | | | | 185 | | | | | 190 | | |
| Ser | Val | Arg | Val | Tyr | Tyr | Lys | Lys | Cys | Pro | Glu | Leu | Leu | Gln | Gly | Leu |
| | | 195 | | | | | 200 | | | | | 205 | | | |
| Ala | His | Phe | Pro | Glu | Thr | Ile | Ala | Gly | Ser | Asp | Ala | Pro | Ser | Leu | Ala |
| | 210 | | | | | 215 | | | | | 220 | | | | |
| Thr | Val | Ala | Gly | Thr | Cys | Val | Asp | His | Ala | Val | Val | Pro | Pro | Gly | Gly |
| 225 | | | | | 230 | | | | | 235 | | | | | 240 |
| Glu | Glu | Pro | Arg | Met | His | Cys | Ala | Val | Asp | Gly | Glu | Trp | Leu | Val | Pro |
| | | | | 245 | | | | | 250 | | | | | 255 | |
| Ile | Gly | Gln | Cys | Leu | Cys | Gln | Ala | Gly | Tyr | Glu | Lys | Val | Glu | Asp | Ala |
| | | | 260 | | | | | 265 | | | | | 270 | | |
| Cys | Gln | Ala | Cys | Ser | Pro | Gly | Phe | Phe | Lys | Phe | Glu | Ala | Ser | Glu | Ser |
| | | 275 | | | | | 280 | | | | | 285 | | | |
| Pro | Cys | Leu | Glu | Cys | Pro | Glu | His | Thr | Leu | Pro | Ser | Pro | Glu | Gly | Ala |
| | 290 | | | | | 295 | | | | | 300 | | | | |
| Thr | Ser | Cys | Glu | Cys | Glu | Glu | Gly | Phe | Phe | Arg | Ala | Pro | Gln | Asp | Pro |
| 305 | | | | | 310 | | | | | 315 | | | | | 320 |
| Ala | Ser | Met | Pro | Cys | Thr | Arg | Pro | Pro | Ser | Ala | Pro | His | Tyr | Leu | Thr |
| | | | | 325 | | | | | 330 | | | | | 335 | |
| Ala | Val | Gly | Met | Gly | Ala | Lys | Val | Glu | Leu | Arg | Trp | Thr | Pro | Pro | Gln |
| | | | 340 | | | | | 345 | | | | | 350 | | |
| Asp | Ser | Gly | Gly | Arg | Glu | Asp | Ile | Val | Tyr | Ser | Val | Thr | Cys | Glu | Gln |
| | | | | 355 | | | | | 360 | | | | | 365 | |
| Cys | Trp | Pro | Glu | Ser | Gly | Glu | Cys | Gly | Pro | Cys | Glu | Ala | Ser | Val | Arg |
| | | 370 | | | | | 375 | | | | | 380 | | | |
| Tyr | Ser | Glu | Pro | Pro | His | Gly | Leu | Thr | Arg | Thr | Ser | Val | Thr | Val | Ser |
| 385 | | | | | 390 | | | | | 395 | | | | | 400 |

```
Asp Leu Glu Pro His Met Asn Tyr Thr Phe Thr Val Glu Ala Arg Asn
                405                 410                 415
Gly Val Ser Gly Leu Val Thr Ser Arg Ser Phe Arg Thr Ala Ser Val
            420                 425                 430
Ser Ile Asn Gln Thr Glu Pro Pro Lys Val Arg Leu Glu Gly Arg Ser
        435                 440                 445
Thr Thr Ser Leu Ser Val Ser Trp Ser Ile Pro Pro Gln Gln Ser
450                 455                 460
Arg Val Trp Lys Tyr Glu Val Thr Tyr Arg Lys Lys Gly Asp Ser Asn
465                 470                 475                 480
Ser Tyr Asn Val Arg Arg Thr Glu Gly Phe Ser Val Thr Leu Asp Asp
                485                 490                 495
Leu Ala Pro Asp Thr Thr Tyr Leu Val Gln Val Gln Ala Leu Thr Gln
            500                 505                 510
Glu Gly Gln Gly Ala Gly Ser Lys Val His Glu Phe Gln Thr Leu Ser
        515                 520                 525
Pro Glu Gly Ser Gly Asn Leu Ala Val Ile Gly Gly Val Ala Val Gly
    530                 535                 540
Val Val Leu Leu Leu Val Leu Ala Gly Val Gly Phe Phe Ile His Arg
545                 550                 555                 560
Arg Arg Lys Asn Gln Arg Ala Arg Gln Ser Pro Glu Asp Val Tyr Phe
                565                 570                 575
Ser Lys Ser Glu Gln Leu Lys Pro Leu Lys Thr Tyr Val Asp Pro His
            580                 585                 590
Thr Tyr Glu Asp Pro Asn Gln Ala Val Leu Lys Phe Thr Thr Glu Ile
        595                 600                 605
His Pro Ser Cys Val Thr Arg Gln Lys Val Ile Gly Ala Gly Glu Phe
    610                 615                 620
Gly Glu Val Tyr Lys Gly Met Leu Lys Thr Ser Ser Gly Lys Lys Glu
625                 630                 635                 640
Val Pro Val Ala Ile Lys Thr Leu Lys Ala Gly Tyr Thr Glu Lys Gln
                645                 650                 655
Arg Val Asp Phe Leu Gly Glu Ala Gly Ile Met Gly Gln Phe Ser His
            660                 665                 670
His Asn Ile Ile Arg Leu Glu Gly Val Ile Ser Lys Tyr Lys Pro Met
        675                 680                 685
Met Ile Ile Thr Glu Tyr Met Glu Asn Gly Ala Leu Asp Lys Phe Leu
    690                 695                 700
Arg Glu Lys Asp Gly Glu Phe Ser Val Leu Gln Leu Val Gly Met Leu
705                 710                 715                 720
Arg Gly Ile Ala Ala Gly Met Lys Tyr Leu Ala Asn Met Asn Tyr Val
                725                 730                 735
His Arg Asp Leu Ala Ala Arg Asn Ile Leu Val Asn Ser Asn Leu Val
            740                 745                 750
Cys Lys Val Ser Asp Phe Gly Leu Ser Arg Val Leu Glu Asp Asp Pro
        755                 760                 765
Glu Ala Thr Tyr Thr Thr Ser Gly Gly Lys Ile Pro Ile Arg Trp Thr
    770                 775                 780
Ala Pro Glu Ala Ile Ser Tyr Arg Lys Phe Thr Ser Ala Ser Asp Val
785                 790                 795                 800
Trp Ser Phe Gly Ile Val Met Trp Glu Val Met Thr Tyr Gly Glu Arg
                805                 810                 815
```

```
Pro Tyr Trp Glu Leu Ser Asn His Glu Val Met Lys Ala Ile Asn Asp
            820                 825                 830
Gly Phe Arg Leu Pro Thr Pro Met Asp Cys Pro Ser Ala Ile Tyr Gln
            835                 840                 845
Leu Met Met Gln Cys Trp Gln Gln Glu Arg Ala Arg Arg Pro Lys Phe
            850                 855                 860
Ala Asp Ile Val Ser Ile Leu Asp Lys Leu Ile Arg Ala Pro Asp Ser
865                 870                 875                 880
Leu Lys Thr Leu Ala Asp Phe Asp Pro Arg Val Ser Ile Arg Leu Pro
            885                 890                 895
Ser Thr Ser Gly Ser Glu Gly Val Pro Phe Arg Thr Val Ser Glu Trp
            900                 905                 910
Leu Glu Ser Ile Lys Met Gln Gln Tyr Thr Glu His Phe Met Ala Ala
            915                 920                 925
Gly Tyr Thr Ala Ile Glu Lys Val Val Gln Met Thr Asn Asp Asp Ile
            930                 935                 940
Lys Arg Ile Gly Val Arg Leu Pro Gly His Gln Lys Arg Ile Ala Tyr
945                 950                 955                 960
Ser Leu Leu Gly Leu Lys Asp Gln Val Asn Thr Val Gly Ile Pro Ile
            965                 970                 975

<210> SEQ ID NO 2
<211> LENGTH: 915
<212> TYPE: DNA
<213> ORGANISM: Homo sapiens
<220> FEATURE:
<221> NAME/KEY: Human cDNA sequence encoding residues 596-900 of EPHA2
<222> LOCATION: (1)..(915)
<223> OTHER INFORMATION:

<400> SEQUENCE: 2
gaccccaacc aggctgtgtt gaagttcact accgagatcc atccatcctg tgtcactcgg      60
cagaaggtga tcggagcagg agagtttggg gaggtgtaca agggcatgct gaagacatcc     120
tcggggaaga aggaggtgcc ggtggccatc aagacgctga agccggcta cagagaaag      180 cagcgagtgg acttcctcgg cgaggccggc atcatgggcc agttcagcca ccacaacatc     240
atccgcctag agggcgtcat ctccaaatac aagcccatga tgatcatcac tgagtacatg     300
gagaatgggg ccctggacaa gttccttcgg gagaaggatg gcgagttcag cgtgctgcag     360
ctggtgggca tgctgcgggg catcgcagct ggcatgaagt acctggccaa catgaactat     420
gtgcaccgtg acctggctgc cgcaacatc ctcgtcaaca gcaacctggt ctgcaaggtg      480
tctgactttg gcctgtcccg cgtgctggag gacgaccccg aggccaccta caccaccagt     540
ggcggcaaga tccccatccg ctggaccgcc cggaggcca tttcctaccg gaagttcacc      600
tctgccagcg acgtgtggag ctttggcatt gtcatgtggg aggtgatgac ctatggcgag     660
cggccctact gggagttgtc caaccacgag gtgatgaaag ccatcaatga tggcttccgg     720
ctccccacac ccatggactg cccctccgcc atctaccagc tcatgatgca gtgctggcag     780
caggagcgtg cccgccgccc caagttcgct gacatcgtca gcatcctgga caagctcatt     840
cgtgcccctg actccctcaa gaccctggct gactttgacc ccgcgtgtc tatccggctc      900 cccagcacga gcggc                                                      915

<210> SEQ ID NO 3
<211> LENGTH: 333
<212> TYPE: PRT
<213> ORGANISM: Homo sapiens
```

-continued

```
<220> FEATURE:
<221> NAME/KEY: Amino acid sequence for residues 596-900 of EPHA2 with a
      cleavable (rTev) N-terminal 6x-histidine tag
<222> LOCATION: (1)..(333)
<223> OTHER INFORMATION:
<220> FEATURE:
<221> NAME/KEY: Cleavable (rTev) N-terminal 6x-histidine tag
<222> LOCATION: (1)..(28)
<223> OTHER INFORMATION:

<400> SEQUENCE: 3

Met Ser Tyr Tyr His His His His His His Asp Tyr Asp Ile Pro Thr
1               5                   10                  15

Thr Glu Asn Leu Tyr Phe Gln Gly Ala Met Gly Ser Asp Pro Asn Gln
            20                  25                  30

Ala Val Leu Lys Phe Thr Thr Glu Ile His Pro Ser Cys Val Thr Arg
        35                  40                  45

Gln Lys Val Ile Gly Ala Gly Glu Phe Gly Glu Val Tyr Lys Gly Met
    50                  55                  60

Leu Lys Thr Ser Ser Gly Lys Lys Glu Val Pro Val Ala Ile Lys Thr
65                  70                  75                  80

Leu Lys Ala Gly Tyr Thr Glu Lys Gln Arg Val Asp Phe Leu Gly Glu
                85                  90                  95

Ala Gly Ile Met Gly Gln Phe Ser His His Asn Ile Ile Arg Leu Glu
            100                 105                 110

Gly Val Ile Ser Lys Tyr Lys Pro Met Met Ile Ile Thr Glu Tyr Met
        115                 120                 125

Glu Asn Gly Ala Leu Asp Lys Phe Leu Arg Glu Lys Asp Gly Glu Phe
    130                 135                 140

Ser Val Leu Gln Leu Val Gly Met Leu Arg Gly Ile Ala Ala Gly Met
145                 150                 155                 160

Lys Tyr Leu Ala Asn Met Asn Tyr Val His Arg Asp Leu Ala Ala Arg
                165                 170                 175

Asn Ile Leu Val Asn Ser Asn Leu Val Cys Lys Val Ser Asp Phe Gly
            180                 185                 190

Leu Ser Arg Val Leu Glu Asp Asp Pro Glu Ala Thr Tyr Thr Thr Ser
        195                 200                 205

Gly Gly Lys Ile Pro Ile Arg Trp Thr Ala Pro Glu Ala Ile Ser Tyr
    210                 215                 220

Arg Lys Phe Thr Ser Ala Ser Asp Val Trp Ser Phe Gly Ile Val Met
225                 230                 235                 240

Trp Glu Val Met Thr Tyr Gly Glu Arg Pro Tyr Trp Glu Leu Ser Asn
                245                 250                 255

His Glu Val Met Lys Ala Ile Asn Asp Gly Phe Arg Leu Pro Thr Pro
            260                 265                 270

Met Asp Cys Pro Ser Ala Ile Tyr Gln Leu Met Met Gln Cys Trp Gln
        275                 280                 285

Gln Glu Arg Ala Arg Arg Pro Lys Phe Ala Asp Ile Val Ser Ile Leu
    290                 295                 300

Asp Lys Leu Ile Arg Ala Pro Asp Ser Leu Lys Thr Leu Ala Asp Phe
305                 310                 315                 320

Asp Pro Arg Val Ser Ile Arg Leu Pro Ser Thr Ser Gly
                325                 330
```